US012454534B2

(12) United States Patent
Li et al.

(10) Patent No.: US 12,454,534 B2
(45) Date of Patent: Oct. 28, 2025

(54) PYRROLO[2,3-B]PYRAZINES AS HPK1 INHIBITOR AND THE USE THEREOF

(71) Applicant: BEIGENE, LTD., Grand Cayman (KY)

(72) Inventors: Jing Li, Beijing (CN); Zhiwei Wang, Beijing (CN); Sanjia Xu, Beijing (CN)

(73) Assignee: BeOne Medicines I GmbH, Basel (CH)

( * ) Notice: Subject to any disclaimer, the term of this patent is extended or adjusted under 35 U.S.C. 154(b) by 902 days.

(21) Appl. No.: 17/623,732

(22) PCT Filed: Jul. 3, 2020

(86) PCT No.: PCT/CN2020/100037
§ 371 (c)(1),
(2) Date: Dec. 29, 2021

(87) PCT Pub. No.: WO2021/000925
PCT Pub. Date: Jan. 7, 2021

(65) Prior Publication Data

US 2022/0267333 A1 Aug. 25, 2022

(30) Foreign Application Priority Data

Jul. 4, 2019 (WO) ................ PCT/CN2019/094749
Dec. 5, 2019 (WO) ................ PCT/CN2019/123268
May 9, 2020 (WO) ................ PCT/CN2020/089498

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC .................................................... C07D 487/04
See application file for complete search history.

(56) References Cited

U.S. PATENT DOCUMENTS

| | | | |
|---|---|---|---|
| 5,942,532 | A | 8/1999 | Ohemeng |
| 10,239,873 | B2 | 3/2019 | Choi et al. |
| 11,566,003 | B2 | 1/2023 | Chan et al. |
| 2006/0122185 | A1 | 6/2006 | Green et al. |
| 2006/0258662 | A1 | 11/2006 | Binch et al. |
| 2007/0087988 | A1 | 4/2007 | Sawasdikosol et al. |
| 2011/0081364 | A1 | 4/2011 | Binch et al. |
| 2016/0214996 | A1 | 7/2016 | Song |
| 2016/0297815 | A1 | 10/2016 | Choi et al. |
| 2018/0072720 | A1 | 3/2018 | Vechorkin et al. |
| 2018/0298009 | A1 | 10/2018 | Ford |
| 2019/0106419 | A1 | 4/2019 | Vechorkin et al. |
| 2021/0380581 | A1 | 12/2021 | Vechorkin et al. |

FOREIGN PATENT DOCUMENTS

| | | | |
|---|---|---|---|
| CA | 3092011 | A1 | 9/2019 |
| CN | 101098872 | A | 1/2008 |
| CN | 101851237 | A | 10/2010 |
| CN | 106336413 | A | 1/2017 |
| CN | 106432246 | A | 2/2017 |
| CN | 108440532 | A | 8/2018 |
| CN | 109923114 | A | 6/2019 |
| JP | 2012012332 | A | 1/2012 |
| TW | 201843139 | A | 12/2018 |
| WO | WO-2005028475 | A2 | 3/2005 |
| WO | 2006015123 | A1 | 2/2006 |
| WO | WO-2006015124 | A2 | 2/2006 |
| WO | WO-2006058074 | A1 | 6/2006 |
| WO | WO-2008124849 | A2 | 10/2008 |
| WO | WO-2010049173 | A1 | 5/2010 |
| WO | 2011149950 | A2 | 12/2011 |
| WO | WO-2014006554 | A1 | 1/2014 |
| WO | WO-2014085795 | A1 | 6/2014 |
| WO | WO-2014093383 | A1 | 6/2014 |
| WO | 2016000615 | A1 | 1/2016 |
| WO | WO-2016164641 | A1 | 10/2016 |
| WO | WO-2016205942 | A1 | 12/2016 |

(Continued)

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*

(Continued)

*Primary Examiner* — Nizal S Chandrakumar
(74) *Attorney, Agent, or Firm* — McNeill PLLC

(57) ABSTRACT

Disclosed herein is a compound of Formula (I), or a stereoisomer thereof, or a pharmaceutically acceptable salt thereof, and pharmaceutical compositions comprising thereof. Also disclosed is a method of treating HPK1 related disorders or diseases by using the compound disclosed herein.

(I)

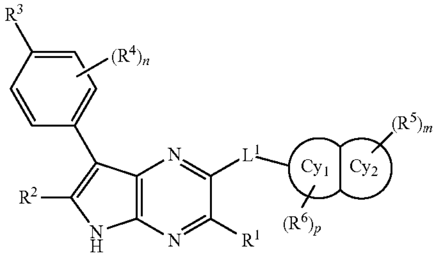

25 Claims, No Drawings

(56) References Cited

FOREIGN PATENT DOCUMENTS

| | | | | | |
|---|---|---|---|---|---|
| WO | WO-2018049152 | A1 | | 3/2018 | |
| WO | WO-2018049191 | A1 | | 3/2018 | |
| WO | WO-2018049200 | A1 | | 3/2018 | |
| WO | WO-2018049214 | A1 | | 3/2018 | |
| WO | WO-2018167147 | A1 | | 9/2018 | |
| WO | 2018183965 | A1 | | 10/2018 | |
| WO | WO-2018183956 | A1 | | 10/2018 | |
| WO | WO-2019167000 | A1 | | 9/2019 | |
| WO | WO-2019227059 | A1 | | 11/2019 | |
| WO | WO-2019238067 | A1 | | 12/2019 | |
| WO | WO-2020103896 | A1 | | 5/2020 | |
| WO | WO 2020227325 | | * | 12/2020 | ........... C07D 410/04 |
| WO | WO-2021000925 | A1 | | 1/2021 | |
| WO | WO-2021013083 | A1 | | 1/2021 | |
| WO | WO-2021032148 | A1 | | 2/2021 | |
| WO | WO-2021057872 | A1 | * | 4/2021 | ........... A61K 38/177 |

OTHER PUBLICATIONS

STN Registry/Zregistry (CAS Registrysm) Sep. 2016 2 pages.*

Venkatesh, J. Pharm. Sci. 89, 145-154 (2000) (p. 146, left column).*

J. G. Cannon, Chapter Nineteen in Burger's Medicinal Chemistry and Drug Discovery, Fifth Edition, vol. I: Principles and Practice, Wiley-Interscience 1995, pp. 783-802, 784.*

Wang, PLoS ONE 15(12): e0243145.*

Dorwald F. A. Side Reactions in Organic Synthesis, 2005, Wiley: VCH, Weinheim p. IX of Preface p. 1-15.*

Alzabin, S. et al., "Hematopoietic progenitor kinase 1 is a critical component of prostaglandin E2-mediated suppression of the anti-tumor immune response," Cancer Immunol Immunother, Mar. 2010, 59(3):419-429.

Alzabin, S. et al., "Hematopoietic progenitor kinase 1 is a negative regulator of dendritic cell activation," J Immunol, May 2009, 182(10):6187-6194.

Batliwalla, F. M. et al., "Microarray Analyses of Peripheral Blood Cells Identifies Unique Gene Expression Signature in Psoriatic Arthritis," Molecular Medicine, vol. 11, No. 1-12, Jan.-Dec. 2005, pp. 21-29.

Ikegami, R. et al., "The Expression of Prostaglandin E Receptors EP2 and EP4 and Their Different Regulation by Lipopolysaccharide in C3H/HeN Peritoneal Macrophages," J Immunol, Apr. 2001, vol. 166, No. 7, pp. 4689-4696.

International Search Report and Written Opinion for International Application No. PCT/CN2019/090922, mailed Sep. 19, 2019, 12 pages.

International Search Report and Written Opinion for International Application No. PCT/CN2019/119896, mailed Feb. 26, 2020, 8 pages.

International Search Report and Written Opinion for International Application No. PCT/CN2020/100037, mailed Oct. 10, 2020, 15 pages.

International Search Report and Written Opinion for International Application No. PCT/CN2020/102647, mailed Sep. 22, 2020, 9 pages.

International Search Report and Written Opinion for International Application No. PCT/CN2020/110171, mailed Nov. 23, 2020, 12 pages.

Liou, J. et al., "HPK1 is activated by lymphocyte antigen receptors and negatively regulates AP-1," Immunity, Apr. 2000, 12(4):399-408.

Sawasdikosol, S. et al., "HPK1 as a novel target for cancer immunotherapy," Immunol Res., Dec. 2012, vol. 54, No. 1-3, pp. 262-265.

Wang, W. et al., "Activation of the Hematopoietic Progenitor Kinase-1 (HPK1)-dependent, Stress-activated c-Jun N-terminal Kinase (JNK) Pathway by Transforming Growth Factor β (TGF-β)-activated Kinase (TAK1), a Kinase Mediator of TGF β Signal Transduction," J. Biol. Chem., Sep. 1997, vol. 272, No. 36, pp. 22771-22775.

Zhou, G. et al., "Hematopoietic Progenitor Kinase 1 Is a Component of Transforming Growth Factor β-induced c-Jun N-terminal Kinase Signaling Cascade," J. Biol. Chem., May 1999, vol. 274, No. 19, pp. 13133-13138.

Kelly et al., Azaindoles I. preparation of 7-azaindoles by thermal indolization of 2-pyridylhydrazones, Canadian Journal of Chemistry 1966, vol. 44, pp. 2455-2459. (Year: 1966).

Gao et al., 2012, "Suzuki coupling reaction catalyzed by aniline-β-imine/PdCl2", China Academic Journal Electronic Publishing House (2 pages).

* cited by examiner

PYRROLO[2,3-B]PYRAZINES AS HPK1 INHIBITOR AND THE USE THEREOF

CROSS-REFERENCE TO RELATED APPLICATIONS

This application is a U.S. National Stage Application under 35 U.S.C. § 371 of International Application No. PCT/CN2020/100037, filed on Jul. 3, 2020, which claims priority to Patent Application Nos. PCT/CN2019/094749 (CN), filed on Jul. 4, 2019, PCT/CN2019/123268 (CN), filed on Dec. 5, 2019, and PCT/CN2019/089498 (CN), filed on May 9, 2020.

FIELD OF THE INVENTION

The disclosure herein provides compounds as well as their compositions and methods of use. The compounds disclosed herein modulate, e.g., inhibit, hematopoietic progenitor kinase 1 (HPK1) activity and are useful in the treatment of various diseases including cancer.

BACKGROUND OF THE INVENTION

HPK1 regulates diverse functions of various immune cells and its kinase activity has been shown to be induced upon activation of T cell receptors (TCR) [Liou J., et al., *Immunity,* 2000. 12 (4): pp. 399-408], B cell receptors (BCR) [Liou J., et al., *Immunity,* 2000. 12 (4): pp. 399-408], transforming growth factor receptor (TGF-βR) [Wang, W., et al., *J Biol Chem,* 1997. 272 (36): pp. 22771-5; Zhou, G., et al., *J Biol Chem,* 1999. 274 (19): pp. 13133-8], or Gs-coupled PGE2 receptors (EP2 and EP4) [Ikegami, R., et al., *J Immunol,* 2001. 166 (7): pp. 4689-96]. Overexpression of HPK1 suppresses TCR-induced activation of AP-1-dependent gene transcription in a kinase-dependent manner, suggesting that HPK1 is required to inhibit the Erk MAPK pathway [Liou J., et al., *Immunity,* 2000. 12 (4): pp. 399-408] and this blockage is thought to be the inhibitory mechanism that negatively regulates TCR-induced IL-2 gene transcription [S. Sawasdikosol., et al., *Immunol Res,* 2012. 54: pp. 262-265].

In vitro HPK1−/− T cells have a lower TCR activation threshold, proliferate robustly, produce enhanced amounts of Th1 cytokines, the HPK1−/− mice experience more severe autoimmune symptoms [S. Sawasdikosol., et al., *Immunol Res,* 2012. 54: pp. 262-265]. In human, HPK1 was downregulated in peripheral blood mononuclear cells of psoriatic arthritis patients or T cells of systemic lupus erythematosus (SLE) patients [Batliwalla F. M., et al., *Mol Med,* 2005. 11 (1-12): pp. 21-9], which indicated that attenuation of HPK1 activity may contribute to autoimmunity in patients. Furthermore, HPK1 may also control anti-tumor immunity via T cell-dependent mechanisms. In the PGE2-producing Lewis lung carcinoma tumor model, the tumors developed more slowly in HPK1 knockout mice as compared to wild-type mice [US patent application No. 2007/0087988]. HPK1 deficient T cells was more effective in controlling tumor growth and metastasis than wild-type T cells [Alzabin, S., et al., *Cancer Immunol Immunother,* 2010. 59 (3): pp. 419-29]. Similarly, BMDCs from HPK1 knockout mice were more efficient to mount a T cell response to eradicate Lewis lung carcinoma as compared to wild-type BMDCs [Alzabin, S., et al., *J Immunol,* 2009. 182 (10): pp. 6187-94]. In all, HPK1 may be a good target for enhancing antitumor immunity.

As HPK1 modulators, WO2016205942 discloses benzoimidazoles, WO2018049152A1 discloses pyrazolopyrmidines, WO2018049191A1 discloses pyrazolopyridones, and WO2008124849, WO2018049200A1 and WO2018049214A1 discloses pyrazolopyridines.

However, there is a need to provide new HPK1 kinase inhibitors useful in treating cancer.

SUMMARY OF THE INVENTION

In the first aspect, disclosed herein is pyrrolo[2, 3-b] pyrazine derivatives of Formula (I), and the methods of use. The first embodiment comprises the following aspects:

Aspect 1: A compound of Formula (I)

(I)

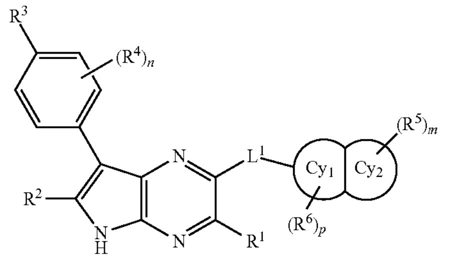

or a pharmaceutically acceptable salt thereof, or a stereoisomer thereof, wherein $R^1$ and $R^2$ are each independently hydrogen, halogen, —$C_{1-8}$alkyl, —$C_{2-8}$alkenyl, —$C_{2-8}$alkynyl, cycloalkyl, heterocyclyl, aryl, heteroaryl, oxo, —CN, —$NO_2$, —$OR^a$, —$SO_2R^a$, —$COR^a$, —$CO_2R^a$, —$CONR^aR^b$, —$C(=NR^a)NR^bR^c$, —$NR^aR^b$, —$NR^aCOR^b$, —$NR^aCONR^bR^c$, —$NR^aCO_2R^b$, —$NR^aSONR^bR^c$, —$NR^aSO_2NR^bR^c$, or —$NR^aSO_2R^b$, each of said —$C_{1-8}$ alkyl, —$C_{2-8}$alkenyl, —$C_{2-8}$alkynyl, cycloalkyl, heterocyclyl, aryl, or heteroaryl is optionally substituted with halogen, hydroxy, —$C_{1-8}$alkyoxy, cycloalkyl, heterocyclyl, aryl, or heteroaryl;

$R^a$, $R^b$, and $R^c$ are each independently hydrogen, —$C_{1-8}$ alkyl, —$C_{2-8}$alkenyl, —$C_{2-8}$alkynyl, cycloalkyl, heterocyclyl, aryl, or heteroaryl;

n is 0, 1, 2, 3 or 4;

$R^3$ and $R^4$, at each of its occurrence, are independently halogen, —$C_{1-8}$alkyl, —$C_{2-8}$alkenyl, —$C_{2-8}$alkynyl, cycloalkyl, heterocyclyl, —$C_{1-8}$alkyl-heterocyclyl, —$C_{1-8}$alkyl-cycloalkyl, aryl, heteroaryl, oxo, —CN, —$NO_2$, —$OR^{3a}$, —$SO_2R^{3a}$, —$SO_2NR^{3a}R^{3b}$, —$COR^{3a}$, —$CO_2R^{3a}$, —$CONR^{3a}R^{3b}$, —$C(=NR^{3a})NR^{3b}R^{3c}$, —$NR^{3a}R^{3b}$, —$NR^{3a}COR^{3b}$, —$NR^{3a}CONR^{3b}R^{3c}$, —$NR^{3a}CO_2R^{3b}$, —$NR^{3a}SONR^{3b}R^{3c}$, —$NR^{3a}SO_2NR^{3b}R^{3c}$, or —$NR^{3a}SO_2R^{3b}$, each of said —$C_{1-8}$alkyl, —$C_{2-8}$alkenyl, —$C_{2-8}$alkynyl, cycloalkyl, heterocyclyl, —$C_{1-8}$alkyl-heterocyclyl, aryl, or heteroaryl is optionally substituted with at least one substituents $R^{3d}$; or $R^3$ and $R^4$, when on adjacent carbon atoms of the phenyl ring, together with the two intervening carbon atoms to which they are attached, form a 5- to 8-membered ring comprising 0, 1 or 2 heteroatoms independently selected from nitrogen, oxygen or optionally oxidized sulfur as ring member (s), said ring is optionally substituted with at least one substituents $R^{3e}$;

or two $R^4$, when on adjacent carbon atoms of the phenyl ring, together with the two intervening carbon atoms to which they are attached, form a 5- to 8-membered ring comprising 0, 1 or 2 heteroatoms independently selected from nitrogen, oxygen or optionally oxidized sulfur as ring member (s).

$R^{3a}$, $R^{3b}$, and $R^{3c}$ are each independently hydrogen, —$C_{1-8}$alkyl, —$C_{2-8}$alkenyl, —$C_{2-8}$alkynyl, cycloalkyl, heterocyclyl, aryl, or heteroaryl, each of said —$C_{1-8}$alkyl, —$C_{2-8}$alkenyl, —$C_{2-8}$alkynyl, cycloalkyl, heterocyclyl, aryl, or heteroaryl is optionally substituted with at least one substituents $R^{3e}$; or ($R^{3a}$ and $R^{3b}$), ($R^{3b}$ and $R^{3c}$), or ($R^{3c}$ and $R^{3a}$), together with the atom (s) to which they are attached, form a 3- to 12-membered ring, said ring comprising 0, 1 or 2 additional heteroatoms independently selected from nitrogen, oxygen or optionally oxidized sulfur as ring member (s), said ring is optionally substituted with at least one substituents $R^{3e}$;

$R^{3d}$ and $R^{3e}$ are each independently halogen, —$C_{1-8}$alkyl, —$C_{2-8}$alkenyl, —$C_{2-8}$alkynyl, cycloalkyl, heterocyclyl, aryl, heteroaryl, oxo, —CN, —$NO_2$, —$OR^{3f}$, —$SO_2R^{3f}$, —$SO_2NR^{3f}R^{3g}$, —$COR^{3f}$, —$CO_2R^{3f}$, —$CONR^{3f}R^{3g}$, —C(=$NR^{3f}$)$NR^{3g}R^{3h}$, —$NR^{3f}R^{3g}$, —$NR^{3f}COR^{3g}$, —$NR^{3f}CONR^{3g}R^{3h}$, —$NR^{3f}CO_2R^{3f}$, —$NR^{3f}SONR^{3f}R^{3g}$, —$NR^{3f}SO_2NR^{3g}R^{3h}$, or —$NR^{3f}SO_2R^{3g}$, each of said —$C_{1-8}$alkyl, —$C_{2-8}$alkenyl, —$C_{2-8}$alkynyl, cycloalkyl, heterocyclyl, aryl, or heteroaryl is optionally substituted with at least one substituents selected from halogen, —$C_{1-8}$alkyl, —$OR^{3i}$, —$NR^{3i}R^{3j}$, cycloalkyl, heterocyclyl, aryl, or heteroaryl;

$R^{3f}$, $R^{3g}$, $R^{3h}$, $R^{3i}$, and $R^{3j}$ are each independently hydrogen, —$C_{1-8}$alkyl, $C_{1-8}$alkoxy-$C_{1-8}$alkyl-, —$C_{2-8}$alkenyl, —$C_{2-8}$alkynyl, cycloalkyl, heterocyclyl, aryl, or heteroaryl;

$L^1$ is a single bond, alkylene, cycloalkylene, $*^1$—O-alkylene-$**^1$, $*^1$-alkylene-O—$**^1$, $*^1$—NH-alkylene-$**^1$, $*^1$-alkylene-NH—$**^1$, $*^1$—NHC(O)—$**^1$, $*^1$—C(O)NH—$**^1$, alkenylene, or alkynylene; wherein $*^1$ refers to the position attached to Cy1, and $**^1$ refers to the position attached to the pyrrolo[2,3-b]prazine ring;

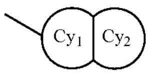

is a fused heterocyclyl, fused heteroaryl, fused aryl, fused cycloalkyl, fused cycloalkenyl, or fused cycloalkynyl,

is optionally substituted with $R^6$;

p is 0, 1, 2, 3, 4;

is optionally substituted with $R^5$, m is 0, 1, 2, 3, 4;

$R^5$ at each of its occurrence, is each independently halogen, —$C_{1-8}$alkyl, —$C_{2-8}$alkenyl, —$C_{2-8}$alkynyl, cycloalkyl, —$C_{1-8}$alkyl-cycloalkyl, heterocyclyl, aryl, heteroaryl, oxo, —CN, —$NO_2$, —$OR^{5a}$, —$SO_2R^{5a}$, —$SO_2NR^{5a}R^{5b}$, —$POR^{5a}R^{5b}$, —$COR^{5a}$, —$CO_2R^{5a}$, —$CONR^{5a}R^{5b}$, —C(=$NR^{5a}$)$NR^{5b}R^{5c}$, —$CH_2CONR^{5a}R^{5b}$, —$CH_2CH_2CONR^{5a}R^{5b}$, —$CH_2CH_2CH_2CONR^{5a}R^{5b}$, —$NR^{5a}R^{5b}$, —$CH_2NR^{5a}R^{5b}$, —$CH_2CH_2NR^{5a}R^{5b}$, —$CH_2CH_2CH_2NR^{5a}R^{5b}$, —$NR^{5a}COR^{5b}$, —$NR^{5a}CONR^{5b}R^{5c}$, —$NR^{5a}CO_2R^{5b}$, —$NR^{5a}SONR^{5b}R^{5c}$, —$NR^{5a}SO_2NR^{5b}R^{5c}$, or —$NR^{5a}SO_2R^{5b}$, each of said —$C_{1-8}$alkyl, —$C_{2-8}$alkenyl, —$C_{2-8}$alkynyl, cycloalkyl, —$C_{1-8}$alkyl-cycloalkyl, heterocyclyl, aryl, or heteroaryl is optionally substituted with at least one substituents $R^{5d}$; or two $R^5$ together with the atoms to which they are attached (provided that the valence theory is met), form a 4-, 5-, 6-, 7- or 8-membered ring, said ring comprising 0, 1 or 2 heteroatoms independently selected from nitrogen, oxygen or optionally oxidized sulfur as ring member (s), said ring is optionally substituted with at least one substituents $R^{5e}$;

$R^{5a}$, $R^{5b}$ and $R^{5c}$ are each independently hydrogen, —$C_{1-8}$ alkyl, —$C_{2-8}$alkenyl, —$C_{2-8}$alkynyl, —$C_{1-8}$alkyl-$C_{1-8}$ alkoxy, cycloalkyl, —$C_{1-8}$alkyl-heterocyclyl, —$C_{1-8}$ alkyl-aryl, heterocyclyl, aryl, or heteroaryl, each of said —$C_{1-8}$alkyl, —$C_{2-8}$alkenyl, —$C_{2-8}$alkynyl, —$C_{1-8}$alkyl-$C_{1-8}$alkoxy, cycloalkyl, —$C_{1-8}$alkyl-heterocyclyl, —$C_{1-8}$alkyl-aryl, heterocyclyl, aryl, or heteroaryl is optionally substituted with at least one substituents $R^{5e}$;

($R^{5a}$ and $R^{5b}$), ($R^{5b}$ and $R^{5c}$), or ($R^{5c}$ and $R^{5a}$), together with the atom (s) to which they are attached, form a 3- to 12-membered ring, said ring comprising 0, 1 or 2 additional heteroatoms independently selected from nitrogen, oxygen or optionally oxidized sulfur as ring member (s), said ring is optionally substituted with at least one substituents $R^{5e}$;

$R^{5d}$ and $R^{5c}$ are each independently hydrogen, halogen, —$C_{1-8}$alkyl, —$C_{2-8}$alkenyl, —$C_{2-8}$alkynyl, cycloalkyl, heterocyclyl, aryl, heteroaryl, oxo, —CN, —$NO_2$, —$CF_3$, —$OR^{5f}$, —$SO_2R^{5f}$, —$SO_2NR^{5f}R^{5g}$, —$POR^{5f}R^{5g}$, —$COR^{5f}$, —$CO_2R^{5f}$, —$CONR^{5f}R^{5g}$, —C(=$NR^{5h}$)$NR^{5f}R^{5g}$, —$NR^{5f}R^{5g}$, —$NR^{5f}COR^{5g}$, —$NR^{5h}CONR^{5f}R^{5g}$, $NR^{5f}CO_2R^{5h}$, —$NR^{5h}SONR^{5f}R^{5g}$, —$NR^{5h}SO_2NR^{5f}R^{5g}$, or —$NR^{5f}SO_2R^{5g}$, each of said —$C_{1-8}$alkyl, —$C_{2-8}$alkenyl, —$C_{2-8}$alkynyl, cycloalkyl, heterocyclyl, aryl, or heteroaryl is optionally substituted with at least one substituents selected from halogen, —$C_{1-8}$alkyl, —$OR^{5i}$, —$NR^{5i}R^{5j}$, cycloalkyl, heterocyclyl, aryl, or heteroaryl;

$R^{5f}$, $R^{5g}$, $R^{5h}$, $R^{5i}$, and $R^{5j}$ are each independently hydrogen, oxo, —$C_{1-8}$alkyl, —$C_{1-8}$alkoxy, hydroxy, $C_{1-8}$alkoxy-$C_{1-8}$alkyl-, —$C_{2-8}$alkenyl, —$C_{2-8}$alkynyl, cycloalkyl, heterocyclyl, aryl, or heteroaryl;

$R^6$ at each of its occurrence, is each independently hydrogen, halogen, —$C_{1-8}$alkyl, —$C_{2-8}$alkenyl, —$C_{2-8}$alkynyl, cycloalkyl, heterocyclyl, aryl, heteroaryl, oxo, —CN, —$NO_2$, —$OR^{6a}$, —$SO_2R^{6a}$, —$SO_2NR^{6a}R^{6b}$, —$COR^{6a}$, —$CO_2R^{6a}$, —$CONR^{6a}R^{6b}$, —C(=$NR^{6a}$)$NR^{6b}R^{6c}$, —$CH_2CONR^{6a}R^{6b}$, —$CH_2CH_2CONR^{6a}R^{6b}$, —$CH_2CH_2CH_2CONR^{6a}R^{6b}$, —$NR^{6a}R^{6b}$, —$CH_2NR^{6a}R^{6b}$, —$CH_2CH_2NR^{6a}R^{6b}$, —$CH_2CH_2CH_2NR^{6a}R^{6b}$, —$NR^{6a}COR^{6b}$, —$NR^{6a}CONR^{6b}R^{6c}$, —$NR^{6a}CO_2R^{6b}$, —$NR^{6a}SONR^{6b}R^{6c}$, —$NR^{6a}SO_2NR^{6b}R^{6c}$, or —$NR^{6a}SO_2R^{6b}$, each of said —$C_{1-8}$alkyl, —$C_{2-8}$alkenyl, —$C_{2-8}$alkynyl, cycloalkyl, heterocyclyl, aryl, or heteroaryl is optionally substituted with at least one substituents $R^{6d}$; or two $R^6$, together with the atoms to which they are attached (provided that the valence theory is met), form a 4-, 5-, 6-, 7- or 8-membered ring, said ring comprising 0, 1 or 2 heteroatoms independently selected from nitrogen, oxygen or optionally oxidized sulfur as ring member (s), said ring is optionally substituted with at least one substituents $R^{6e}$;

$R^{6a}$, $R^{6b}$, and $R^{6c}$ are each independently hydrogen, —$C_{1-8}$alkyl, —$C_{2-8}$alkenyl, —$C_{2-8}$alkynyl, $C_{1-8}$alkoxy-$C_{1-8}$alkyl-, cycloalkyl, heterocyclyl, aryl, or heteroaryl, each of said —$C_{1-8}$alkyl, —$C_{2-8}$alkenyl, —$C_{2-8}$alkynyl, cycloalkyl, heterocyclyl, aryl, or heteroaryl is optionally substituted with at least one substituents $R^{6e}$;

($R^{6a}$ and $R^{6b}$), ($R^{6b}$ and $R^{6c}$), or ($R^{6c}$ and $R^{6a}$), together with the atom (s) to which they are attached, form a 3- to 12-membered ring, said ring comprising 0, 1 or 2 additional heteroatoms independently selected from nitrogen, oxygen or optionally oxidized sulfur as ring member (s), said ring is optionally substituted with at least one substituents $R^{6e}$;

$R^{6d}$ and $R^{6e}$ are each independently hydrogen, halogen, —$C_{1-8}$alkyl, —$C_{2-8}$alkenyl, —$C_{2-8}$alkynyl, cycloalkyl, heterocyclyl, aryl, heteroaryl, oxo, —CN, —$NO_2$, —$OR^{6f}$, —$SO_2R^{6f}$, —$SO_2NR^{6f}R^{6g}$, —$COR^{6f}$, —$CO_2R^{6f}$, —$CONR^{6f}R^{6g}$, —$C(=NR^{6h})NR^{6f}R^{6g}$, —$NR^{6f}R^{6g}$, —$NR^{6f}COR^{6g}$, —$NR^{6h}CONR^{6f}R^{6g}$, —$NR^{6f}CO_2R^{6h}$, —$NR^{6h}SONR^{6f}R^{6g}$, —$NR^{6h}SO_2NR^{6f}R^{6g}$, or —$NR^{6f}SO_2R^{6g}$, each of said —$C_{1-8}$alkyl, —$C_{2-8}$alkenyl, —$C_{2-8}$alkynyl, cycloalkyl, heterocyclyl, aryl, or heteroaryl is optionally substituted with at least one substituents selected from halogen, —$C_{1-8}$alkyl, —$OR^{6i}$, —$NR^{6i}R^{6j}$, cycloalkyl, heterocyclyl, aryl, or heteroaryl;

$R^{6f}$, $R^{6g}$, $R^{6h}$, $R^{6i}$, and $R^{6j}$ are each independently hydrogen, oxo, —$C_{1-8}$alkyl, $C_{1-8}$alkoxy-$C_{1-8}$alkyl-, —$C_{2-8}$alkenyl, —$C_{2-8}$alkynyl, cycloalkyl, heterocyclyl, aryl, or heteroaryl.

Aspect 2: The compound according to Aspect 1, wherein $R^1$ and $R^2$ are each hydrogen or —$C_{1-8}$alkyl (preferably hydrogen or methyl).

Aspect 3: The compound according to Aspect 1 or 2, wherein $R^3$ is —$C_{1-8}$alkyl, —$C_{1-8}$alkyl-heterocyclyl or —$C_{1-8}$alkyl-cycloalkyl, wherein said —$C_{1-8}$alkyl, —$C_{1-8}$alkyl-heterocyclyl or —$C_{1-8}$alkyl-cycloalkyl is optionally substituted with at least one substituents $R^{3d}$; $R^{3d}$ is independently selected from —$C_{1-8}$alkyl or —$OR^{3f}$; $R^{3f}$ is each independently hydrogen, —$C_{1-8}$alkyl. Preferably $R^3$ is

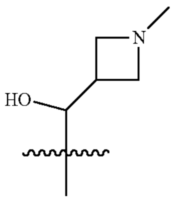

(

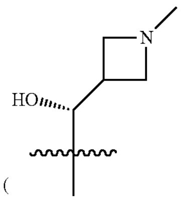

or

-continued

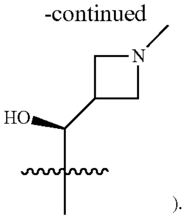

).

Aspect 4: The compound according to Aspect 1 or 2, wherein $R^3$ is —$CONR^{3a}R^{3b}$; $R^{3a}$ and $R^{3b}$ are each independently hydrogen or —$C_{1-8}$alkyl (preferably methyl, ethyl, propyl, butyl, pentyl or hexyl); each of said —$C_{1-8}$alkyl is substituted with at least one substituents selected from hydrogen, —$OR^{3f}$, CN, 3-to-7 membered heterocyclyl comprising 1 or 2 heteroatoms selected from nitrogen, oxygen (for example, piperazinyl, piperidinyl, piperidinyl, tetrahydrofuranyl, tetrahydropyranyl, tetrahydropyranyl, or pyrrolidinyl); $R^{3f}$ is selected from hydrogen or —$C_{1-8}$alkyl (e.g., methyl, ethyl, propyl, butyl, pentyl or hexyl).

Aspect 5: The compound according to any one of Aspect 1-2, wherein $R^3$ is —$CONR^{3a}R^{3b}$ or —$NR^{3a}R^{3b}$; $R^{3a}$ and $R^{3b}$ together with the nitrogen atom to which they are attached is 4- to 12-membered ring comprising 1 or 2 additional nitrogen or oxygen heteroatoms as ring member. (e.g., monocyclic 3- to 8-membered ring or bicyclic spiro 7- to 12-membered ring), said ring is optionally substituted with at least one substituents $R^{3e}$; $R^{3e}$ each is selected from oxo, —$C_{1-8}$alkyl, —$OR^{3f}$, —$NR^{3f}R^{3g}$, said —$C_{1-8}$alkyl is optionally substituted by at least one halogen, wherein $R^{3f}$ and $R^{3g}$ are each independently hydrogen, or —$C_{1-8}$alkyl.

Aspect 6: The compound according to any one of Aspect 1-5, wherein $R^3$ is selected from

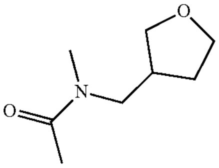

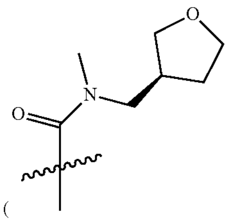

( or

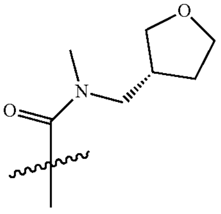

),

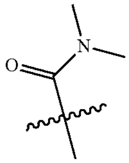

,

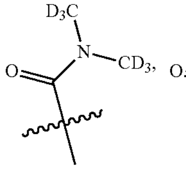

,

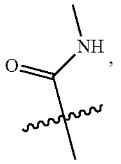

,

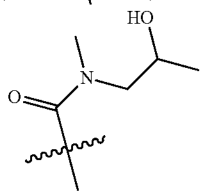

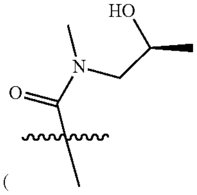

( or

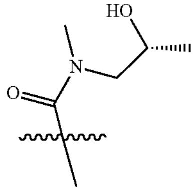

),

-continued

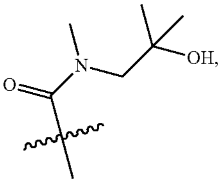 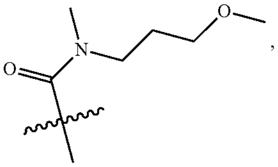

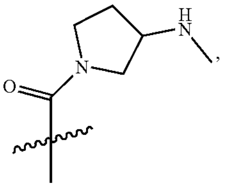

( 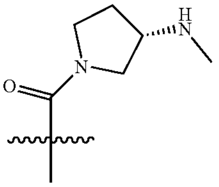 or 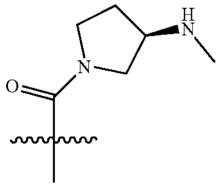 ),

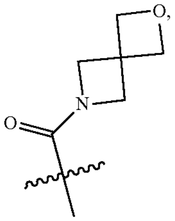 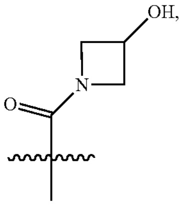

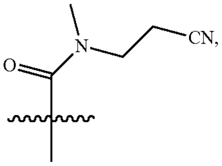 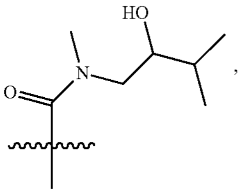

( 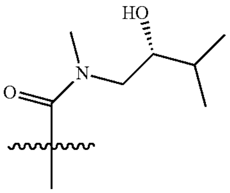 or 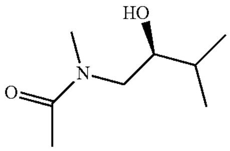 ),

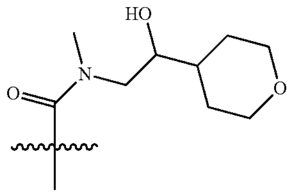

( 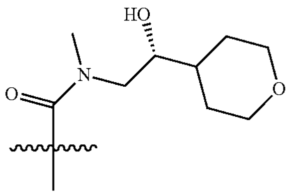 or

-continued

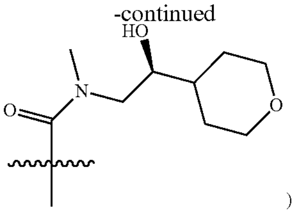 ) or

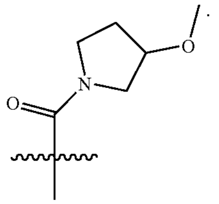

Aspect 7: The compound according to Aspect 5, wherein $R^3$ is selected from

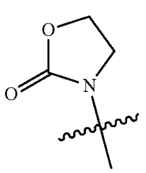 or 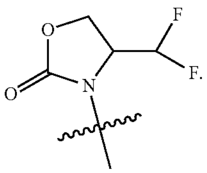

Aspect 8: The compound according to any one of Aspect 1-7, wherein n is 0, 1 or 2; $R^4$ is selected from halogen, —$C_{1-8}$alkyl (preferably methyl), halogen, CN, —$OR^{3a}$ or —$NR^{3a}CONR^{3b}R^{3c}$; said —$C_{1-8}$alkyl is optionally substituted with at least one substituents $R^{3d}$; $R^{3a}$, $R^{3b}$ and $R^{3c}$ are each independently hydrogen, —$C_{1-8}$alkyl (preferably methyl); $R^{3d}$ is each independently halogen or —$C_{1-8}$alkyl.

Aspect 9: The compound according to Aspect 8, wherein n is 1, $R^4$ is selected from —$C_{1-8}$alkyl (preferably methyl), halogen, CN, $OR^{3a}$ or —$NR^{3a}CONR^{3b}R^{3c}$; said —$C_{1-8}$alkyl is optionally substituted with at least one substituents $R^{3d}$; $R^{3a}$, $R^{3b}$ and $R^{3c}$ are each independently hydrogen, or —$C_{1-8}$alkyl (preferably methyl); $R^{3d}$ is each independently halogen or —$C_{1-8}$alkyl.

Aspect 10: The compound according to Aspect 8, wherein n is 2, and $R^4$ is halogen.

Aspect 11: The compound according to Aspect 8, wherein n is 1 or 2, and $R^4$ is selected from methyl, F, OH, CN, —$CHF_2$ or —$NHCOCH_3$.

Aspect 12: The compound according to any one of Aspects 1-8, wherein n is 0, and $R^3$ is selected from

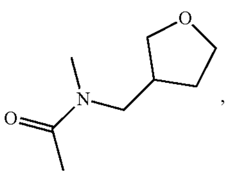, 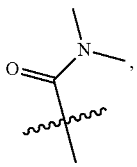, 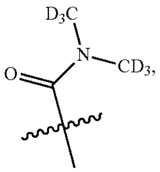

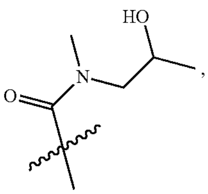, 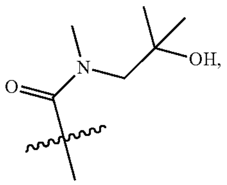

-continued

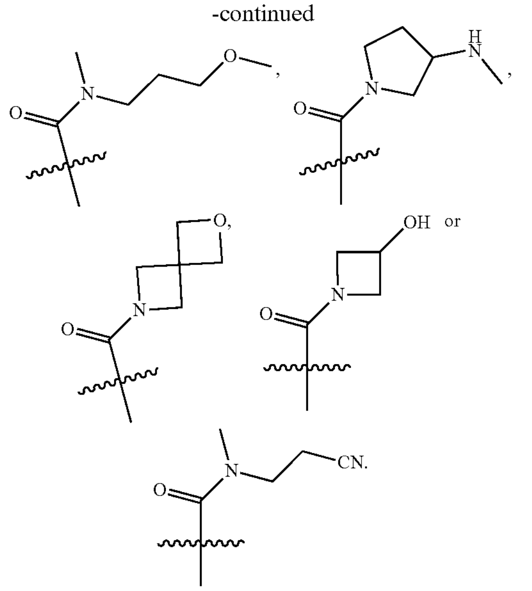

or

Aspect 13: The compound according to any one of Aspects 1-8, 9, 11, wherein n is 1, and $R^3$ is selected from

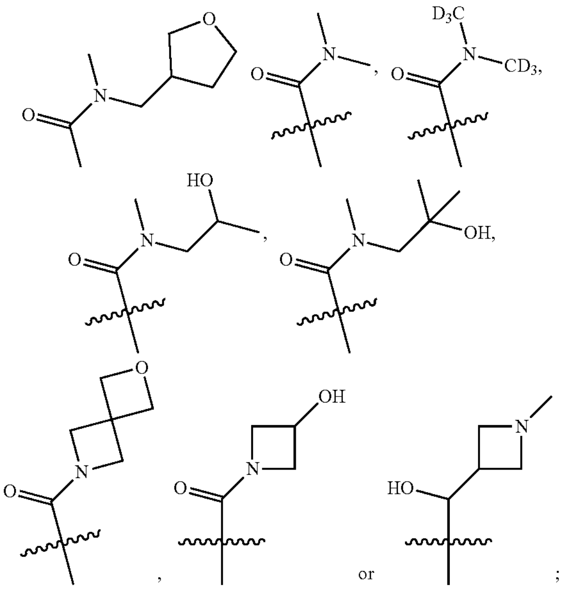

or and $R^4$ is methyl, F, OH, CN, —$CHF_2$ or —$NHCOCH_3$.

Aspect 14: The compound according to any one of Aspects 1-8, and 10-11, wherein n is 2, and $R^3$ is selected from

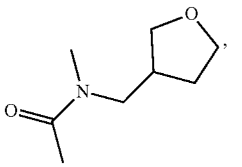

and $R^4$ is F.

Aspect 15: The compound according to any one of Aspects 1-2, wherein $R^3$ and $R^4$, when on adjacent carbon atoms of the phenyl ring, together with the two intervening carbon atoms to which they are attached, form a 5- to 8-membered ring comprising 0, 1 or 2 heteroatoms independently selected from nitrogen, oxygen or optionally oxidized sulfur as ring member (s), said ring is optionally substituted with at least one substituents $R^{3e}$; each $R^{3e}$ is independently selected from —$C_{1-8}$alkyl or oxo.

Aspect 16: The compound according to Aspect 15, wherein

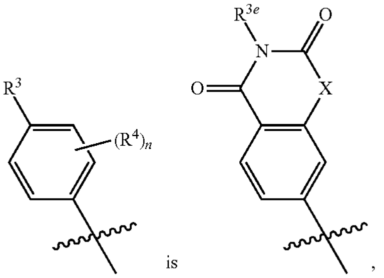

is

X═NH or O, and $R^{3e}$ is —$C_{1-8}$alkyl.

Aspect 17: The compound according to any one of Aspects 1-2, wherein n=2, and two $R^4$, when on adjacent carbon atoms of the phenyl ring, together with the two intervening carbon atoms to which they are attached, form a 5- to 8-membered ring comprising 0, 1 or 2 heteroatoms independently selected from nitrogen, oxygen or optionally oxidized sulfur as ring member (s).

Aspect 18: The compound according to Aspect 17, wherein

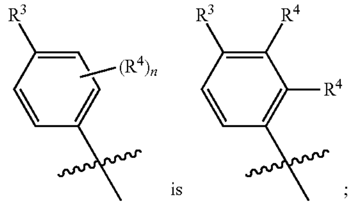

is two $R^4$ when on adjacent carbon atoms of the phenyl ring, together with the two intervening carbon atoms to which they are attached, form a 5-membered ring comprising 2 heteroatoms independently selected from nitrogen, oxygen or optionally oxidized sulfur as ring member (s).

Aspect 19: The compound according to Aspect 18, wherein

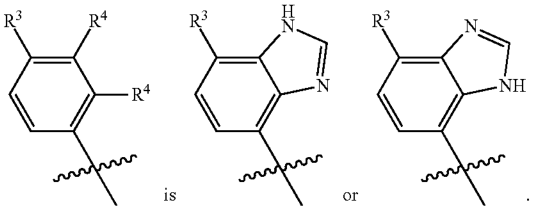

is or

Aspect 20: The compound according to any one of Aspects 1-19, $L^1$ is a single bond.

Aspect 21: The compound according to any one of Aspects 1-20, wherein

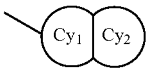

is benzo fused heterocyclyl, benzo fused heteroaryl, benzo fused cycloalkyl, benzo fused cycloalkenyl, benzo fused cycloalkynyl.

Aspect 22: The compound according to Aspect 21, wherein the benzo fused heterocyclyl is indolinyl, isoindolinyl, benzopyranyl, dihydrothiazolopyrimidinyl, tetrahydroquinolyl, tetrahydroisoquinolyl, dihydrobenzofuranyl, dihydrobenzoxazinyl, dihydrobenzoimidazolyl, tetrahydrobenzothienyl, tetrahydrobenzofuranyl, benzodioxolyl, benzodioxonyl, chromanyl, chromenyl, octahydrochromenyl, dihydrobenzodioxynyl, dihydrobenzoxezinyl, dihydrobenzodioxepinyl, dihydrothienodioxynyl, dihydrobenzooxazepinyl, tetrahydrobenzooxazepinyl, dihydrobenzoazepinyl, tetrahydrobenzoazepinyl, isochromanyl, or chromanyl.

Aspect 23: The compound according to any one of Aspects 21-22, wherein the benzo fused heterocyclyl is indolinyl, isoindolinyl, tetrahydroisoquinolyl, dihydrobenzofuranyl, dihydrobenzoimidazolyl, tetrahydrobenzooxazepinyl, tetrahydrobenzoazepinyl, or isochromanyl.

Aspect 24: The compound according to Aspect 23, wherein tetrahydroisoquinolinyl is selected from 1, 2, 3, 4-tetrahydroisoquinolinyl, 1, 2, 3, 4-tetrahydroisoquinolin-6-yl or 1, 2, 3, 4-tetrahydroisoquinolin-7-yl; tetrahydrobenzooxazepinyl is selected from 2, 3, 4, 5-tetrahydrobenzooxazepinyl, 2, 3, 4, 5-tetrahydrobenzo[f][1, 4]oxazepin-8-yl, or 2, 3, 4, 5-tetrahydrobenzo[f][1, 4]oxazepin-7-yl; tetrahydrobenzoazepinyl is selected from 2, 3, 4, 5-tetrahydrobenzoazepinyl, 2, 3, 4, 5-tetrahydro-1H-benzo[c]azepin-7-yl and 2, 3, 4, 5-tetrahydro-1H-benzo[d]azepin-7-yl; isoindolinyl is selected from isoindolin-5-yl; isochromanyl is selected from isochroman-5-yl; dihydroisobenzofuranyl is selected from 1, 3-dihydroisobenzofuran-4-yl.

Aspect 25: The compound according to Aspect 21, wherein the benzo fused heteroaryl is benzisoxazolyl, benzodiazolyl, benzofuranyl, benzofurazanyl, benzofuryl, benzoimidazolyl, benzoisothiazolyl, benzothiadiazolyl, benzothiazolyl, benzothienyl, benzothiophenyl, benzotriazolyl, benzoxadiazolyl, benzoxazolyl, indazolyl, indolyl, isobenzofuryl, isoindolyl, isoquinolinyl (or isoquinolyl), phthalazinyl, pteridinyl, purinyl, quinazolinyl, quinolinyl (or quinolyl), or quinoxalinyl. In some examples, indazolyl is e.g., 1H-indazol-4-yl, 2H-indazol-4-yl, 1H-indazol-5-yl, 2H-indazol-5-yl, 1H-indazol-7-yl; benzodiazolyl is e.g., 1H-benzo[d]imidazol-4-yl, 1H-1, 3-benzodiazol-5-yl or 1H-benzo[d]imidazol-5-yl, 1H-benzo[d]imidazol-4-yl, 1H-benzo[d]imidazol-6-yl; benzooxazolyl is e.g., benzo[d]oxazol-6-yl; benzooxadiazolyl is e.g., benzo[c][1, 2, 5]oxadiazol-4-yl.

Aspect 26: The compound according to Aspect 21, wherein

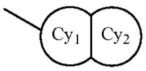

is a bicyclic fused heteroaryl selected from furopyridinyl, furopyrrolyl, imidazopyridinyl, imidazopyridyl, imidazothiazolyl, indolizinyl, naphthyridinyl, pyrazinopyridazinyl, pyrazolopyridinyl, pyrazolopyrimidinyl, pyrazolopyridyl, pyrazolotriazinyl, pyridazolopyridyl, pyrrolopyridinyl, thiazolopyridyl, thienopyrazinyl, thienopyrazolyl, thienopyridyl, thienopyrrolyl, thienothienyl, or triazolopyridyl. In some example, imidazopyridinyl is e.g., imidazo[1, 2-a]pyridin-5-yl or imidazo[1, 5-a]pyridin-5-yl.

Aspect 27: The compound according to Aspect 21, wherein

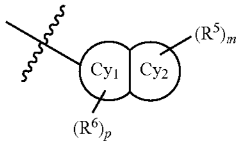

is

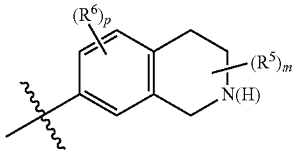

or

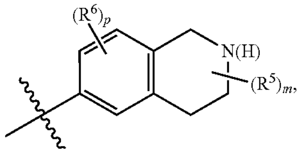

p=0, 1, 2 or 3; m=0, 1, 2, 3 or 4; $R^6$ and $R^5$ are defined for Formula (I).

Aspect 28: The compound according to any one of Aspects 21-27, wherein

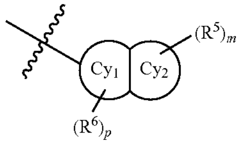

is

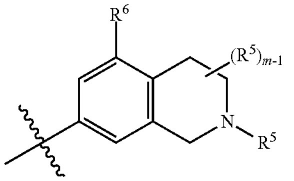

or

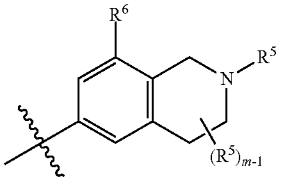

(preferably

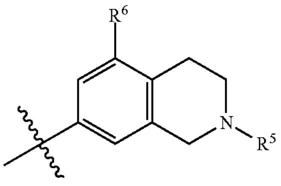

or

-continued

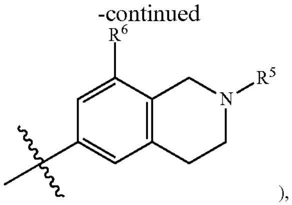

), m=1, 2, 3 or 4; $R^6$ and $R^5$ are defined for Formula (I) (preferably $R^5$ and $R^6$ are independently —$C_{1-8}$alkyl (e.g., methyl, ethyl, 1-propyl, 2-propyl, 1-butyl, 2-methyl-1-propyl, 1-methylpropyl or t-butyl).

Aspect 29: The compound according to Aspect 27 or 28, wherein $R^6$ is selected from —$C_{1-8}$alkyl, —$OR^{6a}$ or —$NR^{6a}R^{6b}$, said —$C_{1-8}$alkyl is optionally substituted with at least one substituents $R^{6d}$, $R^{6a}$ and $R^{6b}$ are each hydrogen or —$C_{1-8}$alkyl; $R^{6d}$ is each independently hydrogen, halogen or —$C_{1-8}$alkyl. preferably $R^6$ is selected from —$CH_3$, —$OCH_3$, —$NHCH_3$, —$CHF_2$, or —$C(CH_3)_2OH$.

Aspect 30: The compound according to any one of Aspects 27-29, wherein each $R^5$ is independently selected from —$C_{1-8}$alkyl, —$C_{1-8}$alkyl-cycloalkyl, heterocyclyl or heteroaryl —$CONR^{3a}R^{3b}$, $CH_2CONR^{5a}R^{5b}$, —$CH_2CH_2CONR^{5a}R^{5b}$, —$NR^{5a}R^{5b}$, —$CH_2NR^{5a}R^{5b}$, —$CH_2CH_2NR^{5a}R^{5b}$, said —$C_{1-8}$alkyl, —$C_{1-8}$alkyl-cycloalkyl or heterocyclyl or heteroaryl is optionally substituted with at least one $R^{5d}$, and $R^{5a}$, $R^{5b}$ and $R^{5d}$ are defined for Formula (I).

Aspect 31: The compound according to any one of Aspects 27-30, wherein $R^5$ is selected from —$C_{1-8}$alkyl (e.g., methyl, ethyl, 1-propyl, 2-propyl, 1-butyl, 2-methyl-1-propyl, 1-methylpropyl or t-butyl), —$C_{1-8}$alkyl-cycloalkyl, heterocyclyl or heteroaryl, said —$C_{1-8}$alkyl, —$C_{1-8}$alkyl-cycloalkyl, heteroaryl or heterocyclyl is optionally substituted with at least one substituents $R^{5d}$; $R^{5d}$ is selected from —$C_{1-8}$alkyl, —$OR^{5f}$, —$NR^{5f}R^{5g}$, —$CO_2R^{5f}$, heteroaryl, heterocyclyl, —$SO_2R^{5f}$, —$POR^{5f}R^{5g}$, —$CONR^{5f}R^{5g}$, oxo or —$CF_3$; $R^{5f}$ and $R^{5g}$ are each independently hydrogen, —$C_{1-8}$alkyl, —$C_{1-8}$alkoxy or hydroxy.

Aspect 32: The compound according to Aspect 31, wherein, $R^5$ is methyl, ethyl, propyl, butyl, pentyl or hexyl, —$CH_2OH$, —$C_2H_4OH$, $C_2H_4NHCH_3$, —$C_2H_4OCH_3$,

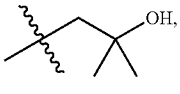, 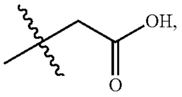,

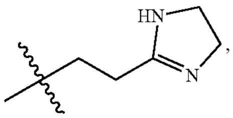, 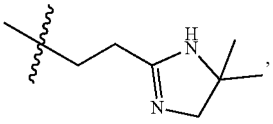,

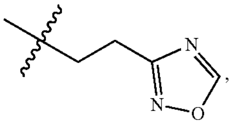, 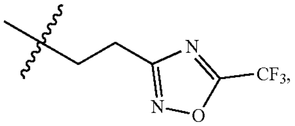,

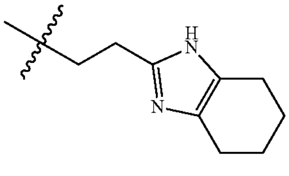,

-continued

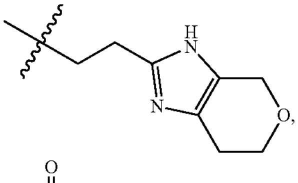,

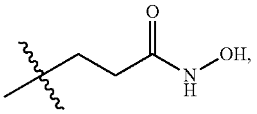, 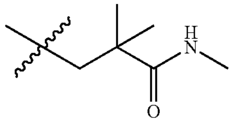,

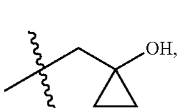, 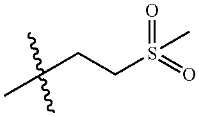,

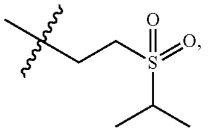, 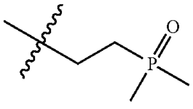 or

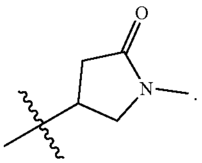.

Aspect 33: The compound according to Aspect 30, wherein $R^5$ is —$NR^{5a}R^{5b}$, —$CH_2NR^{5a}R^{5b}$, —$CH_2CH_2NR^{5a}R^{5b}$; $R^{5a}$ and $R^{5b}$ together with the nitrogen atom to which they are attached form a 4- to 7-membered ring, said ring comprising 0, 1 or 2 additional heteroatoms independently selected from nitrogen, oxygen, said ring is optionally substituted with at least one substituents $R^{5e}$; $R^{5e}$ is each independently selected from $C_{1-8}$alkyl (preferably methyl, ethyl), $OR^{5f}$; $R^{5f}$ is each independently selected from hydrogen or —$C_{1-8}$alkyl (e.g., methyl, ethyl).

Aspect 34: The compound according to Aspect 33, wherein $R^5$ is

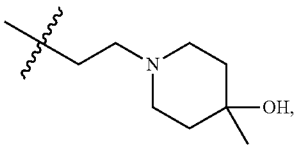, 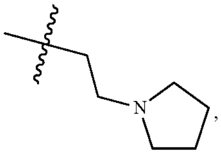,

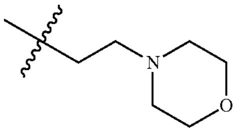 or 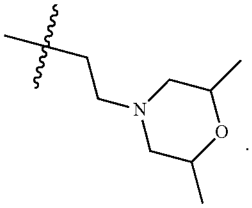.

Aspect 35: The compound according to Aspect 30, wherein $R^5$ is selected from —$CONR^{5a}R^{5b}$, —$CH_2CONR^{5a}R^{5b}$, —$CH_2CH_2CONR^{5a}R^{5b}$, wherein $R^{5a}$ and $R^{5b}$ are each independently hydrogen, —$C_{1-8}$alkyl, $C_{1-8}$alkoxy-$C_{1-8}$alkyl-, cycloalkyl, heterocyclyl, —$C_{1-8}$alkyl-heterocyclyl, —$C_{1-8}$alkyl-aryl, -aryl, or heteroaryl, each of said —$C_{1-8}$alkyl, $C_{1-8}$alkoxy-$C_{1-8}$alkyl-, cycloalkyl, heterocyclyl, —$C_{1-8}$alkyl-heterocyclyl, —$C_{1-8}$alkyl-aryl, -aryl, or heteroaryl is optionally substituted with at least one substituents $R^{5e}$; $R^{5e}$ is independently hydrogen, $OR^{5f}$, —$C_{1-8}$alkyl, heterocyclyl, —$C_{1-8}$alkyl-aryl, or $C_{1-8}$alkoxy-$C_{1-8}$alkyl-; $R^{5f}$ is each independently selected from hydrogen, —$C_{1-8}$alkyl (e.g., methyl, ethyl) and cycloalkyl.

Aspect 36: The compound according to Aspect 35, wherein $R^5$ is selected from —$CONR^{5a}R^{5b}$, —$CH_2CONR^{5a}R^{5b}$, —$CH_2CH_2CONR^{5a}R^{5b}$, wherein $R^{5a}$ is hydrogen or —$C_{1-8}$alkyl (e.g., methyl, ethyl); $R^{5b}$ is selected from —$C_{1-8}$alkyl, cycloalkyl, —$C_{1-8}$alkyl-heterocyclyl, —$C_{1-8}$alkyl-aryl, heterocyclyl, aryl, said —$C_{1-8}$alkyl, cycloalkyl, —$C_{1-8}$alkyl-heterocyclyl, —$C_{1-8}$alkyl-aryl, heterocyclyl, aryl is optionally substituted with at least one substituents $R^{5e}$, $R^{5e}$ is selected from halogen, —$CH_2OH$ or $OR^{5f}$, $R^{5f}$ is selected from hydrogen, cycloalkyl or —$C_{1-8}$alkyl.

Aspect 37: The compound according to Aspect 36, wherein $R^5$ is selected from

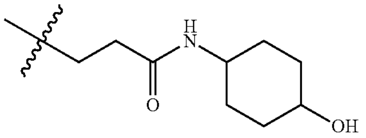

(preferably 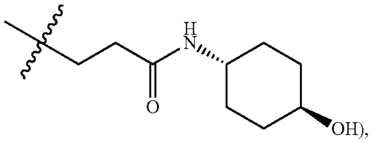

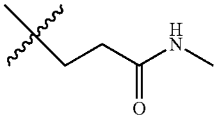 , 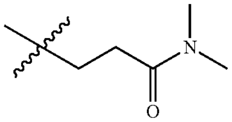 ,

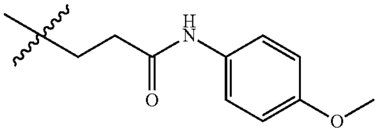 ,

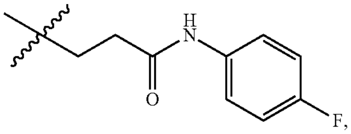

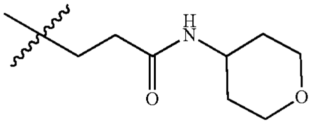

( 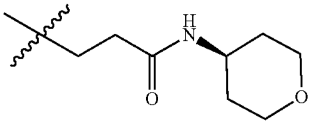 or

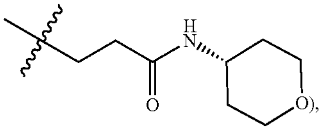

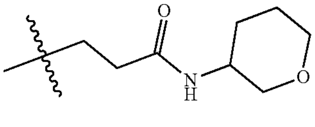

-continued ( 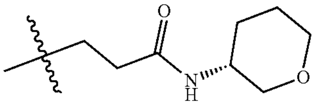 or

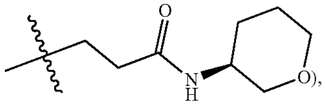

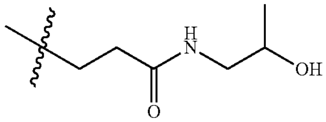

( 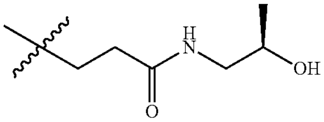 or

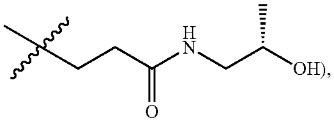

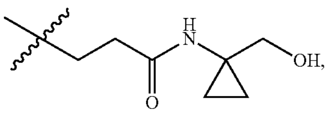

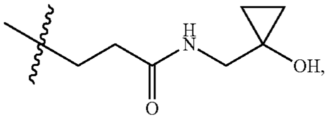

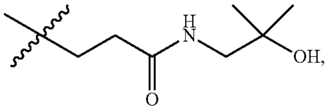

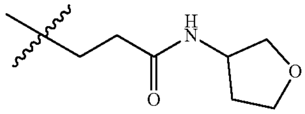

(preferably 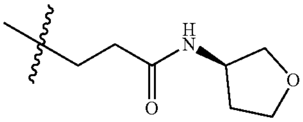 ),

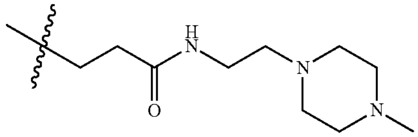 ,

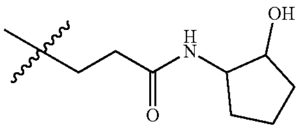

( 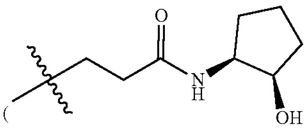 ),

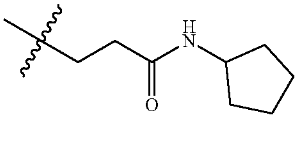 ,

-continued

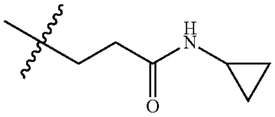,
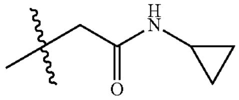,
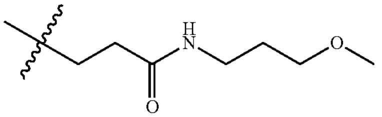,
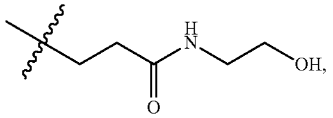
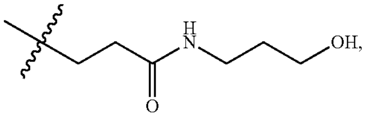
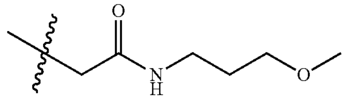,
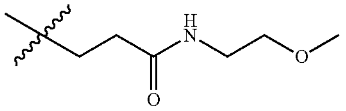,
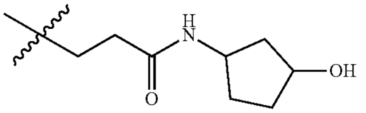
(preferably 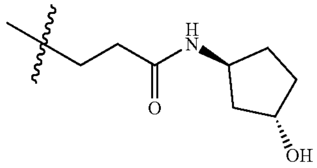),
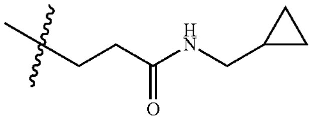,
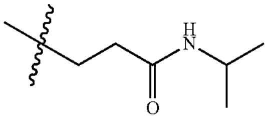,
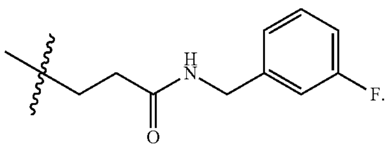

Aspect 38: The compound according to Aspect 35 or 36, wherein $R^5$ is —$CONR^{3a}R^{3b}$, $CH_2CONR^{5a}R^{5b}$ or —$CH_2CH_2CONR^{5a}R^{5b}$, $R^{5a}$ is hydrogen or methyl; and $R^{5b}$ is selected from cycloalkyl, such as cycloalkyl, cyclopropyl, cyclobutyl, cyclopentyl, cyclohexenyl, cyclohexadienyl, cycloheptyl, cyclooctyl, cyclononyl, cyclodecyl, cycloundecyl, and cyclododecyl groups; said cycloalkyl is optionally substituted with OH, —$CH_3$, —$OCH_3$. Preferably $R^5$ is

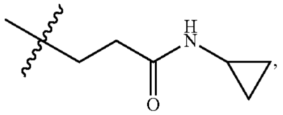
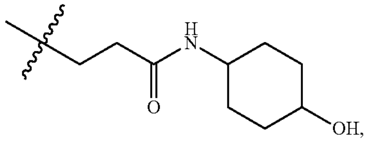
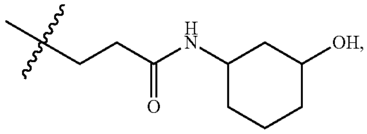
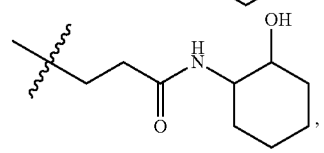
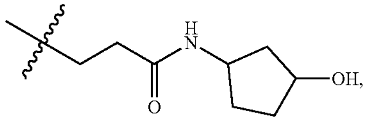
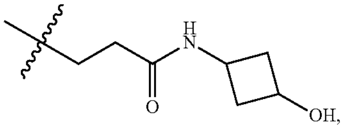
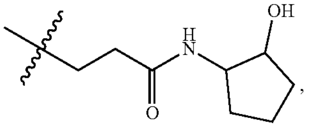
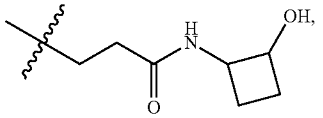
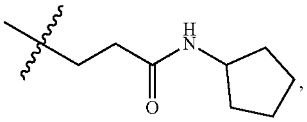
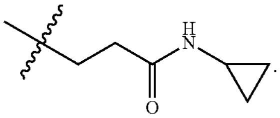

Aspect 39: The compound according to Aspect 35 or 36, wherein $R^5$ is —$CONR^{5a}R^{5b}$, $CH_2CONR^{5a}R^{5b}$ or —$CH_2CH_2CONR^{5a}R^{5b}$, $R^{5a}$ is hydrogen or methyl; and $R^{5b}$ is selected from —$C_{1-8}$alkyl, cycloalkyl or —$C_{1-8}$alkyl-heterocyclyl, said —$C_{1-8}$alkyl, cycloalkyl or —$C_{1-8}$alkyl-heterocyclyl is optionally substituted with at least one substituents $R^{5e}$, $R^{5e}$ is selected from cycloalkyl, —$C_{1-8}$alkyl, —$CH_2OH$ or $OR^{5f}$, $OR^{5f}$ is selected from hydrogen or —$C_{1-8}$alkyl. For example, $R^5$ is selected from

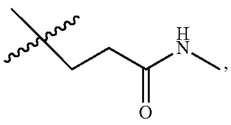, 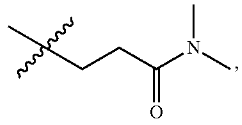,

-continued

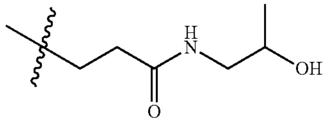

(preferably 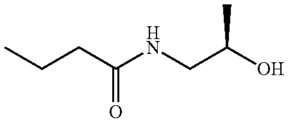),

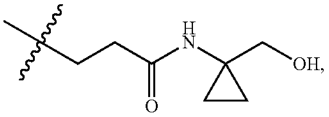

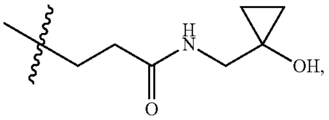

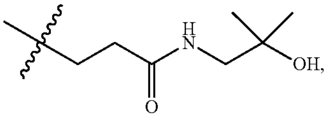

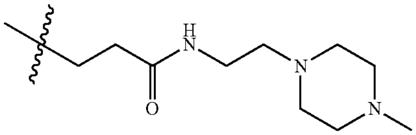,

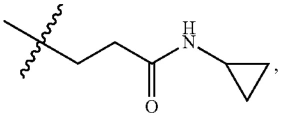

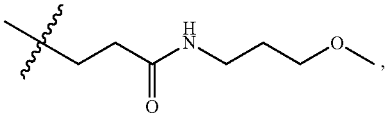

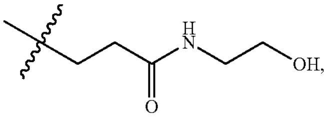

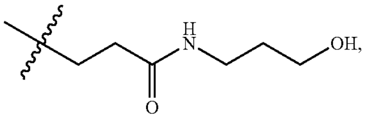

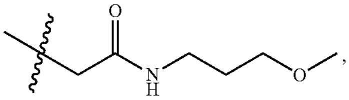

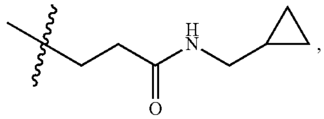

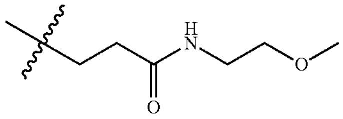 or

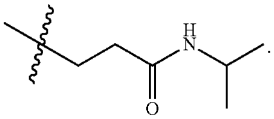

Aspect 40: The compound according to Aspect 35 or 36, wherein $R^5$ is —$CONR^{5a}R^{5b}$, $CH_2CONR^{5a}R^{5b}$ or —$CH_2CH_2CONR^{5a}R^{5b}$, $R^{5a}$ is hydrogen or methyl; and $R^{5b}$ is heterocyclyl (such as

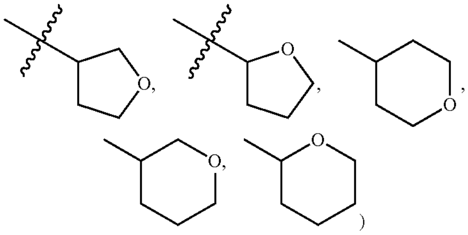)

or aryl (such as phenyl), said heterocyclyl or aryl is optionally substituted with at least one substituents $R^{5e}$ selected from halogen, —$C_{1-8}$alkyl or —$OR^{5f}$; $R^{5f}$ is each independently hydrogen or —$C_{1-8}$alkyl.

Aspect 41: The compound according to Aspect 30, wherein $R^5$ is selected from —$CONR^{5a}R^{5b}$, $CH_2CONR^{5a}R^{5b}$, —$CH_2CH_2CONR^{5a}R^{5b}$, wherein $R^{5a}$ and $R^{5b}$ together with the nitrogen atom to which they are attached, form a 4- to 7-membered ring, said ring comprising 0, 1 or 2 additional heteroatoms independently selected from nitrogen, oxygen or optionally oxidized sulfur as ring member (s), said ring is optionally substituted with at least one substituents $R^{5e}$; $R^{5e}$ is each independently halogen, —$C_{1-8}$alkyl, —$OR^{5f}$, $R^{5f}$ is each independently hydrogen or —$C_{1-8}$alkyl. For example, $R^5$ is

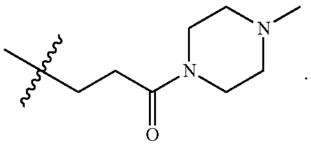 [SMILES: *CCC(=O)N1CCN(C)CC1].

Aspect 42: The compound according to any one of Aspects 1-41, wherein $R^5$ is selected from methyl, ethyl, propyl, butyl, pentyl or hexyl, —$CH_2OH$, —$C_2H_4OH$, $C_2H_4NHCH_3$, —$C_2H_4OCH_3$,

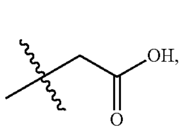

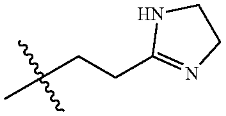,

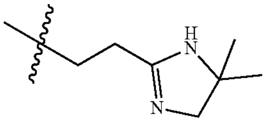

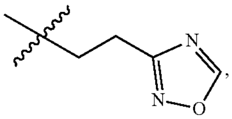

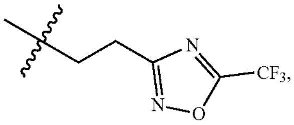

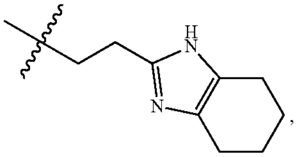

-continued
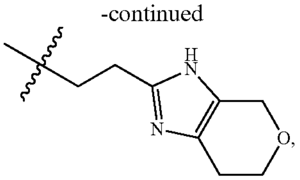
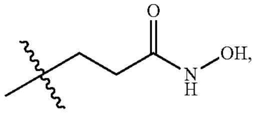
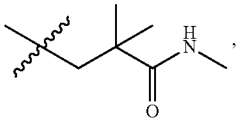
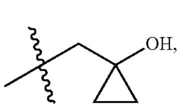
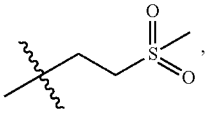
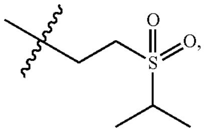
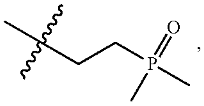
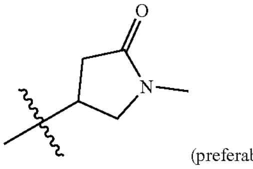
(preferably
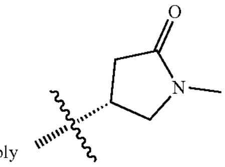
),
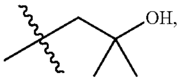
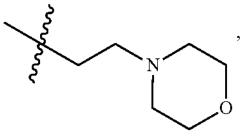
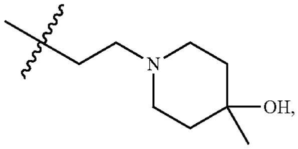
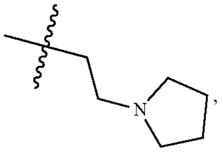
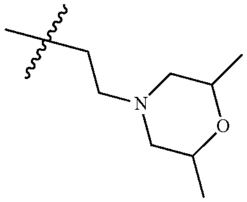
(preferably
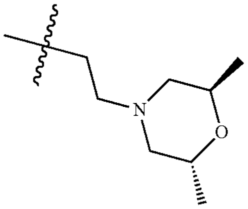
),
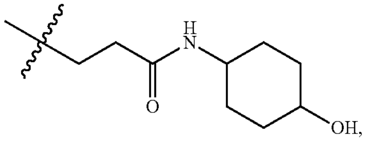
-continued
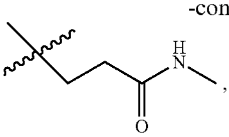
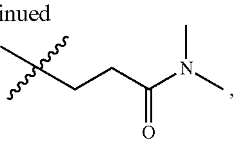
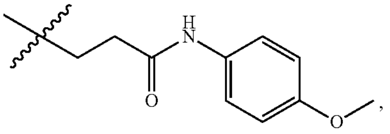
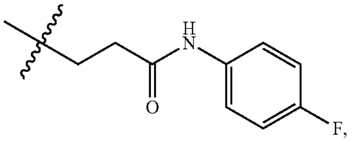
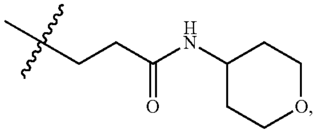
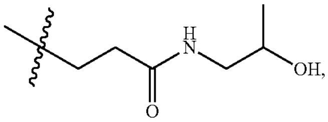
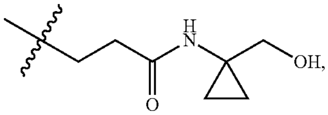
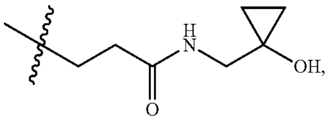
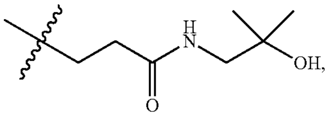
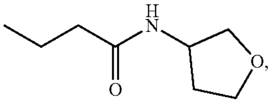
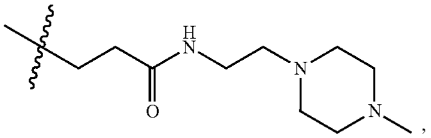
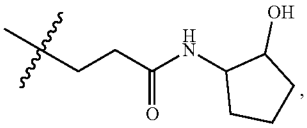
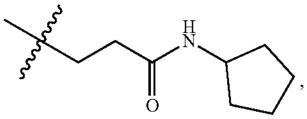
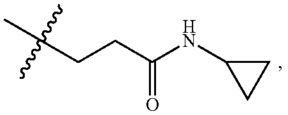
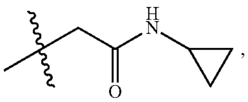

-continued

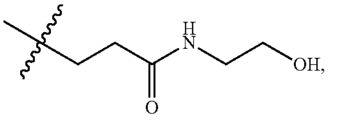

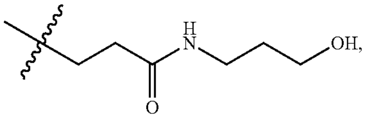

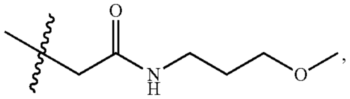

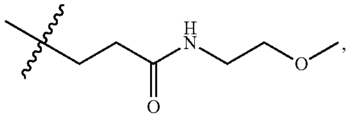

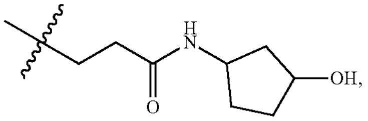

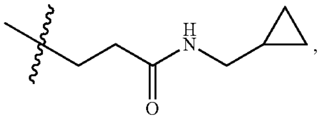

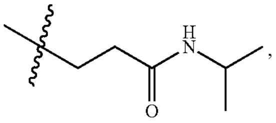

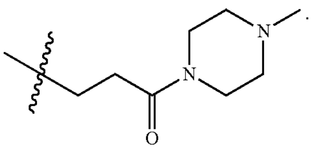

Aspect 43: The compound according to Aspect 28, wherein

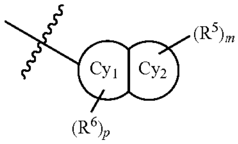 is

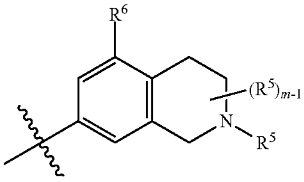 or

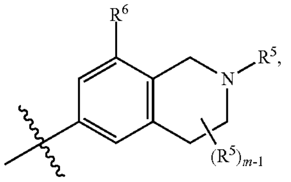

m=2, 3 or 4, $R^5$ is each independently halogen, —$C_{1-8}$alkyl, —$C_{2-8}$alkenyl, —$C_{2-8}$alkynyl, cycloalkyl, —$C_{1-8}$alkyl-cycloalkyl, heterocyclyl, aryl, heteroaryl, oxo, —CN, —$NO_2$, —$OR^{5a}$, —$SO_2R^{5a}$, —$SO_2NR^{5a}R^{5b}$, —$POR^{5a}R^{5b}$, —$COR^{5a}$, —$CO_2R^{5a}$, —$CONR^{5a}R^{5b}$, —C (=$NR^{5a}$)$NR^{5b}R^{5c}$, —$CH_2CONR^{5a}R^{5b}$, —$CH_2CH_2CONR^{5a}R^{5b}$, —$CH_2CH_2CH_2CONR^{5a}R^{5b}$, —$NR^{5a}R^{5b}$, —$CH_2NR^{5a}R^{5b}$, —$CH_2CH_2NR^{5a}R^{5b}$, —$CH_2CH_2CH_2NR^{5a}R^{5b}$, —$NR^{5a}COR^{5b}$, —$NR^{5a}CONR^{5b}R^{5c}$, —$NR^{5a}CO_2R^{5b}$, —$NR^{5a}SONR^{5b}R^{5c}$, —$NR^{5a}SO_2NR^{5b}R^{5c}$, or —$NR^{5a}SO_2R^{5b}$, each of said —$C_{1-8}$alkyl, —$C_{2-8}$alkenyl, —$C_{2-8}$alkynyl, cycloalkyl, —$C_{1-8}$alkyl-cycloalkyl, heterocyclyl, aryl, or heteroaryl is optionally substituted with at least one substituents $R^{5d}$; $R^6$, $R^{5a}$, $R^{5b}$, $R^{5c}$ and $R^{5d}$ are defined for Formula (I).

Aspect 44: The compound according to Aspect 43, wherein

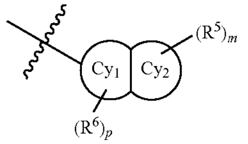 is

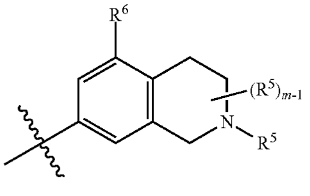 or

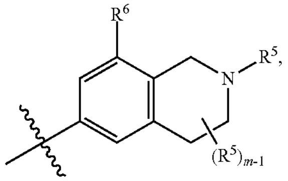

m=2, $R^5$ is each independently —$C_{1-8}$alkyl or —$CONR^{5a}R^{5b}$, $R^{5b}$ and $R^{5d}$ are hydrogen or —$C_{1-8}$alkyl (e.g., methyl, ethyl, propyl, butyl, pentyl or hexyl); $R^6$ is selected from —$C_{1-8}$alkyl, —$OR^{6a}$ or —$NR^{6a}R^{6b}$, said —$C_{1-8}$alkyl is optionally substituted with at least one substituents $R^{6d}$, $R^{6a}$ and $R^{6b}$ are each hydrogen or —$C_{1-8}$alkyl; $R^{6d}$ is each independently hydrogen, halogen or —$C_{1-8}$alkyl. preferably $R^6$ is selected from —$CH_3$, —$OCH_3$, —$NHCH_3$, —$CHF_2$, or —$C(CH_3)_2OH$.

Aspect 45: The compound according to Aspect 44, wherein

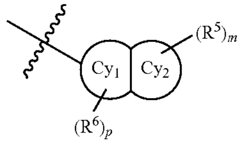 is

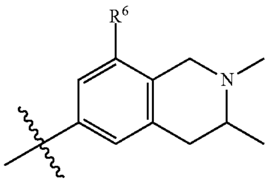 or

-continued
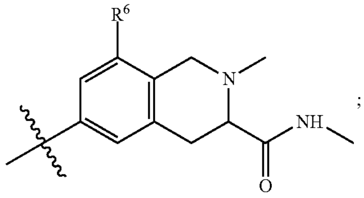
;
$R^6$ is selected from $—CH_3$, $—OCH_3$, $—NHCH_3$, $—CHF_2$, or $—C\ (CH_3)_2OH$.
Aspect 46: The compound according to Aspect 1, selected from:
1
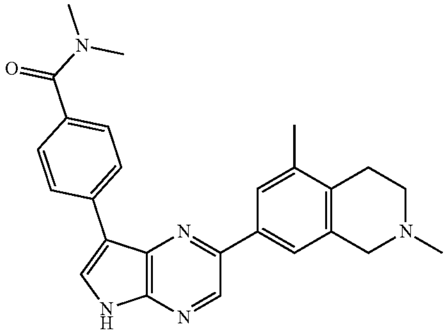
2
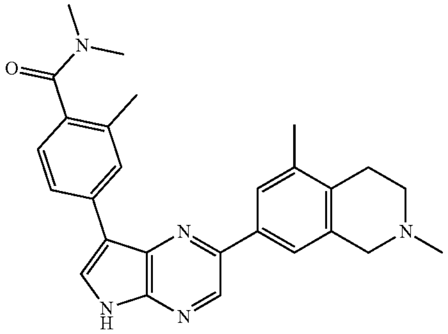
3
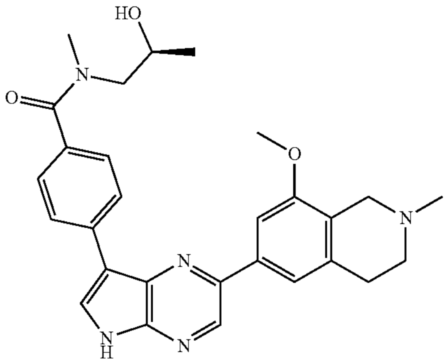
-continued
4
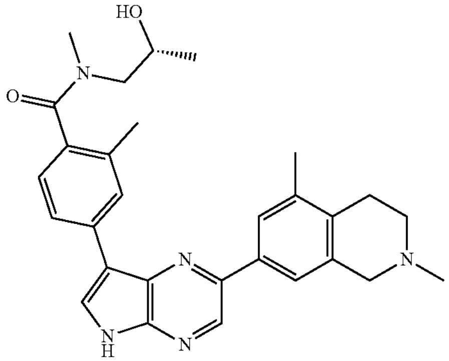
5
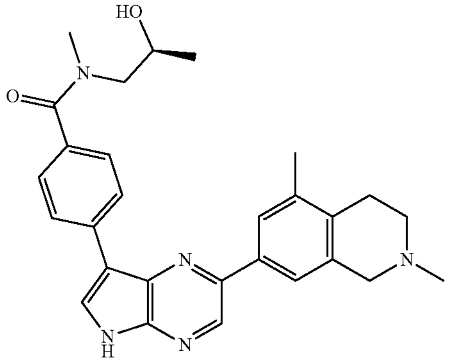
6
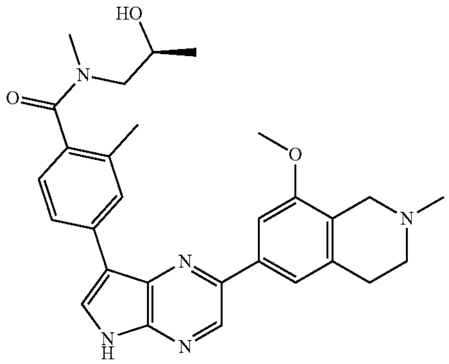
7A
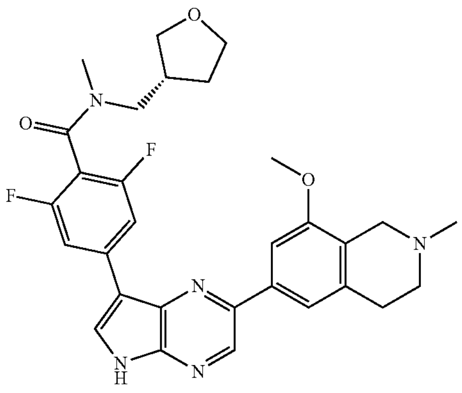

-continued
7B
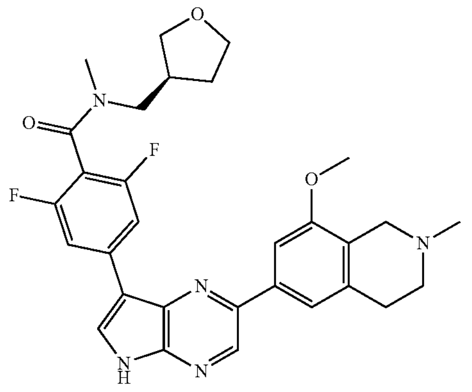
8
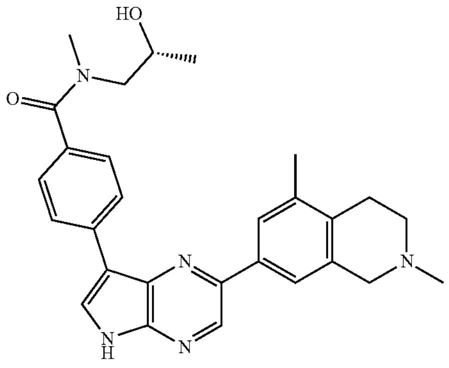
9
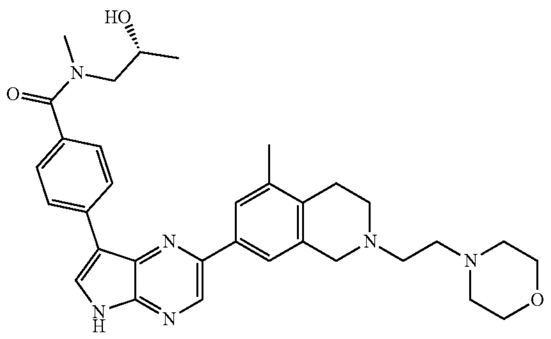
10
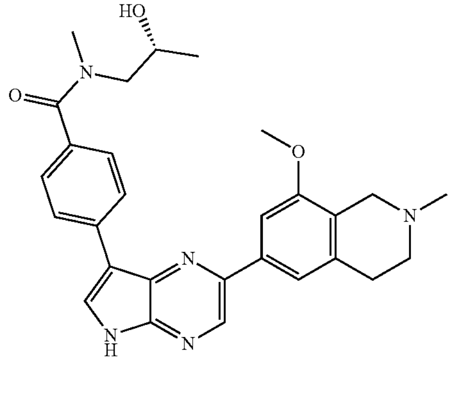
-continued
11
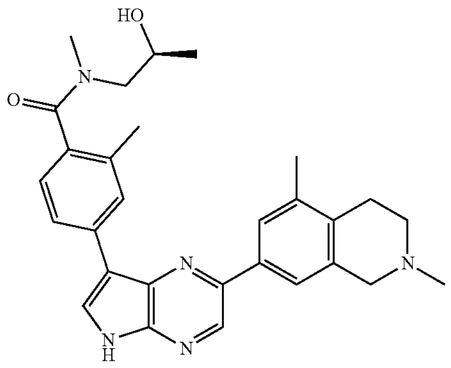
12
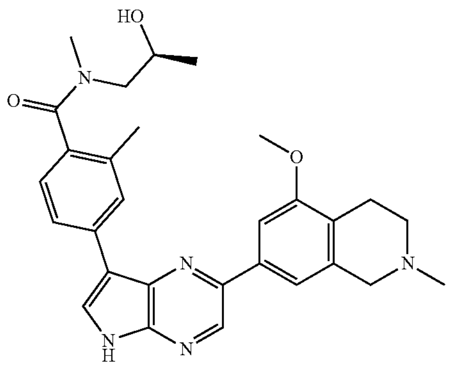
13
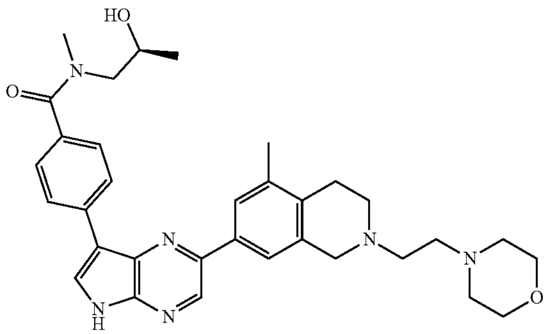
14
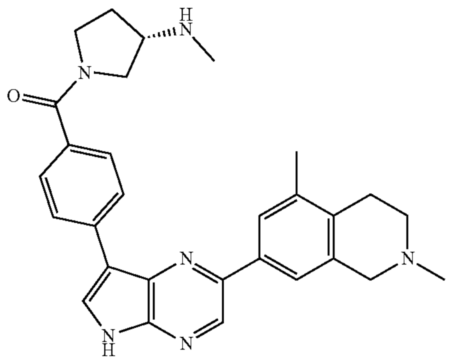

-continued
15
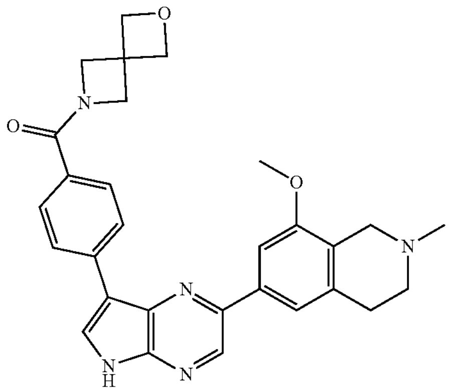
16
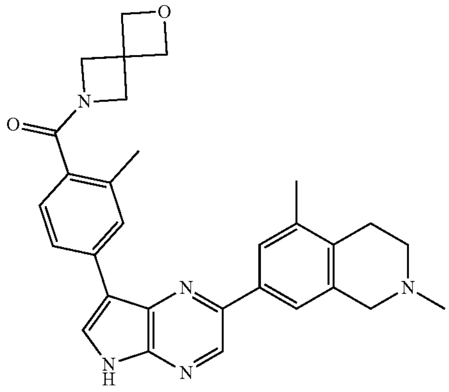
17
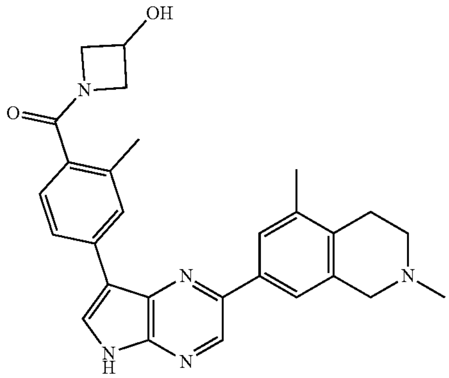
18
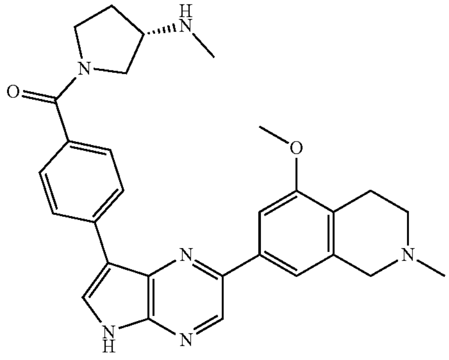
-continued
19
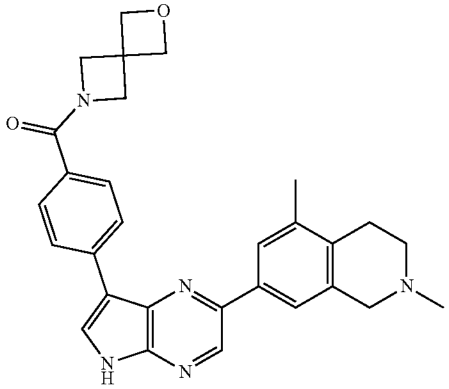
20
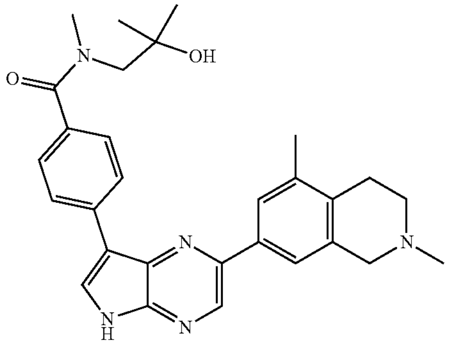
21
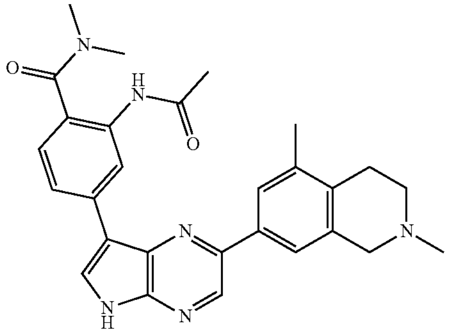
22
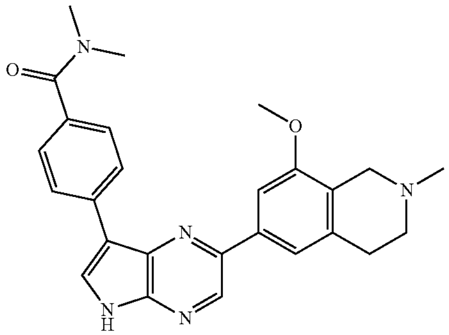

-continued
23
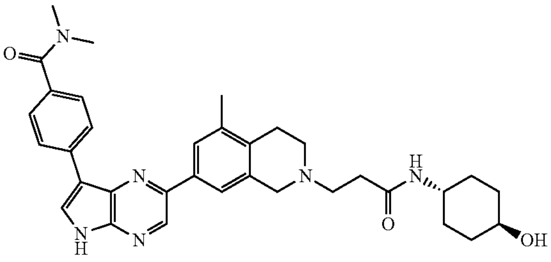
24
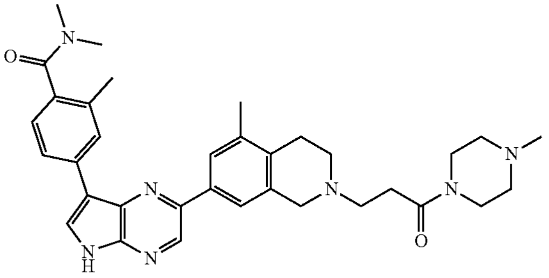
25
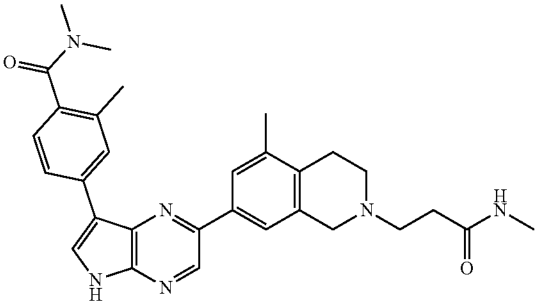
26
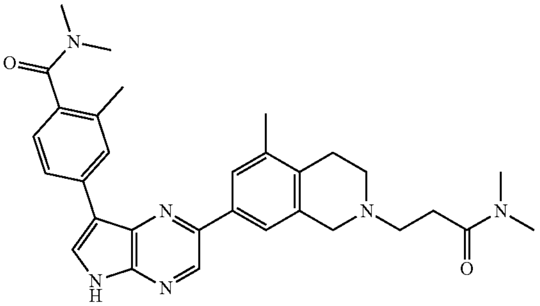
27
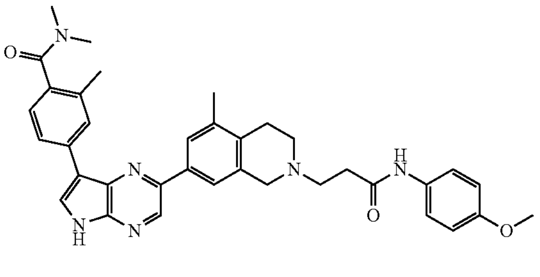
-continued
28
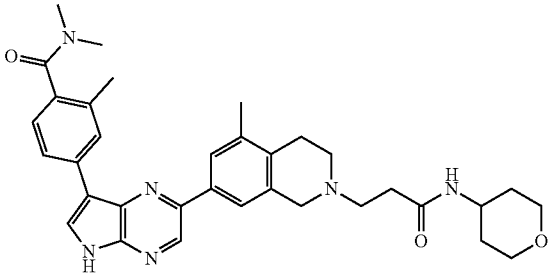
29
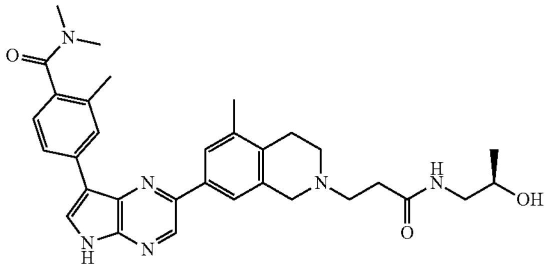
30
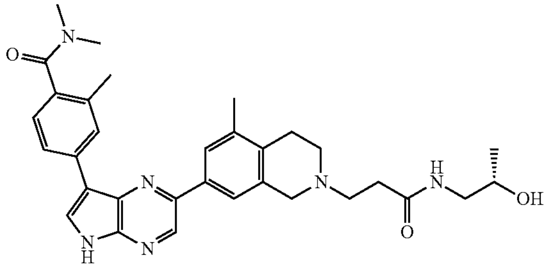
31
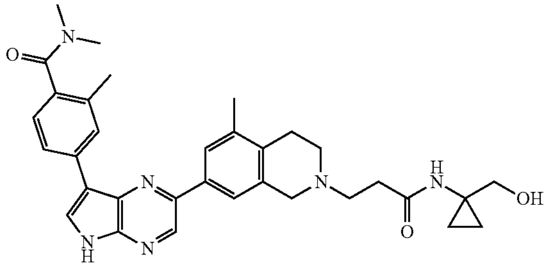
32
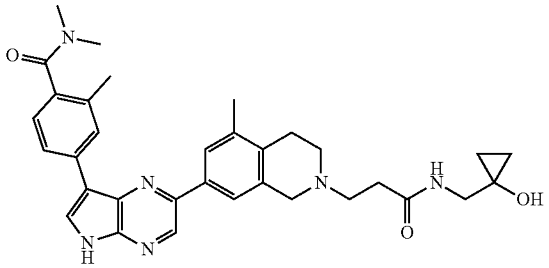

-continued
33
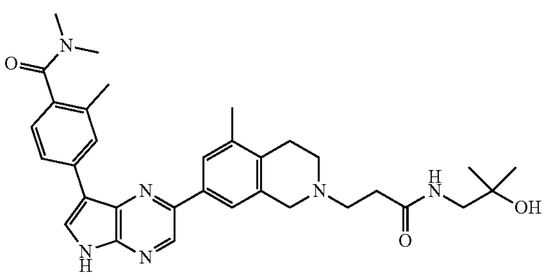
34
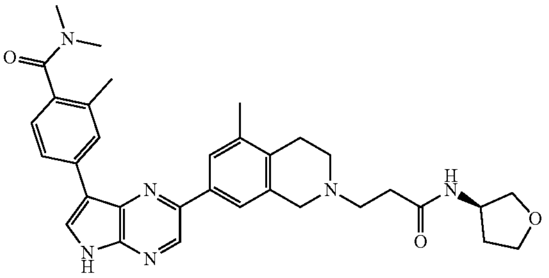
35
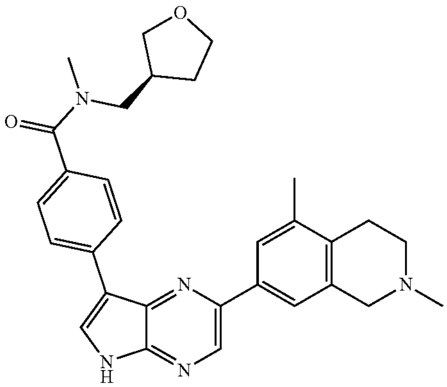
36
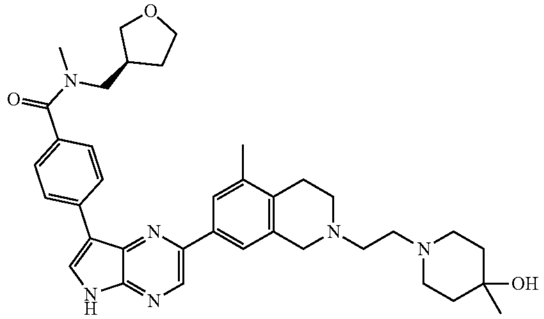
37
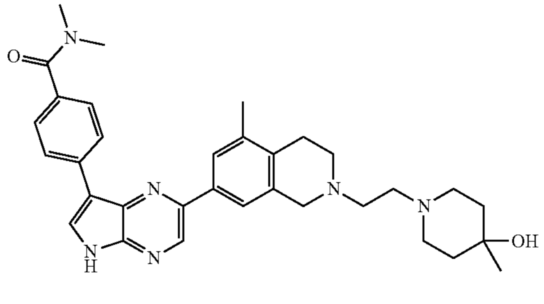
-continued
38
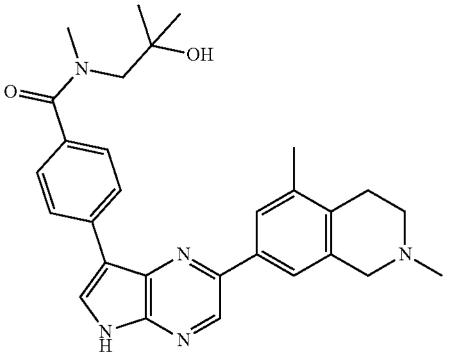
39
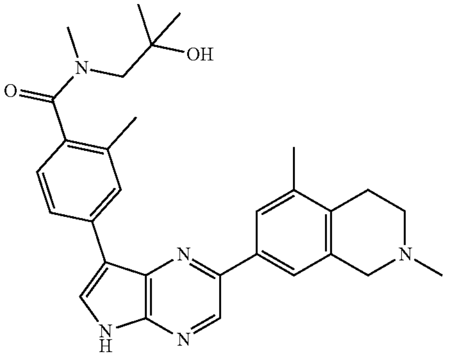
40
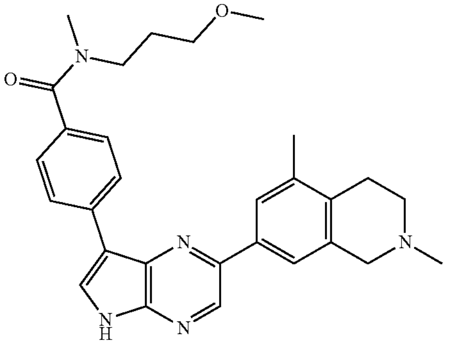
41
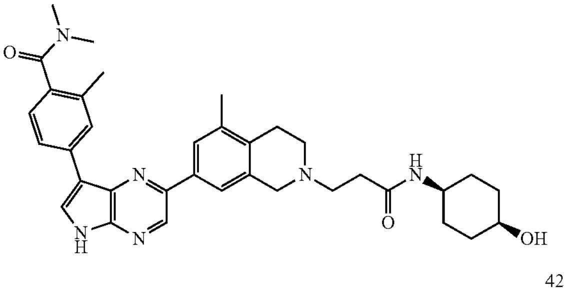
42
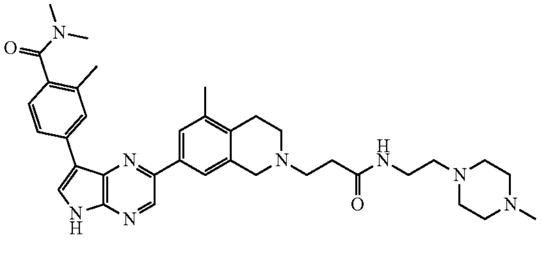

-continued
43
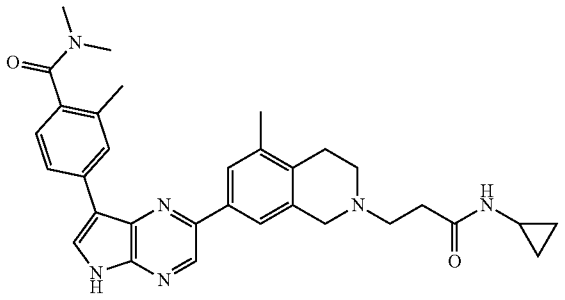
44
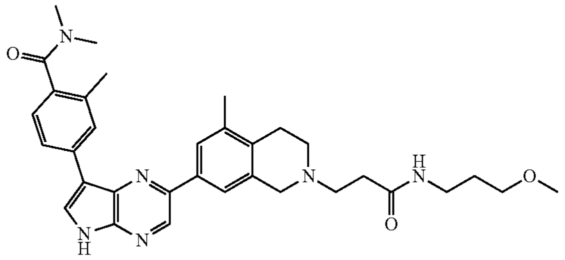
45
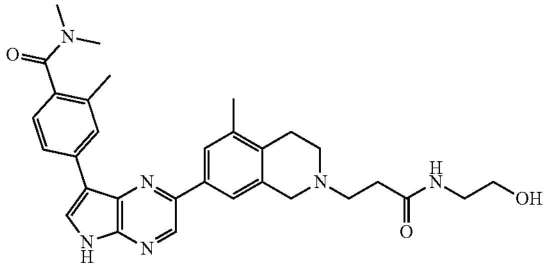
46
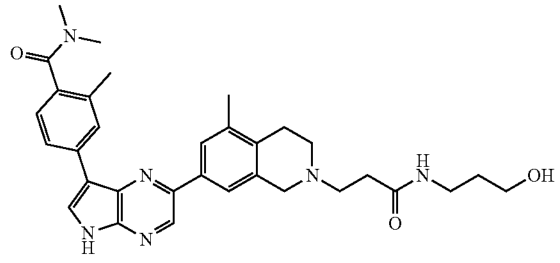
47
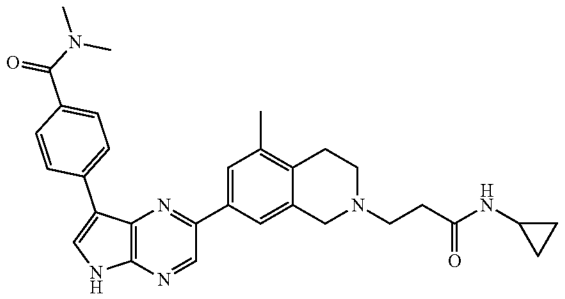
-continued
48
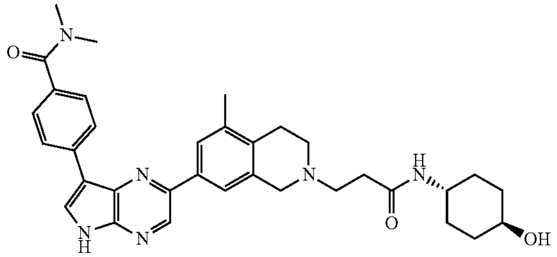
49
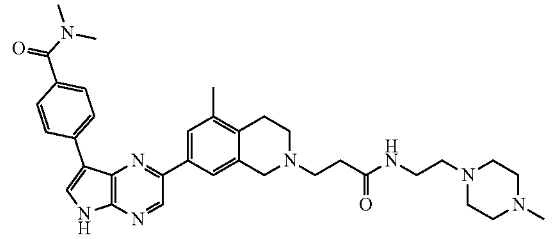
50
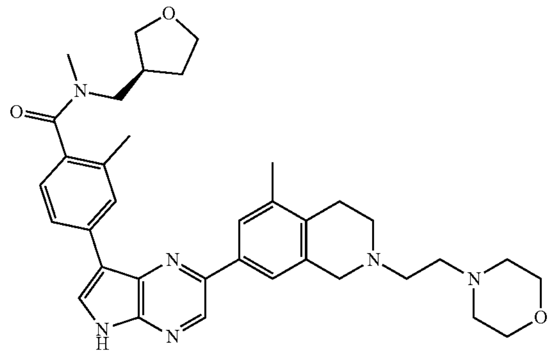
51
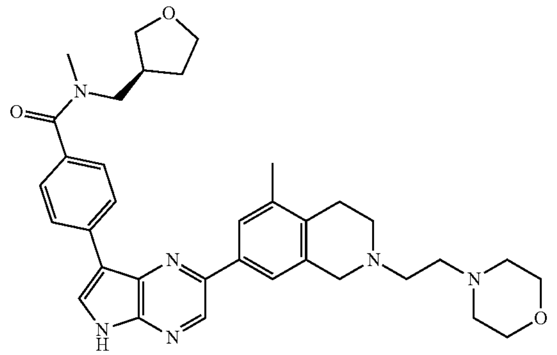
52
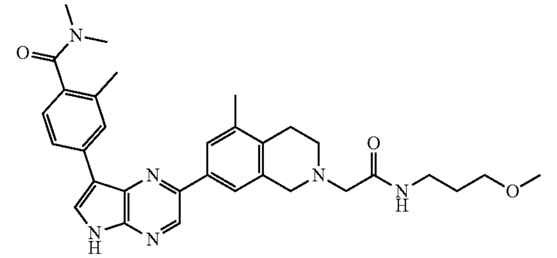

-continued
53
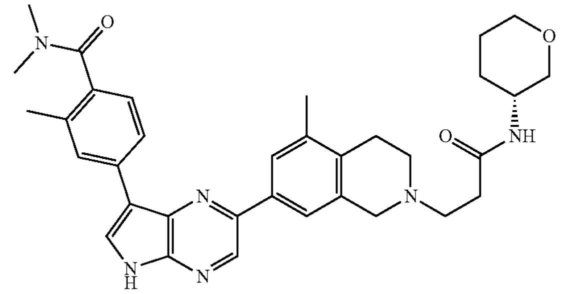
54
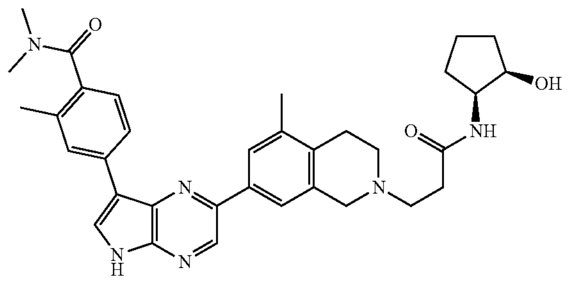
55
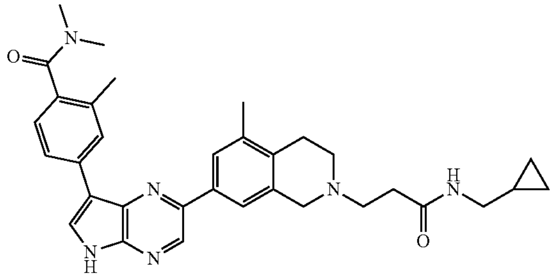
56
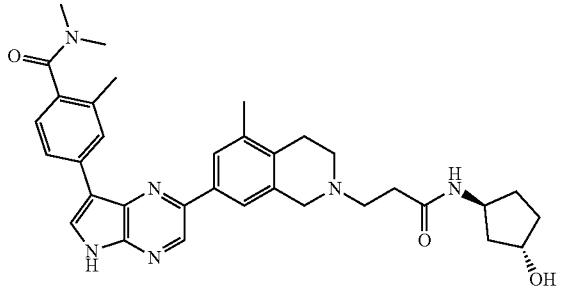
57
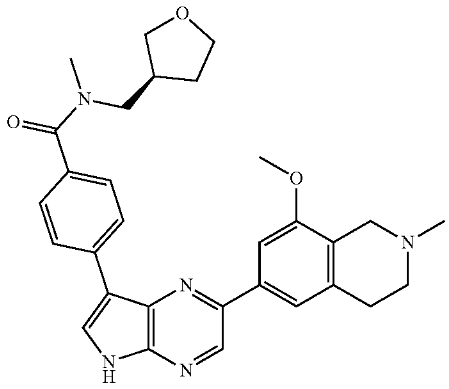
-continued
58
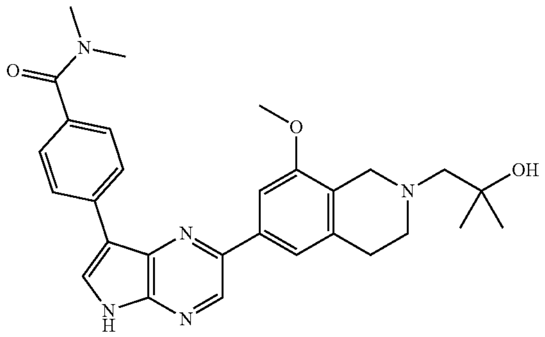
59
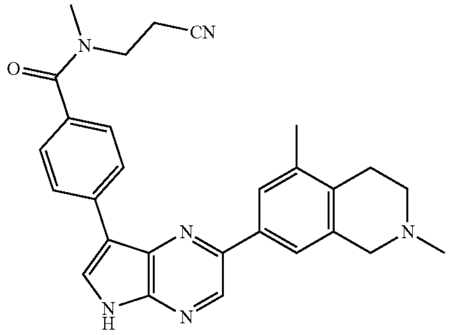
60
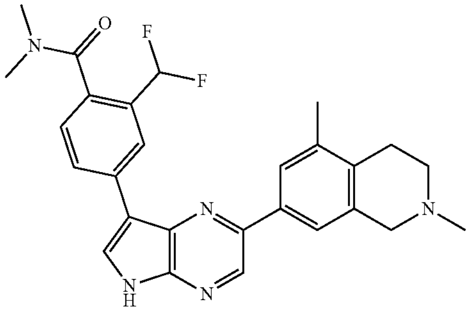
61
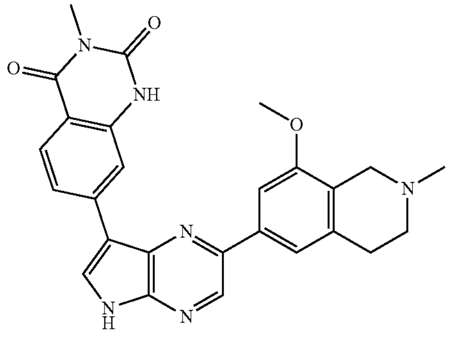

-continued
62
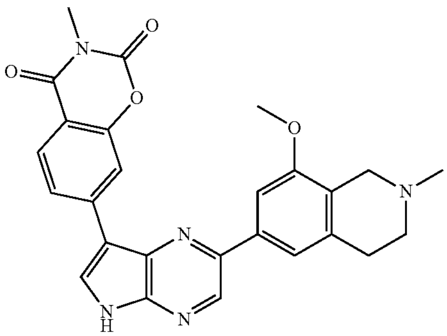
63
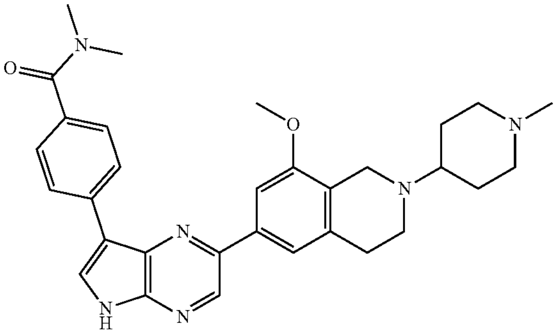
64
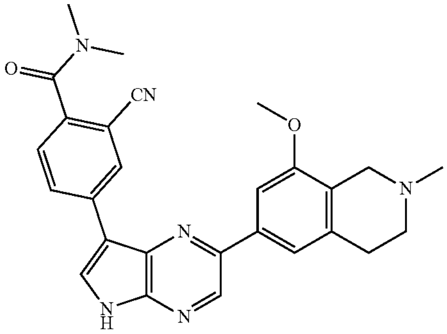
65
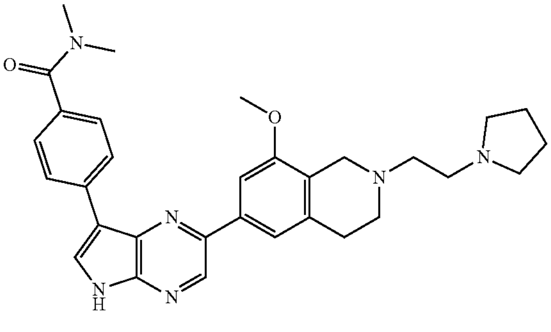
-continued
66
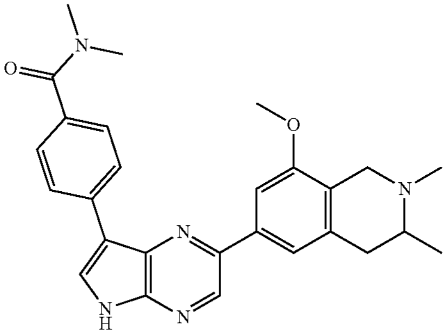
67
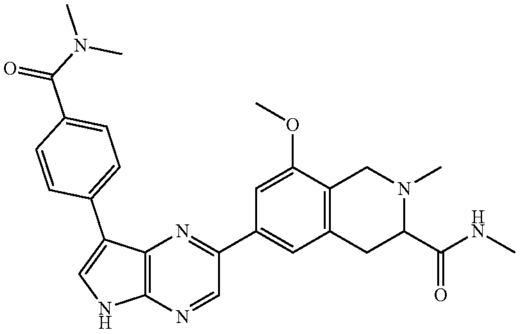
68
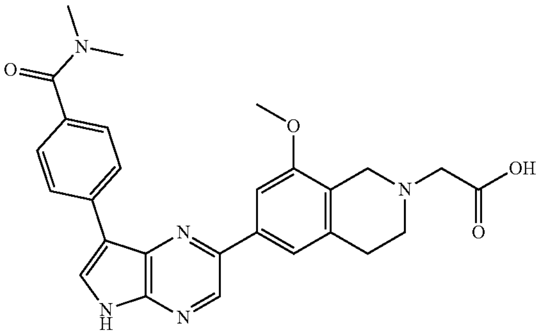
69
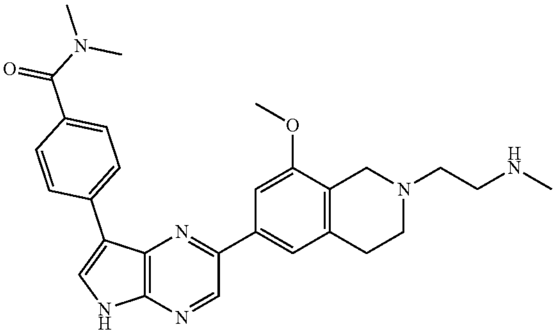

-continued
70
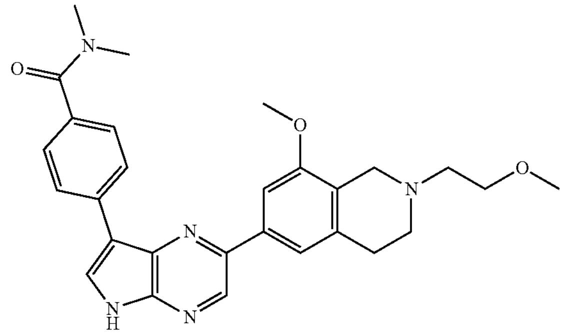
71
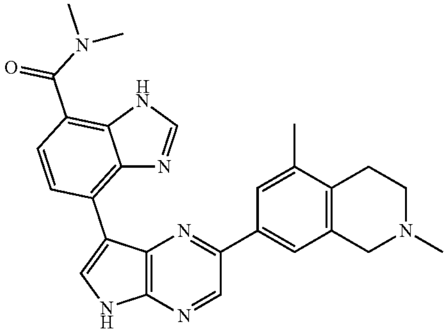
72
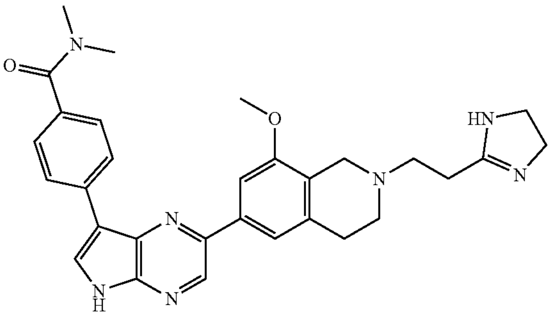
73
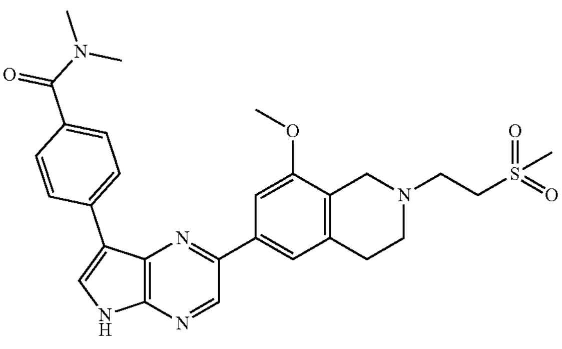
-continued
74
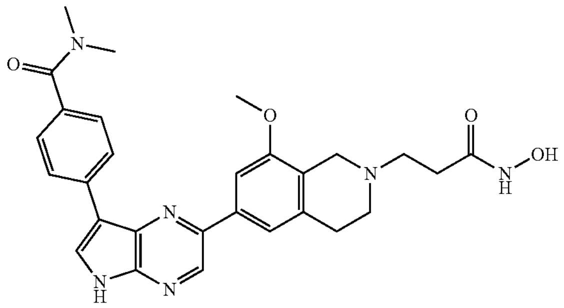
75
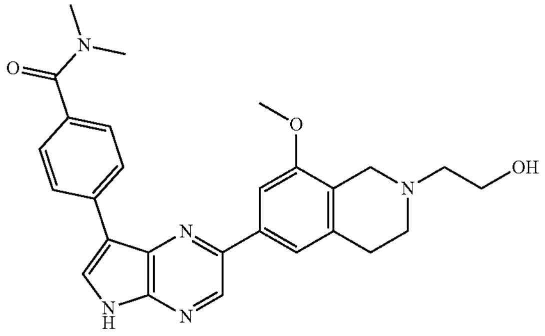
76
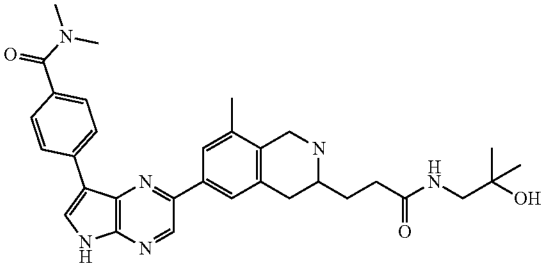
77
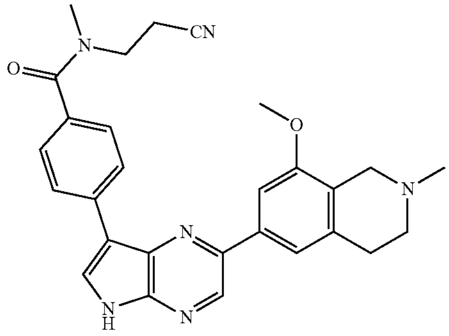

-continued
78
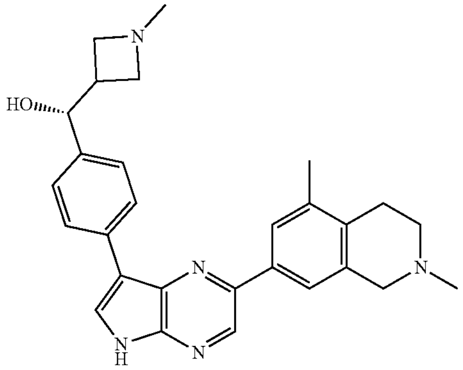
79
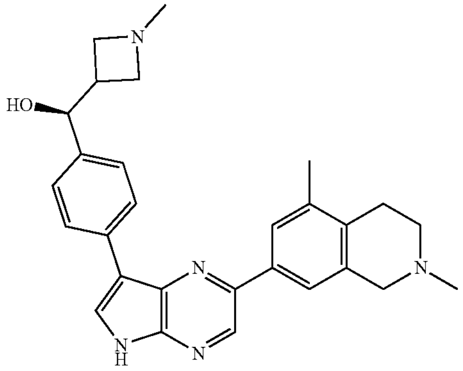
80
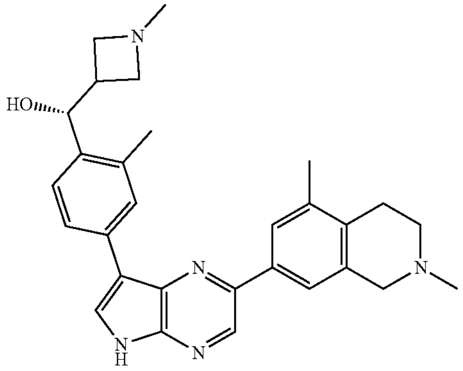
81
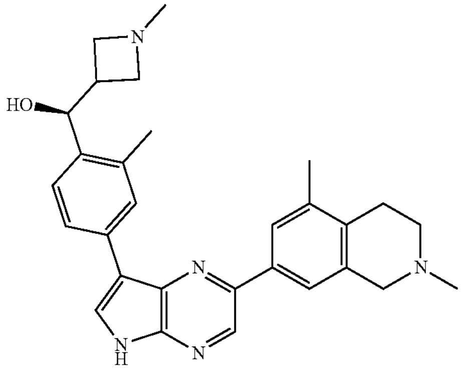
-continued
82
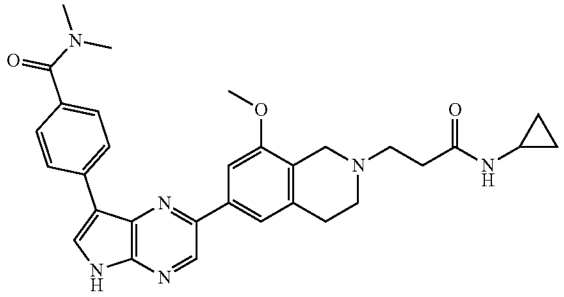
83
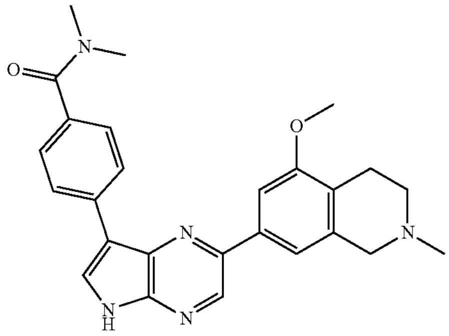
84
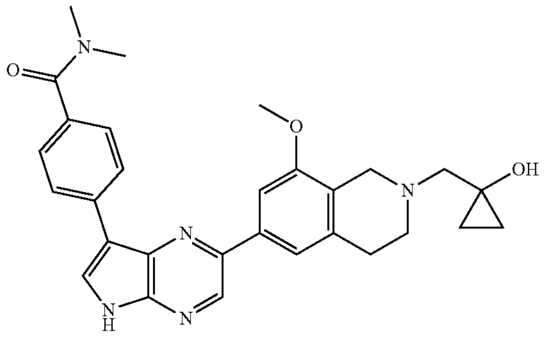
85
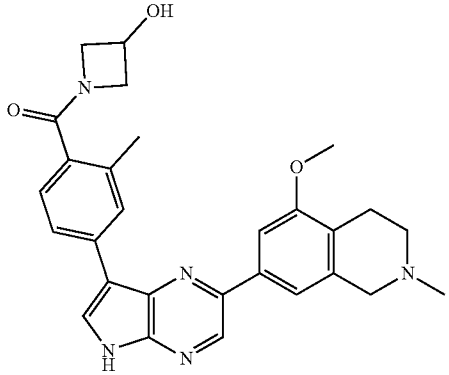

-continued
86
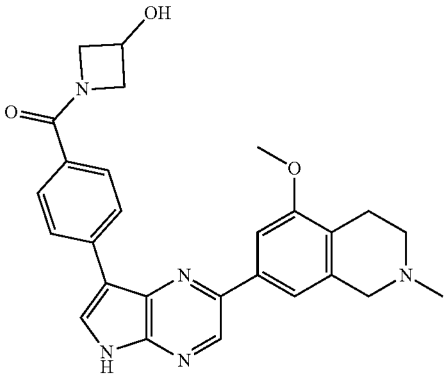
87
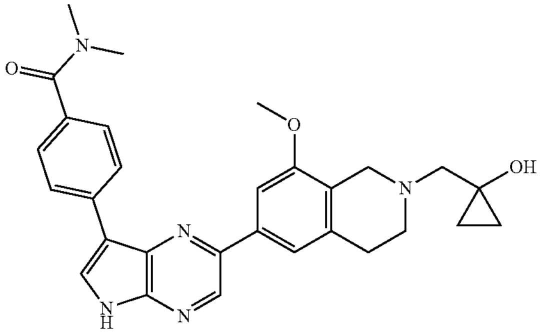
88
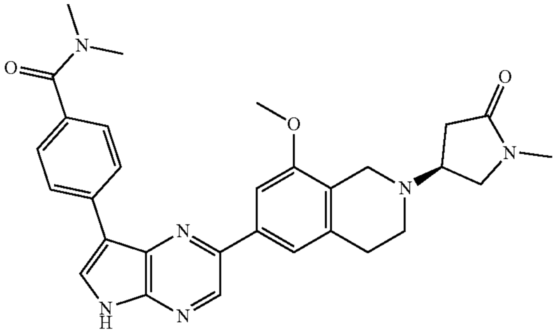
89
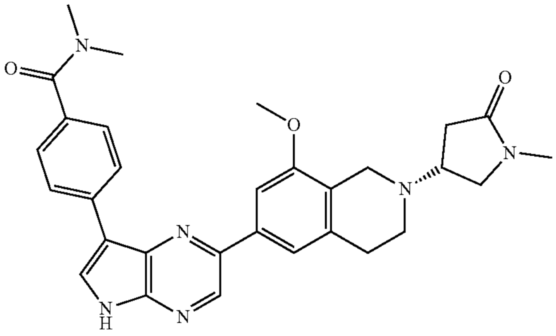
-continued
90
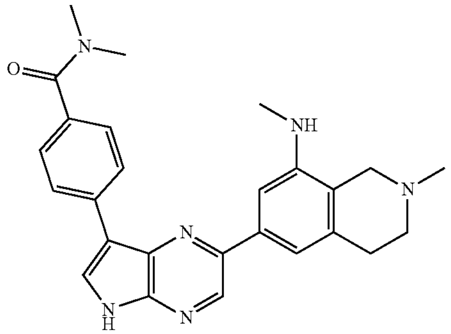
91
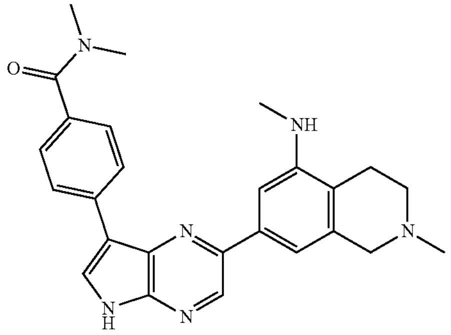
92
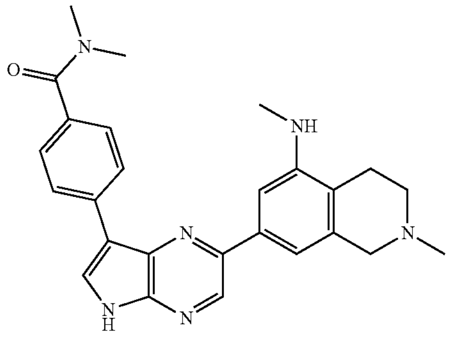
93
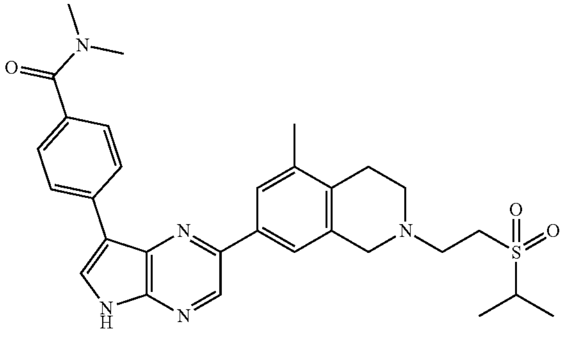

-continued
94
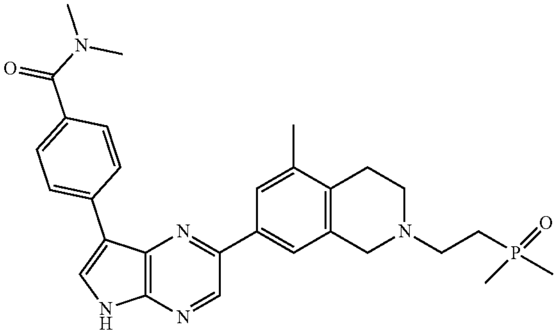
95
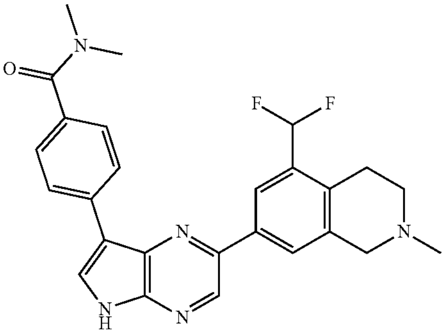
96
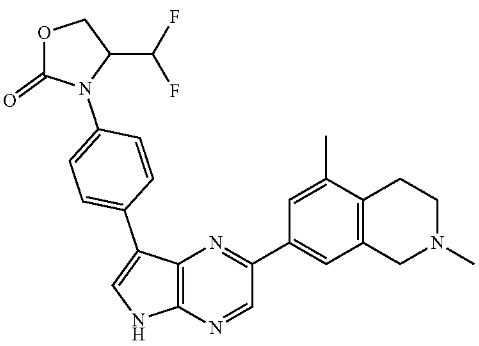
97
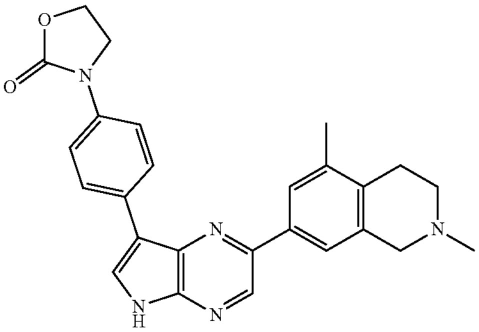
-continued
98
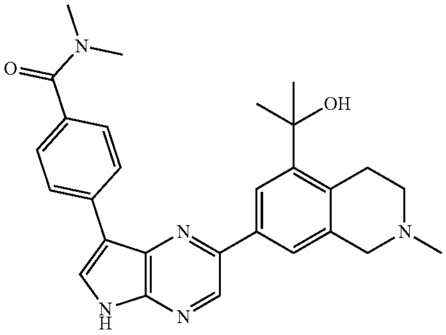
99
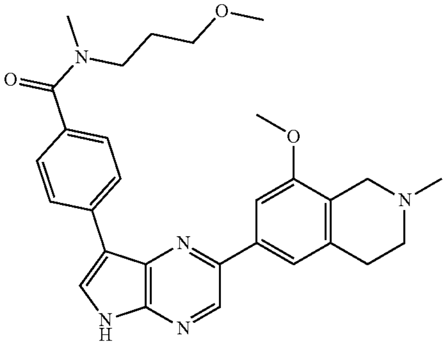
100
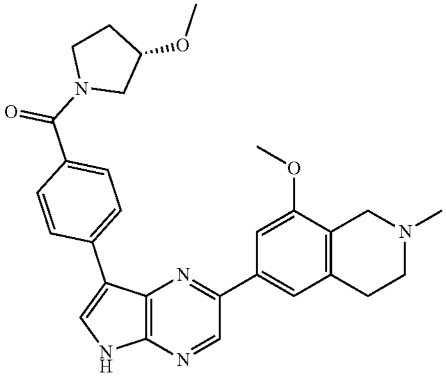
101
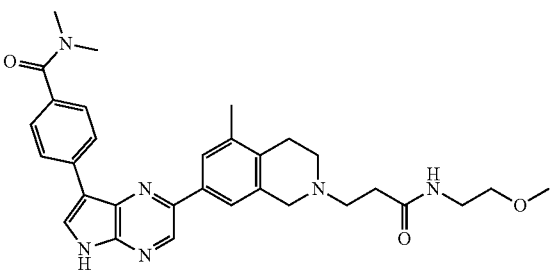

-continued
102
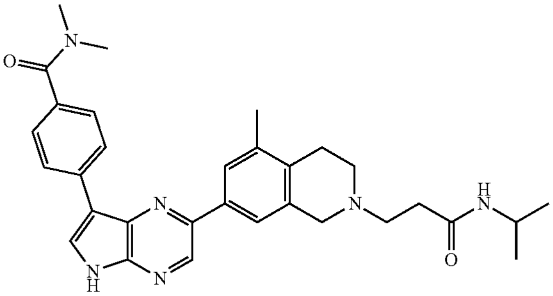
103
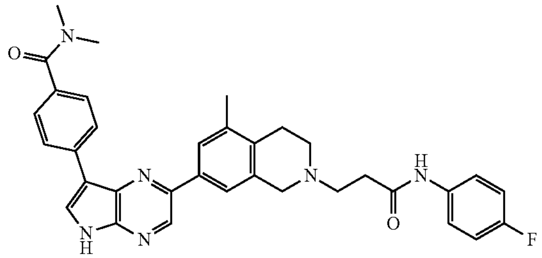
104
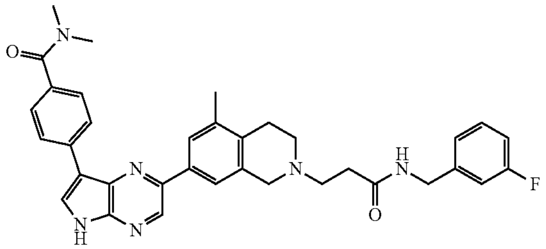
105
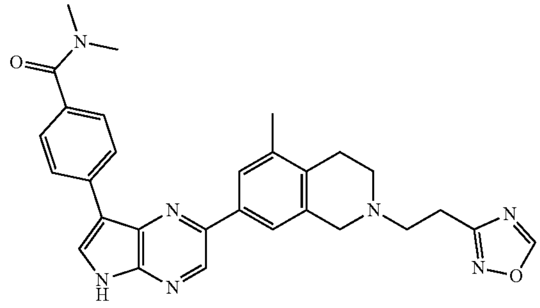
106
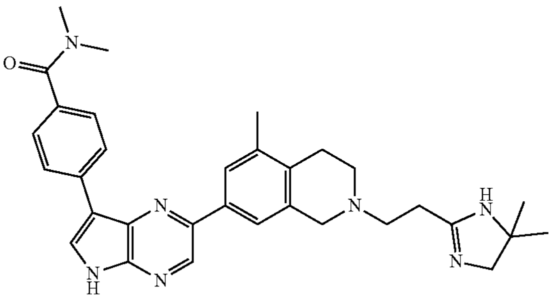
-continued
107
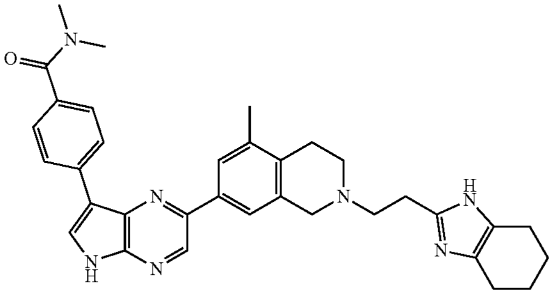
108
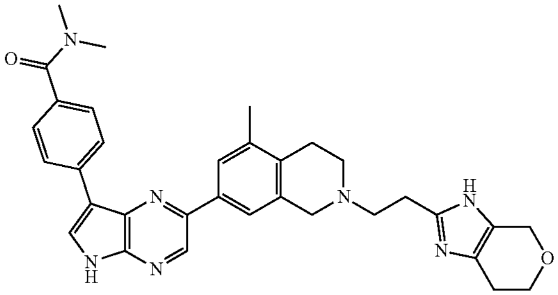
109
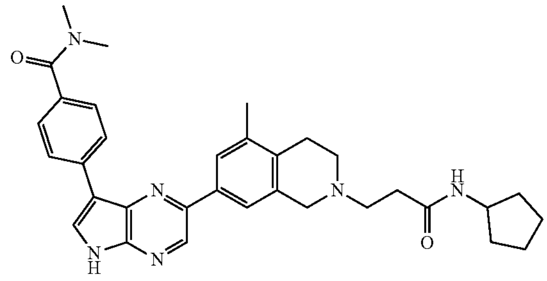
110
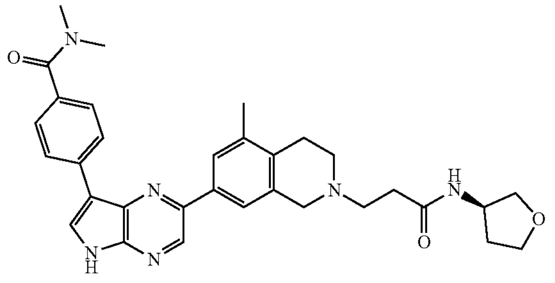
111
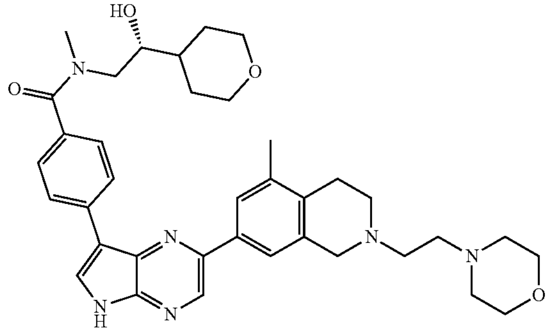

-continued
112
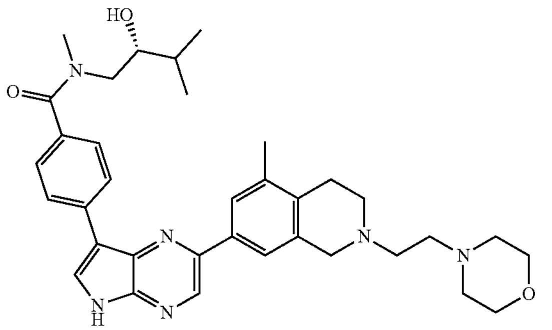
113
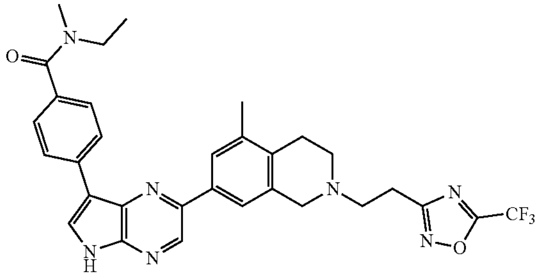
114
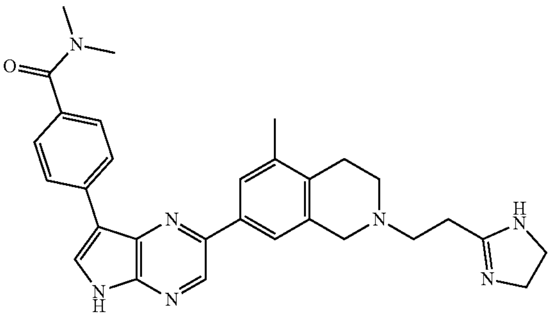
115
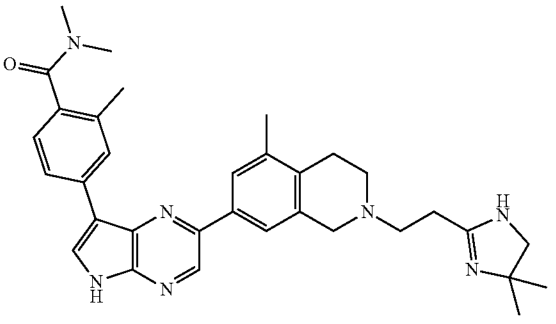
-continued
116
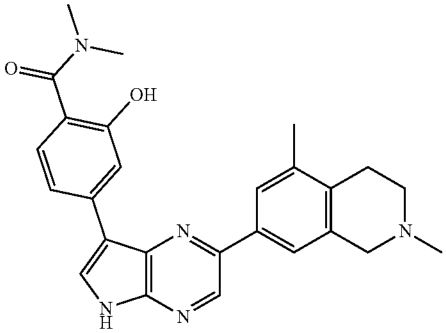
117
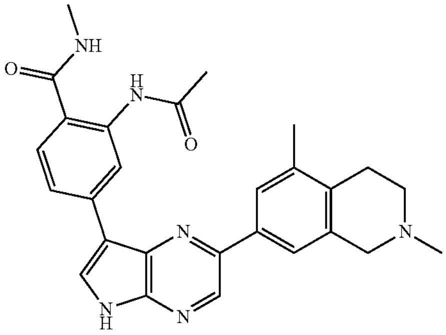
118
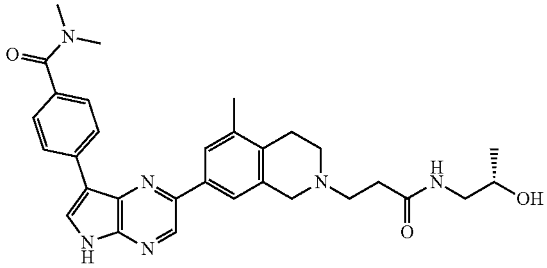
119
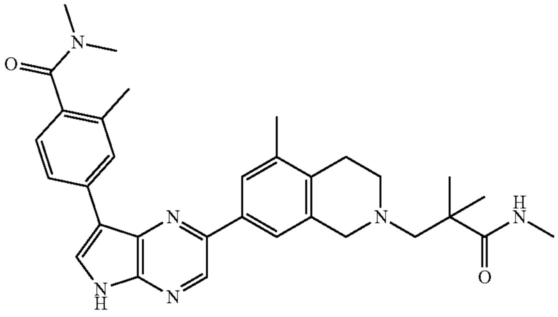
120
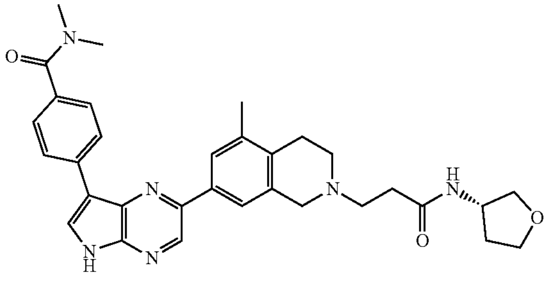

-continued

121

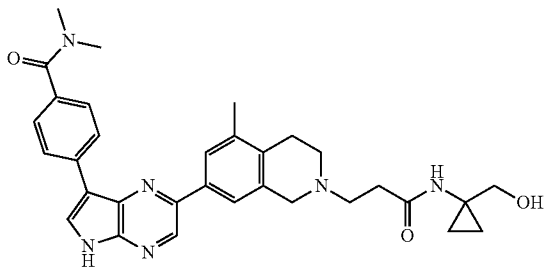

122

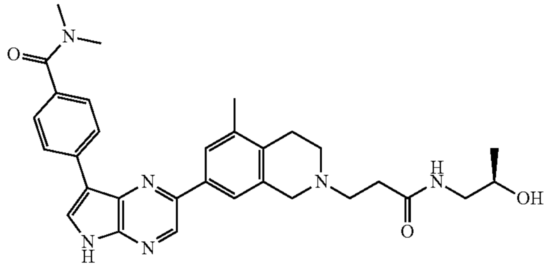

123

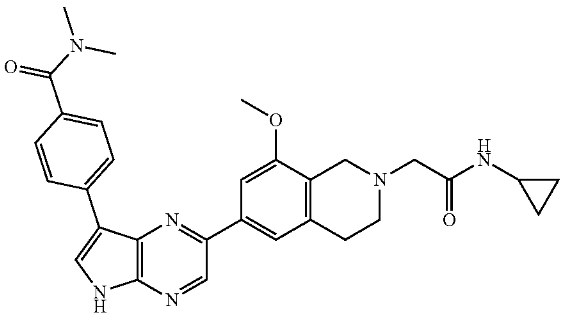

124

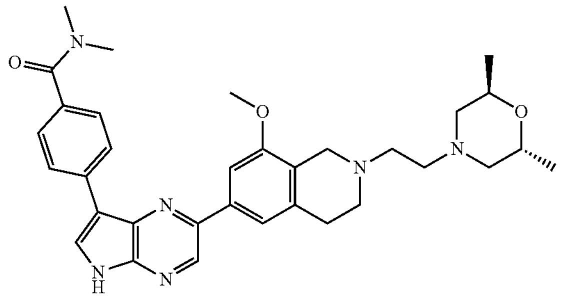

125

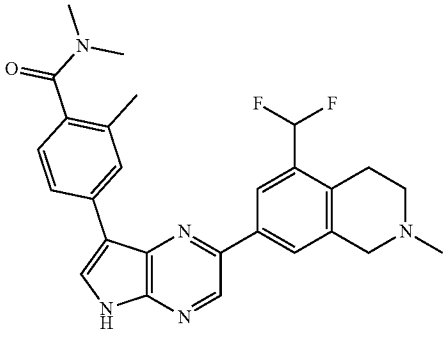

-continued

126

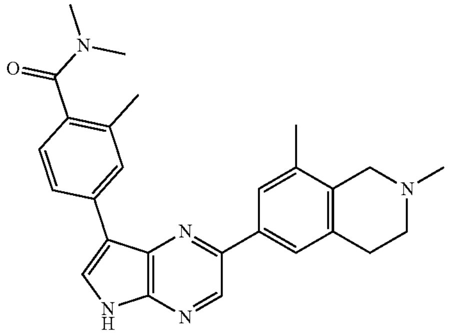

127

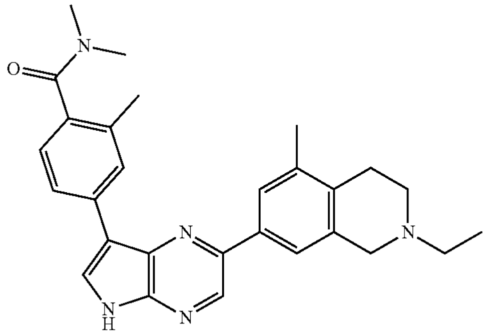

128

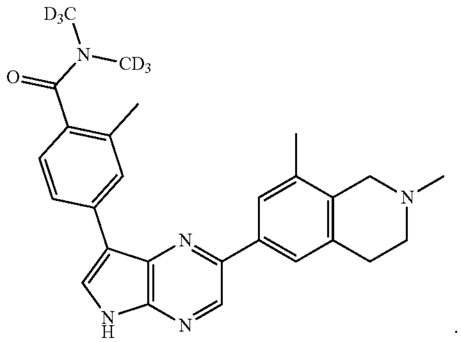

In the second aspect, disclosed herein is a pharmaceutical composition comprising the compound disclosed herein, or a pharmaceutically acceptable salt thereof, and at least one pharmaceutically acceptable carrier or excipient.

In the third aspect, disclosed herein is a method of inhibiting HPK1 activity, which comprise administering to an individual the compound disclosed herein, or a pharmaceutically acceptable salt thereof, including the compound of formula (I) or the specific compounds exemplified herein.

In the fourth aspect, disclosed herein is a method of treating a disease or disorder in a patient comprising administering to the patient a therapeutically effective amount of the compound disclosed herein, or a pharmaceutically acceptable salt thereof as an HPK1 kinase inhibitor, wherein the compound disclosed herein includes the compound of formula (I) or the specific compounds exemplified herein. In some embodiment, the disease or disorder is associated with inhibition of HPK1 interaction. Preferably, the disease or disorder is cancer.

DETAILED DESCRIPTION OF THE INVENTION

The following terms have the indicated meanings throughout the specification:

Unless specifically defined elsewhere in this document, all other technical and scientific terms used herein have the meaning commonly understood by one of ordinary skill in the art to which this invention belongs.

The following terms have the indicated meanings throughout the specification:

As used herein, including the appended claims, the singular forms of words such as "a", "an", and "the", include their corresponding plural references unless the context clearly indicates otherwise.

The term "or" is used to mean, and is used interchangeably with, the term "and/or" unless the context clearly dictates otherwise.

The term "alkyl" refers to a hydrocarbon group selected from linear and branched saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., $C_{1-6}$ alkyl) include, but not limited to, methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1, 1-dimethylethyl or t-butyl ("t-Bu"), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2, 3-dimethyl-2-butyl and 3, 3-dimethyl-2-butyl groups. An alkyl group defined herein is optionally deuterated or tritiated.

The term "propyl" refers to 1-propyl or n-propyl ("n-Pr"), 2-propyl or isopropyl ("i-Pr").

The term "butyl" refers to 1-butyl or n-butyl ("n-Bu"), 2-methyl-1-propyl or isobutyl ("i-Bu"), 1-methylpropyl or s-butyl ("s-Bu"), 1, 1-dimethylethyl or t-butyl ("t-Bu").

The term "pentyl" refers to 1-pentyl, 2-pentyl, 3-pentyl, 2-methyl-2-butyl, 3-methyl-2-butyl, 3-methyl-1-butyl, 2-methyl-1-butyl.

The term "hexyl" refers to 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2, 3-dimethyl-2-butyl and 3, 3-dimethyl-2-butyl.

The term "halogen" refers to fluoro (F), chloro (Cl), bromo (Br) and iodo (I).

The term "haloalkyl" refers to an alkyl group in which one or more hydrogen is/are replaced by one or more halogen atoms such as fluoro, chloro, bromo, and iodo. Examples of the haloalkyl include halo$C_{1-8}$alkyl, halo$C_{1-6}$alkyl or halo $C_{1-4}$alkyl, but not limited to $—CF_3$, $—CH_2Cl$, $—CH_2CF_3$, $—CHCl_2$, $—CF_3$, and the like.

The term "alkenyl" refers to a hydrocarbon group selected from linear and branched hydrocarbon groups comprising at least one C═C double bond and from 2 to 18, such as from 2 to 8, further such as from 2 to 6, carbon atoms. Examples of the alkenyl group, e.g., $C_{2-6}$ alkenyl, include, but not limited to ethenyl or vinyl, prop-1-enyl, prop-2-enyl, 2-methylprop-1-enyl, but-1-enyl, but-2-enyl, but-3-enyl, buta-1, 3-dienyl, 2-methylbuta-1, 3-dienyl, hex-1-enyl, hex-2-enyl, hex-3-enyl, hex-4-enyl, and hexa-1, 3-dienyl groups.

The term "alkynyl" refers to a hydrocarbon group selected from linear and branched hydrocarbon group, comprising at least one C≡C triple bond and from 2 to 18, such as 2 to 8, further such as from 2 to 6, carbon atoms. Examples of the alkynyl group, e.g., $C_{2-6}$ alkynyl, include, but not limited to ethynyl, 1-propynyl, 2-propynyl (propargyl), 1-butynyl, 2-butynyl, and 3-butynyl groups.

The term "cycloalkyl" refers to a hydrocarbon group selected from saturated cyclic hydrocarbon groups, comprising monocyclic and polycyclic (e.g., bicyclic and tricyclic) groups including fused, bridged or spiro cycloalkyl.

For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, cyclohexyl, cycloheptyl, cyclooctyl, cyclononyl, cyclodecyl, cycloundecyl, and cyclododecyl groups. In particular, Examples of the saturated monocyclic cycloalkyl group, e.g., $C_{3-8}$cycloalkyl, include, but not limited to cyclopropyl, cyclobutyl, cyclopentyl, cyclohexyl, cycloheptyl, and cyclooctyl groups. In a preferred embedment, the cycloalkyl is a monocyclic ring comprising 3 to 6 carbon atoms (abbreviated as $C_{3-6}$ cycloalkyl), including but not limited to, cyclopropyl, cyclobutyl, cyclopentyl, and cyclohexyl. Examples of the bicyclic cycloalkyl groups include those having from 7 to 12 ring atoms arranged as a fused bicyclic ring selected from [4, 4], [4, 5], [5, 5], [5, 6] and [6, 6] ring systems, or as a bridged bicyclic ring selected from bicyclo[2.2.1]heptane, bicyclo[2.2.2]octane, and bicyclo[3.2.2]nonane. Further Examples of the bicyclic cycloalkyl groups include those arranged as a bicyclic ring selected from [5, 6] and [6, 6] ring systems.

The term "spiro cycloalkyl" refers to a cyclic structure which contains carbon atoms and is formed by at least two rings sharing one atom. The term "7 to 12 membered spiro cycloalkyl" refers to a cyclic structure which contains 7 to 12 carbon atoms and is formed by at least two rings sharing one atom.

The term "fused cycloalkyl" refers to a bicyclic cycloalkyl group as defined herein which is saturated and is formed by two or more rings sharing two adjacent atoms.

The term "bridged cycloalkyl" refers to a cyclic structure which contains carbon atoms and is formed by two rings sharing two atoms which are not adjacent to each other. The term "7 to 10 membered bridged cycloalkyl" refers to a cyclic structure which contains 7 to 12 carbon atoms and is formed by two rings sharing two atoms which are not adjacent to each other.

The term "cycloalkenyl" refers to non-aromatic cyclic alkyl groups of from 3 to 10 carbon atoms having single or multiple rings and having at least one double bond and preferably from 1 to 2 double bonds. In one embodiment, the cycloalkenyl is cyclopentenyl or cyclohexenyl, 1-cyclopent-1-enyl, 1-cyclopent-2-enyl, 1-cyclopent-3-enyl, 1-cyclohex-1-enyl, 1-cyclohex-2-enyl, 1-cyclohex-3-enyl, cyclohexadienyl, preferably cyclohexenyl.

The term "fused cycloalkenyl" refers to a bicyclic cycloalkyl group as defined herein which contain at least one double bond and is formed by two or more rings sharing two adjacent atoms.

The term "cycloalkynyl" refers to non-aromatic cycloalkyl groups of from 5 to 10 carbon atoms having single or multiple rings and having at least one triple bond.

The term "fused cycloalkynyl" refers to a bicyclic cycloalkyl group as defined herein which contains at least one triple bond and is formed by two or more rings sharing two adjacent atoms.

The term a "benzo fused cycloalkyl" is a bicyclic fused cycloalkyl in which a 4- to 8-membered monocyclic cycloalkyl ring fused to a benzene ring. For example, a benzo fused cycloalkyl is

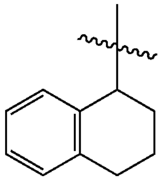

and

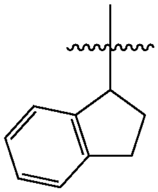

wherein the wavy lines indicate the points of attachment.

The term a "benzo fused cycloalkenyl" is a bicyclic fused cycloalkenyl in which a 4- to 8-membered monocyclic cycloalkenyl ring fused to a benzene ring.

The term a "benzo fused cycloalkynyl" is a bicyclic fused cycloalkynyl in which a 4- to 8-membered monocyclic cycloalkynyl ring fused to a benzene ring.

Examples of fused cycloalkyl, fused cycloalkenyl, or fused cycloalkynyl include but are not limited to bicyclo [1.1.0]butyl, bicyclo[2.1.0]pentyl, bicyclo[3.1.0]hexyl, bicyclo[4.1.0]heptyl, bicyclo[3.3.0]octyl, bicyclo[4.2.0]octyl, decalin, as well as benzo 3 to 8 membered cycloalkyl, benzo $C_{4-6}$ cycloalkenyl, 2, 3-dihydro-1H-indenyl, 1H-indenyl, 1, 2, 3, 4-tetralyl, 1, 4-dihydronaphthyl, etc. Preferred embodiments are 8 to 9 membered fused ring, which refer to cyclic structures containing 8 to 9 ring atoms within the above examples.

The term "aryl" used alone or in combination with other terms refers to a group selected from:

a) 5- and 6-membered carbocyclic aromatic rings, e.g., phenyl;

b) bicyclic ring systems such as 7 to 12 membered bicyclic ring systems, wherein at least one ring is carbocyclic and aromatic, e.g., naphthyl and indanyl; and, c) tricyclic ring systems such as 10 to 15 membered tricyclic ring systems wherein at least one ring is carbocyclic and aromatic, e.g., fluorenyl.

The terms "aromatic hydrocarbon ring" and "aryl" are used interchangeable throughout the disclosure herein. In some embodiments, a monocyclic or bicyclic aromatic hydrocarbon ring has 5 to 10 ring-forming carbon atoms (i.e., $C_{5-10}$ aryl). Examples of a monocyclic or bicyclic aromatic hydrocarbon ring includes, but not limited to, phenyl, naphth-1-yl, naphth-2-yl, anthracenyl, phenanthrenyl, and the like. In some embodiments, the aromatic hydrocarbon ring is a naphthalene ring (naphth-1-yl or naphth-2-yl) or phenyl ring. In some embodiments, the aromatic hydrocarbon ring is a phenyl ring.

Specifically, the term "bicyclic fused aryl" refers to a bicyclic aryl ring as defined herein. The typical bicyclic fused aryl is naphthalene.

The term "heteroaryl" refers to a group selected from:

a) 5-, 6- or 7-membered aromatic, monocyclic rings comprising at least one heteroatom, for example, from 1 to 4, or, in some embodiments, from 1 to 3, in some embodiments, from 1 to 2, heteroatoms, selected from nitrogen (N), sulfur (S) and oxygen (O), with the remaining ring atoms being carbon;

b) 7- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and c) 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. When the heteroaryl group contains more than one heteroatom ring member, the heteroatoms may be the same or different. The nitrogen atoms in the ring (s) of the heteroaryl group can be oxidized to form N-oxides.

Specifically, the term "bicyclic fused heteroaryl" refers to a 7- to 12-membered, preferably 7- to 10-membered, more preferably 9- or 10-membered fused bicyclic heteroaryl ring as defined herein. Typically, a bicyclic fused heteroaryl is 5-membered/5-membered, 5-membered/6-membered, 6-membered/6-membered, or 6-membered/7-membered bicyclic. The group can be attached to the remainder of the molecule through either ring.

Representative examples of bicyclic fused heteroaryl include, but not limited to, the following groups benzisoxazolyl, benzodiazolyl, benzofuranyl, benzofurazanyl, benzofuryl, benzoimidazolyl, benzoisothiazolyl, benzothiadiazolyl, benzothiazolyl, benzothienyl, benzothiophenyl, benzotriazolyl, benzoxadiazolyl, benzoxazolyl, furopyridinyl, furopyrrolyl, imidazopyridinyl, imidazopyridyl, imidazothiazolyl, indazolyl, indolizinyl, indolyl, isobenzofuryl, isoindolyl, isoquinolinyl (or isoquinolyl), naphthyridinyl, phthalazinyl, pteridinyl, purinyl, pyrazinopyridazinyl, pyrazolopyridinyl, pyrazolopyrimidinyl, pyrazolopyridyl, pyrazolotriazinyl, pyridazolopyridyl, pyrrolopyridinyl, quinazolinyl, quinolinyl (or quinolyl), quinoxalinyl, thiazolopyridyl, thienopyrazinyl, thienopyrazolyl, thienopyridyl, thienopyrrolyl, thienothienyl, or triazolopyridyl.

The term a "benzo fused heteroaryl" is a bicyclic fused heteroaryl in which a 5- to 7-membered (preferably, 5- or 6-membered) monocyclic heteroaryl ring as defined herein fused to a benzene ring.

The terms "aromatic heterocyclic ring" and "heteroaryl" are used interchangeable throughout the disclosure herein. In some embodiments, a monocyclic or bicyclic aromatic heterocyclic ring has 5-, 6-, 7-, 8-, 9- or 10-ring forming members with 1, 2, 3, or 4 heteroatom ring members independently selected from nitrogen (N), sulfur (S) and oxygen (O) and the remaining ring members being carbon. In some embodiments, the monocyclic or bicyclic aromatic heterocyclic ring is a monocyclic or bicyclic ring comprising 1 or 2 heteroatom ring members independently selected from nitrogen (N), sulfur (S) and oxygen (O). In some embodiments, the monocyclic or bicyclic aromatic heterocyclic ring is a 5- to 6-membered heteroaryl ring, which is monocyclic and which has 1 or 2 heteroatom ring members independently selected from nitrogen (N), sulfur (S) and oxygen (O). In some embodiments, the monocyclic or bicyclic aromatic heterocyclic ring is an 8- to 10-membered heteroaryl ring, which is bicyclic and which has 1 or 2 heteroatom ring members independently selected from nitrogen, sulfur and oxygen.

Examples of the heteroaryl group or the monocyclic or bicyclic aromatic heterocyclic ring include, but are not limited to, (as numbered from the linkage position assigned priority 1) pyridyl (such as 2-pyridyl, 3-pyridyl, or 4-pyridyl), cinnolinyl, pyrazinyl, 2, 4-pyrimidinyl, 3, 5-pyrimidinyl, 2, 4-imidazolyl, imidazopyridinyl, isoxazolyl, oxazolyl, thiazolyl, isothiazolyl, thiadiazolyl (such as 1, 2, 3-thiadiazolyl, 1, 2, 4-thiadiazolyl, or 1, 3, 4-thiadiazolyl), tetrazolyl, thienyl (such as thien-2-yl, thien-3-yl), triazinyl, benzothienyl, furyl or furanyl, benzofuryl, benzoimidazolyl, indolyl, isoindolyl, oxadiazolyl (such as 1, 2, 3-oxadiazolyl, 1, 2, 4-oxadiazolyl, or 1, 3, 4-oxadiazolyl), phthalazinyl, pyrazinyl, pyridazinyl, pyrrolyl, triazolyl (such as 1, 2, 3-triazolyl, 1, 2, 4-triazolyl, or 1, 3, 4-triazolyl), quinolinyl, isoquinolinyl, pyrazolyl, pyrrolopyridinyl (such as 1H-pyrrolo[2, 3-b]pyridin-5-yl), pyrazolopyridinyl (such as 1H-pyrazolo[3, 4-b]pyridin-5-yl), benzoxazolyl (such as benzo[d]oxazol-6-yl), pteridinyl, purinyl, 1-oxa-2, 3-diazolyl, 1-oxa-2, 4-diazolyl, 1-oxa-2, 5-diazolyl, 1-oxa-3, 4-diazolyl, 1-thia-2, 3-diazolyl, 1-thia-2, 4-diazolyl, 1-thia-2, 5-diazolyl, 1-thia-3, 4-diazolyl, furazanyl (such as furazan-2-yl, furazan-3-yl), benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), and indazolyl (such as 1H-indazol-5-yl).

"Heterocyclyl", "heterocycle" or "heterocyclic" are interchangeable and refer to a non-aromatic heterocyclyl group comprising one or more heteroatoms selected from nitrogen, oxygen or optionally oxidized sulfur as ring members, with the remaining ring members being carbon, including monocyclic, fused, bridged, and spiro ring, i.e., containing monocyclic heterocyclyl, bridged heterocyclyl, spiro heterocyclyl, and fused heterocyclic groups.

The term "optionally oxidized sulfur" used herein refer to S, SO or $SO_2$.

The term "monocyclic heterocyclyl" refers to monocyclic groups in which at least one ring member (e.g., 1-3 heteroatoms, 1 or 2 heteroatoms) is a heteroatom selected from nitrogen, oxygen or optionally oxidized sulfur. A heterocycle may be saturated or partially saturated.

Exemplary monocyclic 4 to 9-membered heterocyclyl groups include, but not limited to, (as numbered from the linkage position assigned priority 1) pyrrolidin-1-yl, pyrrolidin-2-yl, pyrrolidin-3-yl, imidazolidin-2-yl, imidazolidin-4-yl, pyrazolidin-2-yl, pyrazolidin-3-yl, piperidin-1-yl, piperidin-2-yl, piperidin-3-yl, piperidin-4-yl, 2, 5-piperazinyl, pyranyl, morpholinyl, morpholino, morpholin-2-yl, morpholin-3-yl, oxiranyl, aziridin-1-yl, aziridin-2-yl, azocan-1-yl, azocan-2-yl, azocan-3-yl, azocan-4-yl, azocan-5-yl, thiiranyl, azetidin-1-yl, azetidin-2-yl, azetidin-3-yl, oxetanyl, thietanyl, 1, 2-dithietanyl, 1, 3-dithietanyl, dihydropyridinyl, tetrahydropyridinyl, thiomorpholinyl, thioxanyl, piperazinyl, homopiperazinyl, homopiperidinyl, azepan-1-yl, azepan-2-yl, azepan-3-yl, azepan-4-yl, oxepanyl, thiepanyl, 1, 4-oxathianyl, 1, 4-dioxepanyl, 1, 4-oxathiepanyl, 1, 4-oxaazepanyl, 1, 4-dithiepanyl, 1, 4-thiazepanyl and 1, 4-diazepanyl, 1, 4-dithianyl, 1, 4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1, 4-dioxanyl, 1, 3-dioxolanyl, pyrazolinyl, pyrazolidinyl, dithianyl, dithiolanyl, pyrazolidinyl, imidazolinyl, pyrimidinonyl, or 1, 1-dioxo-thiomorpholinyl.

The term "spiro heterocyclyl" refers to a 5 to 20-membered polycyclic heterocyclyl with rings connected through one common carbon atom (called a spiro atom), comprising one or more heteroatoms selected from nitrogen, oxygen or optionally oxidized sulfur as ring members, with the remaining ring members being carbon. One or more rings of a spiro heterocyclyl group may contain one or more double bonds, but none of the rings has a completely conjugated pi-electron system. Preferably a spiro heterocyclyl is 6 to 14-membered, and more preferably 7 to 12-membered. According to the number of common spiro atoms, a spiro heterocyclyl is divided into mono-spiro heterocyclyl, di-spiro heterocyclyl, or poly-spiro heterocyclyl, and preferably refers to mono-spiro heterocyclyl or di-spiro heterocyclyl, and more preferably 4-membered/3-membered, 4-membered/4-membered, 3-membered/5-membered, 4-membered/5-membered, 4-membered/6-membered, 5-membered/5-membered, or 5-membered/6-membered mono-spiro heterocyclyl. Representative examples of spiro heterocyclyls include, but not limited to the following groups: 2, 3-dihydrospiro[indene-1, 2'-pyrrolidine] (e.g., 2, 3-dihydrospiro[indene-1, 2'-pyrrolidine]-1'-yl), 1, 3-dihydrospiro[indene-2, 2'-pyrrolidine] (e.g., 1, 3-dihydrospiro[indene-2, 2'-pyrrolidine]-1'-yl), azaspiro[2.4]heptane (e.g., 5-azaspiro[2.4]heptane-5-yl), 2-oxa-6-azaspiro[3.3]heptane (e.g., 2-oxa-6-azaspiro[3.3]heptan-6-yl), azaspiro[3.4]octane (e.g., 6-azaspiro[3.4]octane-6-yl), 2-oxa-6-azaspiro[3.4]octane (e.g., 2-oxa-6-azaspiro[3.4]octane-6-yl), azaspiro[3.4]octane (e.g., 6-azaspiro[3.4]octan-6-yl), azaspiro[3.4]octane (e.g., 6-azaspiro[3.4]octan-6-yl), 1, 7-dioxaspiro[4.5]decane, 2-oxa-7-aza-spiro[4.4]nonane (e.g., 2-oxa-7-aza-spiro[4.4]non-7-yl), 7-oxa-spiro[3.5]nonyl and 5-oxa-spiro[2.4]heptyl.

The term "fused heterocyclyl" refers to a 5 to 20-membered polycyclic heterocyclyl group, wherein each ring in the system shares an adjacent pair of atoms (carbon and carbon atoms or carbon and nitrogen atoms) with another ring, comprising one or more heteroatoms selected from nitrogen, oxygen or optionally oxidized sulfur as ring members, with the remaining ring members being carbon. One or more rings of a fused heterocyclic group may contain one or more double bonds, but the fused heterocyclic group does not have a completely conjugated pi-electron system. Preferably, a fused heterocyclyl is 6 to 14-membered, and more preferably 7 to 12-membered, or 7- to 10-membered. According to the number of membered rings, a fused heterocyclyl is divided into bicyclic, tricyclic, tetracyclic, or polycyclic fused heterocyclyl. The group can be attached to the remainder of the molecule through either ring.

Specifically, the term "bicyclic fused heterocyclyl" refers to a 7 to 12-membered, preferably 7- to 10-membered, more preferably 9- or 10-membered fused heterocyclyl as defined herein comprising two fused rings and comprising 1 to 4 heteroatoms selected from nitrogen, oxygen or optionally oxidized sulfur as ring members. Typically, a bicyclic fused heterocyclyl is 5-membered/5-membered, 5-membered/6-membered, 6-membered/6-membered, or 6-membered/7-membered bicyclic fused heterocyclyl. Representative examples of (bicyclic) fused heterocycles include, but not limited to, the following groups octahydrocyclopenta[c]pyrrole, octahydropyrrolo[3, 4-c]pyrrolyl, octahydroisoindolyl, isoindolinyl, octahydro-benzo[b][1, 4]dioxin, indolinyl, isoindolinyl, benzopyranyl, dihydrothiazolopyrimidinyl, tetrahydroquinolyl, tetrahydroisoquinolyl (or tetrahydroisoquinolinyl), dihydrobenzofuranyl, dihydrobenzoxazinyl, dihydrobenzoimidazolyl, tetrahydrobenzothienyl, tetrahydrobenzofuranyl, benzodioxolyl, benzodioxonyl, chromanyl, chromenyl, octahydrochromenyl, dihydrobenzodioxynyl, dihydrobenzoxezinyl, dihydrobenzodioxepinyl, dihydrothienodioxynyl, dihydrobenzooxazepinyl, tetrahydrobenzooxazepinyl, dihydrobenzoazepinyl, tetrahydrobenzoazepinyl, isochromanyl, chromanyl, or tetrahydropyrazolopyrimidinyl (e.g., 4, 5, 6, 7-tetrahydropyrazolo[1, 5-a]pyrimidin-3-yl).

The term a "benzo fused heterocyclyl" is a bicyclic fused heterocyclyl in which a monocyclic 4 to 9-membered heterocyclyl as defined herein (preferably 5- or 6-membered) fused to a benzene ring.

The term "bridged heterocyclyl" refers to a 5 to 14-membered polycyclic heterocyclic alkyl group, wherein every two rings in the system share two disconnected atoms, comprising one or more heteroatoms selected from nitrogen, oxygen or optionally oxidized sulfur as ring members, with the remaining ring members being carbon. One or more rings of a bridged heterocyclyl group may contain one or more double bonds, but none of the rings has a completely conjugated pi-electron system. Preferably, a bridged heterocyclyl is 6 to 14-membered, and more preferably 7 to 10-membered. According to the number of membered rings, a bridged heterocyclyl is divided into bicyclic, tricyclic, tetracyclic or polycyclic bridged heterocyclyl, and preferably refers to bicyclic, tricyclic or tetracyclic bridged heterocyclyl, and more preferably bicyclic or tricyclic bridged heterocyclyl. Representative examples of bridged heterocyclyls include, but not limited to, the following groups: 2-azabicyclo[2.2.1]heptyl, azabicyclo[3.1.0]hexyl, 2-azabicyclo[2.2.2]octyl and 2-azabicyclo[3.3.2]decyl.

If amine is substituted by $R^5$, it means that the nitrogen atom in structures of

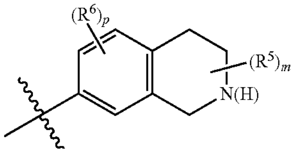

or

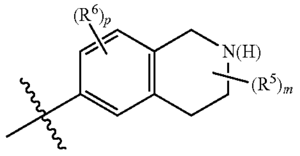

is not bonded to a hydrogen.

The term "at least one substituents" disclosed herein includes, for example, from 1 to 4, such as from 1 to 3, further as 1 or 2, substituents, provided the theory of valence is met. For example, "at least one substituents $R^{6d}$" disclosed herein includes from 1 to 4, such as from 1 to 3, further as 1 or 2, substituents selected from the list of $R^{6d}$ as disclosed herein.

Compounds disclosed herein may contain an asymmetric center and may thus exist as enantiomers. "Enantiomers" refer to two stereoisomers of a compound which are non-superimposable mirror images of one another. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" as used herein means that the target stereoisomer contains no more than 35%, such as no more than 30%, further such as no more than 25%, even further such as no more than 20%, by weight of any other stereoisomer (s). In some embodiments, the term "substantially pure" means that the target stereoisomer contains no more than 10%, for example, no more than 5%, such as no more than 1%, by weight of any other stereoisomer (s).

When compounds disclosed herein contain olefinic double bonds, unless specified otherwise, such double bonds are meant to include both E and Z geometric isomers.

When compounds disclosed herein contain a di-substituted cyclic ring system, substituents found on such ring system may adopt cis and trans formations. Cis formation means that both substituents are found on the upper side of the 2 substituent placements on the carbon, while trans would mean that they were on opposing sides. For example, the di-substituted cyclic ring system may be cyclohexyl or cyclobutyl ring.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

"Diastereomers" refers to stereoisomers of a compound with two or more chiral centers but which are not mirror images of one another. Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. Stereochemistry of Organic Compounds. New York: John Wiley & Sons, Inc., 1994; Lochmuller, C. H., et al. *"Chromatographic resolution of enantiomers: Selective review." J. Chromatogr.,* 113 (3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., *Ed. Drug*

*Stereochemistry: Analytical Methods and Pharmacology*. New York: Marcel Dekker, Inc., 1993.

"Pharmaceutically acceptable salts" refers to those salts which are, within the scope of sound medical judgment, suitable for use in contact with the tissues of humans and lower animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "a pharmaceutically acceptable salt thereof" include salts of at least one compound of Formula (I), and salts of the stereoisomers of the compound of Formula (I), such as salts of enantiomers, and/or salts of diastereomers.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, and rabbit) and most preferably a human.

The term "effective amount" or "therapeutically effective amount" refers to an amount of the active ingredient, such as compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In some embodiments, "therapeutically effective amount" is an amount of at least one compound and/or at least one stereoisomer thereof, and/or at least one pharmaceutically acceptable salt thereof disclosed herein effective to "treat" as defined herein, a disease or disorder in a subject. In the case of combination therapy, the "therapeutically effective amount" refers to the total amount of the combination objects for the effective treatment of a disease, a disorder or a condition.

The pharmaceutical composition comprising the compound disclosed herein can be administrated via oral, inhalation, rectal, parenteral or topical administration to a subject in need thereof. For oral administration, the pharmaceutical composition may be a regular solid formulation such as tablets, powder, granule, capsules and the like, a liquid formulation such as water or oil suspension or other liquid formulation such as syrup, solution, suspension or the like; for parenteral administration, the pharmaceutical composition may be solution, water solution, oil suspension concentrate, lyophilized powder or the like. Preferably, the formulation of the pharmaceutical composition is selected from tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All formulations of the pharmaceutical composition disclosed herein can be produced by the conventional methods in the pharmaceutical field. For example, the active ingredient can be mixed with one or more excipients, then to make the desired formulation. The "pharmaceutically acceptable excipient" refers to conventional pharmaceutical carriers suitable for the desired pharmaceutical formulation, for example: a diluent, a vehicle such as water, various organic solvents, etc., a filler such as starch, sucrose, etc. a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, aromatics, a sweetener, and a dye.

The term "disease" refers to any disease, discomfort, illness, symptoms or indications, and can be interchangeable with the term "disorder" or "condition".

Throughout this specification and the claims which follow, unless the context requires otherwise, the term "comprise", and variations such as "comprises" and "comprising" are intended to specify the presence of the features thereafter, but do not exclude the presence or addition of one or more other features. When used herein the term "comprising" can be substituted with the term "containing", "including" or sometimes "having".

Throughout this specification and the claims which follow, the term "$C_{n-m}$" indicates a range which includes the endpoints, wherein n and m are integers and indicate the number of carbons. Examples include $C_{1-8}$, $C_{1-6}$, and the like.

Unless specifically defined elsewhere in this document, all other technical and scientific terms used herein have the meaning commonly understood by one of ordinary skill in the art to which this invention belongs.

General Synthesis

Compounds disclosed herein, including salts thereof, can be prepared using known organic synthesis techniques and can be synthesized according to any of numerous possible synthetic routes.

The reaction for preparing compounds disclosed herein can be carried out in suitable solvents which can be readily selected by one of skill in the art of organic synthesis.

Suitable solvents can be substantially non-reactive with the starting materials, the intermediates, or products at the temperatures at which the reactions are carried out, e.g., temperatures which can range from room temperature to the solvent's boiling temperature. A given reaction can be carried out in one solvent or mixture of solvents.

The selection of appropriate protecting group, can be readily determined by one skilled in the art.

Reactions can be monitored according to any suitable method known in the art, such as NMR, UV, HPLC, LC-MS and TLC. Compounds can be purified by a variety of methods, including HPLC and normal phase silica chromatography.

Chiral analytic HPLC was used for the retention time analysis of different chiral examples, the conditions were divided into the methods as below according to the column, mobile phase, solvent ration used.

The compounds disclosed herein can be prepared by following Scheme I and Scheme II.

Scheme I

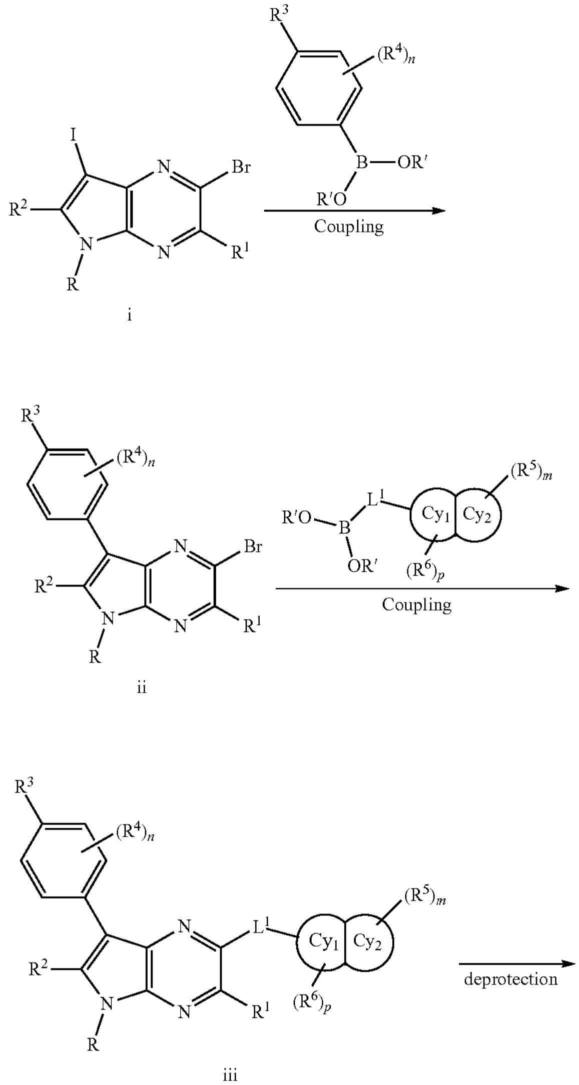

-continued

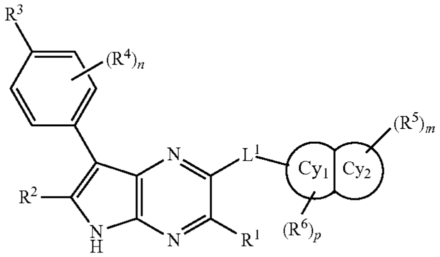

iv

R = Ts or Boc or acyl
R' = H or alkyl
$Cy_1|Cy_2$ is fused ring system

For example, compounds of Formula (I) can be formed as shown in Scheme I. Compound (i) can be reacted with boronic acid or boronic ester using transition metal catalyzed reaction to give compound (ii); compound (ii) can be reacted with boronic acid or boronic ester using transition metal catalyzed reaction to give compound (iii); compound (iii) can be deprotected in situ or stepwise to give compound (iv) [i.e., Formula (I)].

Scheme II

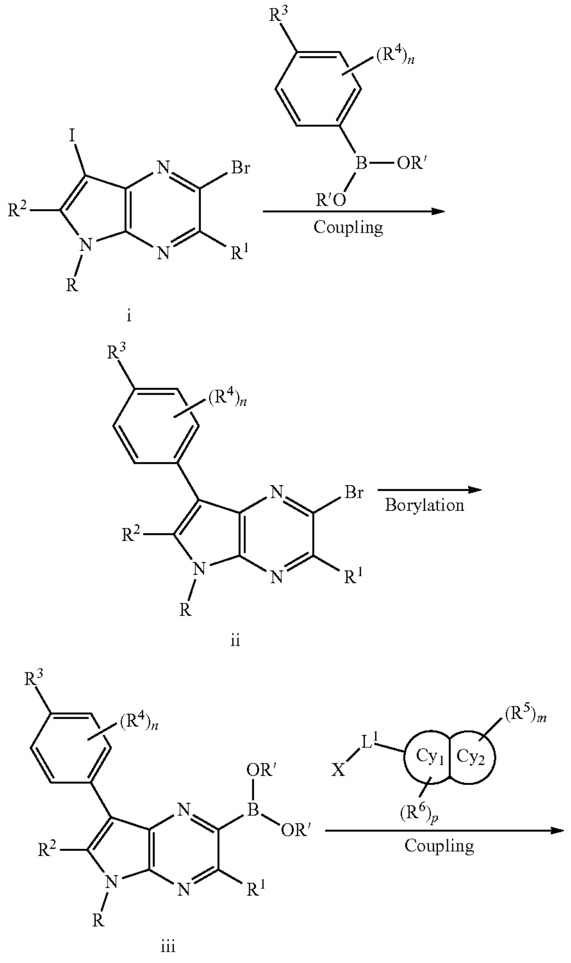

-continued

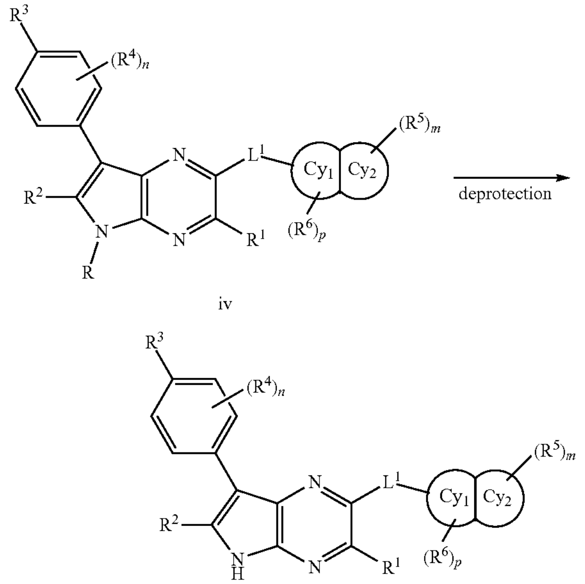

iv v

R = Ts or Boc or acyl
R′ = H or alkyl
X = Cl or Br or I
$Cy_1|Cy_2$ is fused ring system For example, compounds of Formula (I) can be formed as shown in Scheme II. Compound (i) can be reacted with boronic acid or boronic ester using transition metal catalyzed reaction to give compound (ii); compound (ii) can be borylated to give compound (iii); compound (iii) can be reacted with boronic acid or boronic ester using transition metal catalyzed reaction to give compound (iv); compound (iv) can be deprotected in situ or stepwise to give compound (v) [i.e., Formula (I)].

Scheme III

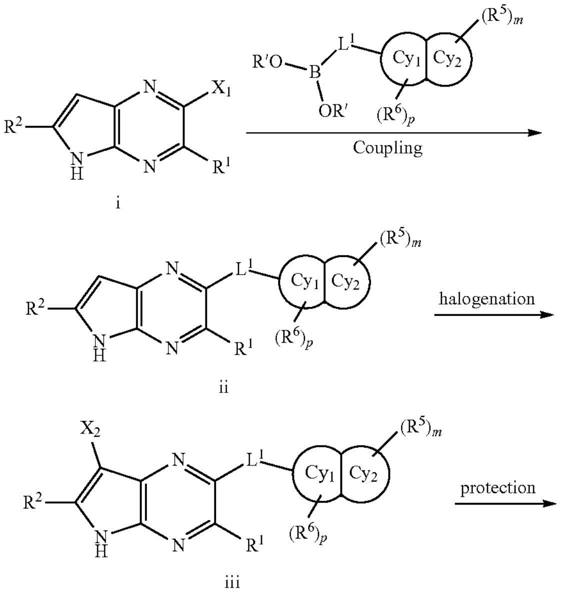

i ii iii

-continued

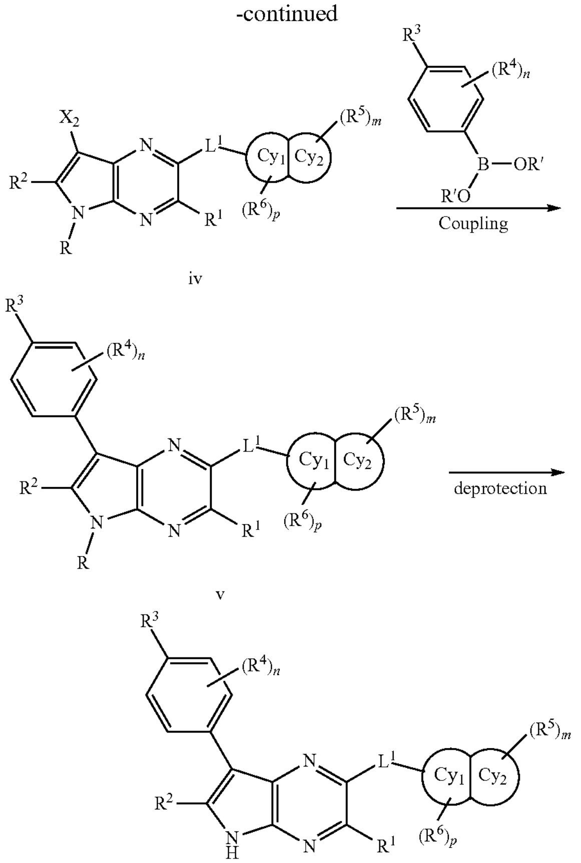

iv v vi

R = Ts or Boc or acyl
R′ = H or alkyl
$X_1$, $X_2$ = Cl or Br or I
$Cy_1|Cy_2$ is fused ring system For example, compounds of Formula (I) can be formed as shown in Scheme III. Compound (i) can be reacted with boronic acid or boronic ester using transition metal catalyzed reaction to give compound (ii); compound (ii) can be selectively halogenated to give compound (iii); compound (iii) can be protected to give compound (iv); compound (iv) can be reacted with boronic acid or boronic ester to give compound (v); compound (v) can be deprotected in situ or stepwise to give compound (vi) [i.e., Formula (I)].

EXAMPLES

The examples below are intended to be purely exemplary and should not be considered to be limiting in any way. Unless otherwise specified, the experimental methods in the Examples described below are conventional methods. Unless otherwise specified, the reagents and materials are all commercially available. All solvents and chemicals employed are of analytical grade or chemical purity. Solvents are all redistilled before use. Anhydrous solvents are all prepared according to standard methods or reference methods.

Abbreviations

Ts p-toluenesulfonyl (tosyl)
THF tetrahydrofuran
DCM dichloromethane

Et ethyl
Ac acetyl
LCMS liquid chromatograph mass spectrometer
Me methyl
dppf 1, 1'-bis (diphenylphosphino)ferrocene
BPD bis (pinacolato)diboron
pin pinacolyl
Boc tert-butyloxycarbonyl
TEA triethylamine
TFA trifluoroacetic acid
TFAA trifluoroacetic anhydride
HPLC high performance liquid chromatography
PE petroleum ether
TLC thin layer chromatography
DMF N, N-dimethylformamide
HATU 2-(7-azabenzotriazol-1-yl)-N, N, N',N'-tetramethyluronium hexafluorophosphate
DIPEA N, N-diisopropylethylamine
DMSO dimethyl sulfoxide
TBS tert-butyldimethylsilyl
MTBE methyl tert-butyl ether
T3P propylphosphonic anhydride
IPA isopropyl alcohol
UV ultraviolet
NIS N-iodosuccinimide
DMAP 4-dimethylaminopyridine Example 1: 4-[2-(2, 5-dimethyl-3, 4-dihydro-1H-isoquinolin-7-yl)-5H-pyrrolo[2, 3-b]pyrazin-7-yl]-N, N-dimethylbenzamide

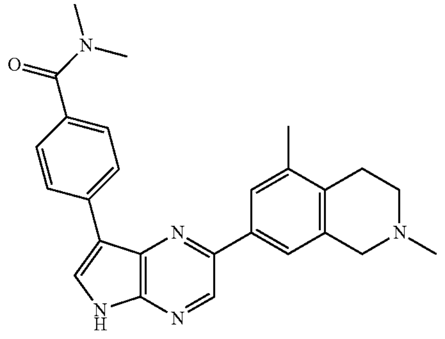 [SMILES: Cc1cc(-c2cnc3[nH]cc(-c4ccc(C(=O)N(C)C)cc4)c3n2)cc2c1CCN(C)C2]

Step 1: 2-bromo-7-iodo-5-tosyl-5H-pyrrolo[2, 3-b]pyrazine

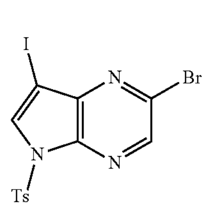 [SMILES: Cc1ccc(S(=O)(=O)n2cc(I)c3nc(Br)cnc32)cc1]

To a solution of 2-bromo-7-iodo-5H-pyrrolo[2, 3-b]pyrazine (162 g, 500 mmol) in anhydrous DMF (1500 mL) was added sodium hydride (30.0 g, 750 mmol) at 0° C. in portions. The resulting mixture was stirred for 15 min at 0° C., and then TsCl (124 g, 650 mmol) was added in portions. The mixture was warmed to room temperature while being stirred. After 3 h, the reaction mixture was poured into ice water (2 L) and the precipitate was collected by filtration. The solid was rinsed with water (200 mL×5) then dried under vacuum to give the title compound (239 g, 99%). LCMS $(M+H)^+$=479.9.

Step 2: 4-(2-bromo-5-tosyl-5H-pyrrolo[2, 3-b]pyrazin-7-yl)-N, N-dimethylbenzamide

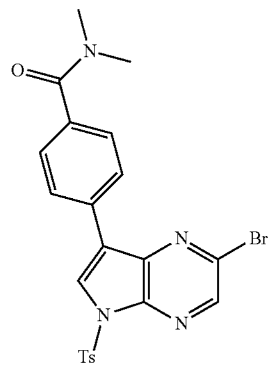 [SMILES: Cc1ccc(S(=O)(=O)n2cc(-c3ccc(C(=O)N(C)C)cc3)c3nc(Br)cnc32)cc1]

To a solution of 2-bromo-7-iodo-5-tosyl-5H-pyrrolo[2, 3-b]pyrazine (240 mg, 0.50 mmol) and [4-(dimethylcarbamoyl)phenyl]boronic acid (106 mg, 0.52 mmol) in 1, 4-dioxane (6 mL) and water (1 mL) was added $K_2CO_3$ (207 mg, 1.42 mmol) and Pd $(dppf)Cl_2 \cdot CH_2Cl_2$ (41 mg, 0.048 mmol). After stirring for 3 h at 70° C. under a nitrogen atmosphere, the reaction mixture was concentrated under reduced pressure. The residue was purified by silica gel column chromatography, eluted with $CHCl_3$/MeOH (9:1) to give the title compound (200 mg, 75%). LCMS $(M+H)^+$=499.2.

Step 3: N, N-dimethyl-4-(2-(4, 4, 5, 5-tetramethyl-1, 3, 2-dioxaborolan-2-yl)-5-tosyl-5H-pyrrolo[2, 3-b]pyrazin-7-yl)benzamide

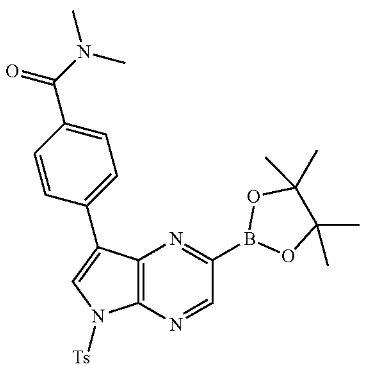 [SMILES: Cc1ccc(S(=O)(=O)n2cc(-c3ccc(C(=O)N(C)C)cc3)c3nc(B4OC(C)(C)C(C)(C)O4)cnc32)cc1]

To a stirred solution of 4-(2-bromo-5-tosyl-5H-pyrrolo[2, 3-b]pyrazin-7-yl)-N, N-dimethylbenzamide (950 mg, 1.90 mmol) and BPD (531 mg, 2.09 mmol) in dioxane (15 mL) was added KOAc (373 mg, 3.80 mmol) and Pd (dppf) $Cl_2 \cdot CH_2Cl_2$ (155 mg, 0.190 mmol). The reaction mixture was stirred for 2 h at 100° C. under nitrogen atmosphere. The mixture was cooled down to room temperature then diluted with water (10 mL). The resulting mixture was extracted with $CH_2Cl_2$ (3×10 mL). The combined organic layers were washed with water (30 mL), dried over anhydrous $Na_2SO_4$ and filtered. The filtrate was concentrated under reduced pressure to give the title compound (1.0 g, 93%). LCMS (M-pin)$^+$=465.1.

Step 4: 2-(4-bromo-2-methylphenyl)ethanamine hydrochloride

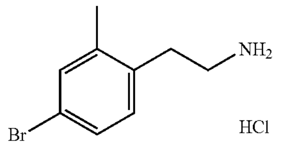

At 0° C., to a solution of 2-(4-bromo-2-methylphenyl) acetonitrile (30.0 g, 0.143 mol) in MeOH (200 mL) was added $NiCl_2·6H_2O$ (3.39 g, 0.0143 mol), $Boc_2O$ (62.3 g, 0.286 mol). Then $NaBH_4$ (64.8 g, 1.71 mol) was added in portions within 15 min. The resulting mixture was stirred for 5 h at room temperature. The reaction mixture was quenched with ice water. The resulting solution was extracted with ethyl acetate (1000 mL×3). The organic phases were combined, washed with brine, dried over $Na_2SO_4$ and concentrated under reduced pressure. To the residue was added HCl in MeOH (7 N, 50 mL, 0.350 mol) at room temperature, and the solution was stirred for 16 h at room temperature. The solvent was concentrated under reduced pressure to give the title compound (35.0 g, crude). LCMS (M+H)$^+$=214.0.

Step 5: N-[2-(4-bromo-2-methylphenyl)ethyl]-2, 2, 2-trifluoroacetamide

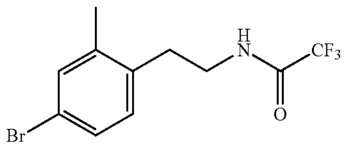 [SMILES: Cc1cc(Br)ccc1CCNC(=O)C(F)(F)F]

At 0° C., to a solution of 2-(4-bromo-2-methylphenyl) ethanamine hydrochloride (350 mg, crude) in DCM (15 mL) was added TEA (345 mg, 3.42 mmol) and TFAA (356 mg, 1.70 mmol) with stirring under nitrogen atmosphere. After 15 h, the reaction was then quenched by the addition of water (20 mL). The resulting solution was extracted with DCM (35 mL×3). The organic phases were combined, washed with brine, dried over $Na_2SO_4$ and concentrated under reduced pressure to give the title compound (271 mg, 61% for 2 steps). LCMS (M+H)$^+$=310.0.

Step 6: 1-(7-bromo-5-methyl-3, 4-dihydro-1H-isoquinolin-2-yl)-2, 2, 2-trifluoroethanone

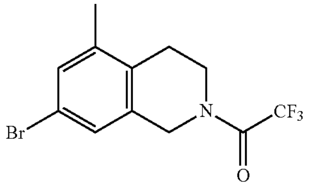 [SMILES: Cc1cc(Br)cc2c1CCN(C(=O)C(F)(F)F)C2]

To a solution of N-[2-(4-bromo-2-methylphenyl)ethyl]-2, 2, 2-trifluoroacetamide (271 mg, 0.874 mmol) in AcOH (3 mL) was added $H_2SO_4$ (2 mL) and paraformaldehyde (176 mg, 1.95 mmol) with stirring at room temperature. After 16 h, the reaction was then diluted by the addition of water (30 mL). The resulting solution was extracted with ethyl acetate (50 mL×3). The organic phases were combined, washed with brine, dried over $Na_2SO_4$ and concentrated under reduced pressure. The residue was purified by C18 column chromatography, eluted with MeCN in water (40% to 70%) to give the title compound (100 mg, 36%). LCMS (M+H)$^+$ =322.2.

Step 7: 7-bromo-5-methyl-1, 2, 3, 4-tetrahydroisoquinoline

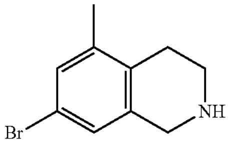

To a solution of 1-(7-bromo-5-methyl-3, 4-dihydro-1H-isoquinolin-2-yl)-2, 2, 2-trifluoroethanone (100 mg, 0.270 mmol) in EtOH (5 mL) and water (1 mL) was added $K_2CO_3$ (147 mg, 1.06 mmol) with stirring at room temperature. The resulting mixture was warmed to 80° C. After 2 h, the reaction was cooled down and diluted with water (10 mL). The resulting mixture was extracted with DCM (30 mL×3). The organic phases were combined, washed with brine, dried over $Na_2SO_4$ and concentrated under reduced pressure to give the title compound (49 mg, 81%). LCMS (M+H)$^+$ =226.1.

Step 8: 7-bromo-2, 5-dimethyl-1, 2, 3, 4-tetrahydroisoquinoline

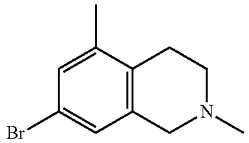

To a stirred solution of 7-bromo-5-methyl-1, 2, 3, 4-tetrahydroisoquinoline (100 mg, 0.398 mmol) and formalin (40%, 45 mg, 0.597 mmol) in MeOH (5 mL) was added $NaBH_3CN$ (39 mg, 0.60 mmol) in portions at room temperature under nitrogen atmosphere. After 3 h, the resulting mixture was concentrated under reduced pressure and the residue was purified by silica gel column chromatography, eluted with DCM/MeOH (10:1) to give the title compound (102 mg, 99%). LCMS (M+H)$^+$=240.0.

Step 9: 4-(2-(2, 5-dimethyl-1, 2, 3, 4-tetrahydroisoquinolin-7-yl)-5-tosyl-5H-pyrrolo[2, 3-b]pyrazin-7-yl)-N, N-dimethylbenzamide

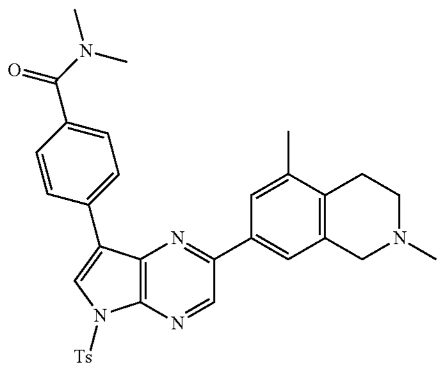 [SMILES: Cc1ccc(S(=O)(=O)n2cc(-c3ccc(C(=O)N(C)C)cc3)c3nc(-c4cc(C)c5c(c4)CN(C)CC5)cnc32)cc1]

To a stirred solution of N, N-dimethyl-4-(2-(4, 4, 5, 5-tetramethyl-1, 3, 2-dioxaborolan-2-yl)-5-tosyl-5H-pyrrolo[2, 3-b]pyrazin-7-yl)benzamide (77 mg, 0.166 mmol) and 7-bromo-2, 5-dimethyl-1, 2, 3, 4-tetrahydroisoquinoline (20 mg, 0.083 mmol) in 1, 4-dioxane (3 mL) and water (0.60 mL) was added $K_2CO_3$ (35 mg, 0.250 mmol) and Pd(dppf)$Cl_2$·$CH_2Cl_2$ (7 mg, 0.008 mmol) under nitrogen atmosphere. The mixture was heated to 100° C. with stirring. After 2 h, the reaction mixture was cooled down and concentrated under reduced pressure. The residue was diluted with DCM (10 mL) and filtered. The filter cake was washed with DCM (6 mL×3). The filtrate was concentrated under reduced pressure. The residue was purified by silica gel column chromatography, eluted with DCM/MeOH (10:1) to give the title compound (27 mg, 16%). LCMS $(M+H)^+$ =580.6.

Step 10: 4-[2-(2, 5-dimethyl-3, 4-dihydro-1H-isoquinolin-7-yl)-5H-pyrrolo[2, 3-b]pyrazin-7-yl]-N, N-dimethylbenzamide

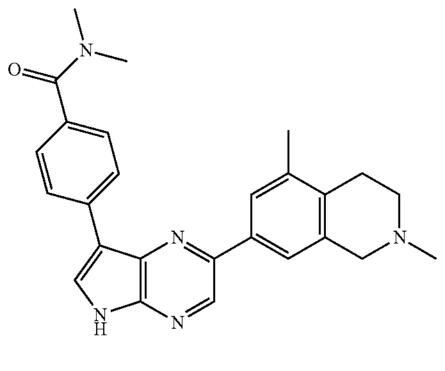 [SMILES: Cc1cc(-c2cnc3[nH]cc(-c4ccc(C(=O)N(C)C)cc4)c3n2)cc2c1CCN(C)C2]

To a stirred mixture of 4-(2-(2, 5-dimethyl-1, 2, 3, 4-tetrahydroisoquinolin-7-yl)-5-tosyl-5H-pyrrolo[2, 3-b]pyrazin-7-yl)-N, N-dimethylbenzamide (34 mg, 0.058 mmol) in MeOH (3 mL) was added $K_2CO_3$ (57 mg, 0.393 mmol) at 70° C. under ambient atmosphere. The mixture was cooled down to room temperature and water (30 mL) was added. The resulting mixture was extracted with $CH_2Cl_2$ (50 mL×3). The combined organic layers were washed with brine (30 mL×2), dried over anhydrous $Na_2SO_4$ and filtered. The filtrate was concentrated under reduced pressure and the residue was purified by prep-HPLC to give Example 1 (9.8 mg, 12%). $^1H$ NMR (400 MHz, DMSO-d6) δ 12.39 (s, 1H), 8.87 (s, 1H), 8.51 (s, 1H), 8.42-8.35 (m, 2H), 7.85 (d, J=1.9 Hz, 1H), 7.73 (d, J=1.9 Hz, 1H), 7.55-7.49 (m, 2H), 3.60 (s, 2H), 3.01 (s, 6H), 2.79-2.71 (m, 2H), 2.71-2.64 (m, 2H), 2.38 (s, 3H), 2.31 (s, 3H). LC-MS $(M+H)^+$=426.4.

Example 2: 4-(2-(2, 5-dimethyl-1, 2, 3, 4-tetrahydroisoquinolin-7-yl)-5H-pyrrolo[2, 3-b]pyrazin-7-yl)-N, N, 2-trimethylbenzamide

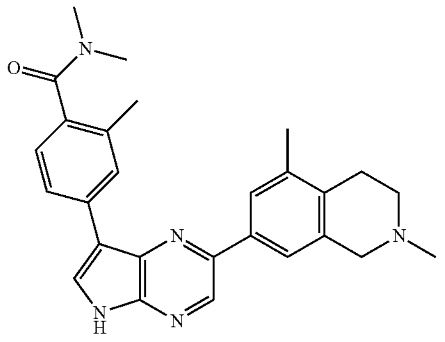 [SMILES: Cc1cc(-c2c[nH]c3ncc(-c4cc(C)c5c(c4)CN(C)CC5)nc23)ccc1C(=O)N(C)C]

Step 1: 4-bromo-N, N, 2-trimethylbenzamide

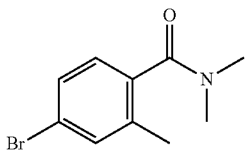

A mixture of 4-bromo-2-methylbenzoic acid (25.0 g, 116 mmol) in $SOCl_2$ (200 mL) was stirred at 60° C. for 3 h. The solvent was removed in vacuo. The residue was re-dissolved in anhydrous DCM (200 mL). Dimethylamine hydrochloride (14.0 g, 174.4 mmol) and TEA (80 mL, 581 mmol) was added at 0° C. The mixture was stirred at room temperature for 2 h. Water (200 mL) was added and the mixture was extracted with DCM (200 mL×3). The combined organic layer was washed with brine (150 mL), dried over $Na_2SO_4$, concentrated under reduced pressure to give the title compound (28.0 g, 99%). LC-MS $(M+H)^+$=242.0, 244.0.

Step 2: N, N, 2-trimethyl-4-(4, 4, 5, 5-tetramethyl-1, 3, 2-dioxaborolan-2-yl)benzamide

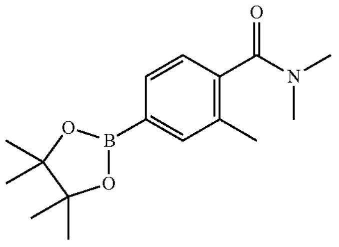

4-bromo-N, N, 2-trimethylbenzamide (28.0 g, 115 mmol), BPD (44.0 g, 174 mmol), Pd (dppf)$Cl_2$ (5.1 g, 6.94 mmol) and AcOK (22.7 g, 231 mmol) was added to dioxane (400 mL) under nitrogen. The reaction mixture was heated to reflux overnight then cooled to room temperature. EtOAc (400 mL) was added and the mixture was washed with brine (300 mL×2). The aqueous layer was extracted with EtOAc (400 mL). The combined organic layer was dried over $Na_2SO_4$ then concentrated under reduced pressure. The residue was purified by silica gel column chromatography, eluted with EtOAc/PE (1:5 to 2:1) to give the title compound (26.0 g, 73%). LC-MS $(M+H)^+$=290.1.

Step 3: 4-(2-bromo-5-tosyl-5H-pyrrolo[2, 3-b]pyrazin-7-yl)-N, N, 2-trimethylbenzamide

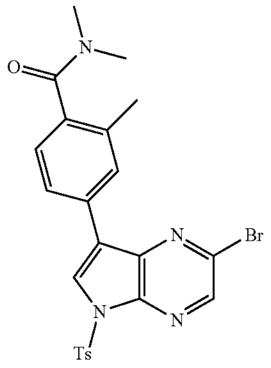 [SMILES: Cc1ccc(S(=O)(=O)n2cc(-c3ccc(C(=O)N(C)C)c(C)c3)c3nc(Br)cnc32)cc1]

To a solution of 2-bromo-7-iodo-5-tosyl-5H-pyrrolo[2, 3-b]pyrazine (16.5 g, 34.6 mmol) and N, N, 2-trimethyl-4-(4, 4, 5, 5-tetramethyl-1, 3, 2-dioxaborolan-2-yl)benzamide (10.0 g, 34.5 mmol) in dioxane (150 mL) and water (50 mL) was added $K_2CO_3$ (9.55 g, 69.2 mmol) and Pd (dppf)$Cl_2$ (1.54 g, 2.07 mmol) under nitrogen atmosphere. After stirring for 5 h at 50° C., the reaction mixture was cooled to room temperature and concentrated under reduced pressure. The residue was purified by silica gel column chromatography, eluted with EtOAc/PE (1:2 to 2:1) to give the title compound (11.0 g, 62%). $^1H$ NMR (400 MHz, DMSO-d6) δ 8.88 (s, 1H), 8.68 (s, 1H), 8.09-8.01 (m, 4H), 7.49-7.44 (m, 2H), 7.29 (d, J=7.8 Hz, 1H), 3.02 (s, 3H), 2.79 (s, 3H), 2.36 (s, 3H), 2.27 (s, 3H). LCMS $(M+H)^+$=513.0.

Step 4: 2, 5-dimethyl-7-(4, 4, 5, 5-tetramethyl-1, 3, 2-dioxaborolan-2-yl)-1, 2, 3, 4-tetrahydroisoquinoline

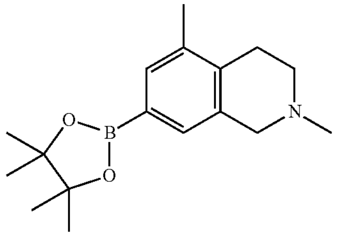

7-bromo-2, 5-dimethyl-1, 2, 3, 4-tetrahydroisoquinoline (2.5 g, 10.4 mmol), BPD (3.96 g, 15.6 mmol), Pd (dppf)$Cl_2$ (457 mg, 0.62 mmol) and AcOK (2.0 g, 20.8 mmol) was added to dioxane (50 mL) under nitrogen. The reaction mixture was heated to reflux overnight then cooled to room temperature. EtOAc (50 mL) was added and the mixture was washed with brine (30 mL×2). The aqueous layer was extracted with EtOAc (50 mL). The combined organic layer was dried over $Na_2SO_4$ then concentrated under reduced pressure. The residue was purified by silica gel column chromatography, eluted with MeOH/DCM (1:15) to give the title compound (2.11 g, 71%). LC-MS $(M+H)^+$=288.1.

Step 5: 4-(2-(2, 5-dimethyl-1, 2, 3, 4-tetrahydroisoquinolin-7-yl)-5H-pyrrolo[2, 3-b]pyrazin-7-yl)-N, N, 2-trimethylbenzamide

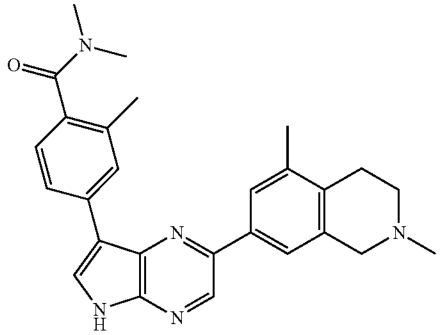 [SMILES: Cc1cc(-c2c[nH]c3ncc(-c4cc(C)c5c(c4)CN(C)CC5)nc23)ccc1C(=O)N(C)C]

4-(2-bromo-5-tosyl-5H-pyrrolo[2, 3-b]pyrazin-7-yl)-N, N, 2-trimethylbenzamide (2.7 g, 5.26 mmol), 2, 5-dimethyl-7-(4, 4, 5, 5-tetramethyl-1, 3, 2-dioxaborolan-2-yl)-1, 2, 3, 4-tetrahydroisoquinoline (2.11 g, 7.37 mmol), Pd (dppf)$Cl_2$ (231 mg, 0.316 mmol) and $K_2CO_3$ (2.18 g, 15.8 mmol) was added to dioxane (50 mL) and water (10 mL) under nitrogen. The reaction mixture was heated to reflux overnight then cooled to room temperature. The reaction mixture was partitioned between EtOAc (40 mL) and water (40 mL) then the aqueous layer was extracted with EtOAc (40 mL×2). The combined organic layer was dried over $Na_2SO_4$ then concentrated under reduced pressure. The residue was purified by silica gel column chromatography, eluted with MeOH/DCM (1:50 to 1:10) to give Example 2 (0.90 g, 39%). $^1H$ NMR (400 MHz, DMSO-d6) δ 12.33 (s, 1H), 8.87 (s, 1H), 8.46 (s, 1H), 8.27-8.18 (m, 2H), 7.87 (s, 1H), 7.74 (s, 1H), 7.25 (d, J=7.9 Hz, 1H), 3.63-3.55 (m, 2H), 3.03 (s, 3H), 2.84 (s, 3H), 2.80-2.63 (m, 4H), 2.39 (s, 3H), 2.34-2.28 (m, 6H). LC-MS $(M+H)^+$=440.4.

Example 3: (S)—N-(2-hydroxypropyl)-4-(2-(8-methoxy-2-methyl-1, 2, 3, 4-tetrahydroisoquinolin-6-yl)-5H-pyrrolo[2, 3-b]pyrazin-7-yl)-N-methylbenzamide

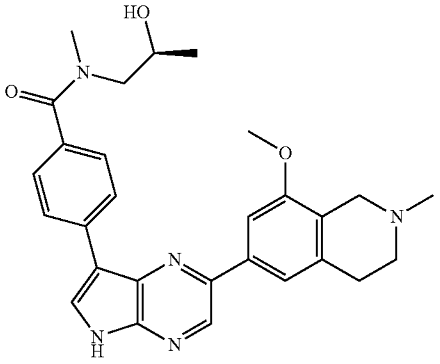 [SMILES: COc1cc(-c2cnc3[nH]cc(-c4ccc(C(=O)N(C)C[C@H](C)O)cc4)c3n2)cc2c1CN(C)CC2]

Step 1: 4-bromo-N-[(2S)-2-hydroxypropyl]benzamide

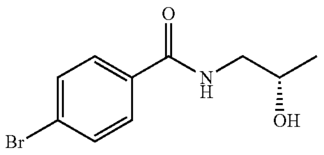

To solution of 4-bromobenzoic acid (11.80 g, 55.8 mmol) in DMF (120 mL) was added DIPEA (10.50 g, 104 mmol), HATU (22.40 g, 58.9 mmol) and (2S)-1-aminopropan-2-ol (4.00 g, 53.3 mmol). The resulting mixture was stirred for 6 h at room temperature. The reaction was quenched by addition of water. The resulting mixture was extracted with EtOAc (600 mL×3). The combined organic layers were washed with brine (100 mL), dried over anhydrous $Na_2SO_4$. After filtration, the filtrate was concentrated under reduced pressure. The residue was purified by silica gel column chromatography, eluted with PE/EtOAc (30:70) to give the title compound (12.0 g, 88%). LC-MS $(M+H)^+$=258.1

Step 2: 4-bromo-N-[(2S)-2-[(tert-butyldimethylsilyl)oxy]propyl]benzamide

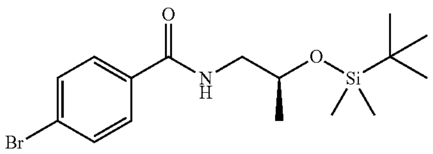 [SMILES: C[C@@H](CNC(=O)c1ccc(Br)cc1)O[Si](C)(C)C(C)(C)C]

To a stirred mixture of 4-bromo-N-[(2S)-2-hydroxypropyl]benzamide (12.0 g, 46.7 mmol) and TBSCl (15.0 g, 59.0 mmol) in DCM (150 mL) was added $Et_3N$ (15.0 g, 1.49 mmol) dropwise at 0° C. The resulting mixture was stirred for 15 h at room temperature. The reaction was quenched by addition of water. The resulting mixture was extracted with DCM (500 mL×3). The combined organic layers were washed with brine (100 mL), dried over anhydrous $Na_2SO_4$. After filtration, the filtrate was concentrated under reduced pressure to provide the title compound (19.0 g, crude). The crude product was used in step 3 directly without further purification. LC-MS $(M+H)^+$=372.2.

Step 3: 4-bromo-N-[(2S)-2-[tert-butyldimethylsilyl)oxy]propyl]-N-methylbenzamide

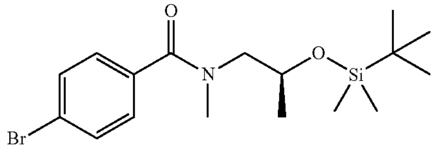 [SMILES: C[C@@H](CN(C)C(=O)c1ccc(Br)cc1)O[Si](C)(C)C(C)(C)C]

To a stirred solution of 4-bromo-N-[(2S)-2-[(tert-butyldimethylsilyl)oxy]propyl]benzamide (19.0 g, crude from step 2) in DMF (120 mL) was added NaH (5.10 g, 60% in mineral oil, 127 mmol) in portions at 0° C. under nitrogen atmosphere. The resulting mixture was stirred for 30 min then $CH_3I$ (9.50 g, 63.6 mmol) was added dropwise at 0° C. The resulting mixture was stirred for 3 h at room temperature under nitrogen atmosphere. The reaction was quenched with ice water at 0° C. The resulting mixture was extracted with EtOAc (700 mL×3). The combined organic layer was washed with brine (150 mL), dried over anhydrous $Na_2SO_4$. After filtration, the filtrate was concentrated under reduced pressure to give the title compound (18.0 g, crude). The crude product was used in step 4 directly without further purification. LC-MS $(M+H)^+$=386.3.

Step 4: 4-bromo-N-[(2S)-2-hydroxypropyl]-N-methylbenzamide

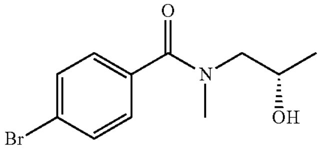

To a solution of 4-bromo-N-[(2S)-2-[(tert-butyldimethylsilyl)oxy]propyl]-N-methylbenzamide (18.0 g, crude from step 3) in THF (200 mL) was added TBAF (1.0 M in THF, 70 mL, 70 mmol). The resulting mixture was stirred for 15 h at room temperature. The reaction mixture was concentrated under vacuum and the residue was purified by silica gel column chromatography, eluted with EtOAc to give the title compound (8.3 g, 65% over 3 steps). LC-MS $(M+H)^+$=272.0.

Step 5: N-[(2S)-2-hydroxypropyl]-N-methyl-4-(4, 4, 5, 5-tetramethyl-1, 3, 2-dioxaborolan-2-yl)benzamide

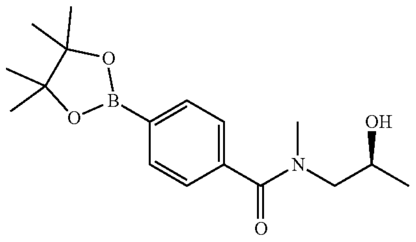 [SMILES: C[C@H](O)CN(C)C(=O)c1ccc(B2OC(C)(C)C(C)(C)O2)cc1]

To a solution of 4-bromo-N-[(2S)-2-hydroxypropyl]-N-methylbenzamide (8.3 g, 30.5 mmol) and BPD (12.0 g, 44.9 mmol) in dioxane (200 mL) was added Pd (dppf)$Cl_2$·DCM (2.60 g, 3.02 mmol) and KOAc (9.30 g, 90.0 mmol). The reaction mixture was stirred for 3 h at 100° C. under nitrogen atmosphere. The mixture was cooled down to room temperature then filtered. The filter cake was rinsed with dioxane (10 mL×3). The filtrate was concentrated under reduced pressure. The residue was purified by silica gel column chromatography, eluted with EtOAc to give the title compound (7.8 g, 80%). LC-MS $(M+H)^+$=320.2.

Step 6: (S)-4-(2-bromo-5-tosyl-5H-pyrrolo[2, 3-b]pyrazin-7-yl)-N-(2-hydroxypropyl)-N-methylbenzamide

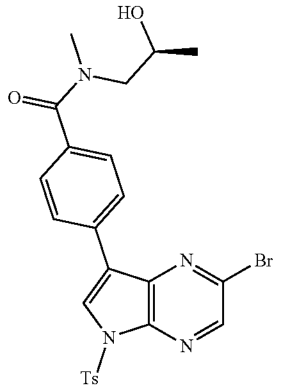 [SMILES: Cc1ccc(S(=O)(=O)n2cc(-c3ccc(C(=O)N(C)C[C@H](C)O)cc3)c3nc(Br)cnc32)cc1]

The title compound (866 mg, 88%) was prepared in a manner similar to that in Example 1 step 2 from N-[(2S)-2-hydroxypropyl]-N-methyl-4-(4, 4, 5, 5-tetramethyl-1, 3, 2-dioxaborolan-2-yl)benzamide and 2-bromo-7-iodo-5-tosyl-5H-pyrrolo[2, 3-b]pyrazine. LC-MS $(M+H)^+$=543.0.

Step 7: tert-butyl (pivaloyloxy)carbamate

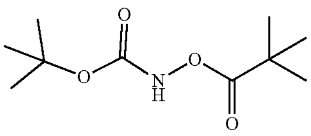

To a stirred solution of pivaloyl anhydride (17.0 g, 86.7 mmol) in $CHCl_3$ (300 mL) was added tert-butyl N-hydroxycarbamate (10.0 g, 71.3 mmol) dropwise at 0° C. The reaction mixture was heated to 70° C. for 16 h. The mixture was cooled down to room temperature and concentrated under vacuum. The residue was partitioned between EtOAc (500 mL) and water (500 mL). The organic layer was dried over $Na_2SO_4$, filtered and concentrated under vacuum to provide the title compound (7.2 g, 46%).

Step 8: O-pivaloylhydroxylamine

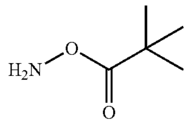

To a solution of tert-butyl (pivaloyloxy)carbamate (26.4 g, 97 mmol) in anhydrous diethyl ether (240 mL) was added TFA (9.6 g, 99 mmol) slowly at room temperature. The resulting mixture was stirred for 1 h then hexane (250 mL) was added. The resulting mixture was rapidly stirred for 10 min. The precipitate was collected by filtration, rinsed with hexane (20 mL×3), and dried in vacuum oven overnight to give the title compound (24.8 g, 91%) as a white solid. LCMS $(M+H)^+$=118.2.

Step 9: 4-bromo-2-methoxy-N-(pivaloyloxy)benzamide

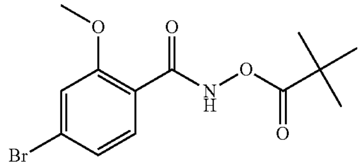 [SMILES: COc1cc(Br)ccc1C(=O)NOC(=O)C(C)(C)C]

To a solution of 4-bromo-2-methoxybenzoic acid (10.0 g, 43.3 mmol) in THF (150 mL) was added T3P (27.6 g, 86.6 mmol) under nitrogen atmosphere at 0° C. The resulting mixture was stirred for 0.5 h at room temperature. Then DIPEA (17.1 g, 132 mmol) and O-pivaloylhydroxylamine (12.0 g, 103 mmol) was added in portions at room temperature. The reaction mixture was stirred for additional 16 h. The reaction was quenched by the addition of water (300 mL), then extracted with ethyl acetate (500 mL×3). The organic phases were combined, washed with brine and dried over $Na_2SO_4$. The solvent was concentrated under reduced pressure and the residue was purified by silica gel column chromatography, eluted with EtOAc/hexane (0:1 to 1:10) to give the title compound (9.83 g, 69%). LCMS $(M+H)^+$=330.2.

Step 10: 6-bromo-8-methoxy-3, 4-dihydroisoquinolin-1 (2H)-one

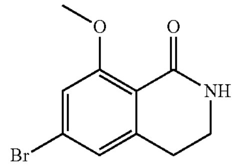

To a stirred solution of 4-bromo-2-methoxy-N-(pivaloyloxy)benzamide (10.0 g, 29.8 mmol) and KOAc (6.67 g, 64.6 mmol) in MeCN (200 mL) was added dichloro (pentamethylcyclopentadienyl)rhodium (III) dimer (968 mg, 1.489 mmol) at room temperature under nitrogen atmosphere. To the mixture was bubbled with ethylene for 1 h at −30° C. The resulting mixture was stirred for additional 16 h at room temperature under 3 bar of ethylene atmosphere. The resulting mixture was concentrated under reduced pressure and the residue was purified by silica gel column chromatography, eluted with DCM/MeOH (10:1) to give the title compound (2.3 g, 28%). LCMS $(M+H)^+$=256.1.

Step 11: 6-bromo-8-methoxy-1, 2, 3, 4-tetrahydroisoquinoline; trifluoroacetic acid

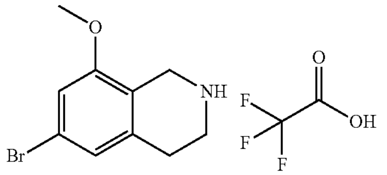

To a stirred solution of 6-bromo-8-methoxy-3, 4-dihydroisoquinolin-1 (2H)-one (400 mg, 1.56 mmol) in THF (20.0 mL) was added $BH_3$-$Me_2S$ (8.00 mL, 84.3 mmol) at 70° C. under nitrogen atmosphere. The resulting mixture was stirred for 12 h at 70° C. then cooled down to room temperature. The reaction was quenched with iced water. To the above mixture was added NaOH (5 M, 30 mL). The resulting mixture was stirred for additional 30 min at 70° C. then cooled down to room temperature. The resulting mixture was extracted with EtOAc (20 mL×3). The combined organic layer was washed with brine (60 mL), dried over anhydrous $Na_2SO_4$. After filtration, the filtrate was concentrated under reduced pressure. The residue was purified by C18 chromatography, eluted with acetonitrile/water (contained 0.05% TFA) (0:1 to 3:7) to give the title compound (240 mg, 43%). LCMS $(M+H)^+$=242.0.

Step 12: 6-bromo-8-methoxy-2-methyl-1, 2, 3, 4-tetrahydroisoquinoline

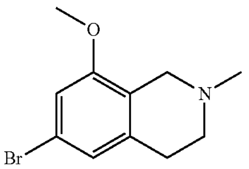

To a stirred solution of 6-bromo-8-methoxy-1, 2, 3, 4-tetrahydroisoquinoline; trifluoroacetic acid (220 mg, 0.620 mmol), HOAc (0.01 mL, 0.173 mmol) and formalin (37%, 104 mg, 1.28 mmol) in MeOH (10 mL) was added $NaBH_3CN$ (85 mg, 1.28 mmol) in portions at 0° C. The resulting mixture was stirred for 2 h at room temperature then concentrated under vacuum. The residue was purified by C18 chromatography, eluted with acetonitrile/water (contained 0.1% $NH_4HCO_3$) (1:1 to 8:2) to give the title compound (90 mg, 57%). LCMS $(M+H)^+$=256.0.

Step 13: 8-methoxy-2-methyl-6-(4, 4, 5, 5-tetramethyl-1, 3, 2-dioxaborolan-2-yl)-1, 2, 3, 4-tetrahydroisoquinoline

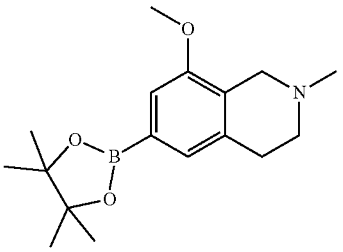

The title compound (210 mg, 81%) was prepared in a manner similar to that in Example 2 step 4 from 6-bromo-8-methoxy-2-methyl-1, 2, 3, 4-tetrahydroisoquinoline and BPD. LC-MS $(M+H)^+$=304.1.

Step 14: (S)—N-(2-hydroxypropyl)-4-(2-(8-methoxy-2-methyl-1, 2, 3, 4-tetrahydroisoquinolin-6-yl)-5-tosyl-5H-pyrrolo[2, 3-b]pyrazin-7-yl)-N-methylbenzamide

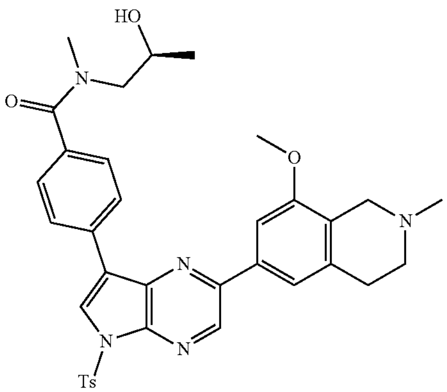 [SMILES: COc1cc(-c2cnc3c(n2)c(-c2ccc(C(=O)N(C)C[C@H](C)O)cc2)cn3S(=O)(=O)c2ccc(C)cc2)cc2c1CN(C)CC2]

The title compound (62 mg, 64%) was prepared in a manner similar to that in Example 2 step 5 from 8-methoxy-2-methyl-6-(4, 4, 5, 5-tetramethyl-1, 3, 2-dioxaborolan-2-yl)-1, 2, 3, 4-tetrahydroisoquinoline and (S)-4-(2-bromo-5-tosyl-5H-pyrrolo[2, 3-b]pyrazin-7-yl)-N-(2-hydroxypropyl)-N-methylbenzamide. LC-MS $(M+H)^+$=640.5.

Step 15: (S)—N-(2-hydroxypropyl)-4-(2-(8-methoxy-2-methyl-1, 2, 3, 4-tetrahydroisoquinolin-6-yl)-5H-pyrrolo[2, 3-b]pyrazin-7-yl)-N-methylbenzamide

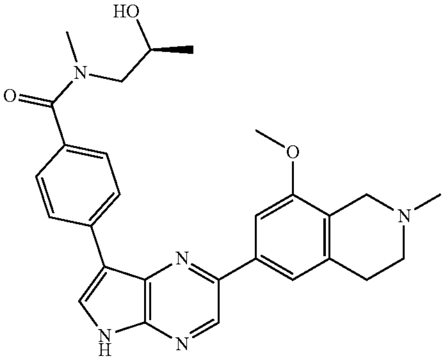 [SMILES: COc1cc(-c2cnc3[nH]cc(-c4ccc(C(=O)N(C)C[C@H](C)O)cc4)c3n2)cc2c1CN(C)CC2]

Example 3 (18 mg, 41%) was prepared in a manner similar to that in in Example 1 step 10 from (S)—N-(2-hydroxypropyl)-4-(2-(8-methoxy-2-methyl-1, 2, 3, 4-tetrahydroisoquinolin-6-yl)-5-tosyl-5H-pyrrolo[2, 3-b]pyrazin-7-yl)-N-methylbenzamide. $^{1}$H NMR (400 MHz, DMSO-d6) δ 12.41 (s, 1H), 8.95 (s, 1H), 8.52 (s, 1H), 8.42-8.37 (m, 2H), 7.60 (d, J=10.7 Hz, 2H), 7.52 (d, J=8.0 Hz, 2H), 4.87-4.82 (m, 1H), 4.07-3.83 (m, 4H), 3.48 (s, 2H), 3.31-3.12 (m, 2H), 3.03 (s, 3H), 2.98-2.90 (m, 2H), 2.67-2.62 (m, 2H), 2.42 (s, 3H), 1.18-0.75 (m, 3H). LC-MS $(M+H)^{+}$=486.5.

Example 4: (R)-4-(2-(2, 5-dimethyl-1, 2, 3, 4-tetrahydroisoquinolin-7-yl)-5H-pyrrolo[2, 3-b]pyrazin-7-yl)-N-(2-hydroxypropyl)-N, 2-dimethylbenzamide

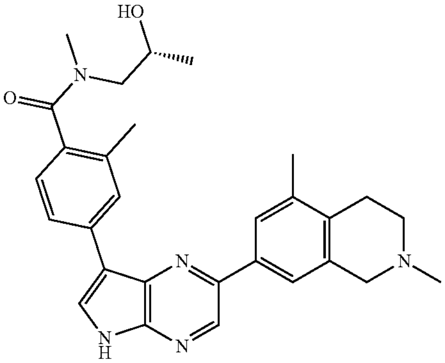 [SMILES: Cc1cc(-c2c[nH]c3ncc(-c4cc(C)c5c(c4)CN(C)CC5)nc23)ccc1C(=O)N(C)C[C@@H](C)O]

Step 1: (R)-4-bromo-N-(2-hydroxypropyl)-2-methylbenzamide

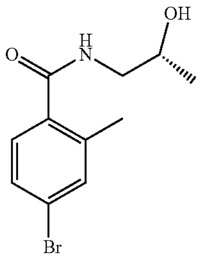

The title compound (24.5 g, 97%) was prepared in a manner similar to that in Example 3 step 1 from 4-bromo-2-methylbenzoic acid and (R)-1-aminopropan-2-ol. LC-MS $(M+H)^{+}$=272.0.

Step 2: (R)-4-bromo-N-(2-(tert-butyldimethylsilyloxy)propyl)-2-methylbenzamide

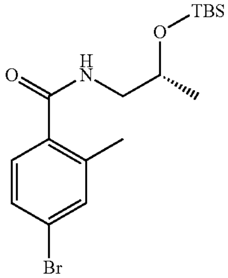

The title compound (48.00 g, crude) was prepared in a manner similar to that in Example 3 step 2 from (R)-4-bromo-N-(2-hydroxypropyl)-2-methylbenzamide. LC-MS $(M+H)^{+}$=386.1.

Step 3: (R)-4-bromo-N-(2-(tert-butyldimethylsilyloxy)propyl)-N, 2-dimethylbenzamide

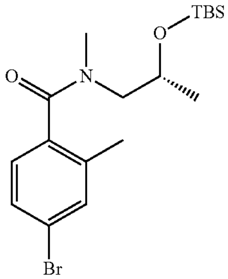

The title compound (32.9 g, 91% over 2 steps) was prepared in a manner similar to that in Example 3 step 3 from (R)-4-bromo-N-(2-(tert-butyldimethylsilyloxy)propyl)-2-methylbenzamide. LC-MS $(M+H)^{+}$=399.9.

Step 4: (R)-4-bromo-N-(2-hydroxypropyl)-N, 2-dimethylbenzamide

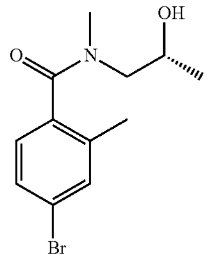 [SMILES: Cc1cc(Br)ccc1C(=O)N(C)C[C@@H](C)O]

The title compound (21.0 g, 80%) was prepared in a manner similar to that in Example 3 step 4 from (R)-4-bromo-N-(2-(tert-butyldimethylsilyloxy)propyl)-N, 2-dimethylbenzamide. LC-MS $(M+H)^+$=286.1.

Step 5: (R)—N-(2-hydroxypropyl)-N, 2-dimethyl-4-(4, 4, 5, 5-tetramethyl-1, 3, 2-dioxaborolan-2-yl) benzamide

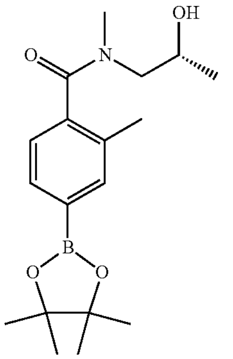 [SMILES: Cc1cc(B2OC(C)(C)C(C)(C)O2)ccc1C(=O)N(C)C[C@@H](C)O]

The title compound (11.5 g, 24%) was prepared in a manner similar to that in Example 3 step 5 from (R)-4-bromo-N-(2-hydroxypropyl)-N, 2-dimethylbenzamide and BPD. LC-MS $(M+H)^+$=334.2.

Step 6: (R)-4-(2-bromo-5-tosyl-5H-pyrrolo[2, 3-b]pyrazin-7-yl)-N-(2-hydroxypropyl)-N, 2-dimethylbenzamide

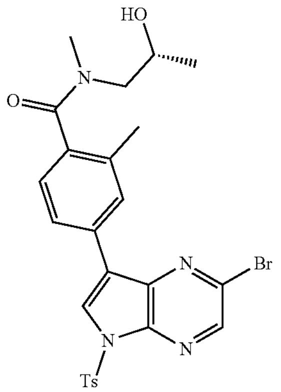 [SMILES: Cc1ccc(S(=O)(=O)n2cc(-c3ccc(C(=O)N(C)C[C@@H](C)O)c(C)c3)c3nc(Br)cnc32)cc1]

The title compound (170 mg, 51%) was prepared in a manner similar to that in Example 1 step 2 from (R)—N-(2-hydroxypropyl)-N, 2-dimethyl-4-(4, 4, 5, 5-tetramethyl-1, 3, 2-dioxaborolan-2-yl)benzamide and 2-bromo-7-iodo-5-tosyl-5H-pyrrolo[2, 3-b]pyrazine. LC-MS $(M+H)^+$ =557.2.

Step 7: (R)—N-(2-hydroxypropyl)-N, 2-dimethyl-4-(2-(4, 4, 5, 5-tetramethyl-1, 3, 2-dioxaborolan-2-yl)-5-tosyl-5H-pyrrolo[2, 3-b]pyrazin-7-yl)benzamide

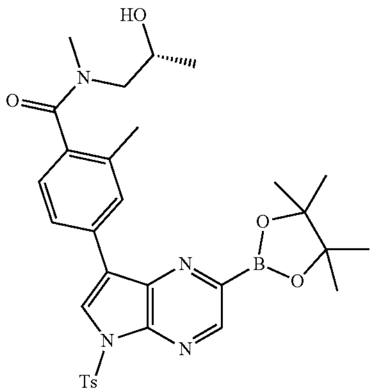 [SMILES: Cc1ccc(S(=O)(=O)n2cc(-c3ccc(C(=O)N(C)C[C@@H](C)O)c(C)c3)c3nc(B4OC(C)(C)C(C)(C)O4)cnc32)cc1]

The title compound (100 mg, 71%) was prepared in a manner similar to that in Example 1 step 3 from (R)-4-(2-bromo-5-tosyl-5H-pyrrolo[2, 3-b]pyrazin-7-yl)-N-(2-hydroxypropyl)-N, 2-dimethylbenzamide and BPD. LC-MS $(M-pin)^+$=523.3.

Step 8: (R)-4-(2-(2, 5-dimethyl-1, 2, 3, 4-tetrahydroisoquinolin-7-yl)-5-tosyl-5H-pyrrolo[2, 3-b] pyrazin-7-yl)-N-(2-hydroxypropyl)-N, 2-dimethylbenzamide

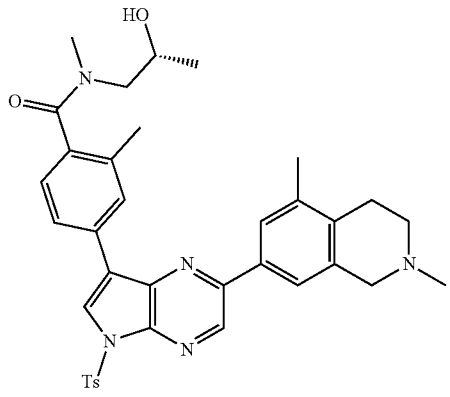 [SMILES: Cc1ccc(S(=O)(=O)n2cc(-c3ccc(C(=O)N(C)C[C@@H](C)O)c(C)c3)c3nc(-c4cc(C)c5c(c4)CN(C)CC5)cnc32)cc1]

The title compound (40 mg, 32%) was prepared in a manner similar to that in Example 1 step 9 from (R)—N-(2-hydroxypropyl)-N, 2-dimethyl-4-(2-(4, 4, 5, 5-tetramethyl-1, 3, 2-dioxaborolan-2-yl)-5-tosyl-5H-pyrrolo[2, 3-b] pyrazin-7-yl)benzamide and 7-bromo-2, 5-dimethyl-1, 2, 3, 4-tetrahydroisoquinoline. LC-MS $(M+H)^+=638.5$.

Step 9: (R)-4-(2-(2, 5-dimethyl-1, 2, 3, 4-tetrahydroisoquinolin-7-yl)-5H-pyrrolo[2, 3-b]pyrazin-7-yl)-N-(2-hydroxypropyl)-N, 2-dimethylbenzamide

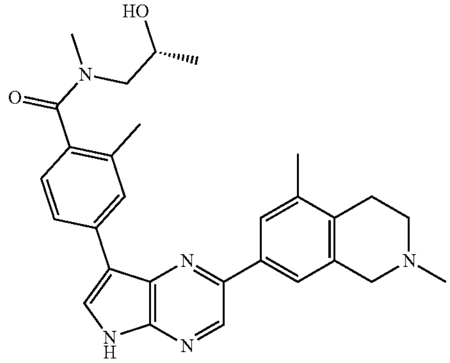 [SMILES: Cc1cc(-c2c[nH]c3ncc(-c4cc(C)c5c(c4)CN(C)CC5)nc23)ccc1C(=O)N(C)C[C@@H](C)O]

Example 4 (5 mg, 12%) was prepared in a manner similar to that in Example 1 step 10 from (R)-4-(2-(2, 5-dimethyl-1, 2, 3, 4-tetrahydroisoquinolin-7-yl)-5-tosyl-5H-pyrrolo[2, 3-b]pyrazin-7-yl)-N-(2-hydroxypropyl)-N, 2-dimethylbenzamide. $^1H$ NMR (400 MHz, DMSO-d6) δ 12.34 (s, 1H), 8.87 (s, 1H), 8.46 (s, 1H), 8.26-8.19 (m, 2H), 8.22-8.15 (m, 1H), 7.88 (s, 1H), 7.74 (s, 1H), 7.26 (d, J=7.8 Hz, 1H), 4.83-4.77 (m, 1H), 4.06-3.75 (m, 1H), 3.63 (s, 2H), 3.57-3.49 (m, 1H), 3.07-3.01 (m, 2H), 2.91-2.86 (m, 2H), 2.79-2.69 (m, 4H), 2.41 (s, 3H), 2.35-2.27 (m, 6H), 1.18-0.86 (m, 3H). LC-MS $(M+H)^+=484.5$.

Example 5: (S)-4-(2-(2, 5-dimethyl-1, 2, 3, 4-tetrahydroisoquinolin-7-yl)-5H-pyrrolo[2, 3-b]pyrazin-7-yl)-N-(2-hydroxypropyl)-N-methylbenzamide

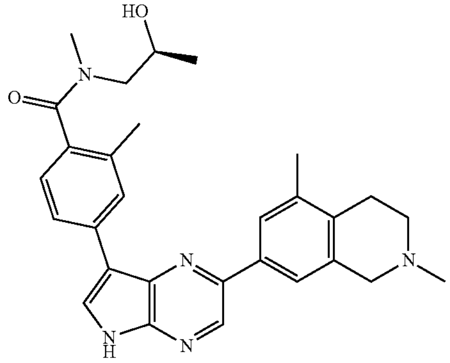 [SMILES: Cc1cc(-c2c[nH]c3ncc(-c4cc(C)c5c(c4)CN(C)CC5)nc23)ccc1C(=O)N(C)C[C@H](C)O]

Step 1: (S)—N-(2-hydroxypropyl)-N-methyl-4-(2-(4, 4, 5, 5-tetramethyl-1, 3, 2-dioxaborolan-2-yl)-5-tosyl-5H-pyrrolo[2, 3-b]pyrazin-7-yl)benzamide

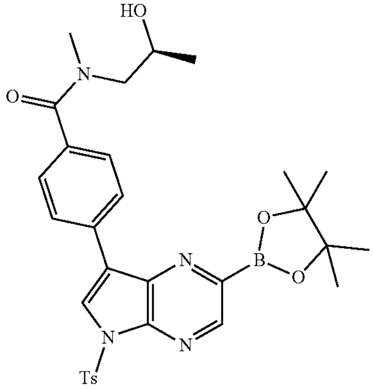 [SMILES: Cc1ccc(S(=O)(=O)n2cc(-c3ccc(C(=O)N(C)C[C@H](C)O)cc3)c3nc(B4OC(C)(C)C(C)(C)O4)cnc32)cc1]

The title compound (71 mg, 83%) was prepared in a manner similar to that in Example 1 step 3 from (S)-4-(2-bromo-5-tosyl-5H-pyrrolo[2, 3-b]pyrazin-7-yl)-N-(2-hydroxypropyl)-N-methylbenzamide and BPD. LC-MS (M-pin)+=509.4.

Step 2: (S)-4-(2-(2, 5-dimethyl-1, 2, 3, 4-tetrahydroisoquinolin-7-yl)-5-tosyl-5H-pyrrolo[2, 3-b]pyrazin-7-yl)-N-(2-hydroxypropyl)-N-methylbenzamide

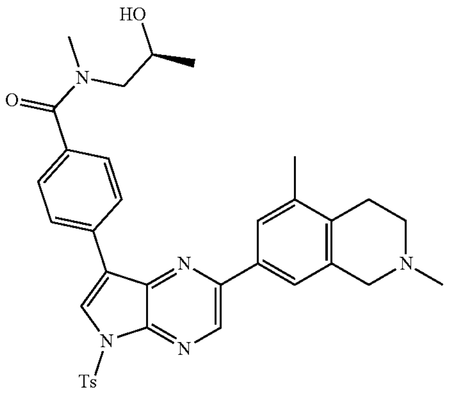 [SMILES: Cc1ccc(S(=O)(=O)n2cc(-c3ccc(C(=O)N(C)C[C@H](C)O)cc3)c3nc(-c4cc(C)c5c(c4)CN(C)CC5)cnc32)cc1]

The title compound (150 mg, 50%) was prepared in a manner similar to that in Example 1 step 9 from (S)—N-(2-hydroxypropyl)-N-methyl-4-(2-(4, 4, 5, 5-tetramethyl-1, 3, 2-dioxaborolan-2-yl)-5-tosyl-5H-pyrrolo[2, 3-b]pyrazin-7-yl)benzamide and 7-bromo-2, 5-dimethyl-1, 2, 3, 4-tetrahydroisoquinoline. LC-MS $(M+H)^+=624.5$.

Step 3: (S)-4-(2-(2, 5-dimethyl-1, 2, 3, 4-tetrahydroisoquinolin-7-yl)-5H-pyrrolo[2, 3-b]pyrazin-7-yl)-N-(2-hydroxypropyl)-N-methylbenzamide

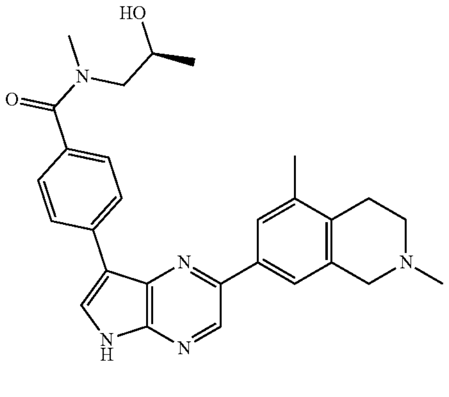 [SMILES: Cc1cc(-c2cnc3[nH]cc(-c4ccc(C(=O)N(C)C[C@H](C)O)cc4)c3n2)cc2c1CCN(C)C2]

Example 5 (4.5 mg, 4.5%) was prepared in a manner similar to that in Example 1 step 10 from (S)-4-(2-(2, 5-dimethyl-1, 2, 3, 4-tetrahydroisoquinolin-7-yl)-5-tosyl-5H-pyrrolo[2, 3-b]pyrazin-7-yl)-N-(2-hydroxypropyl)-N-methylbenzamide. $^1$H NMR (400 MHz, DMSO-d6) δ 12.37 (s, 1H), 8.87 (s, 1H), 8.50 (s, 1H), 8.41-8.34 (m, 2H), 7.85 (s, 1H), 7.73 (d, J=1.9 Hz, 1H), 7.52 (d, J=7.9 Hz, 2H), 4.83 (s, 1H), 4.04-3.87 (m, 1H), 3.60 (s, 2H), 3.52-3.47 (m, 1H), 3.22-3.18 (m, 1H), 3.04 (s, 3H), 2.79-2.72 (m, 2H), 2.71-2.64 (m, 2H), 2.38 (s, 3H), 2.32 (s, 3H), 1.18-0.88 (m, 3H). LC-MS $(M+H)^+=470.5$.

Example 6: (S)—N-(2-hydroxypropyl)-4-(2-(8-methoxy-2-methyl-1, 2, 3, 4-tetrahydroisoquinolin-6-yl)-5H-pyrrolo[2, 3-b]pyrazin-7-yl)-N, 2-dimethylbenzamide

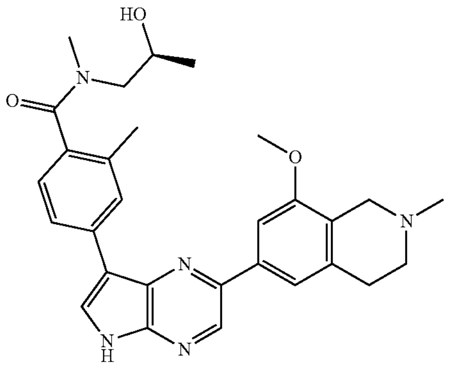 [SMILES: COc1cc(-c2cnc3[nH]cc(-c4ccc(C(=O)N(C)C[C@H](C)O)c(C)c4)c3n2)cc2c1CN(C)CC2]

Step 1: (S)-4-bromo-N-(2-hydroxypropyl)-2-methylbenzamide

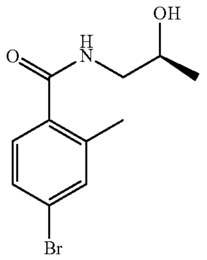

The title compound (14.0 g, 97%) was prepared in a manner similar to that in Example 3 step 1 from (S)-1-aminopropan-2-ol and 3-bromo-5-methylbenzoic acid. LC-MS $(M+H)^+=272.3$.

Step 2: (S)-4-bromo-N-(2-(tert-butyldimethylsilyloxy)propyl)-2-methylbenzamide

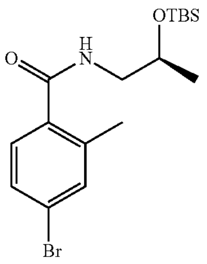 [SMILES: Cc1cc(Br)ccc1C(=O)NC[C@H](C)O[Si](C)(C)C(C)(C)C]

The title compound (21.8 g, 89%) was prepared in a manner similar to that in Example 3 step 2 from (S)-4-bromo-N-(2-hydroxypropyl)-2-methylbenzamide and TBSCL. LC-MS $(M+H)^+=386.2$.

Step 3: (S)-4-bromo-N-(2-(tert-butyldimethylsilyloxy)propyl)-N, 2-dimethylbenzamide

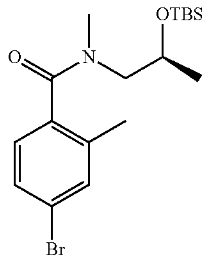 [SMILES: Cc1cc(Br)ccc1C(=O)N(C)C[C@H](C)O[Si](C)(C)C(C)(C)C]

The title compound (13.1 g, 61%) was prepared in a manner similar to that in Example 3 step 3 from (S)-4-bromo-N-(2-(tert-butyldimethylsilyloxy)propyl)-2-methylbenzamide and MeI. LC-MS $(M+H)^+$=400.2.

Step 4: (S)-4-bromo-N-(2-hydroxypropyl)-N, 2-dimethylbenzamide

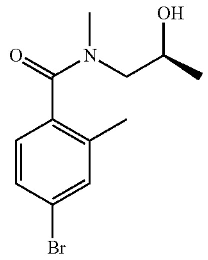 [SMILES: Cc1cc(Br)ccc1C(=O)N(C)C[C@H](C)O]

The title compound (6.36 g, 81%) was prepared in a manner similar to that in Example 3 step 4 from (S)-4-bromo-N-(2-(tert-butyldimethylsilyloxy)propyl)-N, 2-dimethylbenzamide. LC-MS $(M+H)^+$=286.2.

Step 5: (S)—N-(2-hydroxypropyl)-N, 2-dimethyl-4-(4, 4, 5, 5-tetramethyl-1, 3, 2-dioxaborolan-2-yl)benzamide

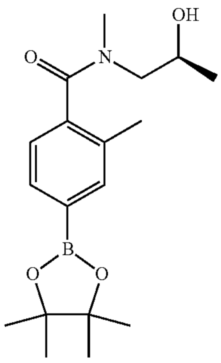 [SMILES: Cc1cc(B2OC(C)(C)C(C)(C)O2)ccc1C(=O)N(C)C[C@H](C)O]

The title compound (7.78 g, 64%) was prepared in a manner similar to that in Example 3 step 5 from (S)-4-bromo-N-(2-hydroxypropyl)-N, 2-dimethylbenzamide and BPD. LC-MS $(M+H)^+$=334.4.

Step 6: (S)-4-(2-bromo-5-tosyl-5H-pyrrolo[2, 3-b]pyrazin-7-yl)-N-(2-hydroxypropyl)-N, 2-dimethylbenzamide

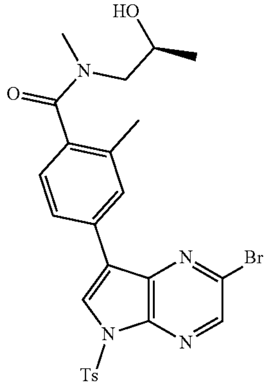 [SMILES: Cc1ccc(S(=O)(=O)n2cc(-c3ccc(C(=O)N(C)C[C@H](C)O)c(C)c3)c3nc(Br)cnc32)cc1]

The title compound (495 mg, 34%) was prepared in a manner similar to that in Example 1 step 2 from (S)—N-(2-hydroxypropyl)-N, 2-dimethyl-4-(4, 4, 5, 5-tetramethyl-1, 3, 2-dioxaborolan-2-yl)benzamide and 2-bromo-7-iodo-5-tosyl-5H-pyrrolo[2, 3-b]pyrazine. LC-MS $(M+H)^+$=557.1.

Step 7: (S)—N-(2-hydroxypropyl)-N, 2-dimethyl-4-(2-(4, 4, 5, 5-tetramethyl-1, 3, 2-dioxaborolan-2-yl)-5-tosyl-5H-pyrrolo[2, 3-b]pyrazin-7-yl)benzamide

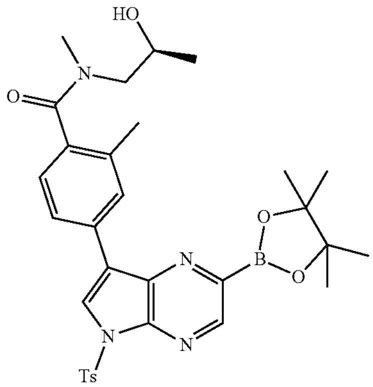 [SMILES: Cc1ccc(S(=O)(=O)n2cc(-c3ccc(C(=O)N(C)C[C@H](C)O)c(C)c3)c3nc(B4OC(C)(C)C(C)(C)O4)cnc32)cc1]

The title compound (330 mg, 60%) was prepared in a manner similar to that in Example 1 step 3 from (S)-4-(2-bromo-5-tosyl-5H-pyrrolo[2, 3-b]pyrazin-7-yl)-N-(2-hydroxypropyl)-N, 2-dimethylbenzamide and BPD. LC-MS $(M-pin)^+$=523.2.

Step 8: (S)—N-(2-hydroxypropyl)-4-(2-(8-methoxy-1, 2, 3, 4-tetrahydroisoquinolin-6-yl)-5-tosyl-5H-pyrrolo[2, 3-b]pyrazin-7-yl)-N, 2-dimethylbenzamide

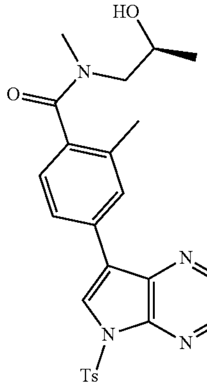

The title compound (203 mg, 59%) was prepared in a manner similar to that in Example 1 step 9 from (S)-7-(4-((2-hydroxypropyl) (methyl)carbamoyl)-3-methylphenyl)-5-tosyl-5H-pyrrolo[2, 3-b]pyrazin-2-ylboronic acid and 6-bromo-8-methoxy-1, 2, 3, 4-tetrahydroisoquinoline; trifluoroacetic acid. LC-MS $(M+H)^+$=640.7.

Step 9: (S)—N-(2-hydroxypropyl)-4-(2-(8-methoxy-2-methyl-1, 2, 3, 4-tetrahydroisoquinolin-6-yl)-5-tosyl-5H-pyrrolo[2, 3-b]pyrazin-7-yl)-N, 2-dimethylbenzamide; trifluoroacetic acid

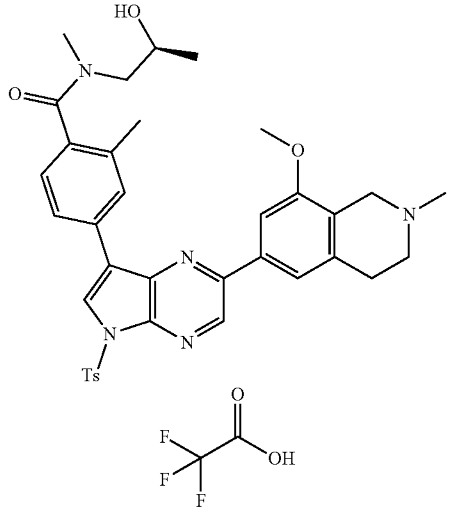

To a stirred solution of (S)—N-(2-hydroxypropyl)-4-(2-(8-methoxy-1, 2, 3, 4-tetrahydroisoquinolin-6-yl)-5-tosyl-5H-pyrrolo[2, 3-b]pyrazin-7-yl)-N, 2-dimethylbenzamide (250 mg, 0.391 mmol) and formalin (30%, 63 mg, 0.63 mmol) in MeOH (10 mL) was added HOAc (1 drop) and $NaBH_3CN$ (39 mg, 0.63 mmol) at room temperature under $N_2$. After 2 h, the reaction mixture was concentrated under reduced pressure. The residue was purified by C18 chromatography, eluted with acetonitrile/water (contained 0.05% TFA) (0:1 to 3:7) to give the title compound (194 mg, 65%). LC-MS $(M+H)^+$=654.5.

Step 10: (S)—N-(2-hydroxypropyl)-4-(2-(8-methoxy-2-methyl-1, 2, 3, 4-tetrahydroisoquinolin-6-yl)-5H-pyrrolo[2, 3-b]pyrazin-7-yl)-N, 2-dimethylbenzamide

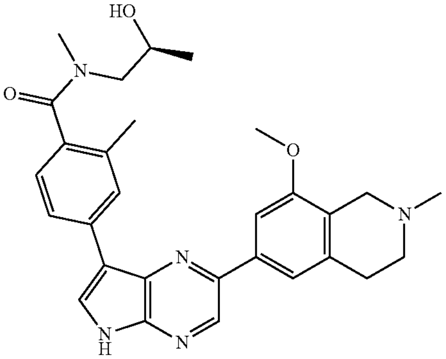 [SMILES: COc1cc(-c2cnc3[nH]cc(-c4ccc(C(=O)N(C)C[C@H](C)O)c(C)c4)c3n2)cc2c1CN(C)CC2]

Example 6 (37 mg, 32%) was prepared in a manner similar to that in Example 1 step 10 from (S)—N-(2-hydroxypropyl)-4-(2-(8-methoxy-2-methyl-1, 2, 3, 4-tetrahydroisoquinolin-6-yl)-5-tosyl-5H-pyrrolo[2, 3-b]pyrazin-7-yl)-N, 2-dimethylbenzamide; trifluoroacetic acid. $^1$H NMR (400 MHz, DMSO-d6) δ 12.36 (s, 1H), 8.96 (s, 1H), 8.48 (s, 1H), 8.37 (d, J=6.2 Hz, 1H), 8.19-8.09 (m, 1H), 7.68 (s, 1H), 7.61 (s, 1H), 7.24 (d, J=8.0 Hz, 1H), 4.83-4.77 (m, 1H), 4.06-3.76 (m, 4H), 3.57-3.46 (m, 3H), 3.16-3.01 (m, 2H), 2.98-2.85 (m, 4H), 2.68-2.60 (m, 2H), 2.41 (s, 3H), 2.34-2.26 (m, 3H), 1.18-0.84 (m, 3H). LC-MS $(M+H)^+$ =500.3.

Example 7A/7B: (S)-2, 6-difluoro-4-(2-(8-methoxy-2-methyl-1, 2, 3, 4-tetrahydroisoquinolin-6-yl)-5H-pyrrolo[2, 3-b]pyrazin-7-yl)-N-methyl-N-((tetrahydrofuran-3-yl) methyl)benzamide & (R)-2, 6-difluoro-4-(2-(8-methoxy-2-methyl-1, 2, 3, 4-tetrahydroisoquinolin-6-yl)-5H-pyrrolo[2, 3-b]pyrazin-7-yl)-N-methyl-N-((tetrahydrofuran-3-yl) methyl)benzamide

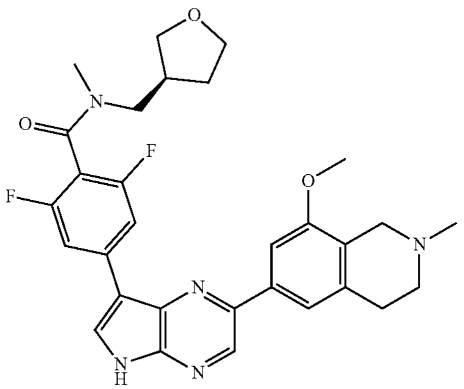

-continued

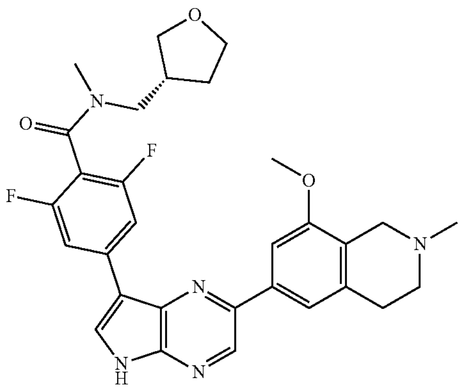

Step 1: 4-bromo-2, 6-difluoro-N-methyl-N-((tetrahydrofuran-3-yl)methyl)benzamide

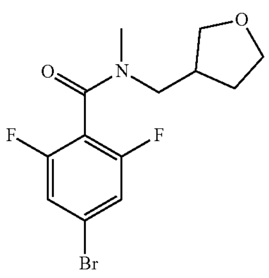 [SMILES: CN(CC1CCOC1)C(=O)c1c(F)cc(Br)cc1F]

The title compound (1.47 g, 56%) was prepared in a manner similar to that in Example 3 step 1 from 4-bromo-2, 6-difluorobenzoic acid and N-methyl (tetrahydrofuran-3-yl) methanamine. LC-MS $(M+H)^+$=334.0.

Step 2: 2, 6-difluoro-N-methyl-N-((tetrahydrofuran-3-yl)methyl)-4-(4, 4, 5, 5-tetramethyl-1, 3, 2-dioxaborolan-2-yl)benzamide

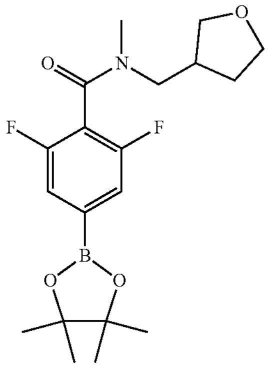 [SMILES: CN(CC1CCOC1)C(=O)c1c(F)cc(B2OC(C)(C)C(C)(C)O2)cc1F]

The title compound (0.90 g, 54%) was prepared in a manner similar to that in Example 3 step 5 from 4-bromo-2, 6-difluoro-N-methyl-N-((tetrahydrofuran-3-yl)methyl)benzamide and BPD. LC-MS $(M+H)^+$=382.2.

Step 3: 4-(2-bromo-5-tosyl-5H-pyrrolo[2, 3-b]pyrazin-7-yl)-2, 6-difluoro-N-methyl-N-(tetrahydrofuran-3-yl)methyl)benzamide

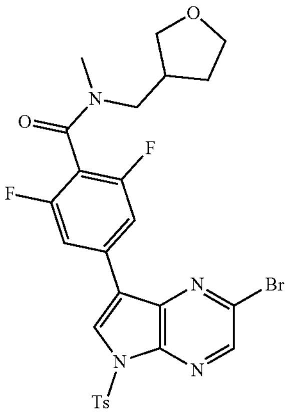 [SMILES: Cc1ccc(S(=O)(=O)n2cc(-c3cc(F)c(C(=O)N(C)CC4CCOC4)c(F)c3)c3nc(Br)cnc32)cc1]

The title compound (47 mg, 76%) was prepared in a manner similar to that in Example 1 step 2 from 2, 6-difluoro-N-methyl-N-((tetrahydrofuran-3-yl)methyl)-4-(4, 4, 5, 5-tetramethyl-1, 3, 2-dioxaborolan-2-yl)benzamide and 2-bromo-7-iodo-5-tosyl-5H-pyrrolo[2, 3-b]pyrazine. LC-MS $(M+H)^+$=605.2.

Step 4: 2, 6-difluoro-N-methyl-N-((tetrahydrofuran-3-yl)methyl)-4-(2-(4, 4, 5, 5-tetramethyl-1, 3, 2-dioxaborolan-2-yl)-5-tosyl-5H-pyrrolo[2, 3-b]pyrazin-7-yl)benzamide

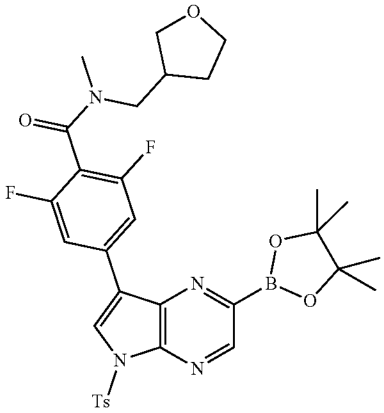 [SMILES: Cc1ccc(S(=O)(=O)n2cc(-c3cc(F)c(C(=O)N(C)CC4CCOC4)c(F)c3)c3nc(B4OC(C)(C)C(C)(C)O4)cnc32)cc1]

The title compound (131 mg, 32%) was prepared in a manner similar to that in Example 1 step 3 from 4-(2-bromo-5-tosyl-5H-pyrrolo[2, 3-b]pyrazin-7-yl)-2, 6-difluoro-N-methyl-N-((tetrahydrofuran-3-yl)methyl)benzamide and BPD. LC-MS $(M-pin)^+$=571.4.

Step 5: 2, 6-difluoro-4-(2-(8-methoxy-1, 2, 3, 4-tetrahydroisoquinolin-6-yl)-5-tosyl-5H-pyrrolo[2, 3-b]pyrazin-7-yl)-N-methyl-N-((tetrahydrofuran-3-yl)methyl)benzamide

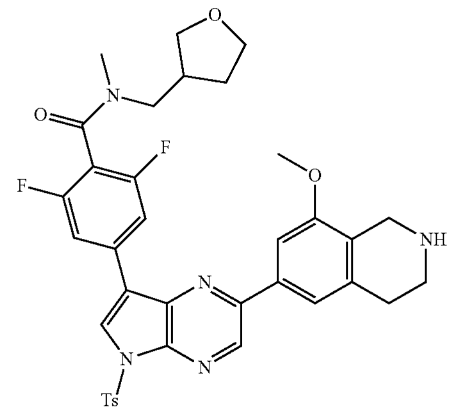 [SMILES: COc1cc(-c2cnc3c(n2)c(-c2cc(F)c(C(=O)N(C)CC4CCOC4)c(F)c2)cn3S(=O)(=O)c2ccc(C)cc2)cc2c1CNCC2]

The title compound (66 mg, 87%) was prepared in a manner similar to that in Example 1 step 9 from 2, 6-difluoro-N-methyl-N-((tetrahydrofuran-3-yl)methyl)-4-(2-(4, 4, 5, 5-tetramethyl-1, 3, 2-dioxaborolan-2-yl)-5-tosyl-5H-pyrrolo[2, 3-b]pyrazin-7-yl)benzamide and 6-bromo-8-methoxy-1, 2, 3, 4-tetrahydroisoquinoline; trifluoroacetic acid. LC-MS $(M+H)^+$=688.5.

Step 6: 2, 6-difluoro-4-(2-(8-methoxy-2-methyl-1, 2, 3, 4-tetrahydroisoquinolin-6-yl)-5-tosyl-5H-pyrrolo[2, 3-b]pyrazin-7-yl)-N-methyl-N-((tetrahydrofuran-3-yl)methyl)benzamide

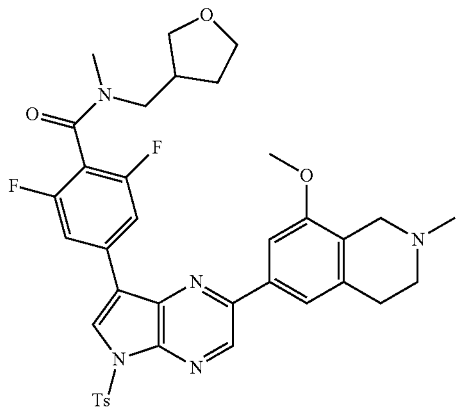 [SMILES: COc1cc(-c2cnc3c(n2)c(-c2cc(F)c(C(=O)N(C)CC4CCOC4)c(F)c2)cn3S(=O)(=O)c2ccc(C)cc2)cc2c1CN(C)CC2]

The title compound (67 mg, 87%) was prepared in a manner similar to that in Example 6 step 9 from 2, 6-difluoro-4-(2-(8-methoxy-1, 2, 3, 4-tetrahydroisoquinolin-6-yl)-5-tosyl-5H-pyrrolo[2, 3-b]pyrazin-7-yl)-N-methyl-N-((tetrahydrofuran-3-yl)methyl)benzamide and formalin. LC-MS $(M+H)^+$=702.4.

Step 7: (S)-2, 6-difluoro-4-(2-(8-methoxy-2-methyl-1, 2, 3, 4-tetrahydroisoquinolin-6-yl)-5H-pyrrolo[2, 3-b]pyrazin-7-yl)-N-methyl-N-((tetrahydrofuran-3-yl)methyl)benzamide & (R)-2, 6-difluoro-4-(2-(8-methoxy-2-methyl-1, 2, 3, 4-tetrahydroisoquinolin-6-yl)-5H-pyrrolo[2, 3-b]pyrazin-7-yl)-N-methyl-N-((tetrahydrofuran-3-yl)methyl)benzamide

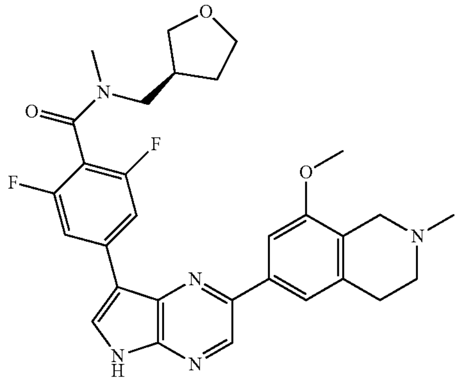

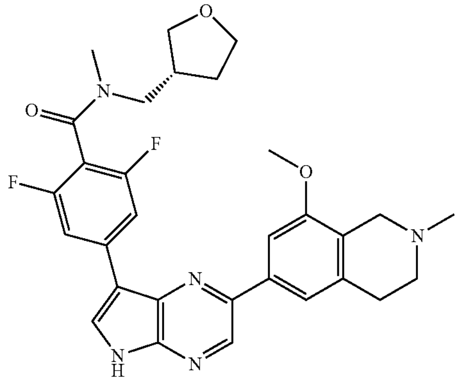

Example 7A/7B was prepared in a manner similar to that in Example 1 step 10 from 2, 6-difluoro-4-(2-(8-methoxy-2-methyl-1, 2, 3, 4-tetrahydroisoquinolin-6-yl)-5-tosyl-5H-pyrrolo[2, 3-b]pyrazin-7-yl)-N-methyl-N-((tetrahydrofuran-3-yl)methyl)benzamide. The 2 isomeric products were identified by separation on Chiral-HPLC under the following conditions: Column, Repaired IC, 0.46×10 cm, 5.0 m. Mobile phase: (Hex:DCM=3:1) (0.2% isopropylamine) in IPA, 70% isocratic in 15 min; detector, UV 254 nm.

Example 7A: (4 mg, 4%). $^1H$ NMR (400 MHz, DMSO-d6) δ 12.64 (s, 1H), 8.99 (s, 1H), 8.71 (s, 1H), 8.28-8.25 (m, 2H), 7.63 (s, 1H), 7.58 (s, 1H), 3.93 (s, 3H), 3.85-3.47 (m, 5H), 3.46 (s, 2H), 3.29-3.22 (m, 1H), 3.06-2.87 (m, 5H), 2.72-2.54 (m, 3H), 2.40 (s, 3H), 2.04-1.85 (m, 1H), 1.69-1.33 (m, 1H). LC-MS $(M+H)^+$=548.4. tR=2.83 m at aforementioned Chiral-HPLC condition.

Example 7B: (4 mg, 4%), $^1H$ NMR (400 MHz, DMSO-d6) δ 12.64 (s, 1H), 8.99 (s, 1H), 8.71 (s, 1H), 8.28-8.25 (m, 2H), 7.63 (s, 1H), 7.58 (s, 1H), 3.93 (s, 3H), 3.85-3.47 (m, 5H), 3.46 (s, 2H), 3.29-3.22 (m, 1H), 3.06-2.87 (m, 5H), 2.72-2.54 (m, 3H), 2.40 (s, 3H), 2.04-1.85 (m, 1H), 1.69-1.33 (m, 1H). LC-MS $(M+H)^+$=548.4. tR=3.86 m at aforementioned Chiral-HPLC condition.

Example 8: (R)-4-(2-(2, 5-dimethyl-1, 2, 3, 4-tetrahydroisoquinolin-7-yl)-5H-pyrrolo[2, 3-b]pyrazin-7-yl)-N-(2-hydroxypropyl)-N-methylbenzamide

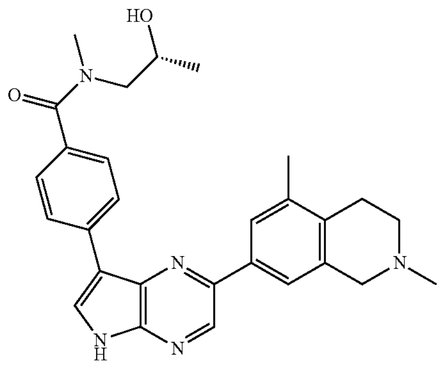 [SMILES: Cc1cc(-c2cnc3[nH]cc(-c4ccc(C(=O)N(C)C[C@@H](C)O)cc4)c3n2)cc2c1CCN(C)C2]

Step 1: 4-bromo-N-[(2R)-2-hydroxypropyl]benzamide

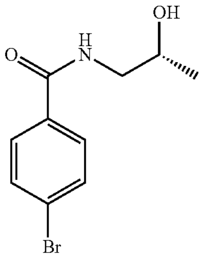

The title compound (4.63 g, 67%) was prepared in a manner similar to that in Example 3 step 1 from 4-bromobenzoic acid and (2R)-1-aminopropan-2-ol. LC-MS $(M+H)^+$=258.1.

Step 2: 4-bromo-N-[(2R)-2-[(tert-butyldimethylsilyl)oxy]propyl]benzamide

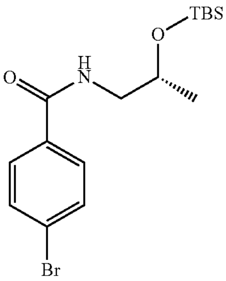

The title compound (12.14 g, 60%) was prepared in a manner similar to that in Example 3 step 2 from 4-bromo-N-[(2R)-2-hydroxypropyl]benzamide and TBSCL. LC-MS $(M+H)^+$=372.3.

Step 3: 4-bromo-N-[(2R)-2-[(tert-butyldimethylsilyl)oxy]propyl]-N-methylbenzamide

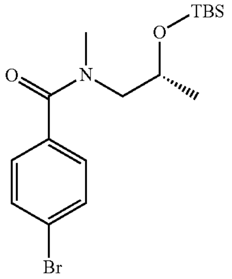

The title compound (9.79 g, 53%) was prepared in a manner similar to that in Example 3 step 3 from 4-bromo-N-[(2R)-2-[(tert-butyldimethylsilyl)oxy]propyl]benzamide and MeI. LC-MS $(M+H)^+$=386.1.

Step 4: 4-bromo-N-[(2R)-2-hydroxypropyl]-N-methylbenzamide

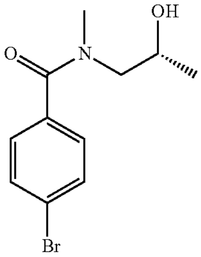

The title compound (5.48 g, 70%) was prepared in a manner similar to that in Example 3 step 4 from 4-bromo-N-[(2R)-2-[(tert-butyldimethylsilyl)oxy]propyl]-N-methylbenzamide. LC-MS $(M+H)^+$=272.0.

Step 5: (R)—N-(2-hydroxypropyl)-N-methyl-4-(4, 4, 5, 5-tetramethyl-1, 3, 2-dioxaborolan-2-yl)benzamide

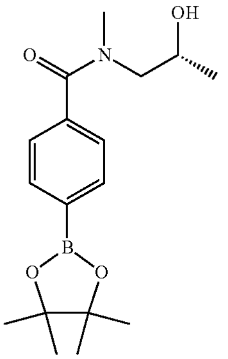 [SMILES: C[C@@H](O)CN(C)C(=O)c1ccc(B2OC(C)(C)C(C)(C)O2)cc1]

The title compound (3.75 g, 47%) was prepared in a manner similar to that in Example 3 step 5 from 4-bromo-N-[(2R)-2-hydroxypropyl]-N-methylbenzamide and BPD. LC-MS $(M+H)^+$=320.1.

Step 6: (R)-4-(2-bromo-5-tosyl-5H-pyrrolo[2, 3-b]pyrazin-7-yl)-N-(2-hydroxypropyl)-N-methylbenzamide

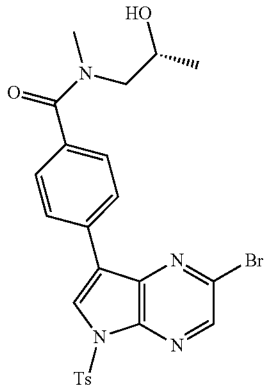 [SMILES: Cc1ccc(S(=O)(=O)n2cc(-c3ccc(C(=O)N(C)C[C@@H](C)O)cc3)c3nc(Br)cnc32)cc1]

The title compound (488 mg, 52%) was prepared in a manner similar to that in Example 1 step 2 from (R)—N-(2-hydroxypropyl)-N-methyl-4-(4, 4, 5, 5-tetramethyl-1, 3, 2-dioxaborolan-2-yl)benzamide and 2-bromo-7-iodo-5-tosyl-5H-pyrrolo[2, 3-b]pyrazine. LC-MS $(M+H)^+$=543.2.

Step 7: (R)—N-(2-hydroxypropyl)-N-methyl-4-(2-(4, 4, 5, 5-tetramethyl-1, 3, 2-dioxaborolan-2-yl)-5-tosyl-5H-pyrrolo[2, 3-b]pyrazin-7-yl)benzamide

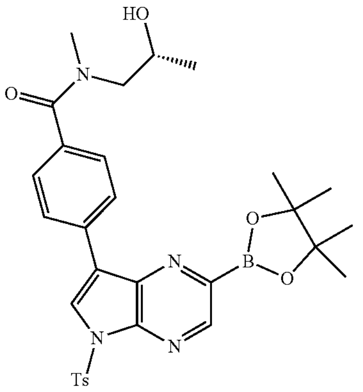 [SMILES: Cc1ccc(S(=O)(=O)n2cc(-c3ccc(C(=O)N(C)C[C@@H](C)O)cc3)c3nc(B4OC(C)(C)C(C)(C)O4)cnc32)cc1]

The title compound (200 mg, crude) was prepared in a manner similar to that in Example 1 step 3 from (R)-4-(2-bromo-5-tosyl-5H-pyrrolo[2, 3-b]pyrazin-7-yl)-N-(2-hydroxypropyl)-N-methylbenzamide and BPD. LC-MS $(M\text{-pin})^+$=509.2.

Step 8: (R)-4-(2-(2, 5-dimethyl-1, 2, 3, 4-tetrahydroisoquinolin-7-yl)-5-tosyl-5H-pyrrolo[2, 3-b]pyrazin-7-yl)-N-(2-hydroxypropyl)-N-methylbenzamide

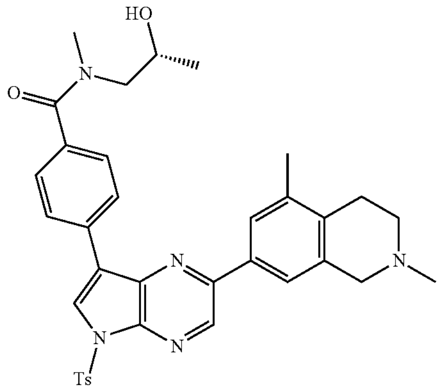 [SMILES: Cc1ccc(S(=O)(=O)n2cc(-c3ccc(C(=O)N(C)C[C@@H](C)O)cc3)c3nc(-c4cc(C)c5c(c4)CN(C)CC5)cnc32)cc1]

The title compound (50 mg, 22% over 2 steps) was prepared in a manner similar to that in Example 1 step 9 from (R)—N-(2-hydroxypropyl)-N-methyl-4-(2-(4, 4, 5, 5-tetramethyl-1, 3, 2-dioxaborolan-2-yl)-5-tosyl-5H-pyrrolo[2, 3-b]pyrazin-7-yl)benzamide and 7-bromo-2, 5-dimethyl-1, 2, 3, 4-tetrahydroisoquinoline. LC-MS $(M+H)^+$=624.5.

Step 9: (R)-4-(2-(2, 5-dimethyl-1, 2, 3, 4-tetrahydroisoquinolin-7-yl)-5H-pyrrolo[2, 3-b]pyrazin-7-yl)-N-(2-hydroxypropyl)-N-methylbenzamide

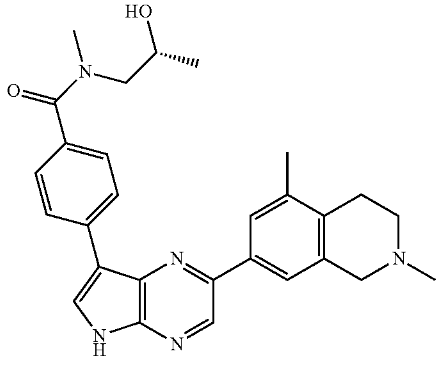 [SMILES: Cc1cc(-c2cnc3[nH]cc(-c4ccc(C(=O)N(C)C[C@@H](C)O)cc4)c3n2)cc2c1CCN(C)C2]

Example 8 (15 mg, 20%) was prepared in a manner similar to that in Example 1 step 10 from (R)-4-(2-(2, 5-dimethyl-1, 2, 3, 4-tetrahydroisoquinolin-7-yl)-5-tosyl-5H-pyrrolo[2, 3-b]pyrazin-7-yl)-N-(2-hydroxypropyl)-N-methylbenzamide. $^1$H NMR (400 MHz, DMSO-d6) δ 12.38 (s, 1H), 8.87 (s, 1H), 8.50 (s, 1H), 8.41-8.35 (m, 2H), 7.85 (s, 1H), 7.73 (s, 1H), 7.55-7.49 (m, 2H), 4.84 (s, 1H), 4.06-3.80 (m, 1H), 3.60 (s, 2H), 3.54-3.47 (m, 1H), 3.27-3.12 (m, 1H), 3.04 (s, 3H), 2.79-2.71 (m, 2H), 2.71-2.63 (m, 2H), 2.38 (s, 3H), 2.31 (s, 3H), 1.20-0.86 (m, 3H). LC-MS $(M+H)^+$=470.5.

Example 9: (R)—N-(2-hydroxypropyl)-N-methyl-4-(2-(5-methyl-2-(2-morpholinoethyl)-1, 2, 3, 4-tetrahydroisoquinolin-7-yl)-5H-pyrrolo[2, 3-b]pyrazin-7-yl)benzamide

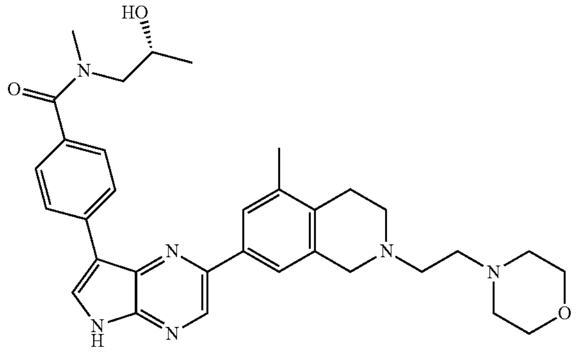 [SMILES: Cc1cc(-c2cnc3[nH]cc(-c4ccc(C(=O)N(C)C[C@@H](C)O)cc4)c3n2)cc2c1CCN(CCN1CCOCC1)C2]

Step 1: (R)—N-(2-hydroxypropyl)-N-methyl-4-(2-(5-methyl-2-(2-morpholinoethyl)-1, 2, 3, 4-tetrahydroisoquinolin-7-yl)-5-tosyl-5H-pyrrolo[2, 3-b] pyrazin-7-yl)benzamide

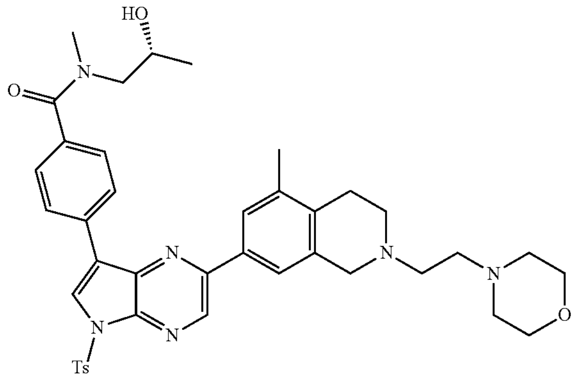 [SMILES: Cc1ccc(S(=O)(=O)n2cc(-c3ccc(C(=O)N(C)C[C@@H](C)O)cc3)c3nc(-c4cc(C)c5c(c4)CN(CCN4CCOCC4)CC5)cnc32)cc1]

The title compound (81 mg, 33%) was prepared in a manner similar to that in Example 2 step 5 from (R)-4-(2-bromo-5-tosyl-5H-pyrrolo[2, 3-b]pyrazin-7-yl)-N-(2-hydroxypropyl)-N-methylbenzamide and 4-(2-(5-methyl-7-(4, 4, 5, 5-tetramethyl-1, 3, 2-dioxaborolan-2-yl)-3, 4-dihydroisoquinolin-2 (1H)-yl)ethyl)morpholine. LC-MS $(M+H)^+$=723.1.

Step 2: (R)—N-(2-hydroxypropyl)-N-methyl-4-(2-(5-methyl-2-(2-morpholinoethyl)-1, 2, 3, 4-tetrahydroisoquinolin-7-yl)-5H-pyrrolo[2, 3-b]pyrazin-7-yl) benzamide

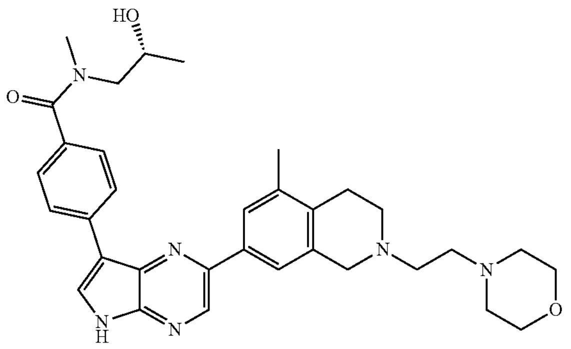 [SMILES: Cc1cc(-c2cnc3[nH]cc(-c4ccc(C(=O)N(C)C[C@@H](C)O)cc4)c3n2)cc2c1CCN(CCN1CCOCC1)C2]

Example 9 (8 mg, 12%) was prepared in a manner similar to that in Example 1 step 10 from (R)—N-(2-hydroxypropyl)-N-methyl-4-(2-(5-methyl-2-(2-morpholinoethyl)-1, 2, 3, 4-tetrahydroisoquinolin-7-yl)-5-tosyl-5H-pyrrolo[2, 3-b] pyrazin-7-yl)benzamide. $^1H$ NMR (400 MHz, DMSO-d6) δ 12.39 (s, 1H), 8.88 (s, 1H), 8.51 (s, 1H), 8.37 (s, 2H), 7.86 (s, 1H), 7.74 (s, 1H), 7.52 (d, J=7.9 Hz, 3H), 4.85 (s, 1H), 4.05-3.83 (m, 1H), 3.76-3.71 (m, 2H), 3.62-3.55 (m, 5H), 3.50-3.46 (m, 2H), 3.03 (s, 3H), 2.84-2.54 (m, 5H), 2.48-2.43 (m, 6H), 2.31 (s, 3H), 1.28-1.19 (m, 1H), 1.18-0.89 (m, 3H). LC-MS $(M+H)^+$=569.1.

Example 10: (R)—N-(2-hydroxypropyl)-4-(2-(8-methoxy-2-methyl-1, 2, 3, 4-tetrahydroisoquinolin-6-yl)-5H-pyrrolo[2, 3-b]pyrazin-7-yl)-N-methylbenzamide

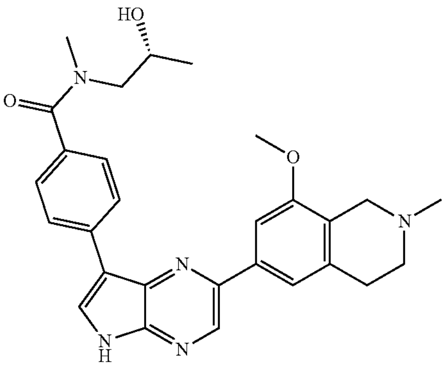 [SMILES: COc1cc(-c2cnc3[nH]cc(-c4ccc(C(=O)N(C)C[C@@H](C)O)cc4)c3n2)cc2c1CN(C)CC2]

Step 1: (R)—N-(2-hydroxypropyl)-4-(2-(8-methoxy-1, 2, 3, 4-tetrahydroisoquinolin-6-yl)-5-tosyl-5H-pyrrolo[2, 3-b]pyrazin-7-yl)-N-methylbenzamide

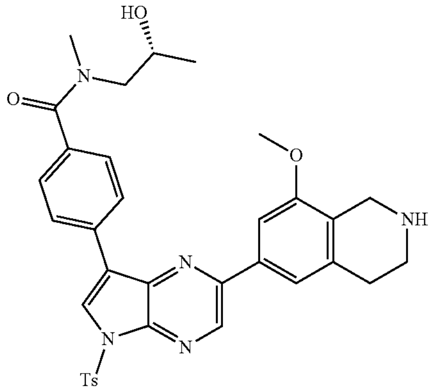 [SMILES: COc1cc(-c2cnc3c(n2)c(-c2ccc(C(=O)N(C)C[C@@H](C)O)cc2)cn3S(=O)(=O)c2ccc(C)cc2)cc2c1CNCC2]

The title compound (33 mg, 22%) was prepared in a manner similar to that in Example 1 step 9 from (R)—N-(2-hydroxypropyl)-N-methyl-4-(2-(4, 4, 5, 5-tetramethyl-1, 3, 2-dioxaborolan-2-yl)-5-tosyl-5H-pyrrolo[2, 3-b]pyrazin-7-yl)benzamide and 6-bromo-8-methoxy-1, 2, 3, 4-tetrahydroisoquinoline; trifluoroacetic acid. LC-MS $(M+H)^+$= 626.3.

Step 2: (R)—N-(2-hydroxypropyl)-4-(2-(8-methoxy-2-methyl-1, 2, 3, 4-tetrahydroisoquinolin-6-yl)-5-tosyl-5H-pyrrolo[2, 3-b]pyrazin-7-yl)-N-methylbenzamide

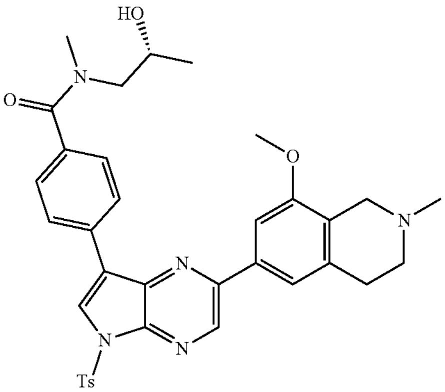 [SMILES: COc1cc(-c2cnc3c(n2)c(-c2ccc(C(=O)N(C)C[C@@H](C)O)cc2)cn3S(=O)(=O)c2ccc(C)cc2)cc2c1CN(C)CC2]

The title compound (25 mg, 83%) was prepared in a manner similar to that in Example 6 step 9 from (R)—N-(2-hydroxypropyl)-4-(2-(8-methoxy-1, 2, 3, 4-tetrahydroisoquinolin-6-yl)-5-tosyl-5H-pyrrolo[2, 3-b]pyrazin-7-yl)-N-methylbenzamide and formalin. LC-MS $(M+H)^+$= 640.4.

Step 3: (R)—N-(2-hydroxypropyl)-4-(2-(8-methoxy-2-methyl-1, 2, 3, 4-tetrahydroisoquinolin-6-yl)-5H-pyrrolo[2, 3-b]pyrazin-7-yl)-N-methylbenzamide

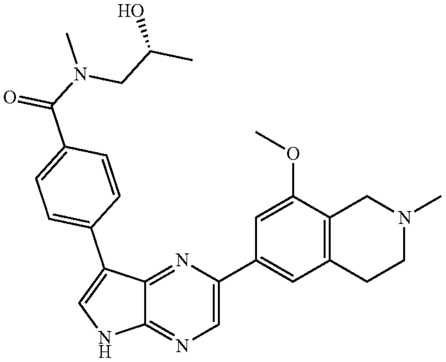 [SMILES: COc1cc(-c2cnc3[nH]cc(-c4ccc(C(=O)N(C)C[C@@H](C)O)cc4)c3n2)cc2c1CN(C)CC2]

Example 10 (6 mg, 36%) was prepared in a manner similar to that in Example 1 step 10 from (R)—N-(2-hydroxypropyl)-4-(2-(8-methoxy-2-methyl-1, 2, 3, 4-tetrahydroisoquinolin-6-yl)-5-tosyl-5H-pyrrolo[2, 3-b]pyrazin-7-yl)-N-methylbenzamide. $^1$H NMR (400 MHz, DMSO-d6) δ 12.41 (s, 1H), 8.94 (s, 1H), 8.52 (s, 1H), 8.42-8.36 (m, 2H), 7.63-7.56 (m, 2H), 7.55-7.48 (m, 2H), 4.85 (s, 1H), 3.94 (s, 3H), 3.45 (s, 2H), 3.35-3.12 (m, 3H), 3.03 (s, 3H), 2.97-2.90 (m, 2H), 2.65-2.58 (m, 2H), 2.40 (s, 3H), 1.19-0.85 (m, 3H). LC-MS $(M+H)^+$=486.4.

Example 11: (S)-4-(2-(2, 5-dimethyl-1, 2, 3, 4-tetrahydroisoquinolin-7-yl)-5H-pyrrolo[2, 3-b]pyrazin-7-yl)-N-(2-hydroxypropyl)-N, 2-dimethylbenzamide

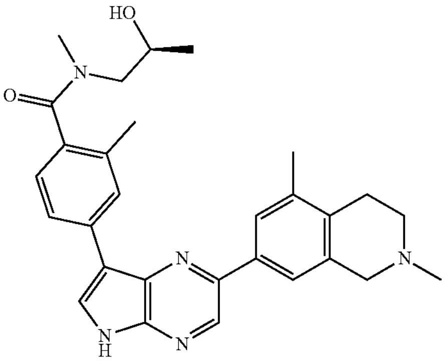 [SMILES: Cc1cc(-c2c[nH]c3ncc(-c4cc(C)c5c(c4)CN(C)CC5)nc23)ccc1C(=O)N(C)C[C@H](C)O]

Step 1: (S)-4-(2-(2, 5-dimethyl-1, 2, 3, 4-tetrahydroisoquinolin-7-yl)-5-tosyl-5H-pyrrolo[2, 3-b] pyrazin-7-yl)-N-(2-hydroxypropyl)-N, 2-dimethylbenzamide

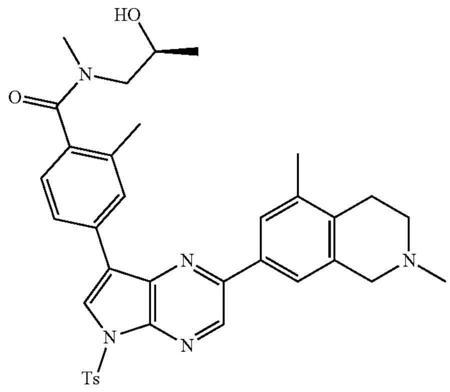 [SMILES: Cc1ccc(S(=O)(=O)n2cc(-c3ccc(C(=O)N(C)C[C@H](C)O)c(C)c3)c3nc(-c4cc(C)c5c(c4)CN(C)CC5)cnc32)cc1]

The title compound (87 mg, 32%) was prepared in a manner similar to that in Example 2 step 5 from (S)-4-(2-bromo-5-tosyl-5H-pyrrolo[2, 3-b]pyrazin-7-yl)-N-(2-hydroxypropyl)-N, 2-dimethylbenzamide and 2, 5-dimethyl-7-(4, 4, 5, 5-tetramethyl-1, 3, 2-dioxaborolan-2-yl)-1, 2, 3, 4-tetrahydroisoquinoline. LC-MS $(M+H)^+$=638.5.

Step 2: (S)-4-(2-(2, 5-dimethyl-1, 2, 3, 4-tetrahydroisoquinolin-7-yl)-5H-pyrrolo[2, 3-b]pyrazin-7-yl)-N-(2-hydroxypropyl)-N, 2-dimethylbenzamide

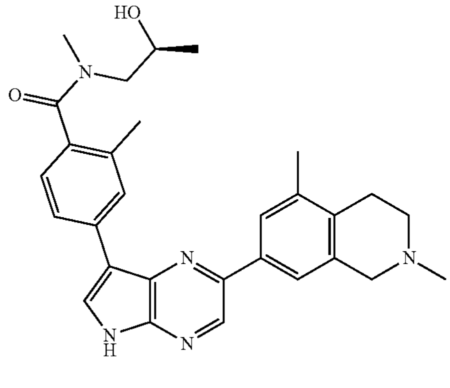 [SMILES: Cc1cc(-c2c[nH]c3ncc(-c4cc(C)c5c(c4)CN(C)CC5)nc23)ccc1C(=O)N(C)C[C@H](C)O]

Example 11 (16 mg, 29%) was prepared in a manner similar to that in Example 1 step 10 from (S)-4-(2-(2, 5-dimethyl-1, 2, 3, 4-tetrahydroisoquinolin-7-yl)-5-tosyl-5H-pyrrolo[2, 3-b]pyrazin-7-yl)-N-(2-hydroxypropyl)-N, 2-dimethylbenzamide. $^1$H NMR (400 MHz, DMSO-d6) δ 12.35 (s, 1H), 8.88 (s, 1H), 8.47 (s, 1H), 8.28-8.17 (m, 2H), 7.90 (s, 1H), 7.77 (s, 1H), 7.29-7.23 (m, 1H), 4.83-4.77 (m, 1H), 4.03-3.97 (m, 1H), 3.78 (s, 2H), 3.58-3.49 (m, 1H), 3.43-3.33 (m, 2H), 3.20-3.02 (m, 2H), 2.91-2.79 (m, 6H), 2.35-2.28 (m, 6H), 1.18-0.83 (m, 3H). LC-MS $(M+H)^+$=484.5.

Example 12: (S)—N-(2-hydroxypropyl)-4-(2-(5-methoxy-2-methyl-1, 2, 3, 4-tetrahydroisoquinolin-7-yl)-5H-pyrrolo[2, 3-b]pyrazin-7-yl)-N, 2-dimethylbenzamide

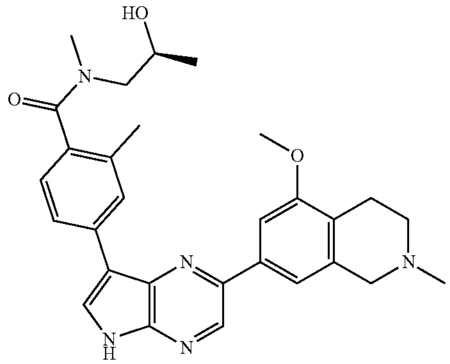 [SMILES: COc1cc(-c2cnc3[nH]cc(-c4ccc(C(=O)N(C)C[C@H](C)O)c(C)c4)c3n2)cc2c1CCN(C)C2]

Step 1 tert-butyl 2-methyl-4-(4, 4, 5, 5-tetramethyl-1, 3, 2-dioxaborolan-2-yl)benzoate

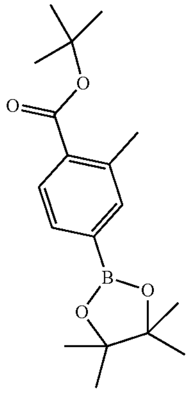 [SMILES: Cc1cc(B2OC(C)(C)C(C)(C)O2)ccc1C(=O)OC(C)(C)C]

The title compound (1.1 g, 81%) was prepared in a manner similar to that in Example 3 step 5 from tert-butyl 4-bromo-2-methylbenzoate and BPD. LC-MS $(M-t-Bu)^+$=263.2.

Step 2: tert-butyl 4-(2-bromo-5-tosyl-5H-pyrrolo[2, 3-b]pyrazin-7-yl)-2-methylbenzoate

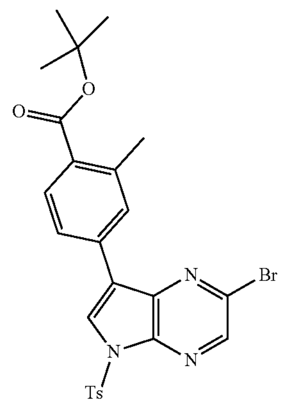 [SMILES: Cc1ccc(S(=O)(=O)n2cc(-c3ccc(C(=O)OC(C)(C)C)c(C)c3)c3nc(Br)cnc32)cc1]

The title compound (1123 mg, 72%) was prepared in a manner similar to that in Example 1 step 2 from 2-bromo-7-iodo-5-tosyl-5H-pyrrolo[2, 3-b]pyrazine and tert-butyl 2-methyl-4-(4, 4, 5, 5-tetramethyl-1, 3, 2-dioxaborolan-2-yl)benzoate. LC-MS $(M+H)^+$=542.1.

Step 3: tert-butyl 2-methyl-4-(2-(4, 4, 5, 5-tetramethyl-1, 3, 2-dioxaborolan-2-yl)-5-tosyl-5H-pyrrolo [2, 3-b]pyrazin-7-yl)benzoate

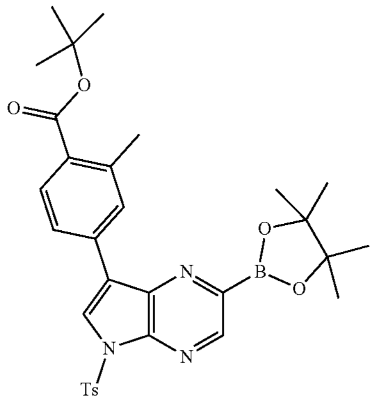 [SMILES: Cc1ccc(S(=O)(=O)n2cc(-c3ccc(C(=O)OC(C)(C)C)c(C)c3)c3nc(B4OC(C)(C)C(C)(C)O4)cnc32)cc1]

The title compound (136 mg, 76%) was prepared in a manner similar to that in Example 1 step 3 from tert-butyl 4-(2-bromo-5-tosyl-5H-pyrrolo[2, 3-b]pyrazin-7-yl)-2-methylbenzoate and BPD. LC-MS $(M\text{-pin})^+$=508.3.

Step 4: N-(3-bromo-5-methoxybenzyl)-2, 2-dimethoxyethanamine

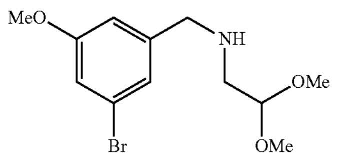 [SMILES: COc1cc(Br)cc(CNCC(OC)OC)c1]

To a solution of 2, 2-dimethoxyethanamine (1.09 g, 10.4 mmol) in toluene (15 mL) was added 3-bromo-5-methoxybenzaldehyde (2.04 g, 9.50 mmol) at room temperature. The resulting mixture was stirred for 15 h at 120° C. under nitrogen atmosphere then cooled down to room temperature. The reaction mixture was concentrated under reduced pressure then re-dissolved in MeOH (15 mL). The mixture was cooled in ice bath and to which was added $NaBH_4$ (4.18 mg, 110 mmol) in portions within 10 min. The resulting mixture was warmed to room temperature. After 5 h, the reaction was quenched with ice water (20 mL). The resulting mixture was extracted with ethyl acetate (50 mL×3). The organic phases were combined, washed with brine and dried over $Na_2SO_4$. The solvent was concentrated under reduced pressure to give the title compound (2.80 g, crude). LCMS $(M+H)^+$=304.4.

Step 5: 7-bromo-5-methoxy-1, 2, 3, 4-tetrahydroisoquinolin-4-ol

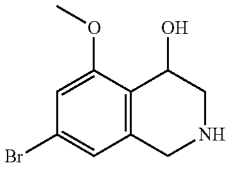

A mixture of N-(3-bromo-5-methoxybenzyl)-2, 2-dimethoxyethanamine (2.80 g, from step 4) in HCl (6 M, 6.0 mL) was stirred for 16 h at 40° C. The mixture cooled down to room temperature and concentrated under reduced pressure. The residue was purified by prep-HPLC to provide the title compound (108 mg, 5% over 2 steps). LCMS $(M+H)^+$=258.1.

Step 6: 7-bromo-5-methoxy-1, 2, 3, 4-tetrahydroisoquinoline

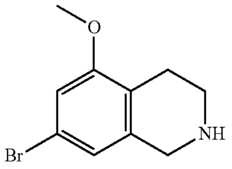

To a stirred mixture of 7-bromo-5-methoxy-1, 2, 3, 4-tetrahydroisoquinolin-4-ol (100 mg, 0.38 mmol) and triethylsilane (1.00 mL, 8.6 mmol) in DCM (5 mL) was added TFA (0.50 mL, 4.4 mmol) dropwise at room temperature under nitrogen atmosphere. The resulting mixture was stirred for 48 h at 40° C. The reaction mixture was cooled down to room temperature and concentrated under reduced pressure. The crude was partitioned between EtOAc (30 mL) and saturated $NaHCO_3$ (30 mL). The combined organic layer was separated, dried over $Na_2SO_4$ and filtered. The filtrate was concentrated under reduced pressure. The residue was purified by C18 chromatography, eluted with MeCN in 0.05% aqueous $NH_4HCO_3$ solution (45% to 70%) to give the title compound (75 mg, 81%). $^1H$ NMR (400 MHz, DMSO-d6) δ 6.92 (d, J=1.9 Hz, 1H), 6.84 (d, J=1.9 Hz, 1H), 3.82-3.74 (m, 5H), 2.90 (t, J=6.0 Hz, 2H), 2.77 (s, 1H), 2.43 (t, J=6.0 Hz, 2H). LCMS $(M+H)^+$=242.1.

Step 7: tert-butyl 4-(2-(5-methoxy-1, 2, 3, 4-tetrahydroisoquinolin-7-yl)-5-tosyl-5H-pyrrolo[2, 3-b]pyrazin-7-yl)-2-methylbenzoate

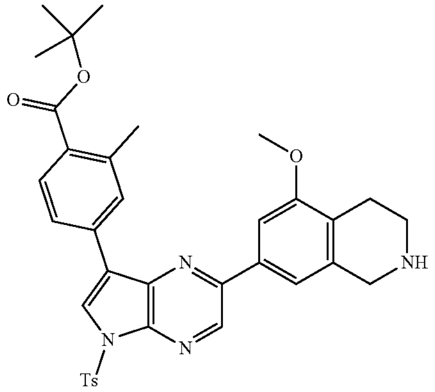 [SMILES: COc1cc(-c2cnc3c(n2)c(-c2ccc(C(=O)OC(C)(C)C)c(C)c2)cn3S(=O)(=O)c2ccc(C)cc2)cc2c1CCNC2]

The title compound (50 mg, 49%) was prepared in a manner similar to that in Example 1 step 9 from tert-butyl 2-methyl-4-(2-(4, 4, 5, 5-tetramethyl-1, 3, 2-dioxaborolan-2-yl)-5-tosyl-5H-pyrrolo[2, 3-b]pyrazin-7-yl)benzoate and 7-bromo-5-methoxy-1, 2, 3, 4-tetrahydroisoquinoline. LC-MS $(M+H)^+$=625.4.

Step 8: tert-butyl 4-(2-(5-methoxy-2-methyl-1, 2, 3, 4-tetrahydroisoquinolin-7-yl)-5-tosyl-5H-pyrrolo[2, 3-b]pyrazin-7-yl)-2-methylbenzoate

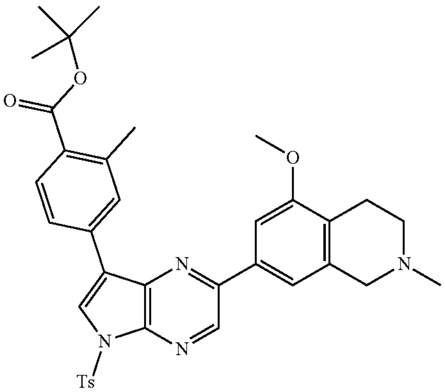 [SMILES: COc1cc(-c2cnc3c(n2)c(-c2ccc(C(=O)OC(C)(C)C)c(C)c2)cn3S(=O)(=O)c2ccc(C)cc2)cc2c1CCN(C)C2]

The title compound (43 mg, 47%) was prepared in a manner similar to that in Example 6 step 9 from tert-butyl 4-(2-(5-methoxy-1, 2, 3, 4-tetrahydroisoquinolin-7-yl)-5-tosyl-5H-pyrrolo[2, 3-b]pyrazin-7-yl)-2-methylbenzoate and formalin. LC-MS $(M+H)^+$=639.4.

Step 9: 4-(2-(5-methoxy-2-methyl-1, 2, 3, 4-tetrahydroisoquinolin-7-yl)-5-tosyl-5H-pyrrolo[2, 3-b]pyrazin-7-yl)-2-methylbenzoic acid; trifluoroacetic acid

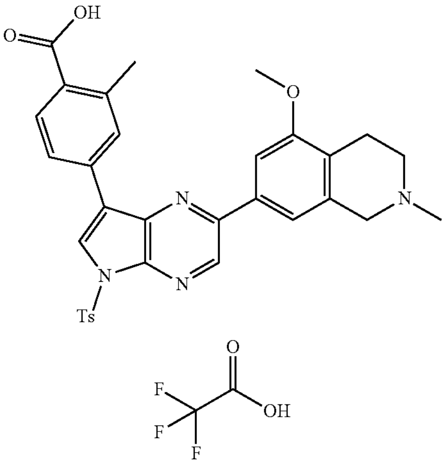 [SMILES: COc1cc(-c2cnc3c(n2)c(-c2ccc(C(=O)O)c(C)c2)cn3S(=O)(=O)c2ccc(C)cc2)cc2c1CCN(C)C2 ; O=C(O)C(F)(F)F]

To a solution of tert-butyl 4-(2-(5-methoxy-2-methyl-1, 2, 3, 4-tetrahydroisoquinolin-7-yl)-5-tosyl-5H-pyrrolo[2, 3-b]pyrazin-7-yl)-2-methylbenzoate (51 mg, 0.076 mmol, 1.00 equiv, 95%) in DCM (2 mL) was added TFA (2 mL) at 0° C. The reaction mixture was stirred for 1.5 h at room temperature then concentrated under reduced pressure to provide the title compound (37 mg, 70%). LC-MS $(M+H)^+$=583.3.

Step 10: (S)—N-(2-hydroxypropyl)-4-(2-(5-methoxy-2-methyl-1, 2, 3, 4-tetrahydroisoquinolin-7-yl)-5-tosyl-5H-pyrrolo[2, 3-b]pyrazin-7-yl)-N, 2-dimethylbenzamide

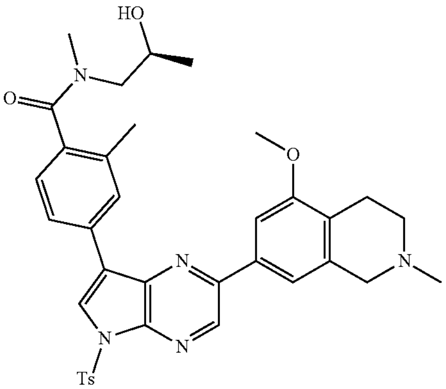 [SMILES: COc1cc(-c2cnc3c(n2)c(-c2ccc(C(=O)N(C)C[C@H](C)O)c(C)c2)cn3S(=O)(=O)c2ccc(C)cc2)cc2c1CCN(C)C2]

The title compound (33 mg, 89%) was prepared in a manner similar to that in Example 3 step 1 from 4-(2-(5-methoxy-2-methyl-1, 2, 3, 4-tetrahydroisoquinolin-7-yl)-5-tosyl-5H-pyrrolo[2, 3-b]pyrazin-7-yl)-2-methylbenzoic acid; trifluoroacetic acid and (S)-1-(methylamino)propan-2-ol. LC-MS $(M+H)^+$=654.4.

Step 11: (S)—N-(2-hydroxypropyl)-4-(2-(5-methoxy-2-methyl-1, 2, 3, 4-tetrahydroisoquinolin-7-yl)-5H-pyrrolo[2, 3-b]pyrazin-7-yl)-N, 2-dimethylbenzamide

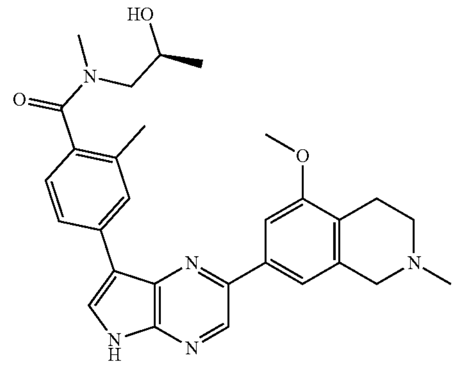 [SMILES: COc1cc(-c2cnc3[nH]cc(-c4ccc(C(=O)N(C)C[C@H](C)O)c(C)c4)c3n2)cc2c1CCN(C)C2]

Example 12 (13 mg, 43%) was prepared in a manner similar to that in Example 1 step 10 from (S)—N-(2-hydroxypropyl)-4-(2-(5-methoxy-2-methyl-1, 2, 3, 4-tetrahydroisoquinolin-7-yl)-5-tosyl-5H-pyrrolo[2, 3-b]pyrazin-7-yl)-N, 2-dimethylbenzamide. $^1$H NMR (400 MHz, DMSO-d6) δ 12.36 (s, 1H), 8.95 (d, J=1.6 Hz, 1H), 8.48 (d, J=2.6 Hz, 1H), 8.36 (d, J=6.6 Hz, 1H), 8.20-8.10 (m, 1H), 7.68 (s, 1H), 7.54 (s, 1H), 7.24 (d, J=8.0 Hz, 1H), 4.84-4.79 (m, 1H), 4.06-3.72 (m, 4H), 3.64-3.48 (m, 3H), 3.17-3.00 (m, 2H), 2.88 (s, 2H), 2.76-2.68 (m, 2H), 2.67-2.60 (m, 2H), 2.38 (s, 3H), 2.34-2.26 (m, 3H), 1.18-0.83 (m, 3H). LC-MS $(M+H)^+$=500.5.

Example 13: (S)—N-(2-hydroxypropyl)-N-methyl-4-(2-(5-methyl-2-(2-morpholinoethyl)-1, 2, 3, 4-tetrahydroisoquinolin-7-yl)-5H-pyrrolo[2, 3-b]pyrazin-7-yl)benzamide

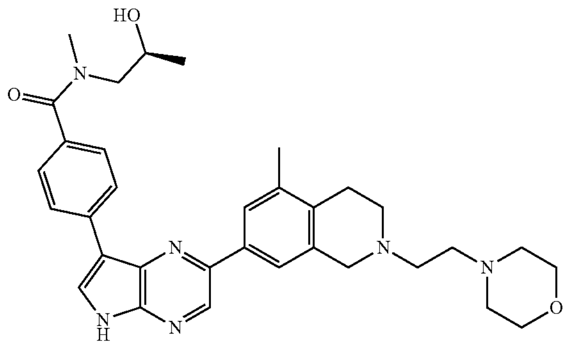 [SMILES: Cc1cc(-c2cnc3[nH]cc(-c4ccc(C(=O)N(C)C[C@H](C)O)cc4)c3n2)cc2c1CCN(CCN1CCOCC1)C2]

Step 1: (S)—N-(2-hydroxypropyl)-N-methyl-4-(2-(5-methyl-2-(2-morpholinoethyl)-1, 2, 3, 4-tetrahydroisoquinolin-7-yl)-5-tosyl-5H-pyrrolo[2, 3-b]pyrazin-7-yl)benzamide

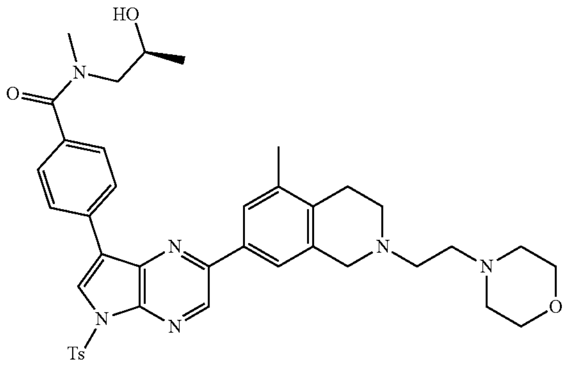 [SMILES: Cc1ccc(S(=O)(=O)n2cc(-c3ccc(C(=O)N(C)C[C@H](C)O)cc3)c3nc(-c4cc(C)c5c(c4)CN(CCN4CCOCC4)CC5)cnc32)cc1]

The title compound (64 mg, 43%) was prepared in a manner similar to that in Example 2 step 5 from 4-(2-(5-methyl-7-(4, 4, 5, 5-tetramethyl-1, 3, 2-dioxaborolan-2-yl)-3, 4-dihydroisoquinolin-2 (1H)-yl)ethyl)morpholine and (S)-4-(2-bromo-5-tosyl-5H-pyrrolo[2, 3-b]pyrazin-7-yl)-N-(2-hydroxypropyl)-N-methylbenzamide. LC-MS $(M+H)^+$= 723.4.

Step 2: (S)—N-(2-hydroxypropyl)-N-methyl-4-(2-(5-methyl-2-(2-morpholinoethyl)-1, 2, 3, 4-tetrahydroisoquinolin-7-yl)-5H-pyrrolo[2, 3-b]pyrazin-7-yl)benzamide

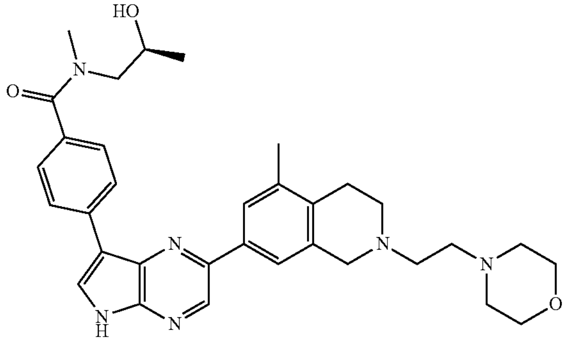 [SMILES: Cc1cc(-c2cnc3[nH]cc(-c4ccc(C(=O)N(C)C[C@H](C)O)cc4)c3n2)cc2c1CCN(CCN1CCOCC1)C2]

Example 13 (17 mg, 36%) was prepared in a manner similar to that in Example 1 step 10 from (S)—N-(2-hydroxypropyl)-N-methyl-4-(2-(5-methyl-2-(2-morpholinoethyl)-1, 2, 3, 4-tetrahydroisoquinolin-7-yl)-5-tosyl-5H-pyrrolo[2, 3-b]pyrazin-7-yl)benzamide. $^1$H NMR (400 MHz, DMSO-d6) δ 12.39 (s, 1H), 8.88 (s, 1H), 8.51 (s, 1H), 8.38 (s, 2H), 7.85 (s, 1H), 7.74 (s, 1H), 7.55-7.49 (m, 2H), 4.85 (s, 1H), 4.07-3.83 (m, 1H), 3.71 (s, 2H), 3.63-3.46 (m, 5H), 3.22-3.18 (m, 1H), 3.07-3.00 (m, 3H), 2.81-2.71 (m, 4H), 2.67-2.60 (m, 2H), 2.58-2.52 (m, 2H), 2.48-2.42 (m, 4H), 2.31 (s, 3H), 1.16-0.90 (m, 3H). LC-MS $(M+H)^+$= 569.3.

Example 14: (S)-(4-(2-(2, 5-dimethyl-1, 2, 3, 4-tetrahydroisoquinolin-7-yl)-5H-pyrrolo[2, 3-b]pyrazin-7-yl)phenyl) (3-(methylamino)pyrrolidin-1-yl) methanone

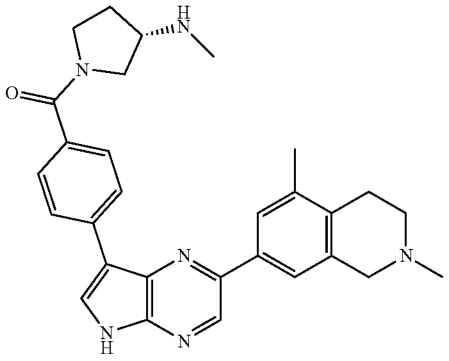 [SMILES: CN[C@H]1CCN(C(=O)c2ccc(-c3c[nH]c4ncc(-c5cc(C)c6c(c5)CN(C)CC6)nc34)cc2)C1]

Step 1: (S)-tert-butyl 1-(4-bromobenzoyl)pyrrolidin-3-yl (methyl)carbamate

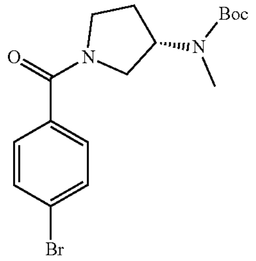 [SMILES: CN(C(=O)OC(C)(C)C)[C@H]1CCN(C(=O)c2ccc(Br)cc2)C1]

The title compound (1.40 g, 73%) was prepared in a manner similar to that in Example 3 step 1 from (S)-tert-butyl methyl (pyrrolidin-3-yl)carbamate and 4-bromobenzoic acid. LC-MS $(M+H)^+=383.2$.

Step 2: (S)-(4-bromophenyl) (3-(methylamino)pyrrolidin-1-yl)methanone; trifluoroacetic acid

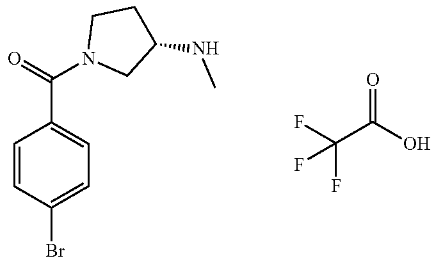 [SMILES: CN[C@H]1CCN(C(=O)c2ccc(Br)cc2)C1 ; O=C(O)C(F)(F)F]

The title compound (1.01 g, 97%) was prepared in a manner similar to that in Example 12 step 9 from (S)-tert-butyl 1-(4-bromobenzoyl)pyrrolidin-3-yl (methyl)carbamate. LC-MS $(M+H)^+=283.1$.

Step 3: (S)-(3-(methylamino)pyrrolidin-1-yl) (4-(4, 4, 5, 5-tetramethyl-1, 3, 2-dioxaborolan-2-yl)phenyl)methanone

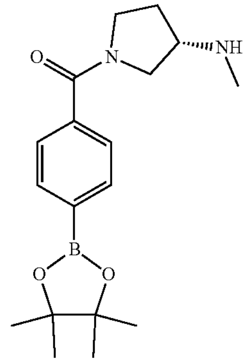

The title compound (881 mg, 75%) was prepared in a manner similar to that in Example 3 step 5 from (S)-(4-bromophenyl) (3-(methylamino)pyrrolidin-1-yl)methanone; trifluoroacetic acid and BPD. LC-MS $(M+H)^+=331.3$.

Step 4: (S)-(4-(2-bromo-5-tosyl-5H-pyrrolo[2, 3-b] pyrazin-7-yl)phenyl) (3-(methylamino)pyrrolidin-1-yl)methanone

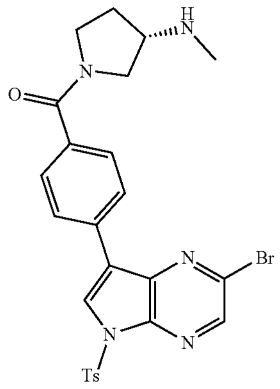 [SMILES: CN[C@H]1CCN(C(=O)c2ccc(-c3cn(S(=O)(=O)c4ccc(C)cc4)c4ncc(Br)nc34)cc2)C1]

The title compound (858 mg, 61%) was prepared in a manner similar to that in Example 1 step 2 from (S)-(3-(methylamino)pyrrolidin-1-yl) (4-(4, 4, 5, 5-tetramethyl-1, 3, 2-dioxaborolan-2-yl)phenyl)methanone and 2-bromo-7-iodo-5-tosyl-5H-pyrrolo[2, 3-b]pyrazine. LC-MS $(M+H)^+=554.3$.

Step 5: (S)-(4-(2-(2, 5-dimethyl-1, 2, 3, 4-tetrahydroisoquinolin-7-yl)-5-tosyl-5H-pyrrolo[2, 3-b]pyrazin-7-yl)phenyl) (3-(methylamino)pyrrolidin-1-yl)methanone

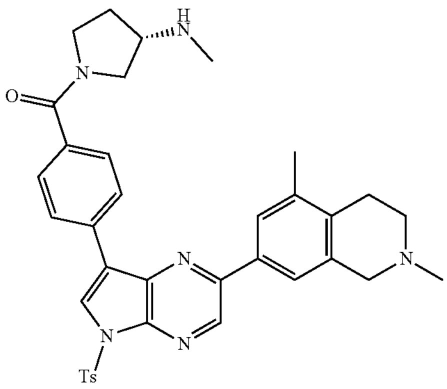 [SMILES: CN[C@H]1CCN(C(=O)c2ccc(-c3cn(S(=O)(=O)c4ccc(C)cc4)c4ncc(-c5cc(C)c6c(c5)CN(C)CC6)nc34)cc2)C1]

The title compound (167 mg, 73%) was prepared in a manner similar to that in Example 2 step 5 from (S)-(4-(2-bromo-5-tosyl-5H-pyrrolo[2, 3-b]pyrazin-7-yl)phenyl) (3-(methylamino)pyrrolidin-1-yl)methanone and 2, 5-dimethyl-7-(4, 4, 5, 5-tetramethyl-1, 3, 2-dioxaborolan-2-yl)-1, 2, 3, 4-tetrahydroisoquinoline. LC-MS $(M+H)^+=635.5$.

Step 6: (S)-(4-(2-(2, 5-dimethyl-1, 2, 3, 4-tetrahydroisoquinolin-7-yl)-5H-pyrrolo[2, 3-b]pyrazin-7-yl)phenyl) (3-(methylamino)pyrrolidin-1-yl)methanone

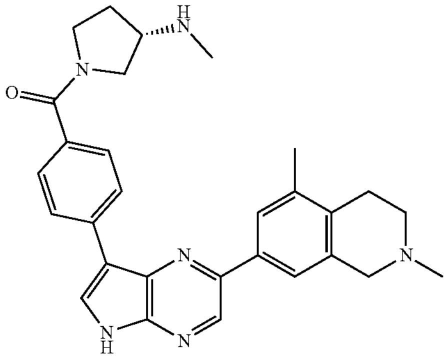 [SMILES: CN[C@H]1CCN(C(=O)c2ccc(-c3c[nH]c4ncc(-c5cc(C)c6c(c5)CN(C)CC6)nc34)cc2)C1]

Example 14 (18 mg, 13%) was prepared in a manner similar to that in Example 1 step 10 from (S)-(4-(2-(2, 5-dimethyl-1, 2, 3, 4-tetrahydroisoquinolin-7-yl)-5-tosyl-5H-pyrrolo[2, 3-b]pyrazin-7-yl)phenyl) (3-(methylamino)pyrrolidin-1-yl)methanone. $^1$H NMR (400 MHz, DMSO-d6) δ 12.41 (s, 1H), 8.88 (s, 1H), 8.52 (s, 1H), 8.42-8.36 (m, 2H), 7.85 (s, 1H), 7.73 (s, 1H), 7.66-7.60 (m, 2H), 3.70-3.55 (m, 4H), 3.53-3.47 (m, 1H), 3.27-3.20 (m, 1H), 3.18-3.12 (m, 1H), 2.78-2.72 (m, 2H), 2.71-2.64 (m, 2H), 2.38 (s, 3H), 2.36-2.20 (m, 6H), 2.05-1.93 (m, 1H), 1.80-1.72 (m, 1H). LC-MS $(M+H)^+=481.4$.

Example 15: (4-(2-(8-methoxy-2-methyl-1, 2, 3, 4-tetrahydroisoquinolin-6-yl)-5H-pyrrolo[2, 3-b]pyrazin-7-yl)phenyl) (2-oxa-6-azaspiro[3.3]heptan-6-yl)methanone

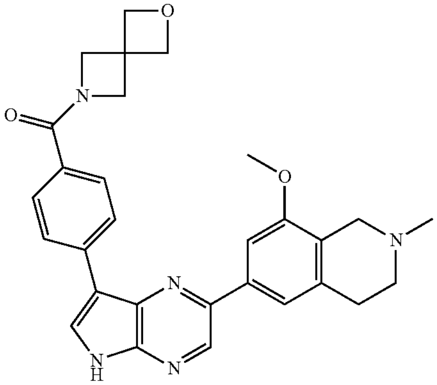 [SMILES: COc1cc(-c2cnc3[nH]cc(-c4ccc(C(=O)N5CC6(COC6)C5)cc4)c3n2)cc2c1CN(C)CC2]

Step 1: (4-(2-oxa-6-azaspiro[3.3]heptane-6-carbonyl)phenyl)boronic acid

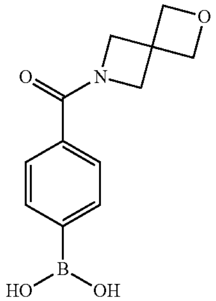 [SMILES: O=C(c1ccc(B(O)O)cc1)N1CC2(COC2)C1]

To a solution of 4-boronobenzoic acid (3.32 g, 19.0 mmol) in DMF (20 mL) at 0° C. was added HATU (10.8 g, 28.5 mmol), DIPEA (7.37 g, 57.0 mmol) and 2-oxa-6-azaspiro[3.3]heptane (1.98 g, 19.0 mmol). The resulting mixture was warmed to room temperature. After 16 h, the mixture was concentrated under vacuum then diluted with water (50 mL). The precipitate was collected by filtration and the solid was washed with water (30 mL×2) to give the title compound (4.7 g, 97%). LC-MS $(M+H)^+=248.1$.

Step 2: (4-(2-bromo-5-tosyl-5H-pyrrolo[2, 3-b] pyrazin-7-yl)phenyl) (2-oxa-6-azaspiro[3.3]heptan-6-yl)methanone

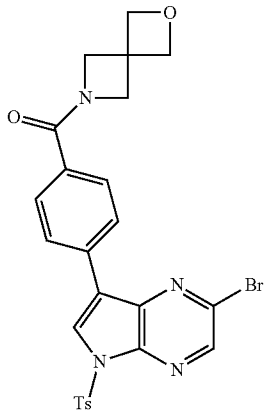 [SMILES: Cc1ccc(S(=O)(=O)n2cc(-c3ccc(C(=O)N4CC5(COC5)C4)cc3)c3nc(Br)cnc32)cc1]

The title compound (350 mg, 76%) was prepared in a manner similar to that in Example 1 step 2 from 2-bromo-7-iodo-5-tosyl-5H-pyrrolo[2, 3-b]pyrazine and (4-(2-oxa-6-azaspiro[3.3]heptane-6-carbonyl)phenyl)boronic acid. LCMS $(M+H)^+=553.1$.

Step 3: (4-(2-(8-methoxy-2-methyl-1, 2, 3, 4-tetrahydroisoquinolin-6-yl)-5-tosyl-5H-pyrrolo[2, 3-b] pyrazin-7-yl)phenyl) (2-oxa-6-azaspiro[3.3]heptan-6-yl)methanone

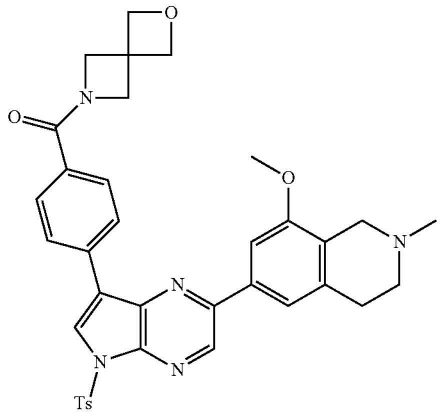 [SMILES: COc1cc(-c2cnc3c(n2)c(-c2ccc(C(=O)N4CC5(COC5)C4)cc2)cn3S(=O)(=O)c2ccc(C)cc2)cc2c1CN(C)CC2]

The title compound (74 mg, 34%) was prepared in a manner similar to that in Example 2 step 5 from 8-methoxy-2-methyl-6-(4, 4, 5, 5-tetramethyl-1, 3, 2-dioxaborolan-2-yl)-1, 2, 3, 4-tetrahydroisoquinoline and (4-(2-bromo-5-tosyl-5H-pyrrolo[2, 3-b]pyrazin-7-yl)phenyl) (2-oxa-6-azaspiro[3.3]heptan-6-yl)methanone. LC-MS $(M+H)^+=650.4$.

Step 4: (4-(2-(8-methoxy-2-methyl-1, 2, 3, 4-tetrahydroisoquinolin-6-yl)-5H-pyrrolo[2, 3-b]pyrazin-7-yl)phenyl) (2-oxa-6-azaspiro[3.3]heptan-6-yl)methanone

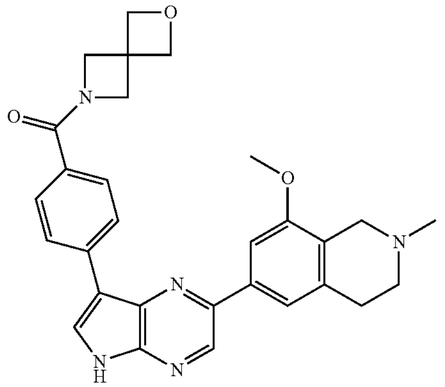 [SMILES: COc1cc(-c2cnc3[nH]cc(-c4ccc(C(=O)N5CC6(COC6)C5)cc4)c3n2)cc2c1CN(C)CC2]

Example 15 (3 mg, 5%) was prepared in a manner similar to that in Example 1 step 10 from (4-(2-(8-methoxy-2-methyl-1, 2, 3, 4-tetrahydroisoquinolin-6-yl)-5-tosyl-5H-pyrrolo[2, 3-b]pyrazin-7-yl)phenyl) (2-oxa-6-azaspiro[3.3]heptan-6-yl)methanone. $^1H$ NMR (400 MHz, DMSO-d6) δ 12.47 (s, 1H), 8.95 (s, 1H), 8.56 (s, 1H), 8.42 (d, J=8.3 Hz, 2H), 7.72 (d, J=8.4 Hz, 2H), 7.62-7.56 (m, 2H), 4.71 (s, 4H), 4.56 (s, 2H), 4.24 (s, 2H), 3.95 (s, 3H), 3.50-3.42 (m, 2H), 2.96-2.90 (m, 2H), 2.67-2.61 (m, 2H), 2.41 (s, 3H). LC-MS $(M+H)^+=496.4$.

Example 16: (4-(2-(2, 5-dimethyl-1, 2, 3, 4-tetrahydroisoquinolin-7-yl)-5H-pyrrolo[2, 3-b]pyrazin-7-yl)-2-methylphenyl) (2-oxa-6-azaspiro[3.3]heptan-6-yl)methanone

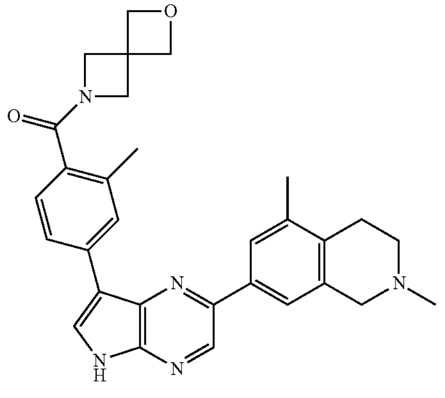 [SMILES: Cc1cc(-c2c[nH]c3ncc(-c4cc(C)c5c(c4)CN(C)CC5)nc23)ccc1C(=O)N1CC2(COC2)C1]

Step 1: 6-(4-bromo-2-methylbenzoyl)-2-oxa-6-azaspiro[3.3]heptane

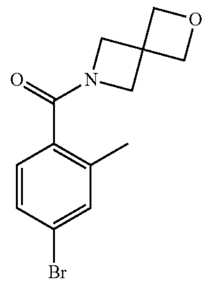 [SMILES: Cc1cc(Br)ccc1C(=O)N1CC2(COC2)C1]

The title compound (250 mg, 78%) was prepared in a manner similar to that in Example 3 step 1 from 4-bromo-2-methylbenzoic acid and 2-oxa-6-azaspiro[3.3]heptane. LCMS $(M+H)^+$=296.0.

Step 2: (2-methyl-4-(4, 4, 5, 5-tetramethyl-1, 3, 2-dioxaborolan-2-yl)phenyl) (2-oxa-6-azaspiro[3.3]heptan-6-yl)methanone

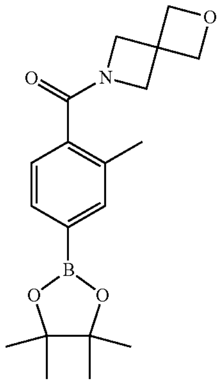 [SMILES: Cc1cc(B2OC(C)(C)C(C)(C)O2)ccc1C(=O)N1CC2(COC2)C1]

The title compound (200 mg, 67%) was prepared in a manner similar to that in Example 3 step 5 from 6-(4-bromo-2-methylbenzoyl)-2-oxa-6-azaspiro[3.3]heptane and BPD. LCMS $(M+H)^+$=344.2.

Step 3: (4-(2-bromo-5-tosyl-5H-pyrrolo[2, 3-b]pyrazin-7-yl)-2-methylphenyl) (2-oxa-6-azaspiro[3.3]heptan-6-yl)methanone

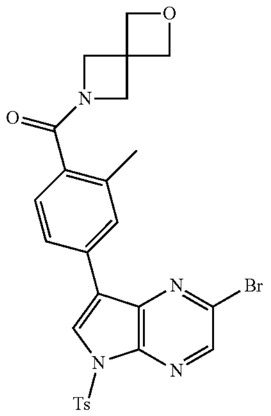 [SMILES: Cc1ccc(S(=O)(=O)n2cc(-c3ccc(C(=O)N4CC5(COC5)C4)c(C)c3)c3nc(Br)cnc32)cc1]

The title compound (185 mg, 67%) was prepared in a manner similar to that in Example 1 step 2 from (2-methyl-4-(4, 4, 5, 5-tetramethyl-1, 3, 2-dioxaborolan-2-yl)phenyl) (2-oxa-6-azaspiro[3.3]heptan-6-yl)methanone and 2-bromo-7-iodo-5-tosyl-5H-pyrrolo[2, 3-b]pyrazine. LC-MS $(M+H)^+$= 567.1.

Step 4: (4-(2-(2, 5-dimethyl-1, 2, 3, 4-tetrahydroisoquinolin-7-yl)-5-tosyl-5H-pyrrolo[2, 3-b]pyrazin-7-yl)-2-methylphenyl) (2-oxa-6-azaspiro[3.3]heptan-6-yl)methanone

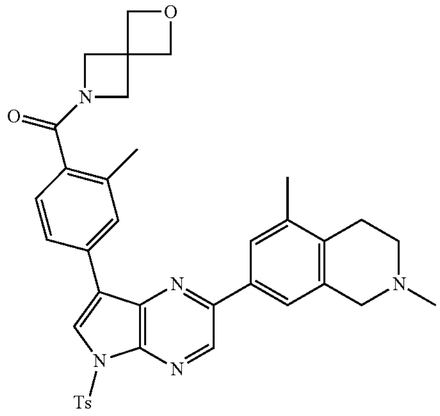 [SMILES: Cc1ccc(S(=O)(=O)n2cc(-c3ccc(C(=O)N4CC5(COC5)C4)c(C)c3)c3nc(-c4cc(C)c5c(c4)CN(C)CC5)cnc32)cc1]

The title compound (91 mg, 30%) was prepared in a manner similar to that in Example 2 step 5 from (4-(2-bromo-5-tosyl-5H-pyrrolo[2, 3-b]pyrazin-7-yl)-2-methylphenyl) (2-oxa-6-azaspiro[3.3]heptan-6-yl)methanone and 2, 5-dimethyl-7-(4, 4, 5, 5-tetramethyl-1, 3, 2-dioxaborolan-2-yl)-1, 2, 3, 4-tetrahydroisoquinoline. LC-MS $(M+H)^+$=648.3.

Step 5: (4-(2-(2, 5-dimethyl-1, 2, 3, 4-tetrahydroisoquinolin-7-yl)-5H-pyrrolo[2, 3-b]pyrazin-7-yl)-2-methylphenyl) (2-oxa-6-azaspiro[3.3]heptan-6-yl)methanone

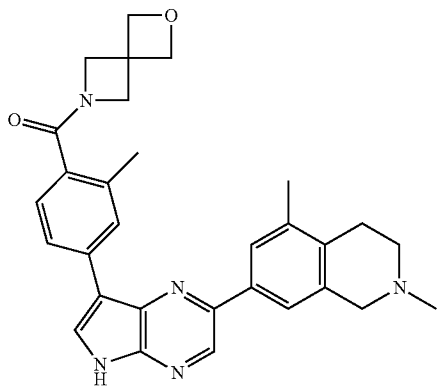 [SMILES: Cc1cc(-c2c[nH]c3ncc(-c4cc(C)c5c(c4)CN(C)CC5)nc23)ccc1C(=O)N1CC2(COC2)C1]

Example 16 (23 mg, 33%) was prepared in a manner similar to that in Example 1 step 10 from (4-(2-(2, 5-dimethyl-1, 2, 3, 4-tetrahydroisoquinolin-7-yl)-5-tosyl-5H-pyrrolo[2, 3-b]pyrazin-7-yl)-2-methylphenyl) (2-oxa-6-azaspiro[3.3]heptan-6-yl)methanone. $^{1}H$ NMR (400 MHz, DMSO-d6) δ 12.36 (s, 1H), 8.88 (s, 1H), 8.49 (s, 1H), 8.27-8.17 (m, 2H), 7.87 (s, 1H), 7.73 (s, 1H), 7.41-7.34 (m, 1H), 4.74-4.64 (m, 4H), 4.22 (s, 2H), 4.16 (s, 2H), 3.60 (s, 2H), 2.78-2.72 (m, 2H), 2.71-2.64 (m, 2H), 2.42-2.36 (m, 6H), 2.32 (s, 3H). LC-MS $(M+H)^+$=494.5.

Example 17: (4-(2-(2, 5-dimethyl-1, 2, 3, 4-tetrahydroisoquinolin-7-yl)-5H-pyrrolo[2, 3-b]pyrazin-7-yl)-2-methylphenyl) (3-hydroxyazetidine-1-yl) methanone

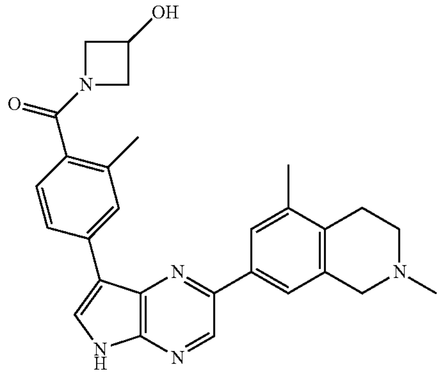 [SMILES: Cc1cc(-c2c[nH]c3ncc(-c4cc(C)c5c(c4)CN(C)CC5)nc23)ccc1C(=O)N1CC(O)C1]

Step 1: (4-bromo-2-methylphenyl) (3-hydroxyazetidine-1-yl)methanone

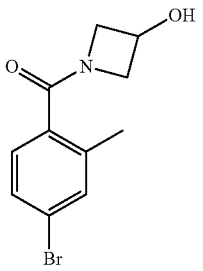

The title compound (750 mg, 61%) was prepared in a manner similar to that in Example 3 step 1 from 4-bromo-2-methylbenzoic acid and azetidin-3-ol hydrochloride. LCMS $(M+H)^+$=270.0.

Step 2: (3-hydroxyazetidine-1-yl) (2-methyl-4-(4, 4, 5, 5-tetramethyl-1, 3, 2-dioxaborolan-2-yl)phenyl) methanone

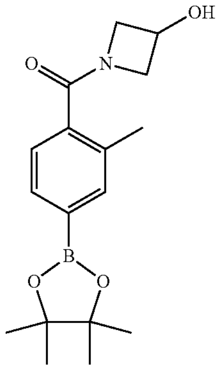 [SMILES: Cc1cc(B2OC(C)(C)C(C)(C)O2)ccc1C(=O)N1CC(O)C1]

The title compound (150 mg, 37%) was prepared in a manner similar to that in Example 3 step 5 from (4-bromo-2-methylphenyl) (3-hydroxyazetidine-1-yl)methanone and BPD. LCMS $(M+H)^+$=318.3.

Step 3: (4-(2-bromo-5-tosyl-5H-pyrrolo[2, 3-b] pyrazin-7-yl)-2-methylphenyl) (3-hydroxyazetidine-1-yl)methanone

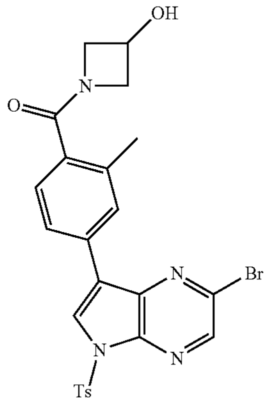 [SMILES: Cc1ccc(S(=O)(=O)n2cc(-c3ccc(C(=O)N4CC(O)C4)c(C)c3)c3nc(Br)cnc32)cc1]

The title compound (854 mg, 75%) was prepared in a manner similar to that in Example 1 step 2 from (3-hydroxyazetidine-1-yl) (2-methyl-4-(4, 4, 5, 5-tetramethyl-1, 3, 2-dioxaborolan-2-yl)phenyl)methanone and 2-bromo-7-iodo-5-tosyl-5H-pyrrolo[2, 3-b]pyrazine. LC-MS $(M+H)^+$=541.2.

Step 4: (4-(2-(2, 5-dimethyl-1, 2, 3, 4-tetrahydroisoquinolin-7-yl)-5-tosyl-5H-pyrrolo[2, 3-b] pyrazin-7-yl)-2-methylphenyl) (3-hydroxyazetidine-1-yl)methanone

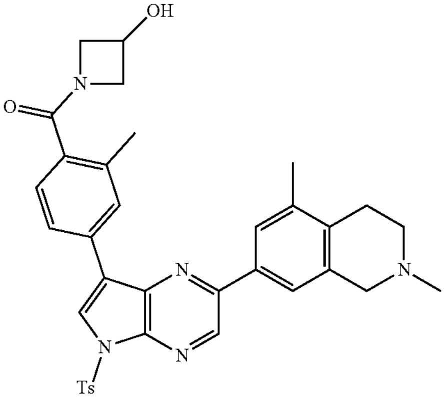 [SMILES: Cc1ccc(S(=O)(=O)n2cc(-c3ccc(C(=O)N4CC(O)C4)c(C)c3)c3nc(-c4cc(C)c5c(c4)CN(C)CC5)cnc32)cc1]

The title compound (60 mg, 36%) was prepared in a manner similar to that in Example 2 step 5 from 2, 5-dimethyl-7-(4, 4, 5, 5-tetramethyl-1, 3, 2-dioxaborolan-2-yl)-1, 2, 3, 4-tetrahydroisoquinoline and (4-(2-bromo-5-tosyl-5H-pyrrolo[2, 3-b]pyrazin-7-yl)-2-methylphenyl) (3-hydroxyazetidine-1-yl)methanone. LC-MS $(M+H)^+$=622.3.

Step 5: ((4-(2-(2, 5-dimethyl-1, 2, 3, 4-tetrahydroisoquinolin-7-yl)-5H-pyrrolo[2, 3-b]pyrazin-7-yl)-2-methylphenyl) (3-hydroxyazetidine-1-yl) methanone

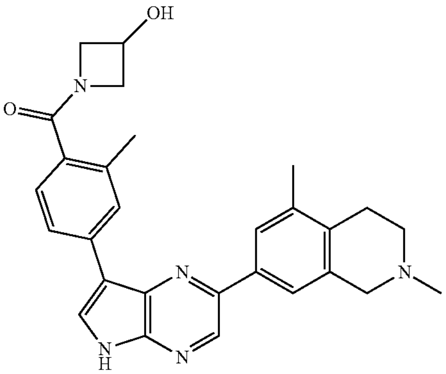 [SMILES: Cc1cc(-c2c[nH]c3ncc(-c4cc(C)c5c(c4)CN(C)CC5)nc23)ccc1C(=O)N1CC(O)C1]

Example 17 (9 mg, 20%) was prepared in a manner similar to that in Example 1 step 10 from (4-(2-(2, 5-dimethyl-1, 2, 3, 4-tetrahydroisoquinolin-7-yl)-5-tosyl-5H-pyrrolo[2, 3-b]pyrazin-7-yl)-2-methylphenyl) (3-hydroxyazetidine-1-yl)methanone. $^1$H NMR (400 MHz, DMSO-d6) δ 12.36 (s, 1H), 8.87 (s, 1H), 8.48 (s, 1H), 8.27-8.17 (m, 2H), 7.87 (s, 1H), 7.73 (d, J=1.9 Hz, 1H), 7.36 (d, J=8.0 Hz, 1H), 5.80-5.74 (m, 1H), 4.54-4.46 (m, 1H), 4.29-4.20 (m, 1H), 4.16-4.08 (m, 1H), 3.82-3.70 (m, 2H), 3.59 (s, 2H), 2.79-2.71 (m, 2H), 2.71-2.64 (m, 2H), 2.44-2.36 (m, 6H), 2.31 (s, 3H). LC-MS $(M+H)^+$=468.5.

Example 18: (S)-(4-(2-(5-methoxy-2-methyl-1, 2, 3, 4-tetrahydroisoquinolin-7-yl)-5H-pyrrolo[2, 3-b] pyrazin-7-yl)phenyl) (3-(methylamino)pyrrolidin-1-yl)methanone

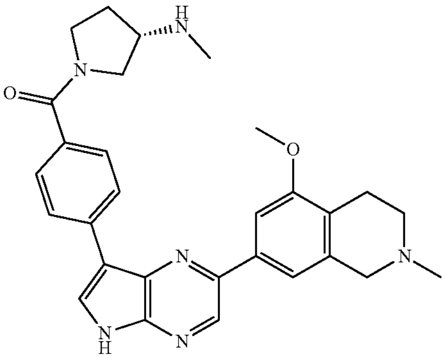 [SMILES: CN[C@H]1CCN(C(=O)c2ccc(-c3c[nH]c4ncc(-c5cc6c(c(OC)c5)CCN(C)C6)nc34)cc2)C1]

Step 1: 7-bromo-5-methoxy-2-methyl-1, 2, 3, 4-tetrahydroisoquinoline

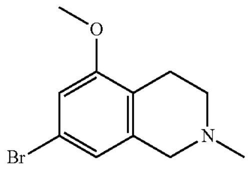

The title compound (600 mg, 99%) was prepared in a manner similar to that in Example 1 step 8 from 7-bromo-5-methoxy-1, 2, 3, 4-tetrahydroisoquinoline. LC-MS $(M+H)^+$=256.0.

Step 2: 5-methoxy-2-methyl-7-(4, 4, 5, 5-tetramethyl-1, 3, 2-dioxaborolan-2-yl)-1, 2, 3, 4-tetrahydroisoquinoline

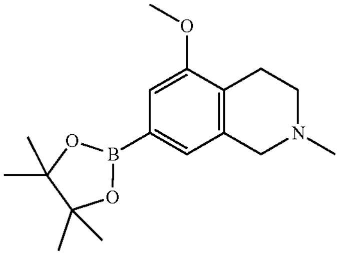

The title compound (705 mg, 99%) was prepared in a manner similar to that in Example 2 step 4 from 7-bromo-5-methoxy-2-methyl-1, 2, 3, 4-tetrahydroisoquinoline. LC-MS $(M+H)^+$=304.2.

Step 3: (S)-(4-(2-(5-methoxy-2-methyl-1, 2, 3, 4-tetrahydroisoquinolin-7-yl)-5-tosyl-5H-pyrrolo[2, 3-b]pyrazin-7-yl)phen (3-(methylamino)pyrrolidin-1-yl)methanone

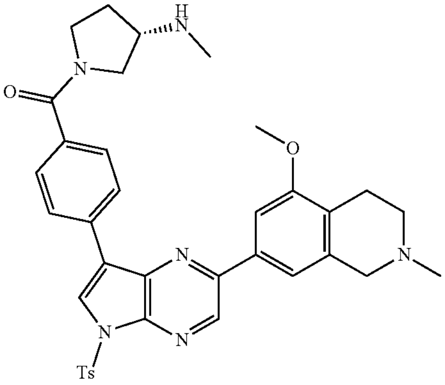 [SMILES: CN[C@H]1CCN(C(=O)c2ccc(-c3cn(S(=O)(=O)c4ccc(C)cc4)c4ncc(-c5cc6c(c(OC)c5)CCN(C)C6)nc34)cc2)C1]

The title compound (62 mg, 24%) was prepared in a manner similar to that in Example 2 step 5 from (S)-(4-(2-bromo-5-tosyl-5H-pyrrolo[2, 3-b]pyrazin-7-yl)phenyl) (3-(methylamino)pyrrolidin-1-yl)methanone and 5-methoxy-2-methyl-7-(4, 4, 5, 5-tetramethyl-1, 3, 2-dioxaborolan-2-yl)-1, 2, 3, 4-tetrahydroisoquinoline. LC-MS $(M+H)^+$=651.6.

Step 4: (S)-(4-(2-(5-methoxy-2-methyl-1, 2, 3, 4-tetrahydroisoquinolin-7-yl)-5H-pyrrolo[2, 3-b]pyrazin-7-yl)phenyl) (3-(methylamino)pyrrolidin-1-yl)methanone

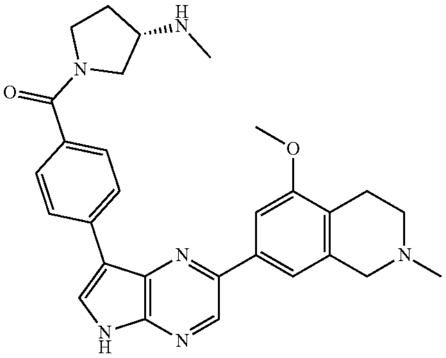 [SMILES: CN[C@H]1CCN(C(=O)c2ccc(-c3c[nH]c4ncc(-c5cc6c(c(OC)c5)CCN(C)C6)nc34)cc2)C1]

Example 18 (9 mg, 13%) was prepared in a manner similar to that in Example 1 step 10 from (S)-(4-(2-(5-methoxy-2-methyl-1, 2, 3, 4-tetrahydroisoquinolin-7-yl)-5-tosyl-5H-pyrrolo[2, 3-b]pyrazin-7-yl)phenyl) (3-(methylamino)pyrrolidin-1-yl)methanone. $^1H$ NMR (400 MHz, DMSO-d6) δ 12.42 (s, 1H), 8.94 (s, 1H), 8.53 (s, 1H), 8.44-8.37 (m, 2H), 7.65-7.55 (m, 4H), 3.94 (s, 3H), 3.67-3.55 (m, 2H), 3.54-3.42 (m, 3H), 3.30-3.07 (m, 2H), 2.96-2.89 (m, 2H), 2.64-2.57 (m, 2H), 2.39 (s, 3H), 2.33-2.16 (m, 3H), 2.05-1.88 (m, 1H), 1.80-1.66 (m, 1H). LC-MS $(M+H)^+$= 497.5.

Example 19: (4-(2-(2, 5-dimethyl-1, 2, 3, 4-tetrahydroisoquinolin-7-yl)-5H-pyrrolo[2, 3-b]pyrazin-7-yl) phenyl) (2-oxa-6-azaspiro[3.3]heptan-6-yl)methanone

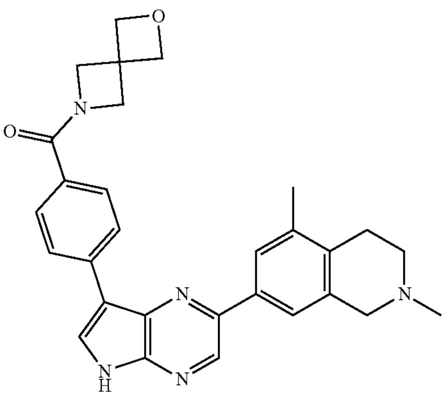 [SMILES: Cc1cc(-c2cnc3[nH]cc(-c4ccc(C(=O)N5CC6(COC6)C5)cc4)c3n2)cc2c1CCN(C)C2]

Step 1: (4-(2-(2, 5-dimethyl-1, 2, 3, 4-tetrahydroisoquinolin-7-yl)-5-tosyl-5H-pyrrolo[2, 3-b]pyrazin-7-yl)phenyl) (2-oxa-6-azaspiro[3.3]heptan-6-yl)methanone

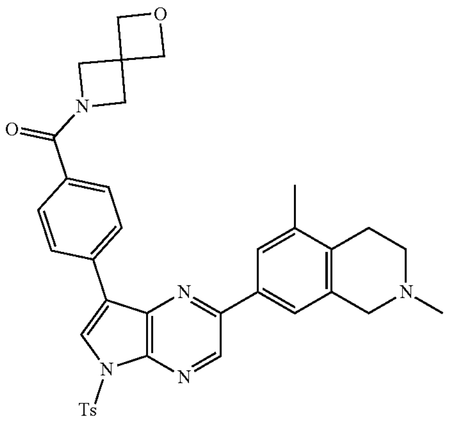 [SMILES: Cc1ccc(S(=O)(=O)n2cc(-c3ccc(C(=O)N4CC5(COC5)C4)cc3)c3nc(-c4cc(C)c5c(c4)CN(C)CC5)cnc32)cc1]

The title compound (78 mg, 56%) was prepared in a manner similar to that in Example 2 step 5 from (4-(2-bromo-5-tosyl-5H-pyrrolo[2, 3-b]pyrazin-7-yl)phenyl) (2-oxa-6-azaspiro[3.3]heptan-6-yl)methanone and 2, 5-dimethyl-7-(4, 4, 5, 5-tetramethyl-1, 3, 2-dioxaborolan-2-yl)-1, 2, 3, 4-tetrahydroisoquinoline. LC-MS $(M+H)^+$=634.5.

Step 2: (4-(2-(2, 5-dimethyl-1, 2, 3, 4-tetrahydroisoquinolin-7-yl)-5H-pyrrolo[2, 3-b]pyrazin-7-yl) phenyl) (2-oxa-6-azaspiro[3.3]heptan-6-yl)methanone

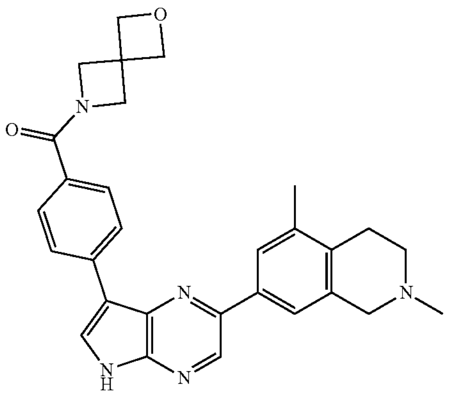 [SMILES: Cc1cc(-c2cnc3[nH]cc(-c4ccc(C(=O)N5CC6(COC6)C5)cc4)c3n2)cc2c1CCN(C)C2]

Example 19 (8 mg, 10%) was prepared in a manner similar to that in Example 1 step 10 from (4-(2-(2, 5-dimethyl-1, 2, 3, 4-tetrahydroisoquinolin-7-yl)-5-tosyl-5H-pyrrolo[2, 3-b]pyrazin-7-yl)phenyl) (2-oxa-6-azaspiro[3.3]heptan-6-yl)methanone. $^1$H NMR (400 MHz, DMSO-d6) δ 12.44 (s, 1H), 8.88 (s, 1H), 8.55 (s, 1H), 8.44-8.38 (m, 2H), 7.85 (s, 1H), 7.76-7.70 (m, 3H), 4.71 (s, 4H), 4.57 (s, 2H), 4.24 (s, 2H), 3.62 (s, 2H), 2.78-2.73 (m, 2H), 2.73-2.67 (m, 2H), 2.40 (s, 3H), 2.32 (s, 3H). LC-MS $(M+H)^+$=480.4.

Example 20: 4-(2-(2, 5-dimethyl-1, 2, 3, 4-tetrahydroisoquinolin-7-yl)-5H-pyrrolo[2, 3-b]pyrazin-7-yl)-N-(2-hydroxy-2-methylpropyl)-N-methylbenzamide

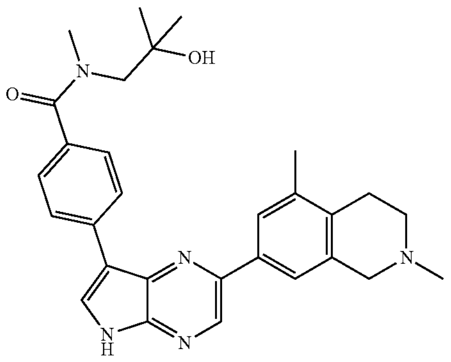 [SMILES: Cc1cc(-c2cnc3[nH]cc(-c4ccc(C(=O)N(C)CC(C)(C)O)cc4)c3n2)cc2c1CCN(C)C2]

Step 1: 4-((2-hydroxy-2-methylpropyl)(methyl)carbamoyl)phenylboronic acid

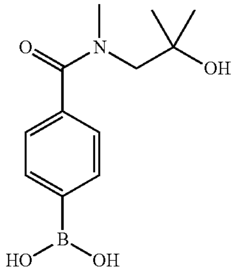 [SMILES: CN(CC(C)(C)O)C(=O)c1ccc(B(O)O)cc1]

The title compound (415 mg, 45%) was prepared in a manner similar to that in Example 15 step 1 from 2-methyl-1-(methylamino)propan-2-ol and 4-boronobenzoic acid. LC-MS $(M+H)^+$=252.2.

Step 2: 4-(2-bromo-5-tosyl-5H-pyrrolo[2, 3-b]pyrazin-7-yl)-N-(2-hydroxy-2-methylpropyl)-N-methylbenzamide

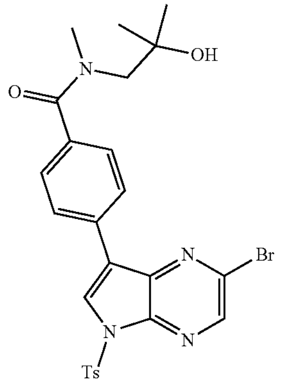 [SMILES: Cc1ccc(S(=O)(=O)n2cc(-c3ccc(C(=O)N(C)CC(C)(C)O)cc3)c3nc(Br)cnc32)cc1]

The title compound (241 mg, 32%) was prepared in a manner similar to that in Example 1 step 1 from 4-((2-hydroxy-2-methylpropyl)(methyl)carbamoyl)phenylboronic acid and 2-bromo-7-iodo-5-tosyl-5H-pyrrolo[2, 3-b]pyrazine. LC-MS $(M+H)^+$=557.2.

Step 3: 4-(2-(2, 5-dimethyl-1, 2, 3, 4-tetrahydroisoquinolin-7-yl)-5-tosyl-5H-pyrrolo[2, 3-b]pyrazin-7-yl)-N-(2-hydroxy-2-methylpropyl)-N-methylbenzamide

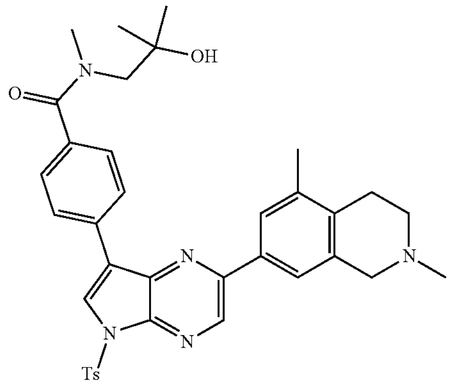 [SMILES: Cc1ccc(S(=O)(=O)n2cc(-c3ccc(C(=O)N(C)CC(C)(C)O)cc3)c3nc(-c4cc(C)c5c(c4)CN(C)CC5)cnc32)cc1]

The title compound (190 mg, 81%) was prepared in a manner similar to that in Example 2 step 5 from 4-(2-bromo-5-tosyl-5H-pyrrolo[2, 3-b]pyrazin-7-yl)-N-(2-hydroxy-2-methylpropyl)-N-methylbenzamide and 2, 5-dimethyl-7-(4, 4, 5, 5-tetramethyl-1, 3, 2-dioxaborolan-2-yl)-1, 2, 3, 4-tetrahydroisoquinoline. LC-MS $(M+H)^+$=638.4.

Step 4: 4-(2-(2, 5-dimethyl-1, 2, 3, 4-tetrahydroisoquinolin-7-yl)-5H-pyrrolo[2, 3-b]pyrazin-7-yl)-N-(2-hydroxy-2-methylpropyl)-N-methylbenzamide

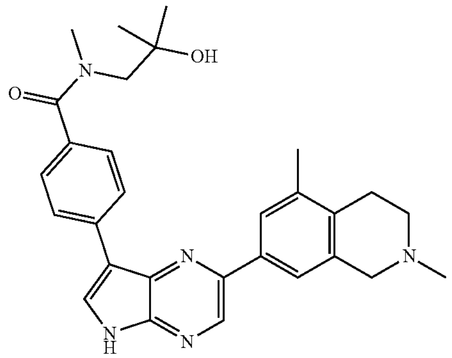 [SMILES: Cc1cc(-c2cnc3[nH]cc(-c4ccc(C(=O)N(C)CC(C)(C)O)cc4)c3n2)cc2c1CCN(C)C2]

Example 20 (34 mg, 29%) was prepared in a manner similar to that in Example 1 step 10 from 4-(2-(2, 5-dimethyl-1, 2, 3, 4-tetrahydroisoquinolin-7-yl)-5-tosyl-5H-pyrrolo[2, 3-b]pyrazin-7-yl)-N-(2-hydroxy-2-methylpropyl)-N-methylbenzamide. $^1$H NMR (400 MHz, DMSO-d6) δ 12.39 (s, 1H), 8.87 (s, 1H), 8.51 (s, 1H), 8.43-8.36 (m, 2H), 7.85 (s, 1H), 7.74 (s, 1H), 7.56-7.42 (m, 2H), 4.70-4.52 (m, 1H), 3.60 (s, 2H), 3.49 (s, 2H), 3.10 (s, 3H), 2.77-2.71 (m, 2H), 2.71-2.63 (m, 2H), 2.38 (s, 3H), 2.31 (s, 3H), 1.25-0.92 (m, 6H). LC-MS $(M+H)^+$=484.4.

Example 21: 2-acetamido-4-(2-(2, 5-dimethyl-1, 2, 3, 4-tetrahydroisoquinolin-7-yl)-5H-pyrrolo[2, 3-b]pyrazin-7-yl)-N, N-dimethylbenzamide

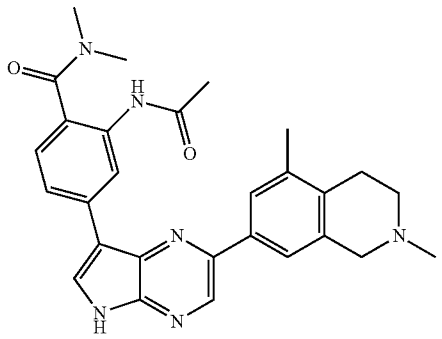 [SMILES: CC(=O)Nc1cc(-c2c[nH]c3ncc(-c4cc(C)c5c(c4)CN(C)CC5)nc23)ccc1C(=O)N(C)C]

Step 1: methyl 2-acetamido-4-bromobenzoate

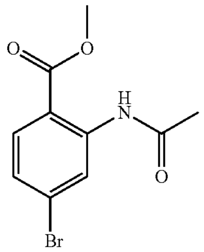

The title compound (980 mg, 87%) was prepared in a manner similar to that in Example 3 step 1 from methyl 2-amino-4-bromobenzoate and AcOH. LC-MS $(M+H)^+$=272.0.

Step 2: 2-acetamido-4-bromobenzoic acid

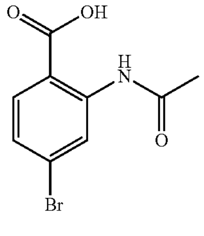

To a solution of methyl 2-acetamido-4-bromobenzoate (980 mg, 3.6 mmol) in THF (10 mL) and water (10 mL) was added LiOH monohydrate (302 mg, 7.2 mmol) at room temperature. After 16 h, THF was evaporated under reduced pressure and the reaction mixture was acidified by HCl (1 M) until pH=1. The solid was collected by filtration and washed with water (20 mL) to give the title compound (850 mg, 92%). LC-MS $(M+H)^+$=258.0.

Step 3: 2-acetamido-4-bromo-N, N-dimethylbenzamide

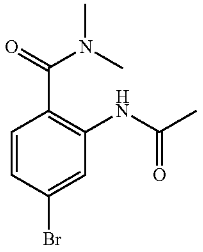 [SMILES: CC(=O)Nc1cc(Br)ccc1C(=O)N(C)C]

The title compound (325 mg, 76%) was prepared in a manner similar to that in Example 3 step 1 from 2-acetamido-4-bromobenzoic acid and dimethylamine hydrochloride. LC-MS $(M+H)^+$=285.1.

Step 4: 2-acetamido-N, N-dimethyl-4-(4, 4, 5, 5-tetramethyl-1, 3, 2-dioxaborolan-2-yl)benzamide

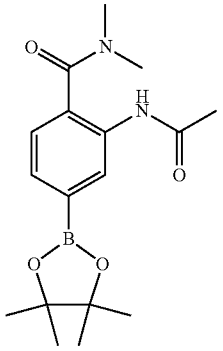 [SMILES: CC(=O)Nc1cc(B2OC(C)(C)C(C)(C)O2)ccc1C(=O)N(C)C]

The title compound (209 mg, 60%) was prepared in a manner similar to that in Example 3 step 5 from 2-acetamido-4-bromo-N, N-dimethylbenzamide and BPD. LC-MS $(M+H)^+$=333.3.

Step 5: 2-acetamido-4-(2-bromo-5-tosyl-5H-pyrrolo [2, 3-b]pyrazin-7-yl)-N, N-dimethylbenzamide

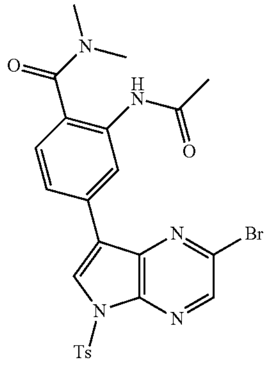 [SMILES: CC(=O)Nc1cc(-c2cn(S(=O)(=O)c3ccc(C)cc3)c3ncc(Br)nc23)ccc1C(=O)N(C)C]

The title compound (199 mg, 81%) was prepared in a manner similar to that in Example 1 step 2 from 2-acetamido-N, N-dimethyl-4-(4, 4, 5, 5-tetramethyl-1, 3, 2-dioxaborolan-2-yl)benzamide and 2-bromo-7-iodo-5-tosyl-5H-pyrrolo[2, 3-b]pyrazine. LC-MS $(M+H)^+$=556.1.

Step 6: 2-acetamido-4-(2-(2, 5-dimethyl-1, 2, 3, 4-tetrahydroisoquinolin-7-yl)-5-tosyl-5H-pyrrolo[2, 3-b]pyrazin-7-yl)-N, N-dimethylbenzamide

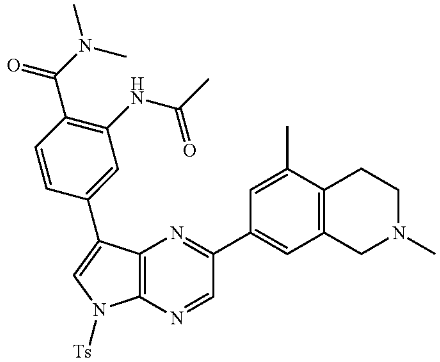 [SMILES: CC(=O)Nc1cc(-c2cn(S(=O)(=O)c3ccc(C)cc3)c3ncc(-c4cc(C)c5c(c4)CN(C)CC5)nc23)ccc1C(=O)N(C)C]

The title compound (125 mg, 57%) was prepared in a manner similar to that in Example 2 step 5 from 2-acetamido-4-(2-bromo-5-tosyl-5H-pyrrolo[2, 3-b]pyrazin-7-yl)-N, N-dimethylbenzamide and 2, 5-dimethyl-7-(4, 4, 5, 5-tetramethyl-1, 3, 2-dioxaborolan-2-yl)-1, 2, 3, 4-tetrahydroisoquinoline. LC-MS $(M+H)^+$=637.4.

Step 7: 2-acetamido-4-(2-(2, 5-dimethyl-1, 2, 3, 4-tetrahydroisoquinolin-7-yl)-5H-pyrrolo[2, 3-b] pyrazin-7-yl)-N, N-dimethylbenzamide

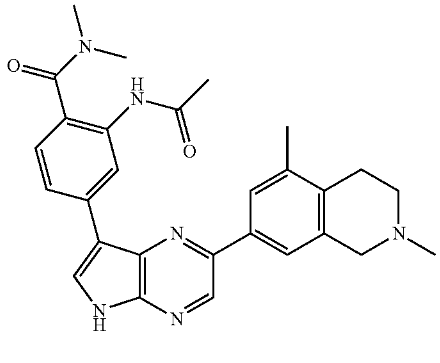 [SMILES: CC(=O)Nc1cc(-c2c[nH]c3ncc(-c4cc(C)c5c(c4)CN(C)CC5)nc23)ccc1C(=O)N(C)C]

Example 21 (25 mg, 27%) was prepared as similar method to Example 1 step 10 from 2-acetamido-4-(2-(2, 5-dimethyl-1, 2, 3, 4-tetrahydroisoquinolin-7-yl)-5-tosyl-5H-pyrrolo[2, 3-b]pyrazin-7-yl)-N, N-dimethylbenzamide. $^1H$ NMR (400 MHz, DMSO-d6) δ 12.36 (s, 1H), 9.60 (s, 1H), 9.08 (s, 1H), 8.92 (s, 1H), 8.48 (s, 1H), 8.00 (s, 1H), 7.97-7.90 (m, 2H), 7.34 (d, J=8.0 Hz, 1H), 3.64 (s, 2H), 3.06-2.86 (m, 6H), 2.78-2.65 (m, 4H), 2.39 (s, 3H), 2.33 (s, 3H), 2.11 (s, 3H). LC-MS $(M+H)^+$=483.4.

Example 22: 4-(2-(8-methoxy-2-methyl-1, 2, 3, 4-tetrahydroisoquinolin-6-yl)-5H-pyrrolo[2, 3-b]pyrazin-7-yl)-N, N-dimethylbenzamide

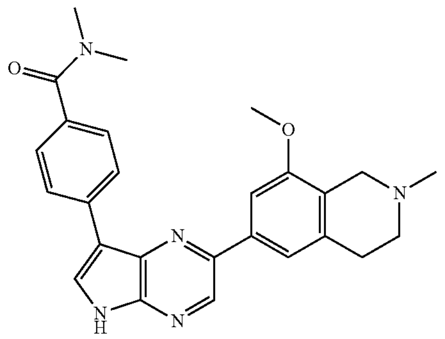 [SMILES: COc1cc(-c2cnc3[nH]cc(-c4ccc(C(=O)N(C)C)cc4)c3n2)cc2c1CN(C)CC2]

Step 1: 4-(2-(8-methoxy-1, 2, 3, 4-tetrahydroisoquinolin-6-yl)-5-tosyl-5H-pyrrolo[2, 3-b]pyrazin-7-yl)-N, N-dimethylbenzamide

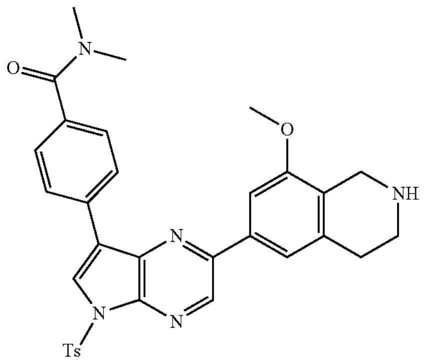 [SMILES: COc1cc(-c2cnc3c(n2)c(-c2ccc(C(=O)N(C)C)cc2)cn3S(=O)(=O)c2ccc(C)cc2)cc2c1CNCC2]

The title compound (390 mg, 65%) was prepared in a manner similar to that in Example 1 step 9 from N, N-dimethyl-4-(2-(4, 4, 5, 5-tetramethyl-1, 3, 2-dioxaborolan-2-yl)-5-tosyl-5H-pyrrolo[2, 3-b]pyrazin-7-yl)benzamide and 6-bromo-8-methoxy-1, 2, 3, 4-tetrahydroisoquinoline; trifluoroacetic acid. LC-MS $(M+H)^+$=582.5.

Step 2: 4-(2-(8-methoxy-2-methyl-1, 2, 3, 4-tetrahydroisoquinolin-6-yl)-5-tosyl-5H-pyrrolo[2, 3-b]pyrazin-7-yl)-N, N-dimethylbenzamide

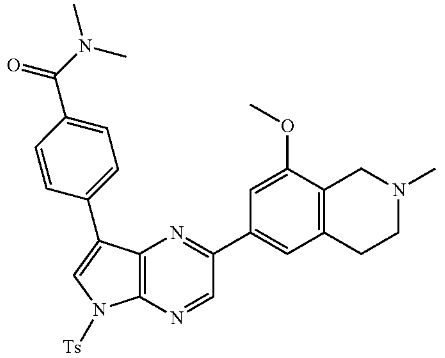 [SMILES: COc1cc(-c2cnc3c(n2)c(-c2ccc(C(=O)N(C)C)cc2)cn3S(=O)(=O)c2ccc(C)cc2)cc2c1CN(C)CC2]

The title compound (290 mg, 89%) was prepared in a manner similar to that in Example 6 step 9 from 4-(2-(8-methoxy-1, 2, 3, 4-tetrahydroisoquinolin-6-yl)-5-tosyl-5H-pyrrolo[2, 3-b]pyrazin-7-yl)-N, N-dimethylbenzamide and formalin. LC-MS $(M+H)^+$=596.3.

Step 3: 4-(2-(8-methoxy-2-methyl-1, 2, 3, 4-tetrahydroisoquinolin-6-yl)-5H-pyrrolo[2, 3-b]pyrazin-7-yl)-N, N-dimethylbenzamide

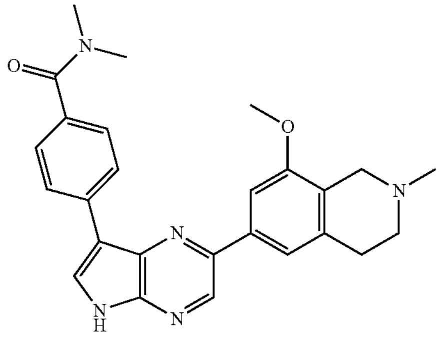 [SMILES: COc1cc(-c2cnc3[nH]cc(-c4ccc(C(=O)N(C)C)cc4)c3n2)cc2c1CN(C)CC2]

Example 22 (36 mg, 19%) was prepared in a manner similar to that in Example 1 step 10 from 4-(2-(8-methoxy-2-methyl-1, 2, 3, 4-tetrahydroisoquinolin-6-yl)-5-tosyl-5H-pyrrolo[2, 3-b]pyrazin-7-yl)-N, N-dimethylbenzamide. $^1H$ NMR (400 MHz, DMSO-d6) δ 12.41 (s, 1H), 8.94 (s, 1H), 8.52 (s, 1H), 8.44-8.37 (m, 2H), 7.63-7.55 (m, 2H), 7.55-7.48 (m, 2H), 3.94 (s, 3H), 3.46 (s, 2H), 3.00 (s, 6H), 2.93 (t, J=5.8 Hz, 2H), 2.62 (t, J=5.7 Hz, 2H), 2.40 (s, 3H). LC-MS $(M+H)^+$=442.3.

Example 23: 4-(2-(2-(3-((trans-4-hydroxycyclohexyl)amino)-3-oxopropyl)-5-methyl-1, 2, 3, 4-tetrahydroisoquinolin-7-yl)-5H-pyrrolo[2, 3-b]pyrazin-7-yl)-N, N, 2-trimethylbenzamide

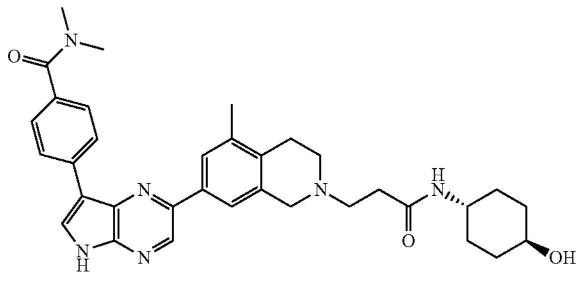 [SMILES: Cc1cc(-c2cnc3[nH]cc(-c4ccc(C(=O)N(C)C)cc4)c3n2)cc2c1CCN(CCC(=O)N[C@H]1CC[C@H](O)CC1)C2]

Step 1: ethyl 3-(7-bromo-5-methyl-3, 4-dihydroisoquinolin-2 (1H)-yl)propanoate

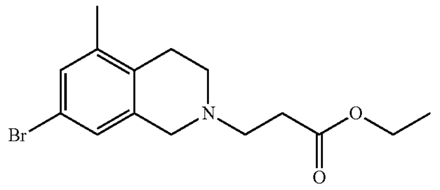 [SMILES: CCOC(=O)CCN1CCc2c(C)cc(Br)cc2C1]

To a 100 mL sealed tube was added 7-bromo-5-methyl-1, 2, 3, 4-tetrahydroisoquinoline (4.5 g, 20 mmol), ethyl acrylate (6.0 g, 60 mmol) and EtOH (30 mL). The mixture was stirred at 50° C. overnight. The mixture was concentrated under vacuum to give the title compound (6.5 g, 99%). LC-MS $(M+H)^+$=325.9, 327.9.

Step 2: ethyl 3-(5-methyl-7-(4, 4, 5, 5-tetramethyl-1, 3, 2-dioxaborolan-2-yl)-3, 4-dihydroisoquinolin-2 (1H)-yl)propanoate

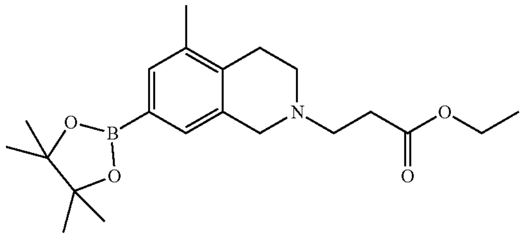 [SMILES: CCOC(=O)CCN1CCc2c(C)cc(B3OC(C)(C)C(C)(C)O3)cc2C1]

To a solution of ethyl 3-(7-bromo-5-methyl-3, 4-dihydroisoquinolin-2 (1H)-yl)propanoate (6.5 g, 20 mmol) and BPD (6.0 g, 24 mmol) in 1, 4-dioxane (100 mL) was added KOAc (7.0 g, 71 mmol) and Pd $(dppf)Cl_2$ (730 mg, 1.0 mmol) under $N_2$. The mixture was stirred at 90° C. overnight. The mixture was cooled and diluted with water (100 mL) then extracted with EtOAc (100 mL×3). The combined organic phase was washed with brine, dried over $Na_2SO_4$ and evaporated under vacuum. The residue was purified by silica gel column chromatography, eluted with EtOAc/PE (1:3) to give the title compound (6.5 g, 87%). LC-MS $(M+H)^+$=374.1.

Step 3: 3-(7-(7-(4-(dimethylcarbamoyl)-3-methylphenyl)-5H-pyrrolo[2, 3-b]pyrazin-2-yl)-5-methyl-3, 4-dihydroisoquinolin-2 (1H)-yl)propanoic acid

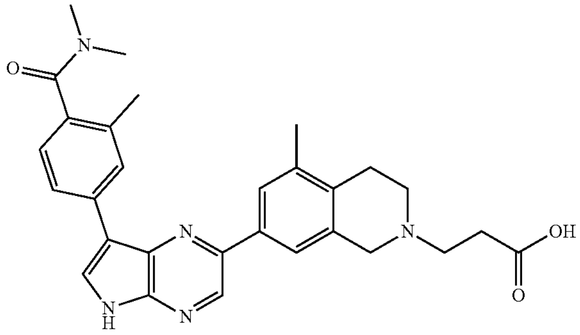 [SMILES: Cc1cc(-c2c[nH]c3ncc(-c4cc(C)c5c(c4)CN(CCC(=O)O)CC5)nc23)ccc1C(=O)N(C)C]

To a solution of ethyl 3-(5-methyl-7-(4, 4, 5, 5-tetramethyl-1, 3, 2-dioxaborolan-2-yl)-3, 4-dihydroisoquinolin-2 (1H)-yl)propanoate (3.2 g, 8.6 mmol) 4-(2-bromo-5-tosyl-5H-pyrrolo[2, 3-b]pyrazin-7-yl)-N, N, 2-trimethylbenzamide (4.3 g, 8.3 mmol) in 1, 4-dioxane (100 mL) and water (50 mL) was added $K_2CO_3$ (3.5 g, 25.4 mmol) and Pd $(dppf)Cl_2$ (310 mg, 0.40 mmol). The mixture was stirred at 100° C. overnight. The mixture was cooled and diluted with water (50 mL). Solid was filtered off and the mixture was neutralized with HCl (2 M) to pH 6. The precipitate was collected by filtration to give the title compound (4.2 g, 99%). LC-MS $(M+H)^+$=498.0.

Step 4: 4-(2-(2-(3-((trans-4-hydroxycyclohexyl)amino)-3-oxopropyl)-5-methyl-1, 2, 3, 4-tetrahydroisoquinolin-7-yl)-5H-pyrrolo[2, 3-b]pyrazin-7-yl)-N, N, 2-trimethylbenzamide

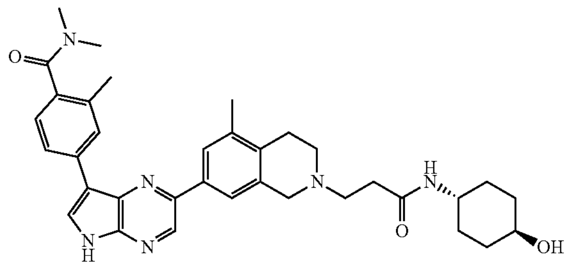 [SMILES: Cc1cc(-c2c[nH]c3ncc(-c4cc(C)c5c(c4)CN(CCC(=O)N[C@H]4CC[C@H](O)CC4)CC5)nc23)ccc1C(=O)N(C)C]

To a solution of 3-(7-(7-(4-(dimethylcarbamoyl)-3-methylphenyl)-5H-pyrrolo[2, 3-b]pyrazin-2-yl)-5-methyl-3, 4-dihydroisoquinolin-2 (1H)-yl)propanoic acid (100 mg, 0.20 mmol) and trans-4-aminocyclohexan-1-ol (35 mg, 0.30 mmol) in DMF (2 mL) was added $Et_3N$ (100 mg, 1.0 mmol) and HATU (110 mg, 0.30 mmol). The mixture was stirred at room temperature for 2 h. The mixture was diluted with water (10 mL), extracted with EtOAc (10 mL×3). The combined organic phase was washed with brine (10 mL×3), dried over $Na_2SO_4$ and evaporated under vacuum. The residue was purified by prep-TLC, developed with DCM/MeOH/25% aqueous $NH_3$ (100/10/0.5) to give Example 23

(40 mg, 33%). $^1$H NMR (400 MHz, DMSO-d6) δ 12.34 (d, J=2.6 Hz, 1H), 8.86 (s, 1H), 8.46 (d, J=2.8 Hz, 1H), 8.25-8.20 (m, 2H), 7.86 (s, 1H), 7.82 (d, J=7.8 Hz, 1H), 7.73 (s, 1H), 7.24 (d, J=7.8 Hz, 1H), 4.50 (d, J=4.4 Hz, 1H), 3.68 (brs, 2H), 3.46 (brs, 1H), 3.03 (s, 3H), 2.83 (s, 3H), 2.73 (brs, 6H), 2.38-2.28 (m, 9H), 1.81-1.69 (m, 4H), 1.20-1.10 (m, 4H). LC-MS $(M+H)^+$=595.5.

Example 24: N, N, 2-trimethyl-4-(2-(5-methyl-2-(3-(4-methylpiperazin-1-yl)-3-oxopropyl)-1, 2, 3, 4-tetrahydroisoquinolin-7-yl)-5H-pyrrolo[2, 3-b]pyrazin-7-yl)benzamide

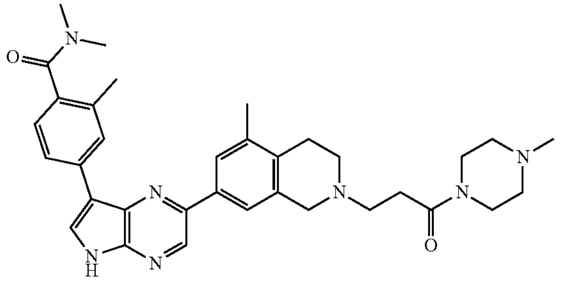 [SMILES: Cc1cc(-c2c[nH]c3ncc(-c4cc(C)c5c(c4)CN(CCC(=O)N4CCN(C)CC4)CC5)nc23)ccc1C(=O)N(C)C]

Step 1: N, N, 2-trimethyl-4-(2-(4, 4, 5, 5-tetramethyl-1, 3, 2-dioxaborolan-2-yl)-5-tosyl-5H-pyrrolo [2, 3-b]pyrazin-7-yl)benzamide

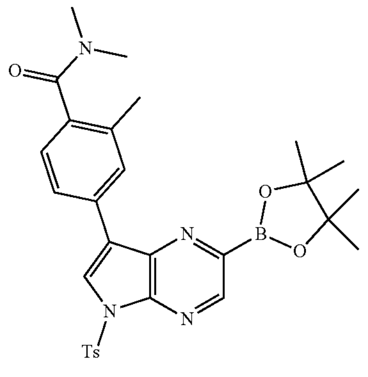 [SMILES: Cc1ccc(S(=O)(=O)n2cc(-c3ccc(C(=O)N(C)C)c(C)c3)c3nc(B4OC(C)(C)C(C)(C)O4)cnc32)cc1]

The title compound (2.3 mg, 97%) was prepared in a manner similar to that in Example 1 step 3 from 4-(2-bromo-5-tosyl-5H-pyrrolo[2, 3-b]pyrazin-7-yl)-N, N, 2-trimethylbenzamide and BPD. LCMS (M-pin)$^+$=479.1.

Step 2: N, N, 2-trimethyl-4-(2-(5-methyl-1, 2, 3, 4-tetrahydroisoquinolin-7-yl)-5-tosyl-5H-pyrrolo[2, 3-b]pyrazin-7-yl)benzamide

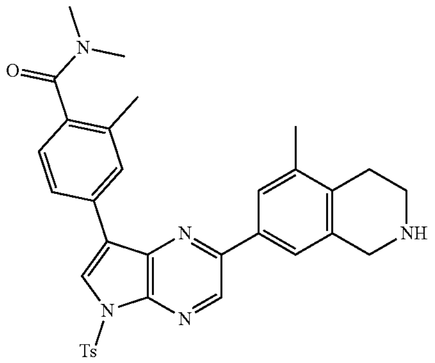 [SMILES: Cc1ccc(S(=O)(=O)n2cc(-c3ccc(C(=O)N(C)C)c(C)c3)c3nc(-c4cc(C)c5c(c4)CNCC5)cnc32)cc1]

The title compound (1.21 g, 58%) was prepared in a manner similar to that in Example 1 step 9 from N, N, 2-trimethyl-4-(2-(4, 4, 5, 5-tetramethyl-1, 3, 2-dioxaborolan-2-yl)-5-tosyl-5H-pyrrolo[2, 3-b]pyrazin-7-yl)benzamide and 7-bromo-5-methyl-1, 2, 3, 4-tetrahydroisoquinoline. LC-MS $(M+H)^+$=580.3.

Step 3: 3-(7-(7-(4-(dimethylcarbamoyl)-3-methylphenyl)-5-tosyl-5H-pyrrolo[2, 3-b]pyrazin-2-yl)-5-methyl-3, 4-dihydroisoquinolin-2 (1H)-yl)propanoic acid

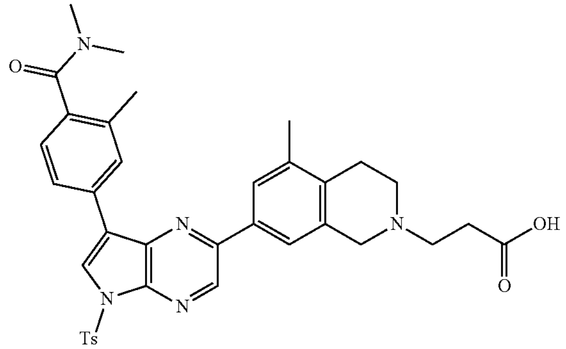 [SMILES: Cc1ccc(S(=O)(=O)n2cc(-c3ccc(C(=O)N(C)C)c(C)c3)c3nc(-c4cc(C)c5c(c4)CN(CCC(=O)O)CC5)cnc32)cc1]

To a mixture of N, N, 2-trimethyl-4-[2-(5-methyl-1, 2, 3, 4-tetrahydroisoquinolin-7-yl)-5-(4-methylbenzenesulfonyl) pyrrolo[2, 3-b]pyrazin-7-yl]benzamide (1.30 g, 2.08 mmol), KI (364 mg, 2.08 mmol) and $Et_3N$ (666 mg, 6.25 mmol) in DMF (15 mL) was added 3-bromopropionic acid (537 mg, 3.33 mmol) in portions at room temperature. The resulting mixture was stirred for 3 h then diluted with water (20 mL). The precipitate was collected by filtration and washed with water (10 mL×3) to give the title compound (1.35 g, 90%). LC-MS $(M+H)^+$=652.2.

Step 4: N, N, 2-trimethyl-4-(2-(5-methyl-2-(3-(4-methylpiperazin-1-yl)-3-oxopropyl)-1, 2, 3, 4-tetrahydroisoquinolin-7-yl)-5-tosyl-5H-pyrrolo[2, 3-b]pyrazin-7-yl)benzamide

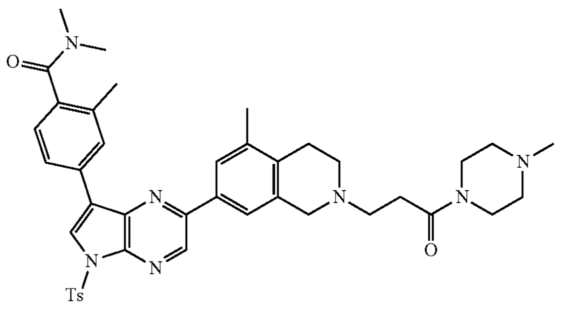 [SMILES: Cc1ccc(S(=O)(=O)n2cc(-c3ccc(C(=O)N(C)C)c(C)c3)c3nc(-c4cc(C)c5c(c4)CN(CCC(=O)N4CCN(C)CC4)CC5)cnc32)cc1]

The title compound (79 mg, 51%) was prepared in a manner similar to that in Example 23 step 4 from 3-(7-(7-(4-(dimethylcarbamoyl)-3-methylphenyl)-5-tosyl-5H-pyrrolo[2, 3-b]pyrazin-2-yl)-5-methyl-3, 4-dihydroisoquinolin-2 (1H)-yl)propanoic acid and 1-methylpiperazine. LC-MS $(M+H)^+$=734.3.

Step 5: N, N, 2-trimethyl-4-(2-(5-methyl-2-(3-(4-methylpiperazin-1-yl)-3-oxopropyl)-1, 2, 3, 4-tetrahydroisoquinolin-7-yl)-5H-pyrrolo[2, 3-b]pyrazin-7-yl)benzamide

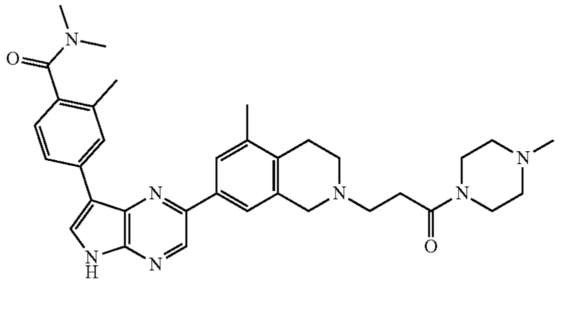 [SMILES: Cc1cc(-c2c[nH]c3ncc(-c4cc(C)c5c(c4)CN(CCC(=O)N4CCN(C)CC4)CC5)nc23)ccc1C(=O)N(C)C]

Example 24 (21 mg, 37%) was prepared in a manner similar to that in Example 1 step 10 from N, N, 2-trimethyl-4-(2-(5-methyl-2-(3-(4-methylpiperazin-1-yl)-3-oxopropyl)-1, 2, 3, 4-tetrahydroisoquinolin-7-yl)-5-tosyl-5H-pyrrolo[2, 3-b]pyrazin-7-yl)benzamide. $^1$H NMR (400 MHz, DMSO-d6) δ 12.33 (s, 1H), 8.86 (s, 1H), 8.46 (s, 1H), 8.26-8.18 (m, 2H), 7.86 (s, 1H), 7.74 (s, 1H), 7.25 (d, J=7.8 Hz, 1H), 3.69 (s, 2H), 3.52-3.42 (m, 4H), 3.03 (s, 3H), 2.83 (s, 3H), 2.81-2.70 (m, 6H), 2.65-2.57 (m, 2H), 2.33-2.26 (m, 8H), 2.26-2.20 (m, 2H), 2.17 (s, 3H). LC-MS $(M+H)^+$=580.3.

Example 25: N, N, 2-trimethyl-4-(2-(5-methyl-2-(3-(methylamino)-3-oxopropyl)-1, 2, 3, 4-tetrahydroisoquinolin-7-yl)-5H-pyrrolo[2, 3-b]pyrazin-7-yl)benzamide

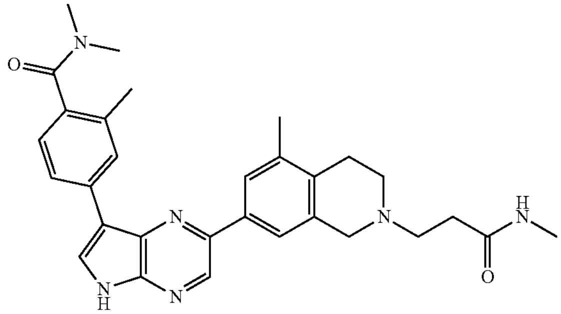 [SMILES: CNC(=O)CCN1CCc2c(C)cc(-c3cnc4[nH]cc(-c5ccc(C(=O)N(C)C)c(C)c5)c4n3)cc2C1]

Step 1: N, N, 2-trimethyl-4-(2-(5-methyl-2-(3-(methylamino)-3-oxopropyl)-1, 2, 3, 4-tetrahydroisoquinolin-7-yl)-5-tosyl-5H-pyrrolo[2, 3-b]pyrazin-7-yl)

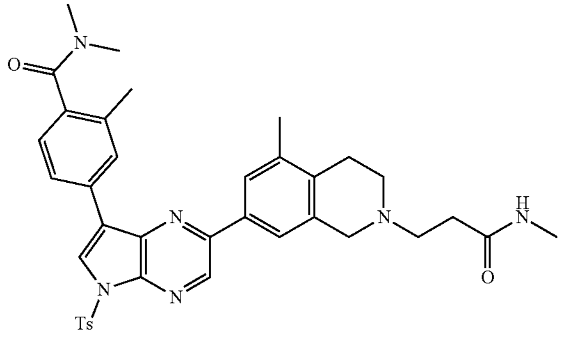 [SMILES: CNC(=O)CCN1CCc2c(C)cc(-c3cnc4c(n3)c(-c3ccc(C(=O)N(C)C)c(C)c3)cn4S(=O)(=O)c3ccc(C)cc3)cc2C1]

The title compound (92 mg, 45%) was prepared in a manner similar to that in Example 23 step 4 from 3-(7-(7-(4-(dimethylcarbamoyl)-3-methylphenyl)-5-tosyl-5H-pyrrolo[2, 3-b]pyrazin-2-yl)-5-methyl-3, 4-dihydroisoquinolin-2 (1H)-yl)propanoic acid and $MeNH_2$. LC-MS $(M+H)^+$=665.0.

Step 2: N, N, 2-trimethyl-4-(2-(5-methyl-2-(3-(methylamino)-3-oxopropyl)-1, 2, 3, 4-tetrahydroisoquinolin-7-yl)-5H-pyrrolo[2, 3-b]pyrazin-7-yl) benzamide

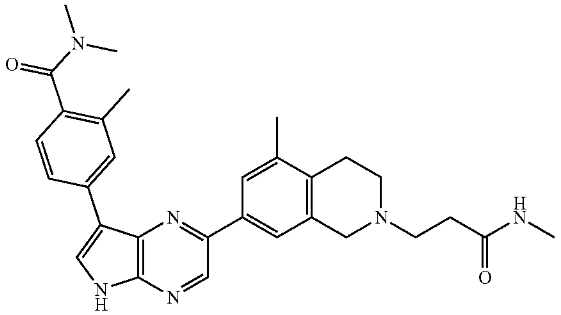 [SMILES: CNC(=O)CCN1CCc2c(C)cc(-c3cnc4[nH]cc(-c5ccc(C(=O)N(C)C)c(C)c5)c4n3)cc2C1]

Example 25 (8 mg, 16%) was prepared in a manner similar to that in Example 1 step 10 from N, N, 2-trimethyl-4-(2-(5-methyl-2-(3-(methylamino)-3-oxopropyl)-1, 2, 3, 4-tetrahydroisoquinolin-7-yl)-5-tosyl-5H-pyrrolo[2, 3-b] pyrazin-7-yl)benzamide. $^1$H NMR (400 MHz, DMSO-d6) δ 12.34 (s, 1H), 8.87 (s, 1H), 8.46 (s, 1H), 8.27-8.18 (m, 2H), 7.89-7.83 (m, 2H), 7.74 (s, 1H), 7.25 (d, J=7.7 Hz, 1H), 3.68 (s, 2H), 3.03 (s, 3H), 2.84 (s, 3H), 2.77-2.69 (m, 6H), 2.58 (d, J=4.6 Hz, 3H), 2.37 (t, J=7.2 Hz, 2H), 2.33-2.28 (m, 6H). LC-MS $(M+H)^+$=511.0.

Example 26: 4-(2-(2-(3-(dimethylamino)-3-oxopropyl)-5-methyl-1, 2, 3, 4-tetrahydroisoquinolin-7-yl)-5H-pyrrolo[2, 3-b]pyrazin-7-yl)-N, N, 2-trimethylbenzamide

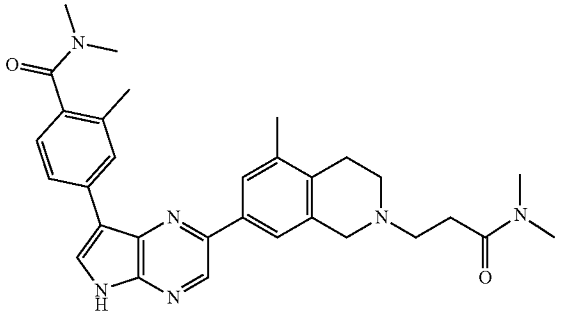 [SMILES: Cc1cc(-c2c[nH]c3ncc(-c4cc(C)c5c(c4)CN(CCC(=O)N(C)C)CC5)nc23)ccc1C(=O)N(C)C]

Step 1: 4-(2-(2-(3-(dimethylamino)-3-oxopropyl)-5-methyl-1, 2, 3, 4-tetrahydroisoquinolin-7-yl)-5-tosyl-5H-pyrrolo[2, 3-b]pyrazin-7-yl)-N, N, 2-trimethylbenzamide

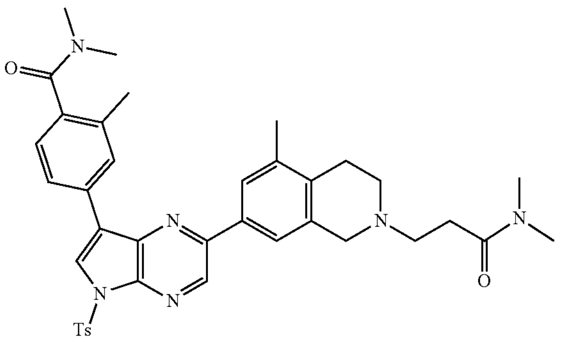 [SMILES: Cc1ccc(S(=O)(=O)n2cc(-c3ccc(C(=O)N(C)C)c(C)c3)c3nc(-c4cc(C)c5c(c4)CN(CCC(=O)N(C)C)CC5)cnc32)cc1]

The title compound (75 mg, 41%) was prepared in a manner similar to that in Example 23 step 4 from 3-(7-(7-(4-(dimethylcarbamoyl)-3-methylphenyl)-5-tosyl-5H-pyrrolo[2, 3-b]pyrazin-2-yl)-5-methyl-3, 4-dihydroisoquinolin-2 (1H)-yl)propanoic acid and $Me_2NH$ hydrochloride. LC-MS $(M+H)^+$=679.0.

Step 2: 4-(2-(2-(3-(dimethylamino)-3-oxopropyl)-5-methyl-1, 2, 3, 4-tetrahydroisoquinolin-7-yl)-5H-pyrrolo[2, 3-b]pyrazin-7-yl)-N, N, 2-trimethylbenzamide

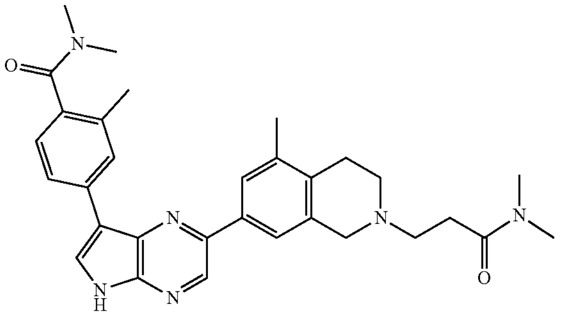 [SMILES: Cc1cc(-c2c[nH]c3ncc(-c4cc(C)c5c(c4)CN(CCC(=O)N(C)C)CC5)nc23)ccc1C(=O)N(C)C]

Example 26 (10 mg, 12%) was prepared in a manner similar to that in Example 1 step 10 from 4-(2-(2-(3-(dimethylamino)-3-oxopropyl)-5-methyl-1, 2, 3, 4-tetrahydroisoquinolin-7-yl)-5-tosyl-5H-pyrrolo[2, 3-b]pyrazin-7-yl)-N, N, 2-trimethylbenzamide. $^1$H NMR (400 MHz, DMSO-d6) δ 12.33 (s, 1H), 8.87 (s, 1H), 8.46 (s, 1H), 8.26-8.18 (m, 2H), 7.86 (s, 1H), 7.74 (s, 1H), 7.25 (d, J=7.9 Hz, 1H), 3.70 (s, 2H), 3.06-2.99 (m, 6H), 2.86-2.81 (m, 6H), 2.80-2.70 (m, 6H), 2.64-2.56 (m, 2H), 2.37-2.28 (m, 6H). LC-MS $(M+H)^+$=525.0.

Example 27: 4-(2-(2-(3-(4-methoxyphenylamino)-3-oxopropyl)-5-methyl-1, 2, 3, 4-tetrahydroisoquinolin-7-yl)-5H-pyrrolo[2, 3-b]pyrazin-7-yl)-N, N, 2-trimethylbenzamide

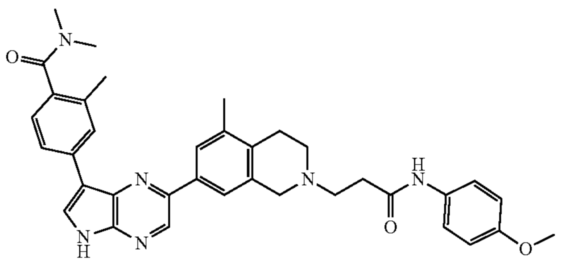 [SMILES: COc1ccc(NC(=O)CCN2CCc3c(C)cc(-c4cnc5[nH]cc(-c6ccc(C(=O)N(C)C)c(C)c6)c5n4)cc3C2)cc1]

Step 1: 4-(2-(2-(3-(4-methoxyphenylamino)-3-oxopropyl)-5-methyl-1, 2, 3, 4-tetrahydroisoquinolin-7-yl)-5-tosyl-5H-pyrrolo[2, 3-b]pyrazin-7-yl)-N, N, 2-trimethylbenzamide

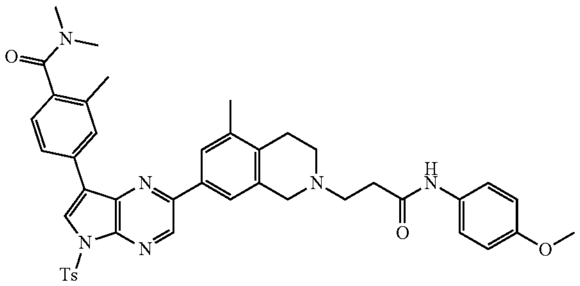 [SMILES: COc1ccc(NC(=O)CCN2CCc3c(C)cc(-c4cnc5c(n4)c(-c4ccc(C(=O)N(C)C)c(C)c4)cn5S(=O)(=O)c4ccc(C)cc4)cc3C2)cc1]

The title compound (103 mg, 54%) was prepared in a manner similar to that in Example 23 step 4 from 3-(7-(7-(4-(dimethylcarbamoyl)-3-methylphenyl)-5-tosyl-5H-pyrrolo[2, 3-b]pyrazin-2-yl)-5-methyl-3, 4-dihydroisoquinolin-2 (1H)-yl)propanoic acid and 4-methoxybenzenamine. LC-MS $(M+H)^{+}$=757.3.

Step 2: 4-(2-(2-(3-(4-methoxyphenylamino)-3-oxopropyl)-5-methyl-1, 2, 3, 4-tetrahydroisoquinolin-7-yl)-5H-pyrrolo[2, 3-b]pyrazin-7-yl)-N, N, 2-trimethylbenzamide

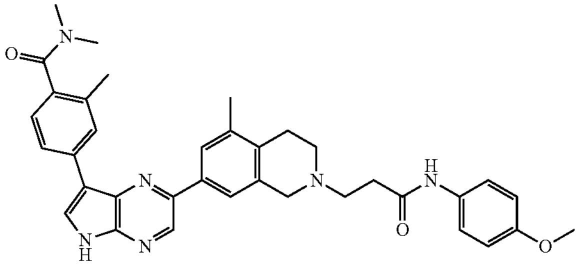 [SMILES: COc1ccc(NC(=O)CCN2CCc3c(C)cc(-c4cnc5[nH]cc(-c6ccc(C(=O)N(C)C)c(C)c6)c5n4)cc3C2)cc1]

Example 27 (35 mg, 42%) was prepared in a manner similar to that in Example 1 step 10 from 4-(2-(2-(3-(4-methoxyphenylamino)-3-oxopropyl)-5-methyl-1, 2, 3, 4-tetrahydroisoquinolin-7-yl)-5-tosyl-5H-pyrrolo[2, 3-b]pyrazin-7-yl)-N, N, 2-trimethylbenzamide. $^{1}H$ NMR (400 MHz, DMSO-d6) δ 12.34 (s, 1H), 9.92 (s, 1H), 8.87 (s, 1H), 8.46 (d, J=2.9 Hz, 1H), 8.25-8.19 (m, 2H), 7.87 (s, 1H), 7.75 (s, 1H), 7.53-7.45 (m, 2H), 7.25 (d, J=8.4 Hz, 1H), 6.90-6.81 (m, 2H), 3.74 (s, 2H), 3.70 (s, 3H), 3.03 (s, 3H), 2.88-2.78 (m, 7H), 2.78-2.70 (m, 2H), 2.62-2.54 (m, 2H), 2.34-2.27 (m, 6H). LC-MS $(M+H)^{+}$=603.5.

Example 28: N, N, 2-trimethyl-4-(2-(5-methyl-2-(3-oxo-3-(tetrahydro-2H-pyran-4-ylamino)propyl)-1, 2, 3, 4-tetrahydroisoquinolin-7-yl)-5H-pyrrolo[2, 3-b]pyrazin-7-yl)benzamide

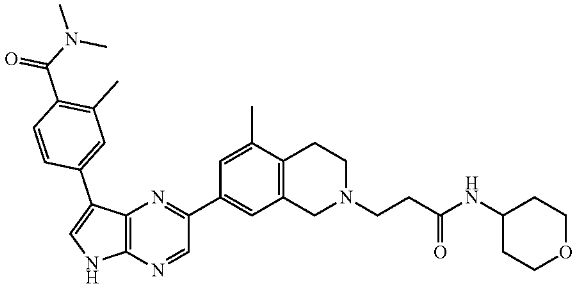 [SMILES: Cc1cc(-c2c[nH]c3ncc(-c4cc(C)c5c(c4)CN(CCC(=O)NC4CCOCC4)CC5)nc23)ccc1C(=O)N(C)C]

Step 1: N, N, 2-trimethyl-4-(2-(5-methyl-2-(3-oxo-3-(tetrahydro-2H-pyran-4-ylamino)propyl)-1, 2, 3, 4-tetrahydroisoquinolin-7-yl)-5-tosyl-5H-pyrrolo[2, 3-b]pyrazin-7-yl)benzamide

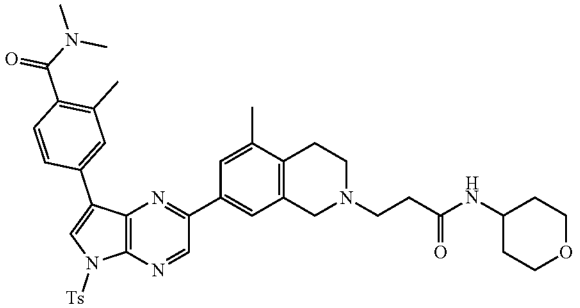 [SMILES: Cc1ccc(S(=O)(=O)n2cc(-c3ccc(C(=O)N(C)C)c(C)c3)c3nc(-c4cc(C)c5c(c4)CN(CCC(=O)NC4CCOCC4)CC5)cnc32)cc1]

The title compound (107 mg, 47%) was prepared in a manner similar to that in Example 23 step 4 from 3-(7-(7-(4-(dimethylcarbamoyl)-3-methylphenyl)-5-tosyl-5H-pyrrolo[2, 3-b]pyrazin-2-yl)-5-methyl-3, 4-dihydroisoquinolin-2 (1H)-yl)propanoic acid and tetrahydro-2H-pyran-4-amine. LC-MS $(M+H)^{+}$=735.3.

Step 2: N, N, 2-trimethyl-4-(2-(5-methyl-2-(3-oxo-3-(tetrahydro-2H-pyran-4-ylamino)propyl)-1, 2, 3, 4-tetrahydroisoquinolin-7-yl)-5H-pyrrolo[2, 3-b]pyrazin-7-yl)benzamide

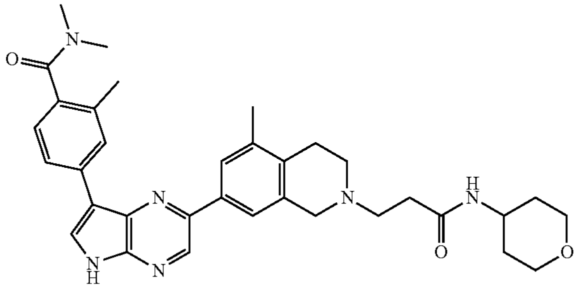 [SMILES: Cc1cc(-c2c[nH]c3ncc(-c4cc(C)c5c(c4)CN(CCC(=O)NC4CCOCC4)CC5)nc23)ccc1C(=O)N(C)C]

Example 28 (30 mg, 37%) was prepared in a manner similar to that in Example 1 step 10 from N, N, 2-trimethyl-4-(2-(5-methyl-2-(3-oxo-3-(tetrahydro-2H-pyran-4-ylamino)propyl)-1, 2, 3, 4-tetrahydroisoquinolin-7-yl)-5-tosyl-5H-pyrrolo[2, 3-b]pyrazin-7-yl)benzamide. $^1$H NMR (400 MHz, DMSO-d6) δ 12.34 (s, 1H), 8.87 (s, 1H), 8.46 (s, 1H), 8.26-8.19 (m, 2H), 7.97 (d, J=7.6 Hz, 1H), 7.86 (s, 1H), 7.73 (s, 1H), 7.25 (d, J=8.4 Hz, 1H), 3.83-3.70 (m, 3H), 3.69 (s, 2H), 3.37-3.34 (m, 1H), 3.32-3.29 (m, 1H), 3.03 (s, 3H), 2.84 (s, 3H), 2.79-2.70 (m, 6H), 2.41-2.33 (m, 2H), 2.33-2.27 (m, 6H), 1.73-1.65 (m, 2H), 1.43-1.29 (m, 2H). LC-MS $(M+H)^+$=581.3.

Example 29: (R)-4-(2-(2-(3-(2-hydroxypropylamino)-3-oxopropyl)-5-methyl-1, 2, 3, 4-tetrahydroisoquinolin-7-yl)-5H-pyrrolo[2, 3-b]pyrazin-7-yl)-N, N, 2-trimethylbenzamide

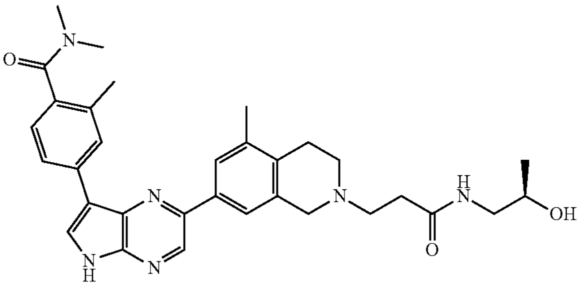 [SMILES: Cc1cc(-c2c[nH]c3ncc(-c4cc(C)c5c(c4)CN(CCC(=O)NC[C@@H](C)O)CC5)nc23)ccc1C(=O)N(C)C]

Step 1: (R)-4-(2-(2-(3-(2-hydroxypropylamino)-3-oxopropyl)-5-methyl-1, 2, 3, 4-tetrahydroisoquinolin-7-yl)-5-tosyl-5H-pyrrolo[2, 3-b]pyrazin-7-yl)-N, N, 2-trimethylbenzamide

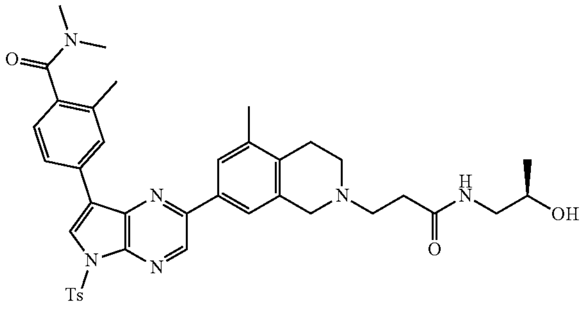 [SMILES: Cc1ccc(S(=O)(=O)n2cc(-c3ccc(C(=O)N(C)C)c(C)c3)c3nc(-c4cc(C)c5c(c4)CN(CCC(=O)NC[C@@H](C)O)CC5)cnc32)cc1]

The title compound (69 mg, 48%) was prepared in a manner similar to that in Example 23 step 4 from 3-(7-(7-(4-(dimethylcarbamoyl)-3-methylphenyl)-5-tosyl-5H-pyrrolo[2, 3-b]pyrazin-2-yl)-5-methyl-3, 4-dihydroisoquinolin-2 (1H)-yl)propanoic acid and (R)-1-aminopropan-2-ol. LC-MS $(M+H)^+$=709.4.

Step 2: (R)-4-(2-(2-(3-(2-hydroxypropylamino)-3-oxopropyl)-5-methyl-1, 2, 3, 4-tetrahydroisoquinolin-7-yl)-5H-pyrrolo[2, 3-b]pyrazin-7-yl)-N, N, 2-trimethylbenzamide

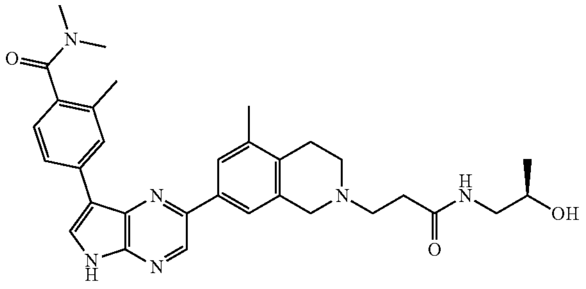 [SMILES: Cc1cc(-c2c[nH]c3ncc(-c4cc(C)c5c(c4)CN(CCC(=O)NC[C@@H](C)O)CC5)nc23)ccc1C(=O)N(C)C]

Example 29 (20 mg, 23%) was prepared in a manner similar to that in Example 1 step 10 from (R)-4-(2-(2-(3-(2-hydroxypropylamino)-3-oxopropyl)-5-methyl-1, 2, 3, 4-tetrahydroisoquinolin-7-yl)-5-tosyl-5H-pyrrolo[2, 3-b]pyrazin-7-yl)-N, N, 2-trimethylbenzamide. $^1$H NMR (400 MHz, DMSO-d6) δ 12.33 (s, 1H), 8.86 (s, 1H), 8.46 (s, 1H), 8.25-8.19 (m, 2H), 8.00-7.93 (m, 1H), 7.86 (s, 1H), 7.73 (s, 1H), 7.28-7.19 (m, 1H), 4.66-4.60 (m, 1H), 3.68 (s, 2H), 3.67-3.57 (m, 1H), 3.05-2.95 (m, 5H), 2.84 (s, 3H), 2.80-2.70 (m, 6H), 2.40 (t, J=7.2 Hz, 2H), 2.33-2.27 (m, 6H), 1.03-0.97 (m, 3H). LC-MS $(M+H)^+$=555.3.

Example 30: (S)-4-(2-(2-(3-(2-hydroxypropylamino)-3-oxopropyl)-5-methyl-1, 2, 3, 4-tetrahydroisoquinolin-7-yl)-5H-pyrrolo[2, 3-b]pyrazin-7-yl)-N, N, 2-trimethylbenzamide

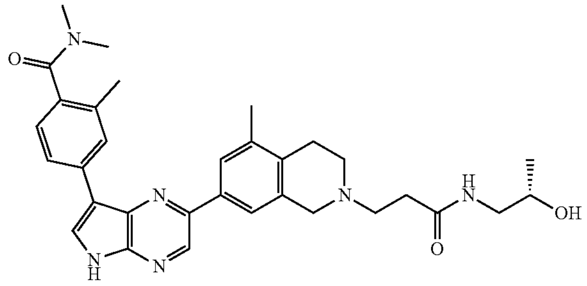 [SMILES: Cc1cc(-c2c[nH]c3ncc(-c4cc(C)c5c(c4)CN(CCC(=O)NC[C@H](C)O)CC5)nc23)ccc1C(=O)N(C)C]

Step 1: (S)-4-(2-(2-(3-(2-hydroxypropylamino)-3-oxopropyl)-5-methyl-1, 2, 3, 4-tetrahydroisoquinolin-7-yl)-5-tosyl-5H-pyrrolo[2, 3-b]pyrazin-7-yl)-N, N, 2-trimethylbenzamide

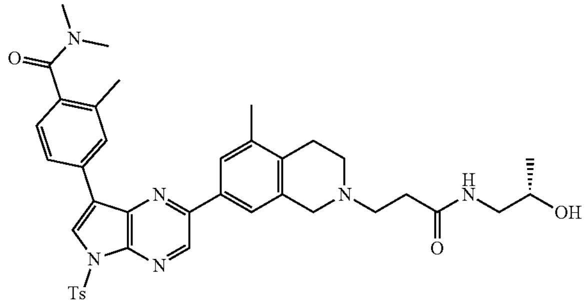 [SMILES: Cc1ccc(S(=O)(=O)n2cc(-c3ccc(C(=O)N(C)C)c(C)c3)c3nc(-c4cc(C)c5c(c4)CN(CCC(=O)NC[C@H](C)O)CC5)cnc32)cc1]

The title compound (74 mg, 54%) was prepared in a manner similar to that in Example 23 step 4 from 3-(7-(7-(4-(dimethylcarbamoyl)-3-methylphenyl)-5-tosyl-5H-pyrrolo[2, 3-b]pyrazin-2-yl)-5-methyl-3, 4-dihydroisoquinolin-2 (1H)-yl)propanoic acid and (S)-1-aminopropan-2-ol. LC-MS $(M+H)^+$=709.6.

Step 2: (S)-4-(2-(2-(3-(2-hydroxypropylamino)-3-oxopropyl)-5-methyl-1, 2, 3, 4-tetrahydroisoquinolin-7-yl)-5H-pyrrolo[2, 3-b]pyrazin-7-yl)-N, N, 2-trimethylbenzamide

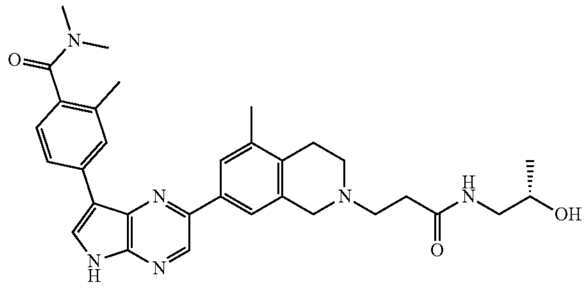 [SMILES: Cc1cc(-c2c[nH]c3ncc(-c4cc(C)c5c(c4)CN(CCC(=O)NC[C@H](C)O)CC5)nc23)ccc1C(=O)N(C)C]

Example 30 (11 mg, 18%) was prepared in a manner similar to that in Example 1 step 10 from (S)-4-(2-(2-(3-(2-hydroxypropylamino)-3-oxopropyl)-5-methyl-1, 2, 3, 4-tetrahydroisoquinolin-7-yl)-5-tosyl-5H-pyrrolo[2, 3-b]pyrazin-7-yl)-N, N, 2-trimethylbenzamide. $^1H$ NMR (400 MHz, DMSO-d6) δ 12.33 (s, 1H), 8.86 (s, 1H), 8.46 (s, 1H), 8.25-8.19 (m, 2H), 8.01-7.94 (m, 1H), 7.86 (s, 1H), 7.73 (s, 1H), 7.28-7.22 (m, 1H), 4.64 (s, 1H), 3.68 (s, 2H), 3.67-3.57 (m, 1H), 3.05-2.95 (m, 5H), 2.84 (s, 3H), 2.80-2.69 (m, 6H), 2.40 (t, J=7.1 Hz, 2H), 2.33-2.27 (m, 6H), 1.03-0.97 (m, 3H). LC-MS $(M+H)^+$=555.5.

Example 31: 4-(2-(2-(3-(1-(hydroxymethyl)cyclopropylamino)-3-oxopropyl)-5-methyl-1, 2, 3, 4-tetrahydroisoquinolin-7-yl)-5H-pyrrolo[2, 3-b]pyrazin-7-yl)-N, N, 2-trimethylbenzamide

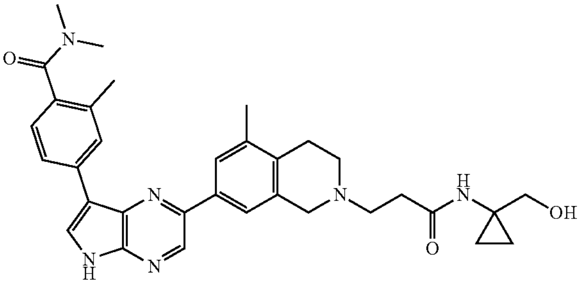 [SMILES: Cc1cc(-c2c[nH]c3ncc(-c4cc(C)c5c(c4)CN(CCC(=O)NC4(CO)CC4)CC5)nc23)ccc1C(=O)N(C)C]

Step 1: 4-(2-(2-(3-(1-(hydroxymethyl)cyclopropylamino)-3-oxopropyl)-5-methyl-1, 2, 3, 4-tetrahydroisoquinolin-7-yl)-5-tosyl-5H-pyrrolo[2, 3-b]pyrazin-7-yl)-N, N, 2-trimethylbenzamide

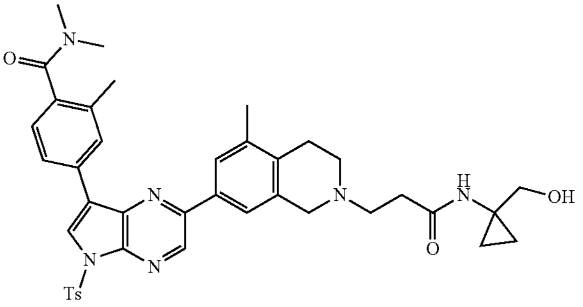 [SMILES: Cc1ccc(S(=O)(=O)n2cc(-c3ccc(C(=O)N(C)C)c(C)c3)c3nc(-c4cc(C)c5c(c4)CN(CCC(=O)NC4(CO)CC4)CC5)cnc32)cc1]

The title compound (81 mg, 73%) was prepared in a manner similar to that in Example 23 step 4 from 3-(7-(7-(4-(dimethylcarbamoyl)-3-methylphenyl)-5-tosyl-5H-pyrrolo[2, 3-b]pyrazin-2-yl)-5-methyl-3, 4-dihydroisoquinolin-2 (1H)-yl)propanoic acid and (1-aminocyclopropyl) methanol. LC-MS $(M+H)^+$=721.1.

Step 2: 4-(2-(2-(3-(1-(hydroxymethyl)cyclopropylamino)-3-oxopropyl)-5-methyl-1, 2, 3, 4-tetrahydroisoquinolin-7-yl)-5H-pyrrolo[2, 3-b]pyrazin-7-yl)-N, N, 2-trimethylbenzamide

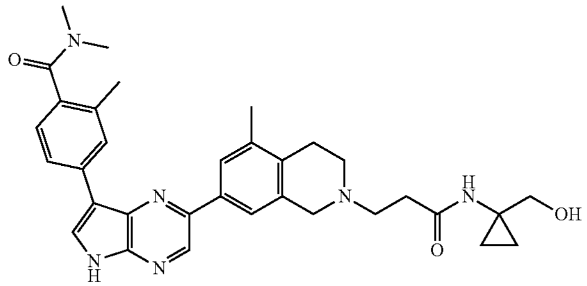 [SMILES: Cc1cc(-c2c[nH]c3ncc(-c4cc(C)c5c(c4)CN(CCC(=O)NC4(CO)CC4)CC5)nc23)ccc1C(=O)N(C)C]

Example 31 (35 mg, 40%) was prepared in a manner similar to that in Example 1 step 10 from 4-(2-(2-(3-(1-(hydroxymethyl)cyclopropylamino)-3-oxopropyl)-5-methyl-1, 2, 3, 4-tetrahydroisoquinolin-7-yl)-5-tosyl-5H-pyrrolo[2, 3-b]pyrazin-7-yl)-N, N, 2-trimethylbenzamide. $^{1}$H NMR (400 MHz, DMSO-d6) δ 12.34 (s, 1H), 8.87 (s, 1H), 8.46 (s, 1H), 8.27-8.19 (m, 3H), 7.86 (s, 1H), 7.73 (s, 1H), 7.25 (d, J=8.3 Hz, 1H), 4.74-4.67 (m, 1H), 3.67 (s, 2H), 3.43-3.38 (m, 2H), 3.03 (s, 3H), 2.84 (s, 3H), 2.75-2.71 (m, 6H), 2.37-2.28 (m, 8H), 0.69-0.58 (m, 2H), 0.61-0.50 (m, 2H). LC-MS (M+H)$^+$=567.3.

Example 32: 4-(2-(2-(3-((1-hydroxycyclopropyl)methylamino)-3-oxopropyl)-5-methyl-1, 2, 3, 4-tetrahydroisoquinolin-7-yl)-5H-pyrrolo[2, 3-b]pyrazin-7-yl)-N, N, 2-trimethylbenzamide

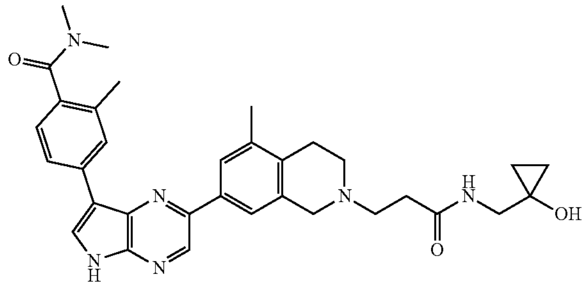 [SMILES: Cc1cc(-c2c[nH]c3ncc(-c4cc(C)c5c(c4)CN(CCC(=O)NCC4(O)CC4)CC5)nc23)ccc1C(=O)N(C)C]

Step 1: 4-(2-(2-(3-((1-hydroxycyclopropyl)methylamino)-3-oxopropyl)-5-methyl-1, 2, 3, 4-tetrahydroisoquinolin-7-yl)-5-tosyl-5H-pyrrolo[2, 3-b]pyrazin-7-yl)-N, N, 2-trimethylbenzamide

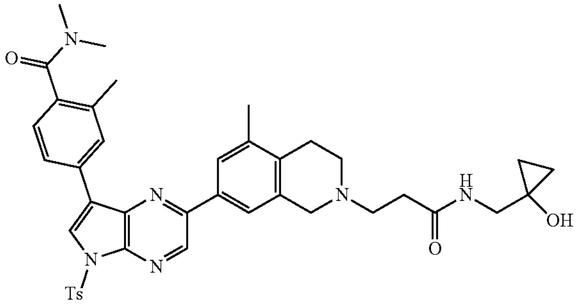 [SMILES: Cc1ccc(S(=O)(=O)n2cc(-c3ccc(C(=O)N(C)C)c(C)c3)c3nc(-c4cc(C)c5c(c4)CN(CCC(=O)NCC4(O)CC4)CC5)cnc32)cc1]

The title compound (106 mg, 52%) was prepared in a manner similar to that in Example 23 step 4 from 3-(7-(7-(4-(dimethylcarbamoyl)-3-methylphenyl)-5-tosyl-5H-pyrrolo[2, 3-b]pyrazin-2-yl)-5-methyl-3, 4-dihydroisoquinolin-2 (1H)-yl)propanoic acid and 1-(aminomethyl) cyclopropanol. LC-MS (M+H)$^+$=721.6.

Step 2: 4-(2-(2-(3-((1-hydroxycyclopropyl)methylamino)-3-oxopropyl)-5-methyl-1, 2, 3, 4-tetrahydroisoquinolin-7-yl)-5H-pyrrolo[2, 3-b]pyrazin-7-yl)-N, N, 2-trimethylbenzamide

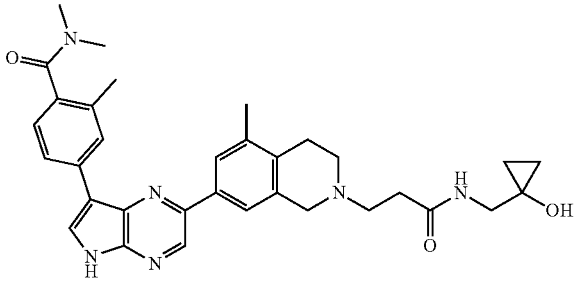 [SMILES: Cc1cc(-c2c[nH]c3ncc(-c4cc(C)c5c(c4)CN(CCC(=O)NCC4(O)CC4)CC5)nc23)ccc1C(=O)N(C)C]

Example 32 (34 mg, 47%) was prepared in a manner similar to that in Example 1 step 10 from 4-(2-(2-(3-((1-hydroxycyclopropyl)methylamino)-3-oxopropyl)-5-methyl-1, 2, 3, 4-tetrahydroisoquinolin-7-yl)-5-tosyl-5H-pyrrolo[2, 3-b]pyrazin-7-yl)-N, N, 2-trimethylbenzamide. $^{1}$H NMR (400 MHz, DMSO-d6) δ 12.34 (s, 1H), 8.87 (s, 1H), 8.46 (s, 1H), 8.26-8.20 (m, 2H), 8.06-8.02 (m, 1H), 7.87 (s, 1H), 7.74 (s, 1H), 7.25 (d, J=8.3 Hz, 1H), 5.28 (s, 1H), 3.70 (s, 2H), 3.22 (d, J=5.7 Hz, 2H), 3.03 (s, 3H), 2.84 (s, 3H), 2.78-2.73 (m, 6H), 2.45-2.40 (m, 2H), 2.34-2.28 (m, 6H), 0.52-0.41 (m, 4H). LC-MS (M+H)$^+$=567.5.

Example 33: 4-(2-(2-(3-(2-hydroxy-2-methylpropylamino)-3-oxopropyl)-5-methyl-1, 2, 3, 4-tetrahydroisoquinolin-7-yl)-5H-pyrrolo[2, 3-b]pyrazin-7-yl)-N, N, 2-trimethylbenzamide

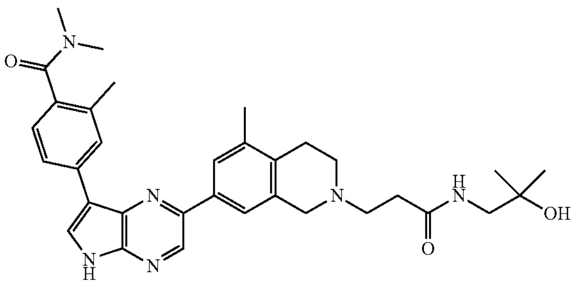 [SMILES: Cc1cc(-c2c[nH]c3ncc(-c4cc(C)c5c(c4)CN(CCC(=O)NCC(C)(C)O)CC5)nc23)ccc1C(=O)N(C)C]

Step 1: 4-(2-(2-(3-(2-hydroxy-2-methylpropylamino)-3-oxopropyl)-5-methyl-1, 2, 3, 4-tetrahydroisoquinolin-7-yl)-5-tosyl-5H-pyrrolo[2, 3-b]pyrazin-7-yl)-N, N, 2-trimethylbenzamide

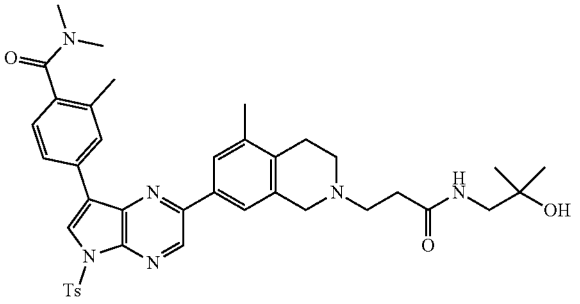 [SMILES: Cc1ccc(S(=O)(=O)n2cc(-c3ccc(C(=O)N(C)C)c(C)c3)c3nc(-c4cc(C)c5c(c4)CN(CCC(=O)NCC(C)(C)O)CC5)cnc32)cc1]

The title compound (93 mg, 63%) was prepared in a manner similar to that in Example 23 step 4 from 3-(7-(7-(4-(dimethylcarbamoyl)-3-methylphenyl)-5-tosyl-5H-pyrrolo[2, 3-b]pyrazin-2-yl)-5-methyl-3, 4-dihydroisoquinolin-2 (1H)-yl)propanoic acid and 1-amino-2-methylpropan-2-ol. LC-MS $(M+H)^+$=723.4.

Step 2: 4-(2-(2-(3-(2-hydroxy-2-methylpropylamino)-3-oxopropyl)-5-methyl-1, 2, 3, 4-tetrahydroisoquinolin-7-yl)-5H-pyrrolo[2, 3-b]pyrazin-7-yl)-N, N, 2-trimethylbenzamide

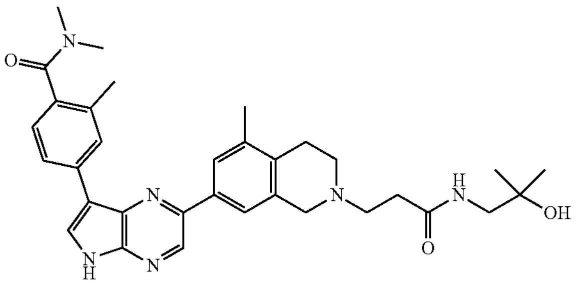 [SMILES: Cc1cc(-c2c[nH]c3ncc(-c4cc(C)c5c(c4)CN(CCC(=O)NCC(C)(C)O)CC5)nc23)ccc1C(=O)N(C)C]

Example 33 (29 mg, 31%) was prepared in a manner similar to that in Example 1 step 10 from 4-(2-(2-(3-(2-hydroxy-2-methylpropylamino)-3-oxopropyl)-5-methyl-1, 2, 3, 4-tetrahydroisoquinolin-7-yl)-5-tosyl-5H-pyrrolo[2, 3-b]pyrazin-7-yl)-N, N, 2-trimethylbenzamide. $^1$H NMR (400 MHz, DMSO-d6) δ 12.33 (s, 1H), 8.86 (s, 1H), 8.46 (s, 1H), 8.26-8.19 (m, 2H), 7.98-7.90 (m, 1H), 7.86 (s, 1H), 7.73 (s, 1H), 7.25 (d, J=8.4 Hz, 1H), 4.40 (s, 1H), 3.71 (s, 2H), 3.06-3.00 (m, 5H), 2.84 (s, 3H), 2.80-2.72 (m, 6H), 2.44 (t, J=6.9 Hz, 2H), 2.33-2.27 (m, 6H), 1.02 (s, 6H). LC-MS $(M+H)^+$=569.4.

Example 34: (R)—N, N, 2-trimethyl-4-(2-(5-methyl-2-(3-oxo-3-(tetrahydrofuran-3-ylamino)propyl)-1, 2, 3, 4-tetrahydroisoquinolin-7-yl)-5H-pyrrolo[2, 3-b]pyrazin-7-yl)benzamide

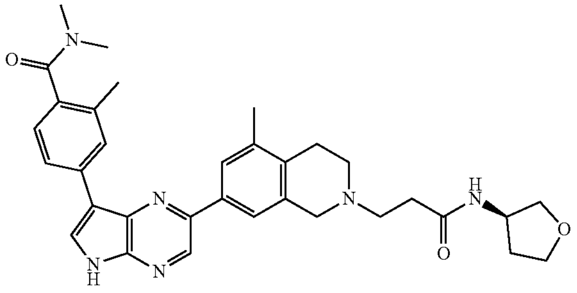 [SMILES: Cc1cc(-c2c[nH]c3ncc(-c4cc(C)c5c(c4)CN(CCC(=O)N[C@@H]4CCOC4)CC5)nc23)ccc1C(=O)N(C)C]

Step 1: (R)—N, N, 2-trimethyl-4-(2-(5-methyl-2-(3-oxo-3-(tetrahydrofuran-3-ylamino)propyl)-1, 2, 3, 4-tetrahydroisoquinolin-7-yl)-5-tosyl-5H-pyrrolo[2, 3-b]pyrazin-7-yl)benzamide

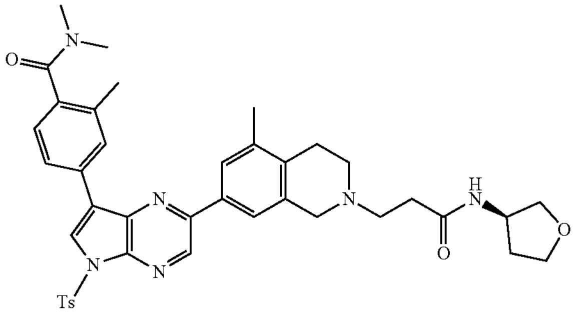 [SMILES: Cc1ccc(S(=O)(=O)n2cc(-c3ccc(C(=O)N(C)C)c(C)c3)c3nc(-c4cc(C)c5c(c4)CN(CCC(=O)N[C@@H]4CCOC4)CC5)cnc32)cc1]

The title compound (103 mg, 51%) was prepared in a manner similar to that in Example 23 step 4 from 3-(7-(7-(4-(dimethylcarbamoyl)-3-methylphenyl)-5-tosyl-5H-pyrrolo[2, 3-b]pyrazin-2-yl)-5-methyl-3, 4-dihydroisoquinolin-2 (1H)-yl)propanoic acid and (R)-tetrahydrofuran-3-amine. LC-MS $(M+H)^+$=721.5.

Step 2: (R)—N, N, 2-trimethyl-4-(2-(5-methyl-2-(3-oxo-3-(tetrahydrofuran-3-ylamino)propyl)-1, 2, 3, 4-tetrahydroisoquinolin-7-yl)-5H-pyrrolo[2, 3-b] pyrazin-7-yl)benzamide

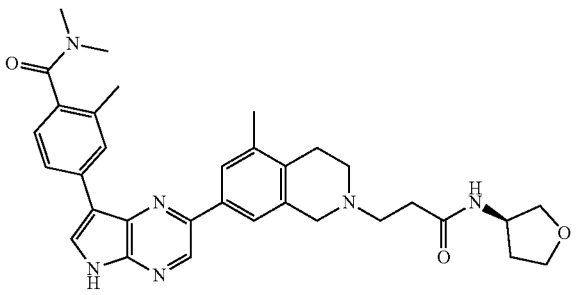 [SMILES: Cc1cc(-c2c[nH]c3ncc(-c4cc(C)c5c(c4)CN(CCC(=O)N[C@@H]4CCOC4)CC5)nc23)ccc1C(=O)N(C)C]

Example 34 (22 mg, 18%) was prepared in a manner similar to that in Example 1 step 10 from (R)—N, N, 2-trimethyl-4-(2-(5-methyl-2-(3-oxo-3-(tetrahydrofuran-3-ylamino)propyl)-1, 2, 3, 4-tetrahydroisoquinolin-7-yl)-5-tosyl-5H-pyrrolo[2, 3-b]pyrazin-7-yl)benzamide. $^1H$ NMR (400 MHz, DMSO-d6) δ 12.34 (s, 1H), 8.87 (s, 1H), 8.46 (s, 1H), 8.26-8.17 (m, 3H), 7.86 (s, 1H), 7.73 (s, 1H), 7.25 (d, J=8.3 Hz, 1H), 4.29-4.18 (m, 1H), 3.79-3.61 (m, 5H), 3.47-3.39 (m, 1H), 3.03 (s, 3H), 2.84 (s, 3H), 2.78-2.70 (m, 6H), 2.38 (t, J=7.2 Hz, 2H), 2.33-2.28 (m, 6H), 2.13-1.99 (m, 1H), 1.75-1.64 (m, 1H). LC-MS $(M+H)^+$=567.4.

Example 35: (S)-4-(2-(2, 5-dimethyl-1, 2, 3, 4-tetrahydroisoquinolin-7-yl)-5H-pyrrolo[2, 3-b]pyrazin-7-yl)-N-methyl-N-((tetrahydrofuran-3-yl)methyl) benzamide Step 1: (S)-4-bromo-N-((tetrahydrofuran-3-yl) methyl)benzamide

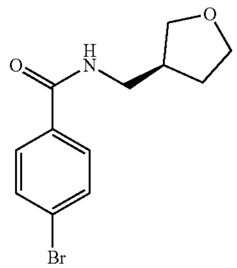 [SMILES: O=C(NC[C@@H]1CCOC1)c1ccc(Br)cc1]

To a solution of 4-bromobenzoic acid (2.0 g, 9.9 mmol) and (S)-(tetrahydrofuran-3-yl)methanamine (1.0 g, 9.9 mmol) in DMF (20 mL) was added HATU (5.64 g, 14.9 mmol) and DIPEA (2.55 g, 19.8 mmol). The resulting solution was stirred at room temperature overnight. Water (20 mL) was added and the solution extracted with EtOAc (20 mL×3). The combined organic layer was washed with brine, dried over $Na_2SO_4$, filtered and concentrated. The residue was purified by silica gel chromatography, eluted with $CH_2Cl_2$/MeOH (100:1) to give the title compound (4.6 g, contained DMF). The material was used in step 2 without further purifications. LC-MS $(M+H)^+$=283.8, 285.8.

Step 2: (S)-4-bromo-N-methyl-N-((tetrahydrofuran-3-yl)methyl)benzamide

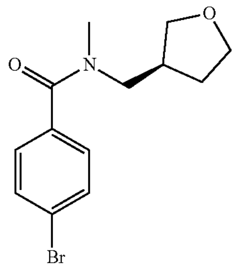 [SMILES: CN(C[C@@H]1CCOC1)C(=O)c1ccc(Br)cc1]

NaH (1.3 g, 32.4 mmol, 60%) was added to a solution of (S)-4-bromo-N-((tetrahydrofuran-3-yl)methyl)benzamide (4.6 g, from step 1) in DMF (30 mL) at 0° C. under $N_2$. The resulting solution was stirred at 0° C. for 1 h, and MeI (3.45 g, 24.3 mmol) was added dropwise. The solution was warmed to room temperature and stirred for 1 h. Water (30 mL) was added and the solution was extracted with EtOAc (30 mL×3). The combined organic layer was washed with brine, dried over $Na_2SO_4$, filtered and concentrated. The residue was purified by silica gel chromatography, eluted with DCM/MeOH (100:1) to give the title compound (2.42 g, 82% for 2 steps). LC-MS $(M+H)^+$=297.8, 299.8.

Step 3: (S)—N-methyl-N-((tetrahydrofuran-3-yl) methyl)-4-(4, 4, 5, 5-tetramethyl-1, 3, 2-dioxaborolan-2-yl)benzamide

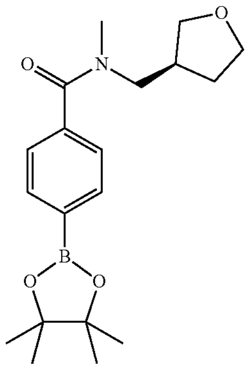 [SMILES: CN(C[C@@H]1CCOC1)C(=O)c1ccc(B2OC(C)(C)C(C)(C)O2)cc1]

To a solution of (S)-4-bromo-N-methyl-N-((tetrahydrofuran-3-yl)methyl)benzamide (2.42 g, 8.12 mmol) in 1, 4-dioxane (50 mL) was added BPD (3.09 g, 12.2 mmol) and Pd (dppf)$Cl_2$·DCM (332 mg, 0.406 mmol) and KOAc (1.59 g, 16.2 mmol) under $N_2$. The resulting solution was stirred at 90° C. overnight. Water (50 mL) was added and the mixture was extracted with EtOAc (50 mL×3). The combined organic layer was washed with brine, dried over $Na_2SO_4$, filtered and concentrated. The residue was purified by silica gel chromatography, eluted with EtOAc/PE (1:3) to give the title compound (2.53 g, 90%). $^1H$ NMR (400 MHz, $CDCl_3$) δ 7.83 (d, J=7.8 Hz, 2H), 7.36 (d, J=7.1 Hz, 2H), 4.02-3.19 (m, 6H), 3.16-2.89 (m, 3H), 2.79-2.45 (m, 1H), 2.15-1.66 (m, 2H), 1.35 (s, 12H). LC-MS $(M+H)^+$=346.0.

Step 4: (S)-4-(2-bromo-5-tosyl-5H-pyrrolo[2, 3-b] pyrazin-7-yl)-N-methyl-N-((tetrahydrofuran-3-yl) methyl)benzamide

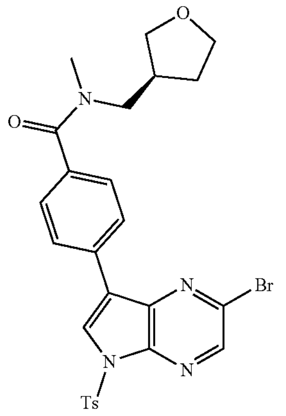 [SMILES: Cc1ccc(S(=O)(=O)n2cc(-c3ccc(C(=O)N(C)C[C@@H]4CCOC4)cc3)c3nc(Br)cnc32)cc1]

To a solution of (S)—N-methyl-N-((tetrahydrofuran-3-yl) methyl)-4-(4, 4, 5, 5-tetramethyl-1, 3, 2-dioxaborolan-2-yl) benzamide (400 mg, 1.16 mmol) and 2-bromo-7-iodo-5-tosyl-5H-pyrrolo[2, 3-b]pyrazine (665 mg, 1.39 mmol) in dioxane (40 mL) and $H_2O$ (8 mL) were added Pd (dppf)$Cl_2$ (85 mg, 0.116 mmol) and $K_2CO_3$ (320 mg, 2.32 mmol) under $N_2$. The mixture was refluxed for 5 h under a condenser. The mixture was cooled to room temperature and diluted with EtOAc (50 mL), then washed with brine (50 mL), dried over $Na_2SO_4$, and concentrated under reduced pressure. The residue was purified by silica gel chromatography, eluted with EtOAc/PE (1:3) to give the title compound (350 mg, 58%). LC-MS $(M+H)^+$=568.9, 570.9.

Step 5: (S)-4-(2-(2, 5-dimethyl-1, 2, 3, 4-tetrahydroisoquinolin-7-yl)-5H-pyrrolo[2, 3-b]pyrazin-7-yl)-N-methyl-N-((tetrahydrofuran-3-yl)methyl)benzamide

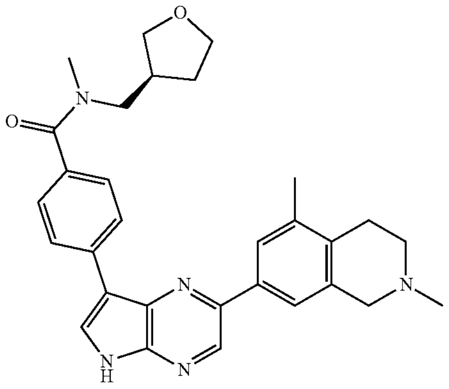 [SMILES: Cc1cc(-c2cnc3[nH]cc(-c4ccc(C(=O)N(C)C[C@@H]5CCOC5)cc4)c3n2)cc2c1CCN(C)C2]

((S)-4-(2-bromo-5-tosyl-5H-pyrrolo[2, 3-b]pyrazin-7-yl)-N-methyl-N-((tetrahydrofuran-3-yl)methyl)benzamide (150 mg, 0.263 mmol), 2, 5-dimethyl-7-(4, 4, 5, 5-tetramethyl-1, 3, 2-dioxaborolan-2-yl)-1, 2, 3, 4-tetrahydroisoquinoline (100 mg, 0.35 mmol), Pd (dppf)$Cl_2$ (19 mg, 0.026 mmol) and $K_2CO_3$ (73 mg, 0.526 mmol) was added to dioxane (10 mL) and water (4 mL) under nitrogen. The reaction mixture was heated to reflux overnight. The mixture was partitioned between EtOAc (10 mL) and water (10 mL) and the aqueous layer was extracted with EtOAc (10 mL×2). The combined organic layer was dried over $Na_2SO_4$ then concentrated under reduced pressure. The residue was purified by prep-TLC, developed with MeOH/DCM (1:10) to give Example 35 (55 mg, 42%). $^1$H NMR (400 MHz, DMSO-d6) δ 12.39 (s, 1H), 8.87 (s, 1H), 8.52 (d, J=2.6 Hz, 1H), 8.43-8.35 (m, 2H), 7.85 (s, 1H), 7.74 (s, 1H), 7.54-7.42 (m, 2H), 3.85-3.44 (m, 8H), 3.00 (s, 3H), 2.79-2.63 (m, 5H), 2.39 (s, 3H), 2.31 (s, 3H), 2.08-1.52 (m, 2H). LC-MS $(M+H)^+$=496.0.

Example 36: (S)-4-(2-(2-(2-(4-hydroxy-4-methylpiperidin-1-yl)ethyl)-5-methyl-1, 2, 3, 4-tetrahydroisoquinolin-7-yl)-5H-pyrrolo[2, 3-b]pyrazin-7-yl)-N-methyl-N-((tetrahydrofuran-3-yl)methyl) benzamide

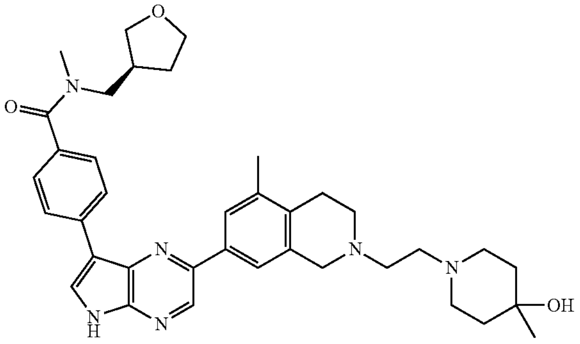 [SMILES: Cc1cc(-c2cnc3[nH]cc(-c4ccc(C(=O)N(C)C[C@@H]5CCOC5)cc4)c3n2)cc2c1CCN(CCN1CCC(C)(O)CC1)C2]

Step 1: 2-(7-bromo-5-methyl-3, 4-dihydroisoquinolin-2 (1H)-yl)ethan-1-ol

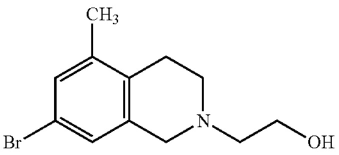

A suspension of 7-bromo-5-methyl-1, 2, 3, 4-tetrahydroisoquinoline (630 mg, 2.79 mmol), 2-bromoethan-1-ol (383 mg, 3.07 mmol) and $K_2CO_3$ (770 mg, 5.58 mmol) in MeCN (20 mL) was stirred at 75° C. overnight. The reaction mixture was cooled and concentrated. The crude was purified by silica gel chromatography, eluted with DCM/MeOH (20:1) to give the title compound (0.50 g, 66%). LCMS $(M+H)^+$=269.9, 271.9.

Step 2: 7-bromo-2-(2-chloroethyl)-5-methyl-1, 2, 3, 4-tetrahydroisoquinoline hydrochloride

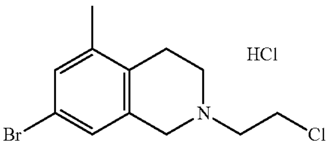

A solution of 2-(7-bromo-5-methyl-3, 4-dihydroisoquinolin-2 (1H)-yl)ethan-1-ol (500 mg, 1.85 mmol) in $SOCl_2$ (5 mL) was stirred at reflux for 2 h. The reaction was cooled to room temperature and the solvent was removed in vacuo to give the title compound (0.60 g, 99%). LCMS $(M+H)^+$ =287.9, 289.9.

Step 3: 1-(2-(7-bromo-5-methyl-3, 4-dihydroisoquinolin-2 (1H)-yl)ethyl)-4-methylpiperidin-4-ol

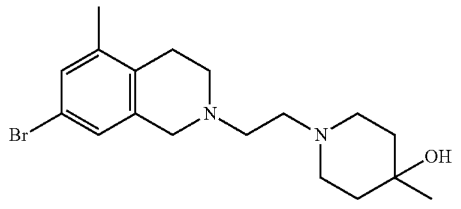 [SMILES: Cc1cc(Br)cc2c1CCN(CCN1CCC(C)(O)CC1)C2]

A suspension of 7-bromo-2-(2-chloroethyl)-5-methyl-1, 2, 3, 4-tetrahydroisoquinoline hydrochloride (600 mg, 1.85 mmol), 4-methylpiperidin-4-ol (213 mg, 1.85 mmol) and $K_2CO_3$ (1.02 g, 7.4 mmol) in MeCN (30 mL) was stirred at 75° C. overnight. The reaction was cooled to room temperature and the solvent was removed in vacuo. The crude was purified by silica gel chromatography, eluted with DCM/MeOH (20:1) to give the title compound (0.48 g, 70%). LCMS $(M+H)^+$=367.0, 369.0.

Step 4: 4-methyl-1-(2-(5-methyl-7-(4, 4, 5, 5-tetramethyl-1, 3, 2-dioxaborolan-2-yl)-3, 4-dihydroisoquinolin-2 (1H)-yl)ethyl)piperidin-4-ol

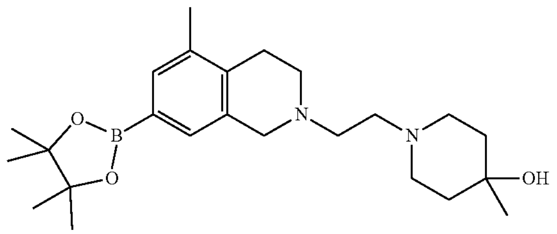 [SMILES: Cc1cc(B2OC(C)(C)C(C)(C)O2)cc2c1CCN(CCN1CCC(C)(O)CC1)C2]

1-(2-(7-bromo-5-methyl-3, 4-dihydroisoquinolin-2 (1H)-yl)ethyl)-4-methylpiperidin-4-ol (480 mg, 1.3 mmol), BPD (497 mg, 1.96 mmol), Pd (dppf)$Cl_2$ (95 mg, 0.13 mmol) and AcOK (255 mg, 2.6 mmol) was added to dioxane (15 mL) under nitrogen. The reaction mixture was stirred at reflux overnight. EtOAc (20 mL) was added and the solution was washed with brine (20 mL×2). The combined organic layer was dried over $Na_2SO_4$ and concentrated. The crude was purified by silica gel chromatography, eluted with DCM/MeOH (50:1 to 30:1) to give the title compound (400 mg, 74%). LC-MS $(M+H)^+$=415.1.

Step 5: (S)-4-(2-(2-(2-(4-hydroxy-4-methylpiperidin-1-yl)ethyl)-5-methyl-1, 2, 3, 4-tetrahydroisoquinolin-7-yl)-5H-pyrrolo[2, 3-b]pyrazin-7-yl)-N-methyl-N-((tetrahydrofuran-3-yl)methyl)benzamide

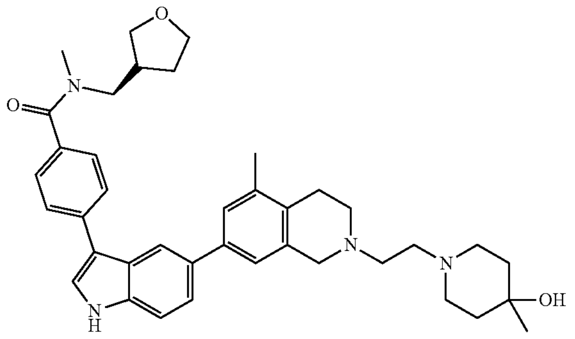

Example 36 (48 mg, 29%) was prepared in a manner similar to that in Example 35 step 5 from ((S)-4-(2-bromo-5-tosyl-5H-pyrrolo[2, 3-b]pyrazin-7-yl)-N-methyl-N-((tetrahydrofuran-3-yl)methyl)benzamide and 4-methyl-1-(2-(5-methyl-7-(4, 4, 5, 5-tetramethyl-1, 3, 2-dioxaborolan-2-yl)-3, 4-dihydroisoquinolin-2 (1H)-yl)ethyl)piperidin-4-ol. $^1H$ NMR (400 MHz, DMSO-d6) δ 12.39 (s, 1H), 8.87 (s, 1H), 8.51 (s, 1H), 8.40 (s, 1H), 8.38 (s, 1H), 7.85 (s, 1H), 7.73 (s, 1H), 7.53-7.43 (m, 2H), 4.13 (s, 1H), 3.85-3.67 (m, 4H), 3.59-3.41 (m, 4H), 2.99 (s, 3H), 2.81-2.71 (m, 4H), 2.67-2.56 (m, 4H), 2.49-2.40 (m, 4H), 2.31 (s, 3H), 2.07-1.82 (m, 2H), 1.70-1.61 (m, 1H), 1.53-1.44 (m, 4H), 1.10 (s, 3H). LC-MS $(M+H)^+$=623.0.

Example 37: 4-(2-(2-(2-(4-hydroxy-4-methylpiperidin-1-yl)ethyl)-5-methyl-1, 2, 3, 4-tetrahydroisoquinolin-7-yl)-5H-pyrrolo[2, 3-b]pyrazin-7-yl)-N, N-dimethylbenzamide

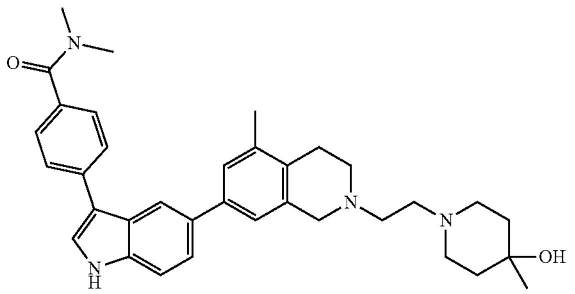 [SMILES: Cc1cc(-c2ccc3[nH]cc(-c4ccc(C(=O)N(C)C)cc4)c3c2)cc2c1CCN(CCN1CCC(C)(O)CC1)C2]

Example 37 (50 mg, 30%) was prepared in a manner similar to that in Example 35 step 5 from 4-(2-bromo-5-tosyl-5H-pyrrolo[2, 3-b]pyrazin-7-yl)-N, N-dimethylbenzamide and 4-methyl-1-(2-(5-methyl-7-(4, 4, 5, 5-tetramethyl-1, 3, 2-dioxaborolan-2-yl)-3, 4-dihydroisoquinolin-2 (1H)-yl)ethyl)piperidin-4-ol. $^1H$ NMR (400 MHz, DMSO-d6) δ 12.39 (s, 1H), 8.87 (s, 1H), 8.51 (s, 1H), 8.39 (s, 1H), 8.37 (s, 1H), 7.84 (s, 1H), 7.72 (s, 1H), 7.53 (s, 1H), 7.50 (s, 1H), 4.09 (s, 1H), 3.69 (s, 2H), 3.01 (s, 6H), 2.80-2.69 (m, 4H), 2.64-2.55 (m, 4H), 2.47-2.38 (m, 4H), 2.30 (s, 3H), 1.50-1.43 (m, 4H), 1.09 (s, 3H). LC-MS $(M+H)^+$=553.0.

Example 38: 4-(2-(2, 5-dimethyl-1, 2, 3, 4-tetrahydroisoquinolin-7-yl)-5H-pyrrolo[2, 3-b]pyrazin-7-yl)-N-(2-hydroxy-2-methylpropyl)-N-methylbenzamide

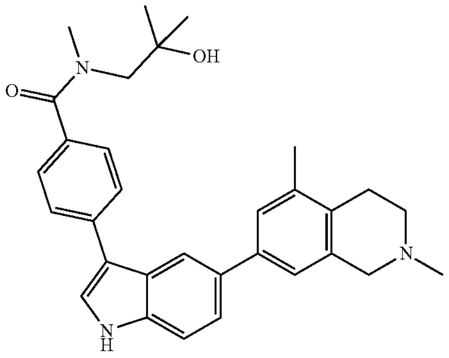 [SMILES: Cc1cc(-c2ccc3[nH]cc(-c4ccc(C(=O)N(C)CC(C)(C)O)cc4)c3c2)cc2c1CCN(C)C2]

Step 1: 4-bromo-N-(2-hydroxy-2-methylpropyl)-N-methylbenzamide

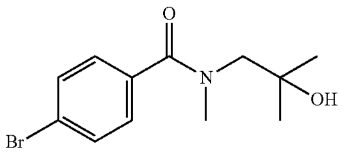 [SMILES: CN(CC(C)(C)O)C(=O)c1ccc(Br)cc1]

4-bromobenzoic acid (1.93 g, 9.61 mmol), 2-methyl-1-(methylamino)propan-2-ol (1.0 g, 9.61 mmol), HATU (4.75 g, 12.5 mmol) and TEA (2.8 mL, 19.2 mmol) was added in DMF (30 mL). The mixture was stirred at room temperature overnight. Water (60 mL) was added and the mixture was extracted with EtOAc (40 mL×3). The combined organic layer was washed with brine (50 mL×3), dried over $Na_2SO_4$, filtered and concentrated under reduced pressure. The residue was purified by silica gel chromatography, eluted with EtOAc/PE (1:5 to 2:1) to give the title compound (2.5 g, 91%). LC-MS $(M+H)^+$=286.0, 288.0.

Step 2: N-(2-hydroxy-2-methylpropyl)-N-methyl-4-(4, 4, 5, 5-tetramethyl-1, 3, 2-dioxaborolan-2-yl)benzamide

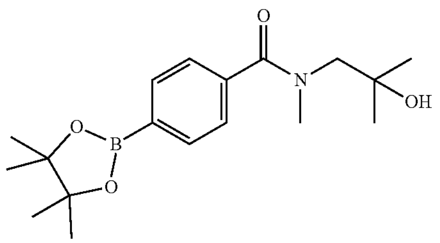 [SMILES: CN(CC(C)(C)O)C(=O)c1ccc(B2OC(C)(C)C(C)(C)O2)cc1]

4-bromo-N-(2-hydroxy-2-methylpropyl)-N-methylbenzamide (2.5 g, 8.7 mmol), BPD (2.2 g, 13 mmol), Pd (dppf)$Cl_2$ (382 mg, 0.52 mmol) and AcOK (1.7 g, 17.4 mmol) was added in dioxane (50 mL) under nitrogen. The reaction mixture was heated to reflux overnight then cooled to room temperature. EtOAc (50 mL) was added and the solution was washed with brine (30 mL×2). The combined organic layer was dried over $Na_2SO_4$, filtered and concentrated under reduced pressure. The residue was purified by silica gel column chromatography, eluted with EtOAc/PE (1:5 to 2:1) to give the title compound (2.8 g, 97%). LC-MS $(M+H)^+$=334.2.

Step 3: 4-(2-bromo-5-tosyl-5H-pyrrolo[2, 3-b]pyrazin-7-yl)-N-(2-hydroxy-2-methylpropyl)-N-methylbenzamide

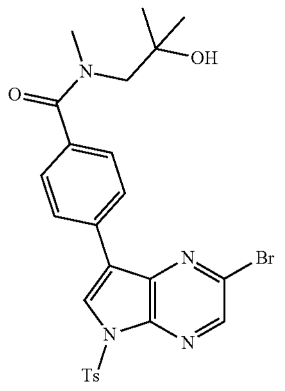 [SMILES: Cc1ccc(S(=O)(=O)n2cc(-c3ccc(C(=O)N(C)CC(C)(C)O)cc3)c3nc(Br)cnc32)cc1]

To a solution of 2-bromo-7-iodo-5-tosyl-5H-pyrrolo[2, 3-b]pyrazine (4.3 g, 9.0 mmol) and N-(2-hydroxy-2-methylpropyl)-N-methyl-4-(4, 4, 5, 5-tetramethyl-1, 3, 2-dioxaborolan-2-yl)benzamide (2.8 g, 8.6 mmol) in dioxane (50 mL) and water (10 mL) was added $K_2CO_3$ (1.6 g, 11.7 mmol) and Pd (dppf)$Cl_2$ (395 mg, 0.54 mmol) under nitrogen atmosphere. After stirring for 5 h at 50° C. under nitrogen atmosphere, the reaction mixture was cooled to room temperature and concentrated under reduced pressure. The crude was purified by silica gel column chromatography, eluted with EtOAc/PE (1:2 to 2:1) to give the title compound (2.5 g, 50%). LCMS $(M+H)^+$=557.0.

Step 4: 4-(2-(2, 5-dimethyl-1, 2, 3, 4-tetrahydroisoquinolin-7-yl)-5H-pyrrolo[2, 3-b]pyrazin-7-yl)-N-(2-hydroxy-2-methylpropyl)-N-methylbenzamide

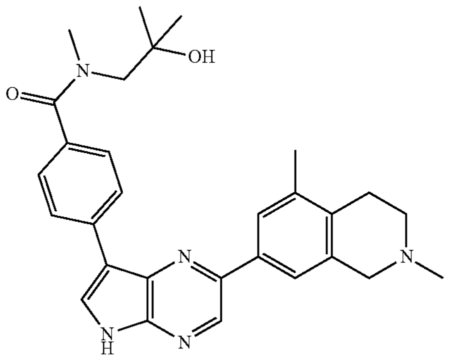 [SMILES: Cc1cc(-c2cnc3[nH]cc(-c4ccc(C(=O)N(C)CC(C)(C)O)cc4)c3n2)cc2c1CCN(C)C2]

Example 38 (28 mg, 21%) was prepared in a manner similar to that in Example 35 step 5 from 4-(2-bromo-5-tosyl-5H-pyrrolo[2, 3-b]pyrazin-7-yl)-N-(2-hydroxy-2-methylpropyl)-N-methylbenzamide and 2, 5-dimethyl-7-(4, 4, 5, 5-tetramethyl-1, 3, 2-dioxaborolan-2-yl)-1, 2, 3, 4-tetrahydroisoquinoline. $^1$H NMR (400 MHz, DMSO-d6) δ 12.45 (s, 1H), 8.93 (s, 1H), 8.57 (d, J=2.8 Hz, 1H), 8.46 (s, 1H), 8.44 (s, 1H), 7.91 (s, 1H), 7.80 (s, 1H), 7.63-7.45 (m, 2H), 4.74 (4.59, 1H), 3.68 (s, 2H), 3.55 (s, 2H), 3.16 (s, 3H), 2.86-2.79 (m, 2H), 2.78-2.73 (m, 2H), 2.45 (s, 3H), 2.38 (s, 3H), 1.28-0.97 (m, 6H). LC-MS $(M+H)^+$=484.0.

Example 39: 4-(2-(2, 5-dimethyl-1, 2, 3, 4-tetrahydroisoquinolin-7-yl)-5H-pyrrolo[2, 3-b]pyrazin-7-yl)-N-(2-hydroxy-2-methylpropyl)-N, 2-dimethylbenzamide

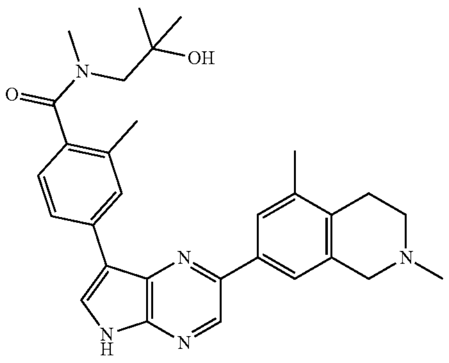 [SMILES: Cc1cc(-c2c[nH]c3ncc(-c4cc(C)c5c(c4)CN(C)CC5)nc23)ccc1C(=O)N(C)CC(C)(C)O]

Step 1: 4-bromo-N-(2-hydroxy-2-methylpropyl)-N, 2-dimethylbenzamide

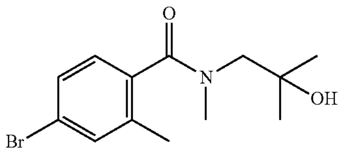 [SMILES: Cc1cc(Br)ccc1C(=O)N(C)CC(C)(C)O]

The title compound (2.5 g, 86%) was prepared in a manner similar to that in Example 38 step 1 from 4-bromo-2-methylbenzoic acid and 2-methyl-1-(methylamino)propan-2-ol. LCMS $(M+H)^+$=300.0, 302.0.

Step 2: N-(2-hydroxy-2-methylpropyl)-N, 2-dimethyl-4-(4, 4, 5, 5-tetramethyl-1, 3, 2-dioxaborolan-2-yl)benzamide

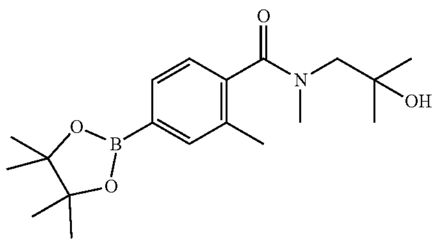 [SMILES: Cc1cc(B2OC(C)(C)C(C)(C)O2)ccc1C(=O)N(C)CC(C)(C)O]

The title compound (2.5 g, 87%) was prepared in a manner similar to that in Example 38 step 2 from 4-bromo-N-(2-hydroxy-2-methylpropyl)-N, 2-dimethylbenzamide and BPD. LC-MS $(M+H)^+$=348.0.

Step 3: 4-(2-bromo-5-tosyl-5H-pyrrolo[2, 3-b]pyrazin-7-yl)-N-(2-hydroxy-2-methylpropyl)-N, 2-dimethylbenzamide

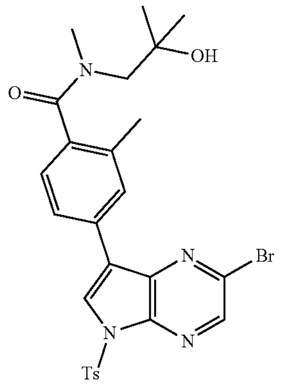 [SMILES: Cc1ccc(S(=O)(=O)n2cc(-c3ccc(C(=O)N(C)CC(C)(C)O)c(C)c3)c3nc(Br)cnc32)cc1]

The title compound (2.5 g, 87%) was prepared in a manner similar to that in Example 38 step 3 from 2-bromo-7-iodo-5-tosyl-5H-pyrrolo[2, 3-b]pyrazine and N-(2-hydroxy-2-methylpropyl)-N, 2-dimethyl-4-(4, 4, 5, 5-tetramethyl-1, 3, 2-dioxaborolan-2-yl)benzamide. LC-MS $(M+H)^+$= 571.0.

Step 4: 4-(2-(2, 5-dimethyl-1, 2, 3, 4-tetrahydroisoquinolin-7-yl)-5H-pyrrolo[2, 3-b]pyrazin-7-yl)-N-(2-hydroxy-2-methylpropyl)-N, 2-dimethylbenzamide

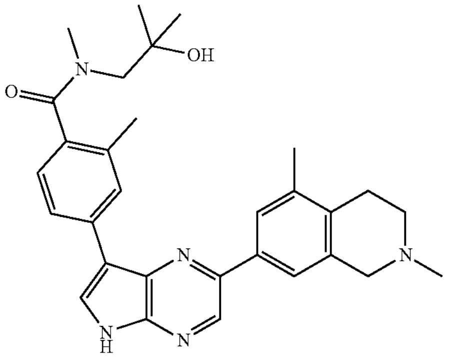 [SMILES: Cc1cc(-c2c[nH]c3ncc(-c4cc(C)c5c(c4)CN(C)CC5)nc23)ccc1C(=O)N(C)CC(C)(C)O]

Example 39 (59 mg, 44%) was prepared in a manner similar to that in Example 35 step 5 from 4-(2-bromo-5-tosyl-5H-pyrrolo[2, 3-b]pyrazin-7-yl)-N-(2-hydroxy-2-methylpropyl)-N, 2-dimethylbenzamide and 2, 5-dimethyl-7-(4, 4, 5, 5-tetramethyl-1, 3, 2-dioxaborolan-2-yl)-1, 2, 3, 4-tetrahydroisoquinoline. $^1$H NMR (400 MHz, DMSO-d6) δ 12.33 (s, 1H), 8.87 (s, 1H), 8.46 (d, J=2.6 Hz, 1H), 8.27-8.18 (m, 2H), 7.86 (s, 1H), 7.74 (s, 1H), 7.25 (d, J=8.3 Hz, 1H), 4.63-4.54 (m, 1H), 3.59 (s, 2H), 3.49 (s, 2H), 3.14-2.93 (m, 3H), 2.78-2.71 (m, 2H), 2.70-2.64 (m, 2H), 2.38 (s, 3H), 2.35-2.77 (m, 6H), 1.22-0.93 (m, 6H). LC-MS $(M+H)^+$= 498.0.

Example 40: 4-(2-(2, 5-dimethyl-1, 2, 3, 4-tetrahydroisoquinolin-7-yl)-5H-pyrrolo[2, 3-b]pyrazin-7-yl)-N-(3-methoxypropyl)-N-methylbenzamide

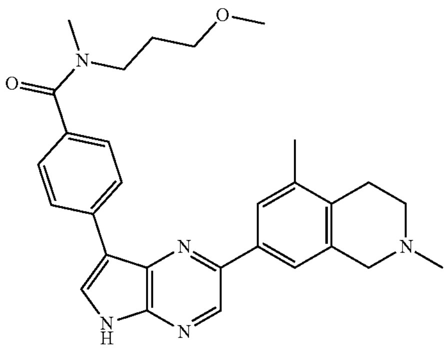 [SMILES: COCCCN(C)C(=O)c1ccc(-c2c[nH]c3ncc(-c4cc(C)c5c(c4)CN(C)CC5)nc23)cc1]

Step 1: 4-bromo-N-(3-methoxypropyl)benzamide

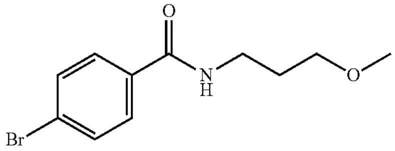

The title compound (1.6 g, 52%) was prepared in a manner similar to that in Example 38 step 1 from 4-bromobenzoic acid and 3-methoxypropan-1-amine. LCMS $(M+H)^+$=272.0, 274.0.

Step 2: 4-bromo-N-(3-methoxypropyl)-N-methylbenzamide

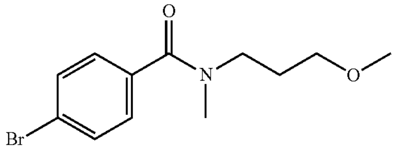 [SMILES: COCCCN(C)C(=O)c1ccc(Br)cc1]

The title compound (1.6 g, 95%) was prepared in a manner similar to that in Example 35 step 2 from 4-bromo-N-(3-methoxypropyl)benzamide and MeI. LC-MS $(M+H)^+$= 286.0, 288.0.

Step 3: N-(3-methoxypropyl)-N-methyl-4-(4, 4, 5, 5-tetramethyl-1, 3, 2-dioxaborolan-2-yl)benzamide

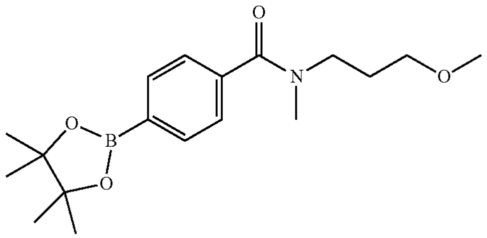

The title compound (2.5 g, 87%) was prepared in a manner similar to that in Example 38 step 2 from 4-bromo-N-(3-methoxypropyl)-N-methylbenzamide and BPD. LC-MS $(M+H)^+$=334.0.

Step 4: 4-(2-bromo-5-tosyl-5H-pyrrolo[2, 3-b]pyrazin-7-yl)-N-(3-methoxypropyl)-N-methylbenzamide

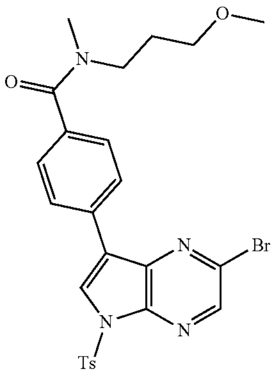 [SMILES: COCCCN(C)C(=O)c1ccc(-c2cn(S(=O)(=O)c3ccc(C)cc3)c3ncc(Br)nc23)cc1]

The title compound (0.80 g, 32%) was prepared in a manner similar to that in Example 38 step 3 from 2-bromo-7-iodo-5-tosyl-5H-pyrrolo[2, 3-b]pyrazine and N-(3-methoxypropyl)-N-methyl-4-(4, 4, 5, 5-tetramethyl-1, 3, 2-dioxaborolan-2-yl)benzamide. LC-MS $(M+H)^+$=557.0, 559.0.

Step 5: 4-(2-(2, 5-dimethyl-1, 2, 3, 4-tetrahydroisoquinolin-7-yl)-5H-pyrrolo[2, 3-b]pyrazin-7-yl)-N-(3-methoxypropyl)-N-methylbenzamide

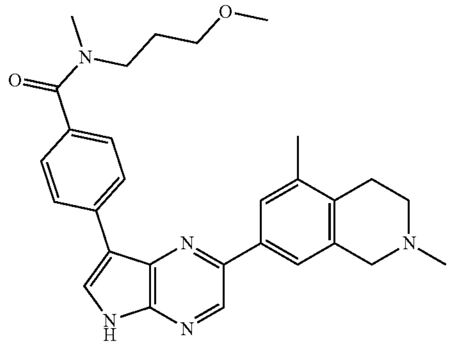 [SMILES: COCCCN(C)C(=O)c1ccc(-c2c[nH]c3ncc(-c4cc(C)c5c(c4)CN(C)CC5)nc23)cc1]

Example 40 (60 mg, 41%) was prepared in a manner similar to that in Example 35 step 5 from 4-(2-bromo-5-tosyl-5H-pyrrolo[2, 3-b]pyrazin-7-yl)-N-(3-methoxypropyl)-N-methylbenzamide and 2, 5-dimethyl-7-(4, 4, 5, 5-tetramethyl-1, 3, 2-dioxaborolan-2-yl)-1, 2, 3, 4-tetrahydroisoquinoline. $^1$H NMR (400 MHz, DMSO-d6) δ 12.39 (s, 1H), 8.87 (s, 1H), 8.51 (s, 1H), 8.30-8.40 (m, 2H), 7.85 (s, 1H), 7.73 (s, 1H), 7.57-7.42 (m, 2H), 3.59 (s, 2H), 3.55-3.37 (m, 3H), 3.29-3.11 (m, 4H), 2.97 (s, 3H), 2.78-2.72 (m, 2H), 2.71-2.64 (m, 2H), 2.37 (s, 3H), 2.31 (s, 3H), 1.89-1.72 (m, 2H). LC-MS $(M+H)^+$=484.8.

Example 41: 4-(2-(2-(3-((cis-4-hydroxycyclohexyl)amino)-3-oxopropyl)-5-methyl-1, 2, 3, 4-tetrahydroisoquinolin-7-yl)-5H-pyrrolo[2, 3-b]pyrazin-7-yl)-N, N, 2-trimethylbenzamide

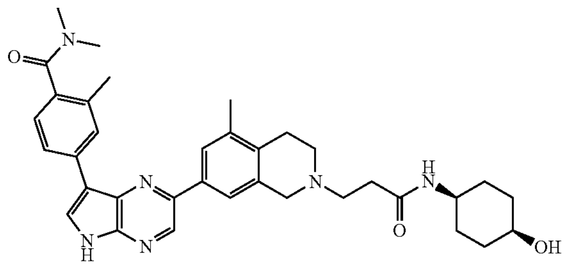 [SMILES: Cc1cc(-c2c[nH]c3ncc(-c4cc(C)c5c(c4)CN(CCC(=O)N[C@H]4CC[C@@H](O)CC4)CC5)nc23)ccc1C(=O)N(C)C]

Example 41 (60 mg, 50%) was prepared in a manner similar to that in Example 23 step 4 from 3-(7-(7-(4-(dimethylcarbamoyl)-3-methylphenyl)-5H-pyrrolo[2, 3-b]pyrazin-2-yl)-5-methyl-3, 4-dihydroisoquinolin-2 (1H)-yl) propanoic acid and cis-4-aminocyclohexan-1-ol. $^1$H NMR (400 MHz, DMSO-d6) δ 12.33 (s, 1H), 8.86 (s, 1H), 8.46 (d, J=2.6 Hz, 1H), 8.25-8.20 (m, 2H), 7.89 (d, J=7.6 Hz, 1H), 7.86 (s, 1H), 7.72 (s, 1H), 7.25 (d, J=8.3 Hz, 1H), 4.36 (d, J=2.8 Hz, 1H), 3.68 (s, 2H), 3.66-3.55 (m, 3H), 3.03 (s, 3H), 2.83 (s, 3H), 2.79-2.69 (m, 6H), 2.37 (t, J=7.0 Hz, 2H), 2.32-2.28 (m, 8H), 1.60-1.49 (m, 4H), 1.49-1.38 (m, 4H). LC-MS $(M+H)^+$=595.5.

Example 42: N, N, 2-trimethyl-4-(2-(5-methyl-2-(3-((2-(4-methylpiperazin-1-yl)ethyl)amino)-3-oxopropyl)-1, 2, 3, 4-tetrahydroisoquinolin-7-yl)-5H-pyrrolo[2, 3-b]pyrazin-7-yl)benzamide

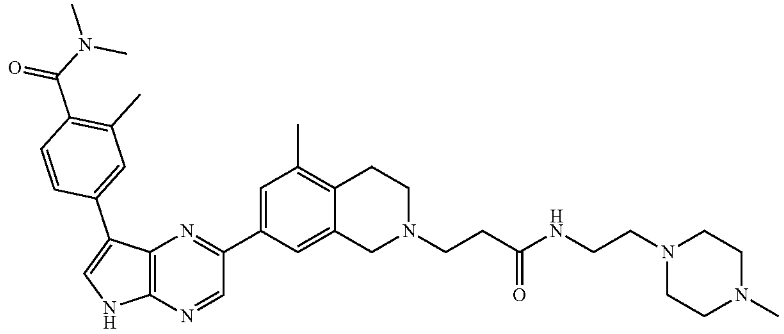 [SMILES: Cc1cc(-c2c[nH]c3ncc(-c4cc(C)c5c(c4)CN(CCC(=O)NCCN4CCN(C)CC4)CC5)nc23)ccc1C(=O)N(C)C]

Example 42 (30 mg, 24%) was prepared in a manner similar to that in Example 23 step 4 from 3-(7-(7-(4-(dimethylcarbamoyl)-3-methylphenyl)-5H-pyrrolo[2, 3-b]pyrazin-2-yl)-5-methyl-3, 4-dihydroisoquinolin-2 (1H)-yl) propanoic acid and 2-(4-methylpiperazin-1-yl)ethan-1-amine. $^1$H NMR (400 MHz, DMSO-d6) δ 12.33 (d, J=2.4 Hz, 1H), 8.86 (s, 1H), 8.46 (d, J=2.4 Hz, 1H), 8.25-8.19 (m, 2H), 7.99 (t, J=5.4 Hz, 1H), 7.86 (s, 1H), 7.73 (s, 1H), 7.24 (d, J=7.8 Hz, 1H), 3.69 (s, 2H), 3.19-3.11 (m, 2H), 3.03 (s, 3H), 2.83 (s, 3H), 2.79-2.68 (m, 6H), 2.37 (t, J=6.8 Hz, 2H), 2.34-2.26 (m, 12H), 2.19 (brs, 4H), 2.05 (s, 3H). LC-MS $(M+H)^+$=623.6.

Example 43: 4-(2-(2-(3-(cyclopropylamino)-3-oxopropyl)-5-methyl-1, 2, 3, 4-tetrahydroisoquinolin-7-yl)-5H-pyrrolo[2, 3-b]pyrazin-7-yl)-N, N, 2-trimethylbenzamide

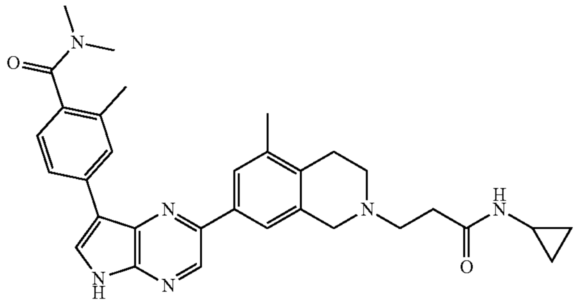 [SMILES: Cc1cc(-c2c[nH]c3ncc(-c4cc(C)c5c(c4)CN(CCC(=O)NC4CC4)CC5)nc23)ccc1C(=O)N(C)C]

Example 43 (30 mg, 27%) was prepared in a manner similar to that in Example 23 step 4 from 3-(7-(7-(4-(dimethylcarbamoyl)-3-methylphenyl)-5H-pyrrolo[2, 3-b]pyrazin-2-yl)-5-methyl-3, 4-dihydroisoquinolin-2 (1H)-yl) propanoic acid and cyclopropylamine. $^1$H NMR (400 MHz, DMSO-d6) δ 12.33 (d, J=2.3 Hz, 1H), 8.86 (s, 1H), 8.46 (d, J=2.8 Hz, 1H), 8.24-8.20 (m, 2H), 7.99 (d, J=4.1 Hz, 1H), 7.86 (s, 1H), 7.72 (s, 1H), 7.24 (d, J=4.5 Hz, 1H), 3.66 (s, 2H), 3.03 (s, 3H), 2.83 (s, 3H), 2.76-2.68 (m, 6H), 2.65-2.57 (m, 1H), 2.34-2.28 (m, 8H), 0.64-0.55 (m, 2H), 0.40-0.31 (m, 2H). LC-MS $(M+H)^+$=537.5.

Example 44: 4-(2-(2-(3-((3-methoxypropyl)amino)-3-oxopropyl)-5-methyl-1, 2, 3, 4-tetrahydroisoquinolin-7-yl)-5H-pyrrolo[2, 3-b]pyrazin-7-yl)-N, N, 2-trimethylbenzamide

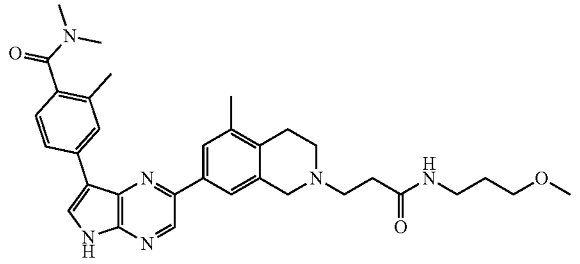 [SMILES: COCCCNC(=O)CCN1CCc2c(C)cc(-c3cnc4[nH]cc(-c5ccc(C(=O)N(C)C)c(C)c5)c4n3)cc2C1]

Example 44 (60 mg, 52%) was prepared in a manner similar to that in Example 23 step 4 from 3-(7-(7-(4-(dimethylcarbamoyl)-3-methylphenyl)-5H-pyrrolo[2, 3-b]pyrazin-2-yl)-5-methyl-3, 4-dihydroisoquinolin-2 (1H)-yl) propanoic acid and 3-methoxypropan-1-amine. $^1$H NMR (400 MHz, DMSO-d6) δ 12.33 (d, J=2.6 Hz, 1H), 8.86 (s, 1H), 8.46 (d, J=2.8 Hz, 1H), 8.24-8.20 (m, 2H), 7.95 (t, J=5.6 Hz, 1H), 7.86 (s, 1H), 7.73 (s, 1H), 7.25 (d, J=8.5 Hz, 1H), 3.68 (s, 2H), 3.28 (t, J=6.6 Hz, 2H), 3.15 (s, 3H), 3.08 (dd, J=12.7, 6.7 Hz, 2H), 3.03 (s, 3H), 2.83 (s, 3H), 2.78-2.69 (m, 6H), 2.36 (t, J=7.1 Hz, 2H), 2.33-2.25 (m, 6H), 1.60 (p, J=6.7 Hz, 2H). LC-MS $(M+H)^+$=569.5.

Example 45: 4-(2-(2-(3-((2-hydroxyethyl)amino)-3-oxopropyl)-5-methyl-1, 2, 3, 4-tetrahydroisoquinolin-7-yl)-5H-pyrrolo[2, 3-b]pyrazin-7-yl)-N, N, 2-trimethylbenzamide

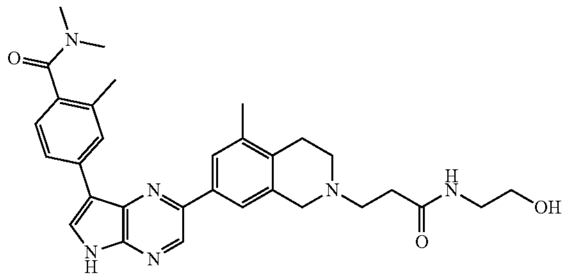 [SMILES: Cc1cc(-c2c[nH]c3ncc(-c4cc(C)c5c(c4)CN(CCC(=O)NCCO)CC5)nc23)ccc1C(=O)N(C)C]

Example 45 (30 mg, 27%) was prepared in a manner similar to that in Example 23 step 4 from 3-(7-(7-(4-(dimethylcarbamoyl)-3-methylphenyl)-5H-pyrrolo[2, 3-b]pyrazin-2-yl)-5-methyl-3, 4-dihydroisoquinolin-2 (1H)-yl) propanoic acid and 2-aminoethane-1-ol. $^1$H NMR (400 MHz, DMSO-d6) δ 12.33 (d, J=2.7 Hz, 1H), 8.87 (s, 1H), 8.46 (d, J=2.8 Hz, 1H), 8.24-8.20 (m, 2H), 7.98 (t, J=5.3 Hz, 1H), 7.86 (s, 1H), 7.73 (s, 1H), 7.25 (d, J=8.5 Hz, 1H), 4.64 (t, J=5.4 Hz, 1H), 3.68 (s, 2H), 3.38 (q, J=5.9 Hz, 2H), 3.12 (q, J=5.9 Hz, 2H), 3.03 (s, 3H), 2.83 (s, 3H), 2.74 (s, 6H), 2.38 (t, J=7.2 Hz, 2H), 2.30 (d, J=4.9 Hz, 6H). LC-MS $(M+H)^+$=541.5.

Example 46: 4-(2-(2-(3-((3-hydroxypropyl)amino)-3-oxopropyl)-5-methyl-1, 2, 3, 4-tetrahydroisoquinolin-7-yl)-5H-pyrrolo[2, 3-b]pyrazin-7-yl)-N, N, 2-trimethylbenzamide

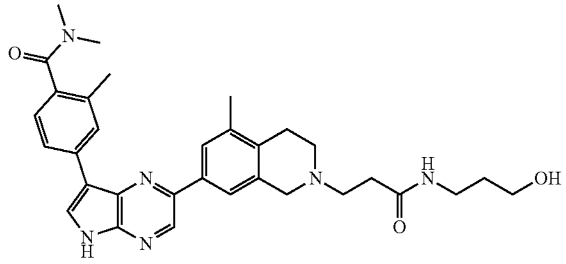 [SMILES: Cc1cc(-c2c[nH]c3ncc(-c4cc(C)c5c(c4)CN(CCC(=O)NCCCO)CC5)nc23)ccc1C(=O)N(C)C]

Example 46 (30 mg, 27%) was prepared in a manner similar to that in Example 23 step 4 from 3-(7-(7-(4-(dimethylcarbamoyl)-3-methylphenyl)-5H-pyrrolo[2, 3-b]pyrazin-2-yl)-5-methyl-3, 4-dihydroisoquinolin-2 (1H)-yl) propanoic acid and 3-aminopropan-1-ol. $^1$H NMR (400 MHz, DMSO-d6) δ 12.33 (d, J=2.5 Hz, 1H), 8.87 (s, 1H), 8.46 (d, J=2.7 Hz, 1H), 8.24-8.20 (m, 2H), 7.93 (t, J=5.5 Hz, 1H), 7.86 (s, 1H), 7.73 (s, 1H), 7.25 (d, J=8.5 Hz, 1H), 4.41 (t, J=5.2 Hz, 1H), 3.67 (s, 2H), 3.39 (dd, J=11.6, 6.1 Hz, 2H), 3.10 (dd, J=12.7, 6.7 Hz, 2H), 3.03 (s, 3H), 2.83 (s, 3H), 2.72 (d, J=7.3 Hz, 6H), 2.36 (t, J=7.1 Hz, 2H), 2.30 (d, J=4.5 Hz, 6H), 1.53 (p, J=6.6 Hz, 2H). LC-MS $(M+H)^+$=555.5.

Example 47: 4-(2-(2-(3-(cyclopropylamino)-3-oxopropyl)-5-methyl-1, 2, 3, 4-tetrahydroisoquinolin-7-yl)-5H-pyrrolo[2, 3-b]pyrazin-7-yl)-N, N-dimethylbenzamide

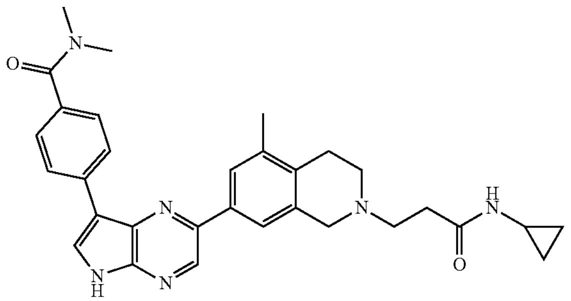 [SMILES: Cc1cc(-c2cnc3[nH]cc(-c4ccc(C(=O)N(C)C)cc4)c3n2)cc2c1CCN(CCC(=O)NC1CC1)C2]

Step 1: 3-(7-(7-(4-(dimethylcarbamoyl)phenyl)-5H-pyrrolo[2, 3-b]pyrazin-2-yl)-5-methyl-3, 4-dihydroisoquinolin-2 (1H)-yl)propanoic acid

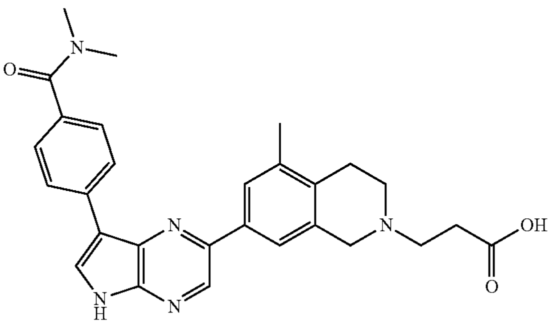 [SMILES: Cc1cc(-c2cnc3[nH]cc(-c4ccc(C(=O)N(C)C)cc4)c3n2)cc2c1CCN(CCC(=O)O)C2]

The title compound (400 mg, crude) was prepared in a manner similar to that in Example 23 step 3 from 4-(2-bromo-5-tosyl-5H-pyrrolo[2, 3-b]pyrazin-7-yl)-N, N-dimethylbenzamide and ethyl 3-(5-methyl-7-(4, 4, 5, 5-tetramethyl-1, 3, 2-dioxaborolan-2-yl)-3, 4-dihydroisoquinolin-2 (1H)-yl)propanoate. LC-MS $(M+H)^+$=484.1.

Step 2: 4-(2-(2-(3-(cyclopropylamino)-3-oxopropyl)-5-methyl-1, 2, 3, 4-tetrahydroisoquinolin-7-yl)-5H-pyrrolo[2, 3-b]pyrazin-7-yl)-N, N-dimethylbenzamide

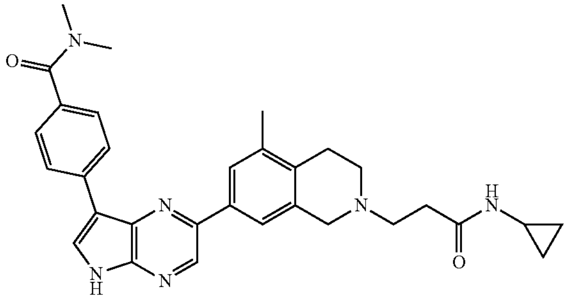 [SMILES: Cc1cc(-c2cnc3[nH]cc(-c4ccc(C(=O)N(C)C)cc4)c3n2)cc2c1CCN(CCC(=O)NC1CC1)C2]

Example 47 (30 mg, 28%) was prepared in a manner similar to that in Example 23 step 4 from 3-(7-(7-(4-(dimethylcarbamoyl)-phenyl)-5H-pyrrolo[2, 3-b]pyrazin-2-yl)-5-methyl-3, 4-dihydroisoquinolin-2 (1H)-yl)propanoic acid and cyclopropylamine. $^1$H NMR (400 MHz, DMSO-d6) δ 12.39 (d, J=2.5 Hz, 1H), 8.87 (s, 1H), 8.51 (d, J=2.8 Hz, 1H), 8.38 (d, J=8.3 Hz, 2H), 7.99 (d, J=3.9 Hz, 1H), 7.84 (s, 1H), 7.72 (s, 1H), 7.52 (d, J=8.3 Hz, 2H), 3.67 (s, 2H), 3.01 (s, 6H), 2.77-2.69 (m, 6H), 2.65-2.57 (m, 1H), 2.36-2.28 (m, 5H), 0.63-0.54 (m, 2H), 0.39-0.32 (m, 2H). LC-MS $(M+H)^+$=523.5.

Example 48: 4-(2-(2-(3-(((1r, 4r)-4-hydroxycyclohexyl)amino)-3-oxopropyl)-5-methyl-1, 2, 3, 4-tetrahydroisoquinolin-7-yl)-5H-pyrrolo[2, 3-b]pyrazin-7-yl)-N, N-dimethylbenzamide

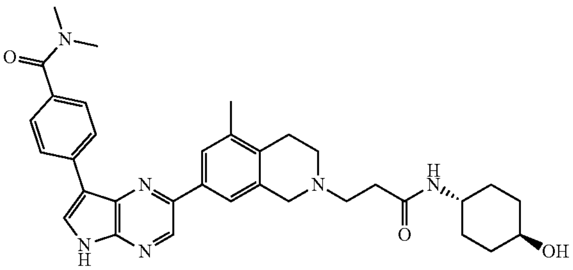 [SMILES: Cc1cc(-c2cnc3[nH]cc(-c4ccc(C(=O)N(C)C)cc4)c3n2)cc2c1CCN(CCC(=O)N[C@H]1CC[C@H](O)CC1)C2]

Example 48 (10 mg, 17%) was prepared in a manner similar to that in Example 23 step 4 from 3-(7-(7-(4-(dimethylcarbamoyl)-phenyl)-5H-pyrrolo[2, 3-b]pyrazin-2-yl)-5-methyl-3, 4-dihydroisoquinolin-2 (1H)-yl)propanoic acid and trans-4-aminocyclohexan-1-ol. $^1$H NMR (400 MHz, DMSO-d6) δ 12.47 (s, 1H), 10.59 (s, 1H), 8.92 (s, 1H), 8.54 (s, 1H), 8.38 (d, J=8.3 Hz, 2H), 8.03 (s, 1H), 7.89 (s, 1H), 7.52 (d, J=8.4 Hz, 2H), 4.72-4.58 (m, 1H), 4.57-4.51 (m, 1H), 4.51-4.37 (m, 1H), 3.84-3.71 (s, 1H), 3.57-3.39 (m, 3H), 3.09-2.94 (m, 8H), 2.81-2.69 (m, 2H), 2.40-2.31 (m, 4H), 1.85-1.70 (m, 4H), 1.23-1.12 (m, 5H). LC-MS $(M+H)^+$= 580.9.

Example 49: N, N-dimethyl-4-(2-(5-methyl-2-(3-((2-(4-methylpiperazin-1-yl)ethyl)amino)-3-oxopropyl)-1, 2, 3, 4-tetrahydroisoquinolin-7-yl)-5H-pyrrolo[2, 3-b]pyrazin-7-yl)benzamide

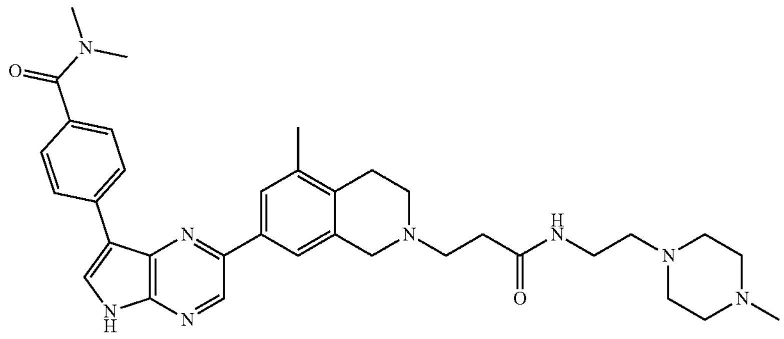 [SMILES: Cc1cc(-c2cnc3[nH]cc(-c4ccc(C(=O)N(C)C)cc4)c3n2)cc2c1CCN(CCC(=O)NCCN1CCN(C)CC1)C2]

Example 49 (10 mg, 16%) was prepared in a manner similar to that in Example 23 step 4 from 3-(7-(7-(4-(dimethylcarbamoyl)-phenyl)-5H-pyrrolo[2, 3-b]pyrazin-2-yl)-5-methyl-3, 4-dihydroisoquinolin-2 (1H)-yl)propanoic acid and 2-(4-methylpiperazin-1-yl)ethan-1-amine. $^1$H NMR (400 MHz, DMSO-d6) δ 12.39 (s, 1H), 8.86 (s, 1H), 8.51 (d, J=2.3 Hz, 1H), 8.38 (d, J=8.3 Hz, 2H), 8.00 (t, J=5.4 Hz, 1H), 7.84 (s, 1H), 7.73 (s, 1H), 7.51 (d, J=8.4 Hz, 2H), 3.69 (s, 2H), 3.15 (dd, J=12.3, 6.4 Hz, 2H), 3.01 (s, 6H), 2.79-2.69 (m, 6H), 2.43-2.10 (m, 15H), 2.05 (s, 3H). LC-MS $(M+H)^+$=609.0.

Example 50: (S)—N, 2-dimethyl-4-(2-(5-methyl-2-(2-morpholinoethyl)-1, 2, 3, 4-tetrahydroisoquinolin-7-yl)-5H-pyrrolo[2, 3-b]pyrazin-7-yl)-N-((tetrahydrofuran-3-yl)methyl)benzamide

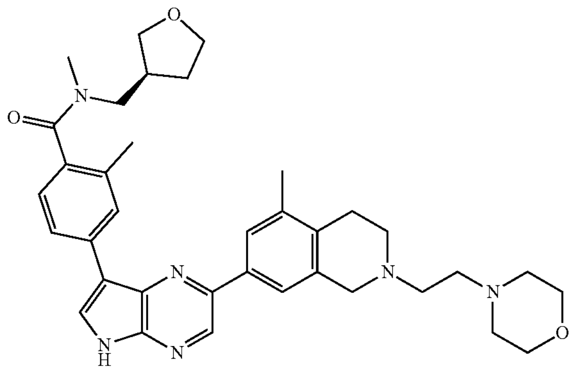 [SMILES: Cc1cc(-c2c[nH]c3ncc(-c4cc(C)c5c(c4)CN(CCN4CCOCC4)CC5)nc23)ccc1C(=O)N(C)C[C@@H]1CCOC1]

Step 1: (S)-4-bromo-2-methyl-N-((tetrahydrofuran-3-yl)methyl)benzamide

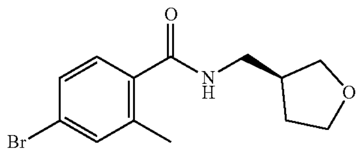 [SMILES: Cc1cc(Br)ccc1C(=O)NC[C@@H]1CCOC1]

The title compound (1.10 g, 81%) was prepared in a manner similar to that in Example 35 step 1 from 4-bromo-2-methylbenzoic acid and (S)-(tetrahydrofuran-3-yl)methanamine. LC-MS $(M+H)^+$=298.0, 300.0.

Step 2: (S)-4-bromo-N, 2-dimethyl-N-((tetrahydrofuran-3-yl)methyl)benzamide

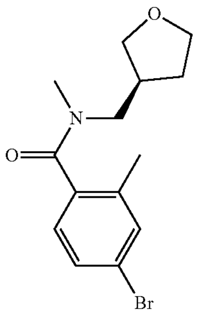 [SMILES: Cc1cc(Br)ccc1C(=O)N(C)C[C@@H]1CCOC1]

The title compound (1.07 g, 93%) was prepared in a manner similar to that in Example 35 step 2 from (S)-4-bromo-2-methyl-N-((tetrahydrofuran-3-yl)methyl)benzamide and iodomethane. LC-MS $(M+H)^+$=311.9, 313.9.

Step 3: (S)—N, 2-dimethyl-N-((tetrahydrofuran-3-yl)methyl)-4-(4, 4, 5, 5-tetramethyl-1, 3, 2-dioxaborolan-2-yl)benzamide

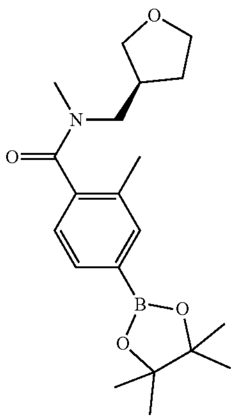 [SMILES: Cc1cc(B2OC(C)(C)C(C)(C)O2)ccc1C(=O)N(C)C[C@@H]1CCOC1]

The title compound (1.20 g, 99%) was prepared in a manner similar to that in Example 35 step 3 from (S)-4-bromo-N, 2-dimethyl-N-((tetrahydrofuran-3-yl)methyl)benzamide and BPD. LC-MS $(M+H)^+$=359.9.

Step 4: (S)-4-(2-bromo-5-tosyl-5H-pyrrolo[2, 3-b]pyrazin-7-yl)-N, 2-dimethyl-N-((tetrahydrofuran-3-yl)methyl)benzamide

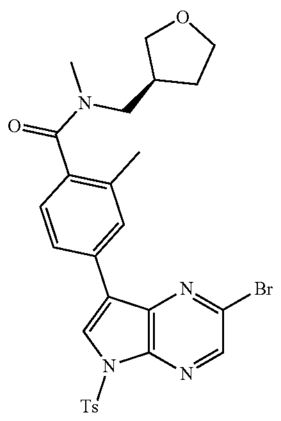 [SMILES: Cc1ccc(S(=O)(=O)n2cc(-c3ccc(C(=O)N(C)C[C@@H]4CCOC4)c(C)c3)c3nc(Br)cnc32)cc1]

The title product (400 mg, 41%) was prepared in a manner similar to that in Example 35 step 4 from 2-bromo-7-iodo-5-tosyl-5H-pyrrolo[2, 3-b]pyrazine and (S)—N, 2-dimethyl-N-((tetrahydrofuran-3-yl)methyl)-4-(4, 4, 5, 5-tetramethyl-1, 3, 2-dioxaborolan-2-yl)benzamide. LC-MS $(M+H)^+$=582.9, 584.9.

Step 5: 4-(2-(7-bromo-5-methyl-3, 4-dihydroisoquinolin-2 (1H)-yl)ethyl)morpholine

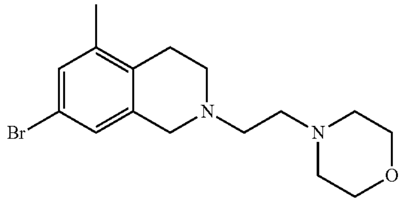 [SMILES: Cc1cc(Br)cc2c1CCN(CCN1CCOCC1)C2]

7-bromo-2, 5-dimethyl-1, 2, 3, 4-tetrahydroisoquinoline (1.0 g, 4.5 mmol), 4-(2-bromoethyl)morpholine hydrogen bromide (1.6 g, 5.9 mmol) and $K_2CO_3$ (1.87 g, 13.6 mmol) was dissolved in $CH_3CN$ (30 mL). The mixture was heated to reflux overnight then cooled to room temperature. Solvent was removed in vacuo and the residue was purified by silica gel column chromatography, eluted with MeOH/DCM (1:50) to give the title compound (1.0 g, 67%). LC-MS $(M+H)^+$=339.0.

Step 6: 4-(2-(5-methyl-7-(4, 4, 5, 5-tetramethyl-1, 3, 2-dioxaborolan-2-yl)-3, 4-dihydroisoquinolin-2 (1H)-yl)ethyl)morpholine

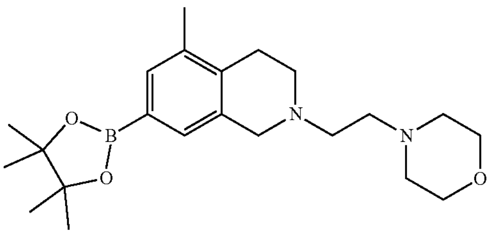 [SMILES: Cc1cc(B2OC(C)(C)C(C)(C)O2)cc2c1CCN(CCN1CCOCC1)C2]

The title product (90 mg, 33%) was prepared in a manner similar to that in Example 36 step 4 from 4-(2-(7-bromo-5-methyl-3, 4-dihydroisoquinolin-2 (1H)-yl)ethyl)morpholine and BPD. LC-MS $(M+H)^+$=387.0.

Step 7: (S)—N, 2-dimethyl-4-(2-(5-methyl-2-(2-morpholinoethyl)-1, 2, 3, 4-tetrahydroisoquinolin-7-yl)-5H-pyrrolo[2, 3-b]pyrazin-7-yl)-N-((tetrahydrofuran-3-yl)methyl)benzamide

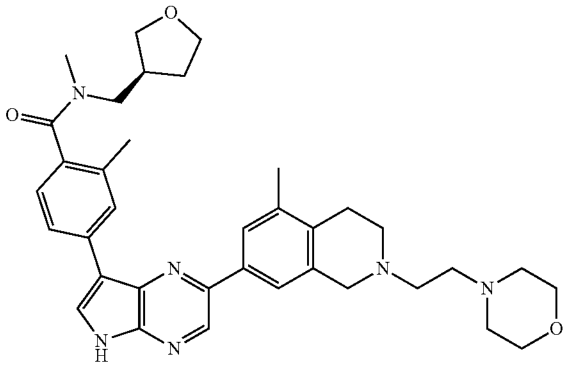 [SMILES: Cc1cc(-c2c[nH]c3ncc(-c4cc(C)c5c(c4)CN(CCN4CCOCC4)CC5)nc23)ccc1C(=O)N(C)C[C@@H]1CCOC1]

Example 50 (60 mg, 29%) was prepared in a manner similar to that in Example 35 step 5 from (S)-4-(2-bromo-5-tosyl-5H-pyrrolo[2, 3-b]pyrazin-7-yl)-N, 2-dimethyl-N-((tetrahydrofuran-3-yl)methyl)benzamide and 4-(2-(5-methyl-7-(4, 4, 5, 5-tetramethyl-1, 3, 2-dioxaborolan-2-yl)-3, 4-dihydroisoquinolin-2 (1H)-yl)ethyl)morpholine. $^1H$ NMR (400 MHz, DMSO-d6) δ 12.34 (s, 1H), 8.87 (s, 1H), 8.47 (s, 1H), 8.30-8.17 (m, 2H), 7.86 (s, 1H), 7.73 (s, 1H), 7.27-7.18 (m, 1H), 3.84-3.77 (m, 1H), 3.74-3.60 (m, 3H), 3.60-3.54 (m, 4H), 3.54-3.42 (m, 2H), 3.19 (brs, 1H), 3.01 (s, 1H), 2.82 (s, 2H), 2.76-2.72 (m, 3H), 2.68-2.58 (m, 2H), 2.53-2.51 (m, 2H), 2.43 (s, 4H), 2.30 (brs, 6H), 2.04-1.96 (m, 1H), 1.70-1.61 (m, 1H). LC-MS $(M+H)^+$=609.0.

Example 51: (S)—N-methyl-4-(2-(5-methyl-2-(2-morpholinoethyl)-1, 2, 3, 4-tetrahydroisoquinolin-7-yl)-5H-pyrrolo[2, 3-b]pyrazin-7-yl)-N-((tetrahydrofuran-3-yl)methyl)benzamide

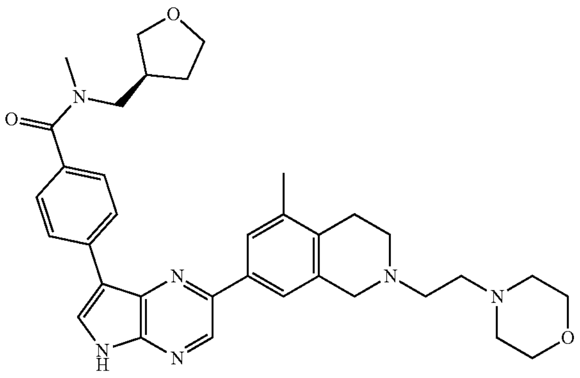 [SMILES: Cc1cc(-c2cnc3[nH]cc(-c4ccc(C(=O)N(C)C[C@@H]5CCOC5)cc4)c3n2)cc2c1CCN(CCN1CCOCC1)C2]

Example 51 (27 mg, 17%) was prepared in a manner similar to that in Example 35 step 5 from (S)-4-(2-bromo-5-tosyl-5H-pyrrolo[2, 3-b]pyrazin-7-yl)-N-methyl-N-((tetrahydrofuran-3-yl)methyl)benzamide and 4-(2-(5-methyl-7-(4, 4, 5, 5-tetramethyl-1, 3, 2-dioxaborolan-2-yl)-3, 4-dihydroisoquinolin-2 (1H)-yl)ethyl)morpholine. $^1$H NMR (400 MHz, DMSO-d6) δ 12.39 (s, 1H), 8.87 (s, 1H), 8.52 (d, J=2.0 Hz, 1H), 8.40 (s, 1H), 8.38 (s, 1H), 7.85 (s, 1H), 7.74 (s, 1H), 7.50-7.48 (m, 2H), 3.77-3.72 (m, 4H), 3.58 (s, 5H), 3.43 (brs, 3H), 2.99 (s, 3H), 2.78 (brs, 2H), 2.73 (brs, 2H), 2.64 (brs, 3H), 2.55 (brs, 2H), 2.44 (s, 4H), 2.31 (s, 3H), 1.95 (brs, 1H), 1.64 (brs, 1H). LC-MS $(M+H)^+$=594.9.

Example 52: 4-(2-(2-(2-((3-methoxypropyl)amino)-2-oxoethyl)-5-methyl-1, 2, 3, 4-tetrahydroisoquinolin-7-yl)-5H-pyrrolo[2, 3-b]pyrazin-7-yl)-N, N, 2-trimethylbenzamide Step 1: methyl 2-(7-bromo-5-methyl-3, 4-dihydroisoquinolin-2 (1H)-yl)acetate

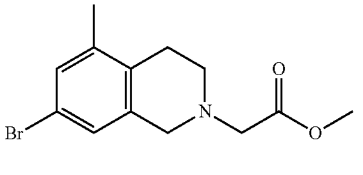 [SMILES: COC(=O)CN1CCc2c(C)cc(Br)cc2C1]

A mixture of 7-bromo-5-methyl-1, 2, 3, 4-tetrahydroisoquinoline (2.3 g, 10 mmol), methyl 2-chloroacetate (1.09 g, 10 mmol) and $Cs_2CO_3$ (3.28 g, 7.75 mmol) in DMF (40 mL) was stirred at room temperature overnight. Solid was filtered off and the filtrate was concentrated under reduced pressure. The residue was purified by silica gel column, eluted with EtOAc/PE (1:4) to give the title compound (2.07 g, 70%). LC-MS $(M+H)^+$=297.9, 299.9.

Step 2: methyl 2-(5-methyl-7-(4, 4, 5, 5-tetramethyl-1, 3, 2-dioxaborolan-2-yl)-3, 4-dihydroisoquinolin-2 (1H)-yl)acetate

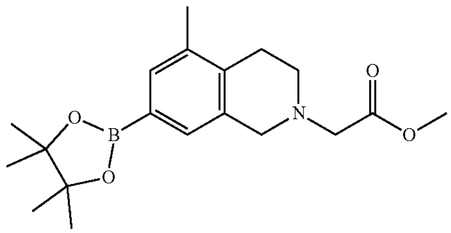

To methyl 2-(7-bromo-5-methyl-3, 4-dihydroisoquinolin-2 (1H)-yl)acetate (2.07 g, 6.95 mmol), BPD (2.65 g, 10.4 mmol), Pd (dppf)$Cl_2$ (512 mg, 0.70 mmol) and AcOK (1.36 g, 13.9 mmol) was added dioxane (40 mL) under nitrogen. The reaction mixture was stirred at reflux overnight then cooled to room temperature. EtOAc (30 mL) was added and the mixture was washed with brine (30 mL×2). The combined organic layer was dried over $Na_2SO_4$, filtered and concentrated under reduced pressure. The residue was purified by silica gel column chromatography, eluted with EtOAc/PE (1:2) to give the title compound (2.64 g, 100%). LC-MS $(M+H)^+$=346.0.

Step 3: 2-(7-(7-(4-(dimethylcarbamoyl)-3-methylphenyl)-5H-pyrrolo[2, 3-b]pyrazin-2-yl)-5-methyl-3, 4-dihydroisoquinolin-2 (1H)-yl)acetic acid

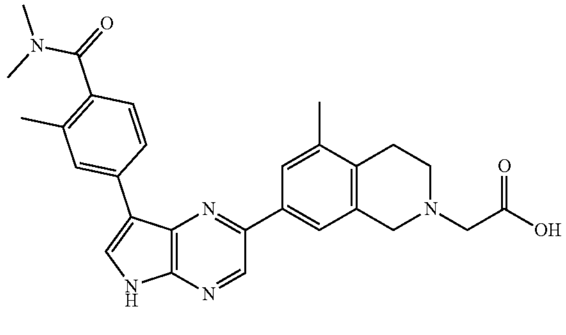 [SMILES: Cc1cc(-c2c[nH]c3ncc(-c4cc(C)c5c(c4)CN(CC(=O)O)CC5)nc23)ccc1C(=O)N(C)C]

The title compound (1.2 g, 44%) was prepared in a manner similar to that in Example 23 step 3 from 4-(2-bromo-5-tosyl-5H-pyrrolo[2, 3-b]pyrazin-7-yl)-N, N, 2-trimethylbenzamide and methyl 2-(5-methyl-7-(4, 4, 5, 5-tetramethyl-1, 3, 2-dioxaborolan-2-yl)-3, 4-dihydroisoquinolin-2 (1H)-yl)acetate. LC-MS $(M+H)^+$=484.0.

Step 4: 4-(2-(2-(2-((3-methoxypropyl)amino)-2-oxoethyl)-5-methyl-1, 2, 3, 4-tetrahydroisoquinolin-7-yl)-5H-pyrrolo[2, 3-b]pyrazin-7-yl)-N, N, 2-trimethylbenzamide

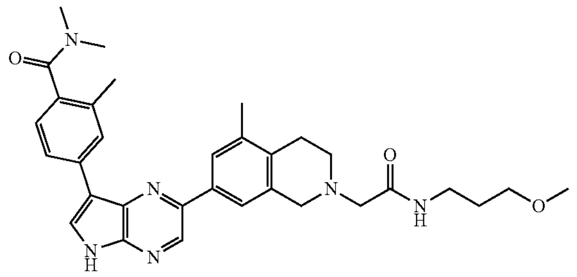 [SMILES: COCCCNC(=O)CN1CCc2c(C)cc(-c3cnc4[nH]cc(-c5ccc(C(=O)N(C)C)c(C)c5)c4n3)cc2C1]

Example 52 (35 mg, 30%) was prepared in a manner similar to that in Example 23 step 4 from 2-(7-(7-(4-(dimethylcarbamoyl)-3-methylphenyl)-5H-pyrrolo[2, 3-b] pyrazin-2-yl)-5-methyl-3, 4-dihydroisoquinolin-2 (1H)-yl) acetic acid and 3-methoxypropan-1-amine. $^{1}$H NMR (400 MHz, DMSO-d6) δ 12.33 (s, 1H), 8.88 (s, 1H), 8.46 (d, J=2.4 Hz, 1H), 8.24 (s, 1H), 8.20 (d, J=8.1 Hz, 1H), 7.89 (s, 1H), 7.88-7.85 (m, 1H), 7.75 (s, 1H), 7.24 (d, J=7.9 Hz, 1H), 3.74 (s, 2H), 3.37-3.30 (m, 2H), 3.20-3.15 (m, 5H), 3.12 (s, 2H), 3.03 (s, 3H), 2.83 (s, 3H), 2.79 (s, 4H), 2.32 (s, 3H), 2.29 (s, 3H), 1.70-1.63 (m, 2H). LC-MS $(M+H)^+$=555.0.

Example 53: (R)—N, N, 2-trimethyl-4-(2-(5-methyl-2-(3-oxo-3-((tetrahydro-2H-pyran-3-yl) amino)propyl)-1, 2, 3, 4-tetrahydroisoquinolin-7-yl)-5H-pyrrolo[2, 3-b]pyrazin-7-yl)benzamide

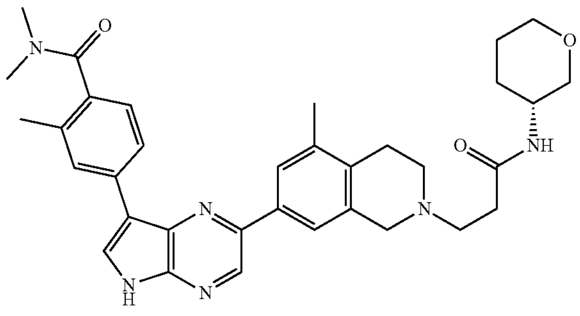 [SMILES: Cc1cc(-c2c[nH]c3ncc(-c4cc(C)c5c(c4)CN(CCC(=O)N[C@@H]4CCCOC4)CC5)nc23)ccc1C(=O)N(C)C]

Example 53 (10 mg, 9%) was prepared in a manner similar to that in Example 23 step 4 from 3-(7-(7-(4-(dimethylcarbamoyl)-3-methylphenyl)-5H-pyrrolo[2, 3-b] pyrazin-2-yl)-5-methyl-3, 4-dihydroisoquinolin-2 (1H)-yl) propanoic acid and (R)-tetrahydro-2H-pyran-3-amine hydrochloride. $^{1}$H NMR (400 MHz, DMSO-d6) δ 12.40 (s, 1H), 8.91 (s, 1H), 8.49 (s, 1H), 8.26-8.17 (m, 3H), 8.02 (s, 1H), 7.86 (s, 1H), 7.25 (d, J=7.9 Hz, 1H), 3.74-3.61 (m, 4H), 3.55-3.36 (m, 4H), 3.18-2.08 (m, 2H), 3.06-3.02 (m, 4H), 2.88-2.70 (m, 6H), 2.40-2.25 (m, 7H), 1.86-1.78 (m, 1H), 1.72-1.62 (m, 1H), 1.54-1.42 (m, 2H). LC-MS $(M+H)^+$=581.0.

Example 54: 4-(2-(2-(3-(((1S, 2R)-2-hydroxycyclopentyl)amino)-3-oxopropyl)-5-methyl-1, 2, 3, 4-tetrahydroisoquinolin-7-yl)-5H-pyrrolo[2, 3-b]pyrazin-7-yl)-N, N, 2-trimethylbenzamide

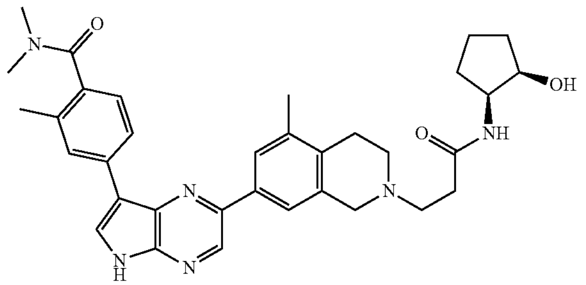 [SMILES: Cc1cc(-c2c[nH]c3ncc(-c4cc(C)c5c(c4)CN(CCC(=O)N[C@H]4CCC[C@H]4O)CC5)nc23)ccc1C(=O)N(C)C]

Example 54 (10 mg, 9%) was prepared in a manner similar to that in Example 23 step 4 from 3-(7-(7-(4-(dimethylcarbamoyl)-3-methylphenyl)-5H-pyrrolo[2, 3-b] pyrazin-2-yl)-5-methyl-3, 4-dihydroisoquinolin-2 (1H)-yl) propanoic acid and (1R, 2S)-2-aminocyclopentan-1-ol hydrochloride. $^{1}$H NMR (400 MHz, DMSO-d6) δ 10.32-10.13 (m, 1H), 8.90 (s, 1H), 8.48 (s, 1H), 8.26-8.18 (m, 2H), 7.86 (s, 3H), 7.25 (d, J=7.9 Hz, 1H), 4.70-4.55 (m, 1H), 3.96-3.80 (m, 2H), 3.31 (s, 3H), 3.07-2.70 (m, 11H), 2.40-2.25 (m, 7H), 1.80-1.60 (m, 3H), 1.60-1.40 (m, 3H). LC-MS $(M+H)^+$=581.0.

Example 55: 4-(2-(2-(3-((cyclopropylmethyl) amino)-3-oxopropyl)-5-methyl-1, 2, 3, 4-tetrahydroisoquinolin-7-yl)-5H-pyrrolo[2, 3-b]pyrazin-7-yl)-N, N, 2-trimethylbenzamide

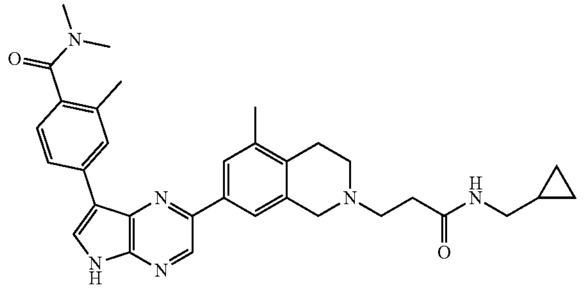 [SMILES: Cc1cc(-c2c[nH]c3ncc(-c4cc(C)c5c(c4)CN(CCC(=O)NCC4CC4)CC5)nc23)ccc1C(=O)N(C)C]

To a stirring solution of 3-(7-(7-(4-(dimethylcarbamoyl)-3-methylphenyl)-5H-pyrrolo[2, 3-b]pyrazin-2-yl)-5-methyl-3, 4-dihydroisoquinolin-2 (1H)-yl)propanoic acid (150 mg, 0.301 mmol) and cyclopropylmethanamine (22 mg, 0.301 mmol) in DMF (5 mL) was added HATU (172 mg, 0.452 mmol) and $Et_3N$ (456 mg, 0.452 mmol). The resulting solution was stirred at r.t for 2 h. Water (10 mL) was added and the mixture was extracted with EtOAc (10 mL×3). The combined organic layer was washed with brine, dried over $Na_2SO_4$, filtered and concentrated. The residue was purified by silica gel column, eluted with MeOH/DCM (1:20) then by prep-TLC, developed with MeOH/DCM (1:15) to give Example 55 (24 mg, 15%). $^{1}$H NMR (400 MHz, DMSO-d6) δ 12.33 (s, 1H), 8.86 (s, 1H), 8.46 (s, 1H), 8.25-8.19 (m, 2H), 8.04 (t, J=5.5 Hz, 1H), 7.86 (s, 1H), 7.73 (s, 1H), 7.27-7.22 (m, 1H), 3.72-3.64 (m, 2H), 3.03 (s, 3H), 2.94 (t, J=6.1 Hz, 2H), 2.83 (s, 3H), 2.79-2.69 (m, 6H), 2.37 (t, J=7.1 Hz, 2H), 2.34-2.26 (m, 6H), 0.92-0.80 (m, 1H), 0.40-0.31 (m, 2H), 0.17-0.09 (m, 2H). LC-MS $(M+H)^+$=551.5

Example 56: 4-(2-(2-(3-(((1S, 3S)-3-hydroxycyclopentyl)amino)-3-oxopropyl)-5-methyl-1, 2, 3, 4-tetrahydroisoquinolin-7-yl)-5H-pyrrolo[2, 3-b]pyrazin-7-yl)-N, N, 2-trimethylbenzamide

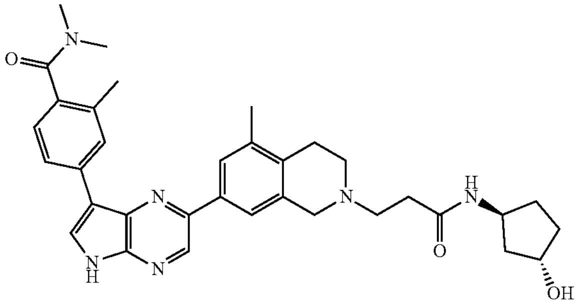 [SMILES: Cc1cc(-c2c[nH]c3ncc(-c4cc(C)c5c(c4)CN(CCC(=O)N[C@H]4CC[C@H](O)C4)CC5)nc23)ccc1C(=O)N(C)C]

Example 56 (25 mg, 21%) was prepared in a manner similar to that in Example 55 from 3-(7-(7-(4-(dimethylcarbamoyl)-3-methylphenyl)-5H-pyrrolo[2, 3-b]pyrazin-2-yl)-5-methyl-3, 4-dihydroisoquinolin-2 (1H)-yl)propanoic acid and (1S, 3S)-3-aminocyclopentan-1-ol. $^1$H NMR (400 MHz, DMSO-d6) δ 12.38 (s, 1H), 10.48-10.12 (m, 1H), 8.89 (s, 1H), 8.48 (d, J=2.5 Hz, 1H), 8.27-8.18 (m, 2H), 8.18-7.70 (m, 3H), 7.25 (d, J=7.8 Hz, 1H), 4.82-4.27 (m, 2H), 4.26-4.10 (m, 2H), 4.09-3.36 (m, 3H), 3.03 (s, 3H), 3.00-2.85 (m, 2H), 2.83 (s, 3H), 2.81-2.55 (m, 3H), 2.34 (s, 3H), 2.30 (s, 3H), 2.04-1.91 (m, 1H), 1.89-1.72 (m, 2H), 1.56-1.47 (m, 1H), 1.46-1.37 (m, 1H), 1.37-1.26 (s, 1H). LC-MS $(M+H)^+$=581.6.

Example 57: (S)-4-(2-(8-methoxy-2-methyl-1, 2, 3, 4-tetrahydroisoquinolin-6-yl)-5H-pyrrolo[2, 3-b]pyrazin-7-yl)-N-methyl-N-((tetrahydrofuran-3-yl)methyl)benzamide

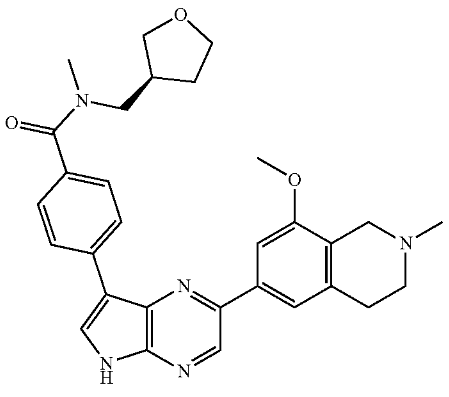 [SMILES: COc1cc(-c2cnc3[nH]cc(-c4ccc(C(=O)N(C)C[C@@H]5CCOC5)cc4)c3n2)cc2c1CN(C)CC2]

Step 1: (S)-4-(2-(8-methoxy-2-methyl-1, 2, 3, 4-tetrahydroisoquinolin-6-yl)-5-tosyl-5H-pyrrolo[2, 3-b]pyrazin-7-yl)-N-methyl-N-((tetrahydrofuran-3-yl)methyl)benzamide

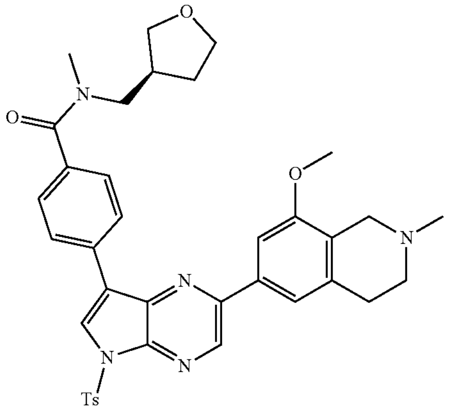 [SMILES: COc1cc(-c2cnc3c(n2)c(-c2ccc(C(=O)N(C)C[C@@H]4CCOC4)cc2)cn3S(=O)(=O)c2ccc(C)cc2)cc2c1CN(C)CC2]

The title compound (70 mg, 58%) was prepared in a manner similar to that in Example 2 step 5 from (S)-4-(2-bromo-5-tosyl-5H-pyrrolo[2, 3-b]pyrazin-7-yl)-N-methyl-N-((tetrahydrofuran-3-yl)methyl)benzamide and 8-methoxy-2-methyl-6-(4, 4, 5, 5-tetramethyl-1, 3, 2-dioxaborolan-2-yl)-1, 2, 3, 4-tetrahydroisoquinoline. LC-MS $(M+H)^+$=666.4.

Step 2: (S)-4-(2-(8-methoxy-2-methyl-1, 2, 3, 4-tetrahydroisoquinolin-6-yl)-5H-pyrrolo[2, 3-b]pyrazin-7-yl)-N-methyl-N-(tetrahydrofuran-3-yl)methyl)benzamide

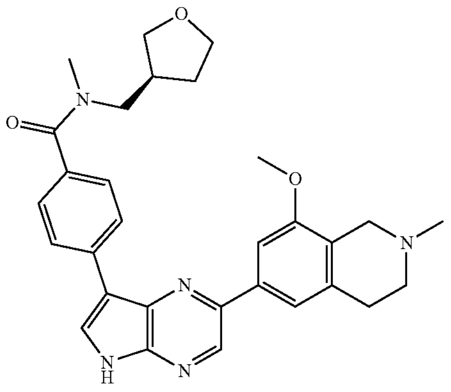 [SMILES: COc1cc(-c2cnc3[nH]cc(-c4ccc(C(=O)N(C)C[C@@H]5CCOC5)cc4)c3n2)cc2c1CN(C)CC2]

Example 57 (8 mg, 12%) was prepared in a manner similar to that in Example 1 step 10 from (S)-4-(2-(8-methoxy-2-methyl-1, 2, 3, 4-tetrahydroisoquinolin-6-yl)-5-tosyl-5H-pyrrolo[2, 3-b]pyrazin-7-yl)-N-methyl-N-((tetrahydrofuran-3-yl)methyl)benzamide. $^1$H NMR (400 MHz, DMSO-d6) δ 12.42 (d, J=2.4 Hz, 1H), 8.95 (s, 1H), 8.54 (d, J=2.8 Hz, 1H), 8.41 (d, J=8.4 Hz, 2H), 7.60 (d, J=7.6 Hz, 2H), 7.53-7.45 (m, 2H), 3.94 (s, 3H), 3.89-3.40 (m, 7H), 3.30-3.20 (m, 1H), 3.00 (s, 3H), 2.97-2.91 (m, 2H), 2.71-2.60 (m, 3H), 2.41 (s, 3H), 2.10-1.80 (m, 1H), 1.70-1.30 (m, 1H). LC-MS $(M+H)^+$=512.3.

Example 58: 4-(2-(2-(2-hydroxy-2-methylpropyl)-8-methoxy-1, 2, 3, 4-tetrahydroisoquinolin-6-yl)-5H-pyrrolo[2, 3-b]pyrazin-7-yl)-N, N-dimethylbenzamide

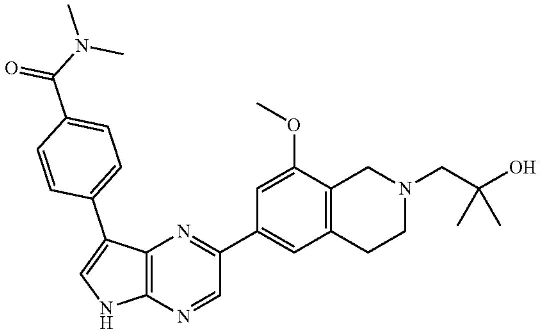 [SMILES: COc1cc(-c2cnc3[nH]cc(-c4ccc(C(=O)N(C)C)cc4)c3n2)cc2c1CN(CC(C)(C)O)CC2]

Step 1: 1-(6-bromo-8-methoxy-3, 4-dihydroisoquinolin-2 (1H)-yl)-2-methylpropan-2-ol; trifluoroacetic acid

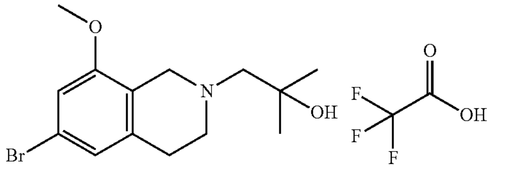

A solution of 6-bromo-8-methoxy-1, 2, 3, 4-tetrahydroisoquinoline (250 mg, 1.03 mmol) and 2, 2-dimethyloxirane (112 mg, 1.55 mmol) in EtOH (5 mL) was irradiated under microwave for 90 min at 110° C. The mixture was cooled down to room temperature and concentrated under reduced pressure. The residue was purified by C18 chromatography, eluted with acetonitrile/water (contained 0.05% TFA) (0:1 to 1:1) to give the title compound (300 mg, 70%). LC-MS $(M+H)^+$=314.0.

Step 2: 4-(2-(2-(2-hydroxy-2-methylpropyl)-8-methoxy-1, 2, 3, 4-tetrahydroisoquinolin-6-yl)-5-tosyl-5H-pyrrolo[2, 3-b]pyrazin-7-yl)-N, N-dimethylbenzamide

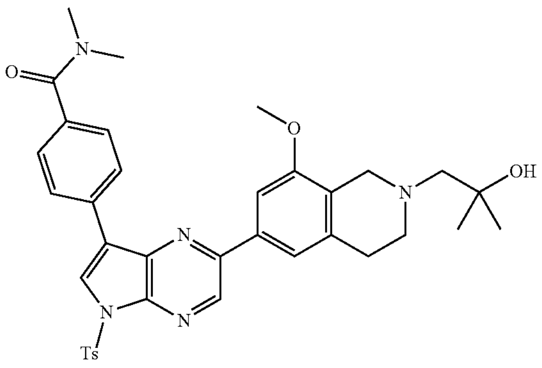 [SMILES: COc1cc(-c2cnc3c(n2)c(-c2ccc(C(=O)N(C)C)cc2)cn3S(=O)(=O)c2ccc(C)cc2)cc2c1CN(CC(C)(C)O)CC2]

The title compound (300 mg, 65%) was prepared in a manner similar to that in Example 1 step 9 from N, N-dimethyl-4-(2-(4, 4, 5, 5-tetramethyl-1, 3, 2-dioxaborolan-2-yl)-5-tosyl-5H-pyrrolo[2, 3-b]pyrazin-7-yl)benzamide and 1-(6-bromo-8-methoxy-3, 4-dihydroisoquinolin-2 (1H)-yl)-2-methylpropan-2-ol; trifluoroacetic acid. LC-MS $(M+H)^+$ =654.3.

Step 3: 4-(2-(2-(2-hydroxy-2-methylpropyl)-8-methoxy-1, 2, 3, 4-tetrahydroisoquinolin-6-yl)-5H-pyrrolo[2, 3-b]pyrazin-7-yl)-N, N-dimethylbenzamide

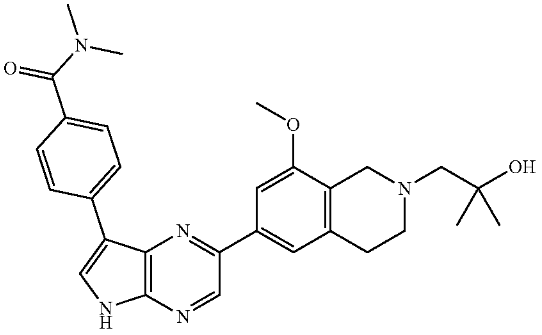 [SMILES: COc1cc(-c2cnc3[nH]cc(-c4ccc(C(=O)N(C)C)cc4)c3n2)cc2c1CN(CC(C)(C)O)CC2]

Example 58 (35 mg, 18%) was prepared in a manner similar to that in Example 1 step 10 from 4-(2-(2-(2-hydroxy-2-methylpropyl)-8-methoxy-1, 2, 3, 4-tetrahydroisoquinolin-6-yl)-5-tosyl-5H-pyrrolo[2, 3-b]pyrazin-7-yl)-N, N-dimethylbenzamide. $^1$H NMR (400 MHz, DMSO-d6) δ 12.41 (s, 1H), 8.94 (s, 1H), 8.53 (s, 1H), 8.41 (d, J=8.4 Hz, 2H), 7.64-7.54 (m, 2H), 7.52 (d, J=8.4 Hz, 2H), 4.18 (s, 1H), 3.93 (s, 3H), 3.79-3.60 (m, 2H), 3.09-2.98 (m, 6H), 2.97-2.88 (m, 2H), 2.88-2.75 (m, 2H), 2.48-2.37 (m, 2H), 1.14 (s, 6H). LC-MS $(M+H)^+$=500.3.

Example 59: N-(2-cyanoethyl)-4-(2-(2, 5-dimethyl-1, 2, 3, 4-tetrahydroisoquinolin-7-yl)-5H-pyrrolo[2, 3-b]pyrazin-7-yl)-N-methylbenzamide

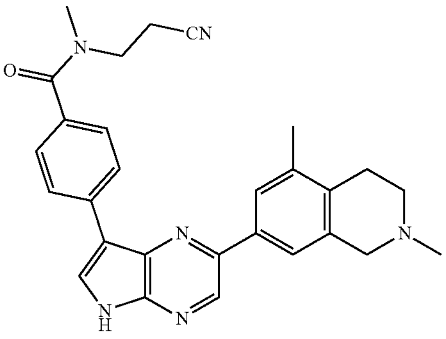 [SMILES: Cc1cc(-c2cnc3[nH]cc(-c4ccc(C(=O)N(C)CCC#N)cc4)c3n2)cc2c1CCN(C)C2]

Step 1: (4-((2-cyanoethyl)(methyl)carbamoyl)phenyl)boronic acid

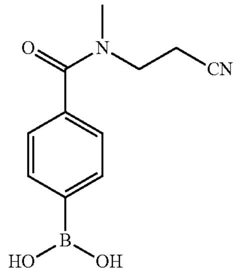 [SMILES: CN(CCC#N)C(=O)c1ccc(B(O)O)cc1]

The title compound (2.4 g, 63%) was prepared in a manner similar to that in Example 15 step 1 from 4-boronobenzoic acid and 3-(methylamino)propanenitrile. LC-MS $(M+H)^+$=233.1.

Step 2: 4-(2-bromo-5-tosyl-5H-pyrrolo[2, 3-b]pyrazin-7-yl)-N-(2-cyanoethyl)-N-methylbenzamide

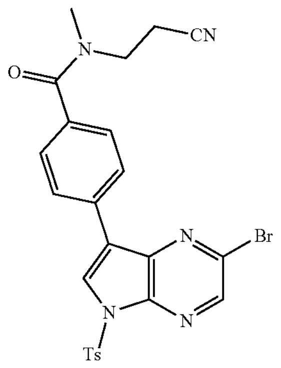 [SMILES: Cc1ccc(S(=O)(=O)n2cc(-c3ccc(C(=O)N(C)CCC#N)cc3)c3nc(Br)cnc32)cc1]

The title compound (330 mg, 44%) was prepared in a manner similar to that in Example 1 step 2 from 2-bromo-7-iodo-5-tosyl-5H-pyrrolo[2, 3-b]pyrazine and (4-((2-cyanoethyl) (methyl)carbamoyl)phenyl)boronic acid. LCMS $(M+H)^+$=538.1.

Step 3: N-(2-cyanoethyl)-4-(2-(2, 5-dimethyl-1, 2, 3, 4-tetrahydroisoquinolin-7-yl)-5-tosyl-5H-pyrrolo[2, 3-b]pyrazin-7-yl)-N-methylbenzamide

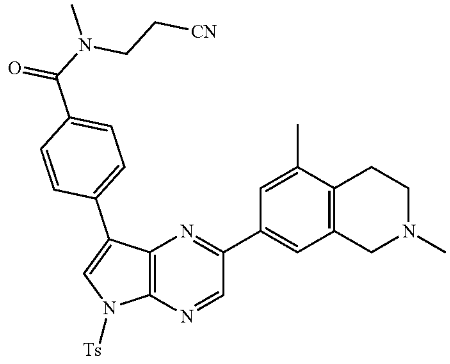 [SMILES: Cc1ccc(S(=O)(=O)n2cc(-c3ccc(C(=O)N(C)CCC#N)cc3)c3nc(-c4cc(C)c5c(c4)CN(C)CC5)cnc32)cc1]

The title compound (185 mg, 55%) was prepared in a manner similar to that in Example 2 step 5 from 4-(2-bromo-5-tosyl-5H-pyrrolo[2, 3-b]pyrazin-7-yl)-N-(2-cyanoethyl)-N-methylbenzamide and 2, 5-dimethyl-7-(4, 4, 5, 5-tetramethyl-1, 3, 2-dioxaborolan-2-yl)-1, 2, 3, 4-tetrahydroisoquinoline. LC-MS $(M+H)^+$=619.4.

Step 4: N-(2-cyanoethyl)-4-(2-(2, 5-dimethyl-1, 2, 3, 4-tetrahydroisoquinolin-7-yl)-5H-pyrrolo[2, 3-b]pyrazin-7-yl)-N-methylbenzamide

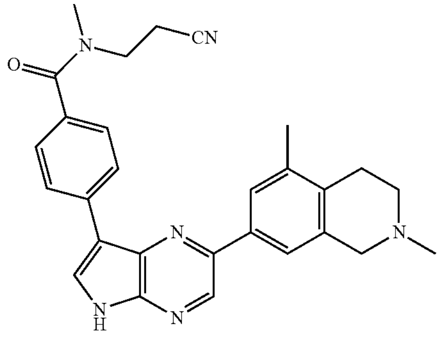 [SMILES: Cc1cc(-c2cnc3[nH]cc(-c4ccc(C(=O)N(C)CCC#N)cc4)c3n2)cc2c1CCN(C)C2]

Example 59 (29 mg, 12%) was prepared in a manner similar to that in Example 1 step 10 from N-(2-cyanoethyl)-4-(2-(2, 5-dimethyl-1, 2, 3, 4-tetrahydroisoquinolin-7-yl)-5-tosyl-5H-pyrrolo[2, 3-b]pyrazin-7-yl)-N-methylbenzamide. $^1$H NMR (400 MHz, DMSO-d6) δ 12.41 (d, J=2.4 Hz, 1H), 8.88 (s, 1H), 8.53 (d, J=2.4 Hz, 1H), 8.41 (d, J=8.0 Hz, 2H), 7.86 (s, 1H), 7.74 (s, 1H), 7.53 (d, J=8.4 Hz, 2H), 3.87-3.56 (m, 4H), 3.04 (s, 3H), 2.98-2.86 (m, 2H), 2.81-2.65 (m, 4H), 2.40 (s, 3H), 2.32 (s, 3H). LC-MS $(M+H)^+$=465.3.

Example 95: 4-(2-(5-(difluoromethyl)-2-methyl-1, 2, 3, 4-tetrahydroisoquinolin-7-yl)-5H-pyrrolo[2, 3-b]pyrazin-7-yl)-N, N-dimethylbenzamide

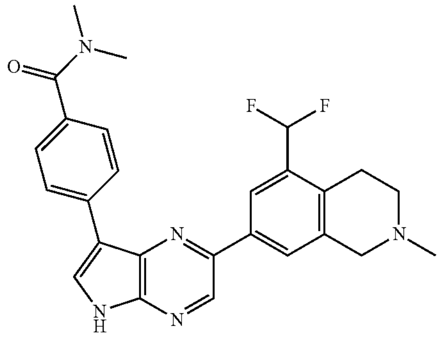 [SMILES: CN1CCc2c(cc(-c3cnc4[nH]cc(-c5ccc(C(=O)N(C)C)cc5)c4n3)cc2C(F)F)C1]

Step 1: methyl 2-methyl-1, 2, 3, 4-tetrahydroisoquinoline-5-carboxylate

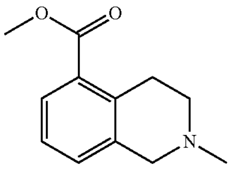

The title compound (830 mg, 71%) was prepared in a manner similar to that in Example 1 step 8 from methyl 1, 2, 3, 4-tetrahydroisoquinoline-5-carboxylate and formalin. LC-MS $(M+H)^+=206.1$.

Step 2: methyl 7-bromo-2-methyl-1, 2, 3, 4-tetrahydroisoquinoline-5-carboxylate

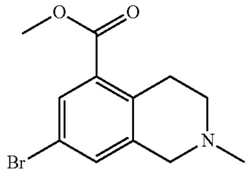

To a stirred mixture of methyl 2-methyl-1, 2, 3, 4-tetrahydroisoquinoline-5-carboxylate (200 mg, 0.97 mmol) in aqueous $H_2SO_4$ (55%, 1.0 mL) was added $KBrO_3$ (170 mg, 0.97 mmol) in portions at 0° C. The mixture was stirred for 15 h at room temperature then quenched with water (10 mL) at 0° C. The mixture was basified to pH 8 with NaOH (4 M) then successively extracted with DCM (30 mL×2). The combined organic layer was dried over anhydrous $Na_2SO_4$. After filtration, the filtrate was concentrated under reduced pressure. The residue was purified by silica gel column chromatography, eluted with MeOH/DCM (1:10) to give the title compound (82 mg, 30%). $^1H$ NMR (400 MHz, DMSO-d6) δ 7.77 (s, 1H), 7.54 (s, 1H), 3.82 (s, 3H), 3.51 (s, 2H), 3.04-2.96 (m, 2H), 2.60-2.54 (m, 2H), 2.31 (s, 3H). LC-MS $(M+H)^+=284.0$.

Step 3: (7-bromo-2-methyl-1, 2, 3, 4-tetrahydroisoquinolin-5-yl)methanol

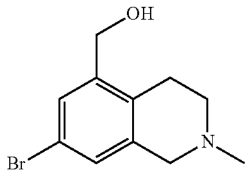

At 0° C., to a solution of methyl 7-bromo-2-methyl-1, 2, 3, 4-tetrahydroisoquinoline-5-carboxylate (507 mg, 1.78 mmol) in THF (12 mL) was added $LiBH_4$ in THF (2.0 M, 5.0 mL, 10 mmol) dropwise. To the mixture was added MeOH (3 mL). The solution was stirred for 15 h at 70° C. The mixture was cooled to room temperature then quenched with water (15 mL). The mixture was extracted with ethyl acetate (25 mL×3). The organic phases were combined, washed with brine and dried over $Na_2SO_4$. The solvent was concentrated under reduced pressure and the residue was purified by silica gel flash chromatography eluting with MeOH/DCM (0:1 to 1:9) to give the title compound (190 mg, 41%). LC-MS $(M+H)^+=256.1$.

Step 4: 7-bromo-2-methyl-1, 2, 3, 4-tetrahydroisoquinoline-5-carbaldehyde

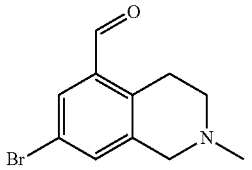

At 0° C., to a solution of (7-bromo-2-methyl-1, 2, 3, 4-tetrahydroisoquinolin-5-yl)methanol (60 mg, 0.233 mmol) in DCM (3 mL) was added Dess-Martin periodinane (119 mg, 0.280 mmol) under nitrogen. The mixture was stirred for 2 h at room temperature then quenched with saturated $NaHCO_3$ (20 mL). The mixture was extracted with DCM (20 mL×3). The combined organic layer was washed with brine (20 mL) and dried over $Na_2SO_4$ then filtered. The filtrate was concentrated under reduced pressure and the residue was purified by silica gel flash chromatography, eluted with EtOAc/hexane (0:1 to 1:9) to give the title compound (38 mg, 65%). LC-MS $(M+H)^+=254.1$.

Step 5: 7-bromo-5-(difluoromethyl)-2-methyl-1, 2, 3, 4-tetrahydroisoquinoline

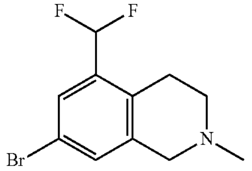

At 0° C., to a solution of 7-bromo-2-methyl-1, 2, 3, 4-tetrahydroisoquinoline-5-carbaldehyde (38 mg, 0.151 mmol) in DCM (4 mL) was added diethylaminosulfur trifluoride (148 mg, 0.914 mmol) dropwise. The mixture was stirred for 3 h at room temperature under nitrogen then quenched with saturated $NaHCO_3$ (15 mL) The mixture was extracted with ethyl acetate (15 mL×3). The combined organic layer was washed with brine (15 mL) and dried over $Na_2SO_4$. The solvent was concentrated under reduced pressure and the residue was purified by silica gel flash chromatography, eluted with MeOH/DCM (0:1 to 1:9) to give the title compound (27 mg, 65%). LC-MS $(M+H)^+=276.1$.

Step 6: 4-(2-(5-(difluoromethyl)-2-methyl-1, 2, 3, 4-tetrahydroisoquinolin-7-yl)-5H-pyrrolo[2, 3-b]pyrazin-7-yl)-N, N-dimethylbenzamide Example 95 (19 mg, 42%) was prepared in a manner similar to that in Example 1 step 9 from 7-bromo-5-(difluoromethyl)-2-methyl-1, 2, 3, 4-tetrahydroisoquinoline and 7-(4-(dimethylcarbamoyl)phenyl)-5-tosyl-5H-pyrrolo[2, 3-b]pyrazin-2-ylboronic acid. $^1H$ NMR (400 MHz, DMSO-d6) δ 12.47 (s, 1H), 8.95 (s, 1H), 8.54 (s, 1H), 8.38 (d, J=8.0 Hz, 2H), 8.23 (s, 1H), 8.07 (s, 1H), 7.52 (d, J=7.9 Hz, 2H), 7.24 (t, J=54.8 Hz, 1H), 3.68 (s, 2H), 3.01 (app s, 8H), 2.71-2.64 (m, 2H), 2.39 (s, 3H). LC-MS $(M+H)^+$=462.3.

Example 126: 4-(2-(2, 8-dimethyl-1, 2, 3, 4-tetrahydroisoquinolin-6-yl)-5H-pyrrolo[2, 3-b]pyrazin-7-yl)-N, N, 2-trimethylbenzamide

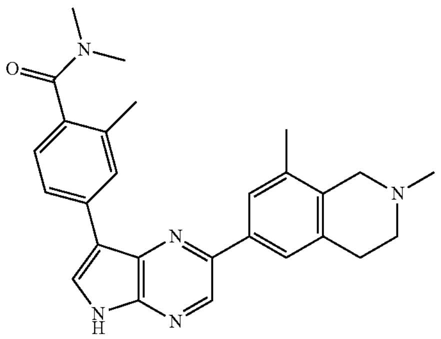 [SMILES: Cc1cc(-c2c[nH]c3ncc(-c4cc(C)c5c(c4)CCN(C)C5)nc23)ccc1C(=O)N(C)C]

Step 1: O-pivaloylhydroxylamine trifluoromethanesulfonate salt

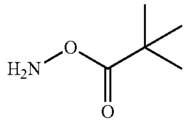

TfOH (18.9 g, 125.7 mmol) was added to a solution of tert-butyl (pivaloyloxy)carbamate (24.8 g, 114.3 mmol) in MTBE (230 mL) at 0° C. and stirred at room temperature for 4 h. The volume of solution was reduced to about 100 mL under reduced pressure and the precipitate was collected by filtration. The solid was dried under vacuum to give the title compound (26.0 g, 85%). LC-MS $(M+H)^+$=118.0.

Step 2: 4-bromo-2-methyl-N-(pivaloyloxy)benzamide

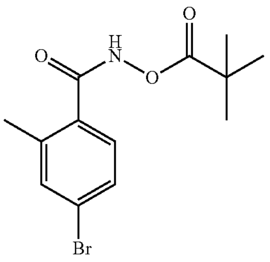 [SMILES: Cc1cc(Br)ccc1C(=O)NOC(=O)C(C)(C)C]

DIPEA (15.7 g, 121.6 mmol) was added to a solution of 4-bromo-2-methylbenzoic acid (8.82 g, 40.52 mmol) in THF (150 mL) at 0° C., followed by T3P (25.8 g, 81.1 mmol) and O-pivaloylhydroxylamine trifluoromethanesulfonate salt (26.0 g, 97.3 mmol). The reaction was stirred at room temperature overnight. Brine (100 mL) was added and the mixture was extracted with ethyl acetate (100 mL×3). The combined organic layer was dried over $Na_2SO_4$, filtered and concentrated under reduced pressure. The residue was purified by silica gel column chromatography to give the title compound (7.5 g, 59%). LC-MS $(M+H)^+$=314.0.

Step 3: 6-bromo-8-methyl-3, 4-dihydroisoquinolin-1 (2H)-one

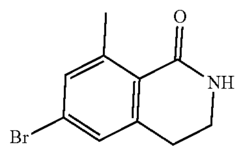

KOAc (5.16 g, 52.5 mmol) and dichloro (pentamethylcyclopentadienyl)rhodium (III) dimer (737.7 mg, 1.19 mmol) were added to a solution of 4-bromo-2-methyl-N-(pivaloyloxy)benzamide (7.5 g, 23.9 mmol) in acetonitrile (150 mL). The solution was stirred under an ethylene atmosphere (3 bar) at room temperature for overnight. The solvent was removed in vacuo and the residue was partitioned between water (20 mL) and ethyl acetate (50 mL). The organic layer was dried over $Na_2SO_4$, filtered and concentrated. The residue was purified by silica gel column chromatography to give the title compound (4.67 g, 82%). LC-MS $(M+H)^+$=240.0.

Step 4: 6-bromo-8-methyl-1, 2, 3, 4-tetrahydroisoquinoline

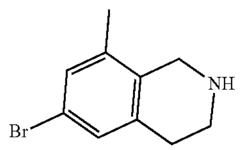

To 6-bromo-8-methyl-3, 4-dihydroisoquinolin-1 (2H)-one (4.67 g, 19.5 mmol) was added $BH_3$ in THF (1.0 M, 77.8 mL, 77.8 mmol) and the reaction mixture was refluxed overnight. The mixture was cooled to 0° C. and MeOH (5 mL) was added followed by HCl (2 M, 25 mL). The solution was heated to 80° C. for 3 h. The mixture was cooled to room temperature and solvent was removed in vacuo. The residue was dissolved in DCM (50 mL) and the solution was successively washed with saturated $NaHCO_3$ (30 mL) and brine (30 mL), dried over $Na_2SO_4$, filtered and concentrated. The residue was purified by silica gel column chromatography to give the title compound (3.79 g, 86%). LC-MS $(M+H)^+$=226.0.

Step 5: 6-bromo-2, 8-dimethyl-1, 2, 3, 4-tetrahydroisoquinoline

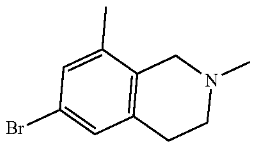

Formalin (37%, 3.48 g, 42.90 mmol) was added to a solution of 6-bromo-8-methyl-1, 2, 3, 4-tetrahydroisoquinoline (1.94 g, 8.58 mmol) in DCM (30 mL). After 5 min, NaBH $(OAc)_3$ (3.64 g, 17.2 mmol) was added and the mixture was stirred at room temperature overnight. Saturated $NaHCO_3$ (20 mL) was added and the mixture was extracted with DCM (30 mL×2). The combined organic layer was dried over $Na_2SO_4$, filtered and concentrated. The residue was purified by silica gel column chromatography to give the title compound (1.85 g, 90%). LC-MS $(M+H)^+$ =240.0.

Step 6: 2, 8-dimethyl-6-(4, 4, 5, 5-tetramethyl-1, 3, 2-dioxaborolan-2-yl)-1, 2, 3, 4-tetrahydroisoquinoline

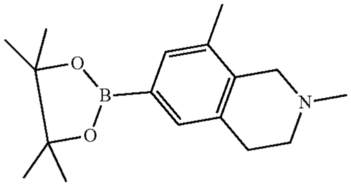

6-bromo-2, 8-dimethyl-1, 2, 3, 4-tetrahydroisoquinoline (1.85 g, 7.71 mmol), BPD (3.92 g, 15.4 mmol), Pd (dppf)Cl2 (282 mg, 0.385 mmol) and KOAc (2.27 g, 23.1 mmol) were added to 1, 4-dioxane (25 mL) and the mixture was heated to 95° C. under $N_2$ overnight. After cooled to room temperature, the mixture was concentrated in vacuo. The residue was purified by silica gel column chromatography to give the title compound (1.77 g, 80%). LC-MS $(M+H)^+$=288.0.

Step 7: 4-(2-(2, 8-dimethyl-1, 2, 3, 4-tetrahydroisoquinolin-6-yl)-5H-pyrrolo[2, 3-b]pyrazin-7-yl)-N, N, 2-trimethylbenzamide 4-(2-bromo-5-tosyl-5H-pyrrolo[2, 3-b]pyrazin-7-yl)-N, N, 2-trimethylbenzamide (879 mg, 1.71 mmol), 2, 8-dimethyl-6-(4, 4, 5, 5-tetramethyl-1, 3, 2-dioxaborolan-2-yl)-1, 2, 3, 4-tetrahydroisoquinoline (590 mg, 2.06 mmol), $K_2CO_3$ (473 mg, 3.43 mmol) and Pd $(dppf)Cl_2$ (63 mg, 0.086 mmol) was added to 1, 4-dioxane (20 mL) and water (3 mL), and the mixture was heated to 100° C. under $N_2$ then stirred for overnight. The mixture was cooled to room temperature and concentrated in vacuo. The residue was diluted with water (30 mL) and extracted with DCM (30 mL×2). The combined organic layer was washed with brine (30 mL), dried over $Na_2SO_4$, filtered and concentrated. The crude was purified by silica gel flash chromatography to give Example 126 (120 mg, 16%). $^1H$ NMR (400 MHz, DMSO-d6) δ 12.34 (s, 1H), 8.88 (s, 1H), 8.46 (s, 1H), 8.27 (s, 1H), 8.20 (d, J=7.9 Hz, 1H), 7.84 (s, 1H), 7.80 (s, 1H), 7.24 (d, J=7.9 Hz, 1H), 3.47 (s, 2H), 3.03 (s, 3H), 2.98-2.91 (m, 2H), 2.83 (s, 3H), 2.67-2.60 (m, 2H), 2.42 (s, 3H), 2.33-2.25 (m, 6H). LC-MS $(M+H)^+$=440.0.

Example 127: 4-(2-(2-ethyl-5-methyl-1, 2, 3, 4-tetrahydroisoquinolin-7-yl)-5H-pyrrolo[2, 3-b]pyrazin-7-yl)-N, N, 2-trimethylbenzamide

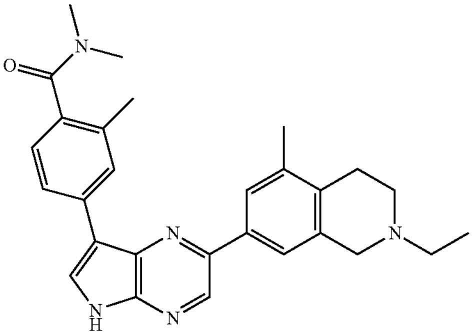 [SMILES: CCN1CCc2c(C)cc(-c3cnc4[nH]cc(-c5ccc(C(=O)N(C)C)c(C)c5)c4n3)cc2C1]

Step 1: 7-bromo-2-ethyl-5-methyl-1, 2, 3, 4-tetrahydroisoquinoline

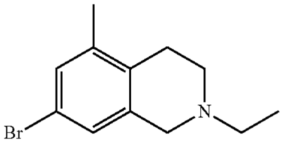

The title compound (787 mg, 100%) was prepared in the same manner which described in Example 1 step 8 from 7-bromo-5-methyl-1, 2, 3, 4-tetrahydroisoquinoline and acetaldehyde. LCMS $(M+H)^+$=254.0, 256.0.

Step 2: 2-ethyl-5-methyl-7-(4, 4, 5, 5-tetramethyl-1, 3, 2-dioxaborolan-2-yl)-1, 2, 3, 4-tetrahydroisoquinoline

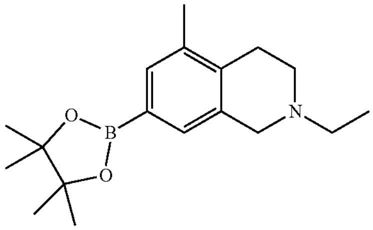 [SMILES: CCN1CCc2c(C)cc(B3OC(C)(C)C(C)(C)O3)cc2C1]

The title compound (530 mg, 57%) was prepared in the same manner which described in Example 2 step 4 from 7-bromo-2-ethyl-5-methyl-1, 2, 3, 4-tetrahydroisoquinoline. LCMS $(M+H)^+$=302.1.

Step 3: 4-(2-(2-ethyl-5-methyl-1, 2, 3, 4-tetrahydroisoquinolin-7-yl)-5H-pyrrolo[2, 3-b]pyrazin-7-yl)-N, N, 2-trimethylbenzamide Example 127 (120 mg, 22%) was prepared in a manner similar to that in Example 2 step 5 from 4-(2-bromo-5-tosyl-5H-pyrrolo[2, 3-b]pyrazin-7-yl)-N, N, 2-trimethylbenzamide and 2-ethyl-5-methyl-7-(4, 4, 5, 5-tetramethyl-1, 3, 2-dioxaborolan-2-yl)-1, 2, 3, 4-tetrahydroisoquinoline. $^1H$ NMR (400 MHz, DMSO-d6) δ 12.32 (s, 1H), 8.86 (s, 1H), 8.45 (s, 1H), 8.27-8.20 (m, 2H), 7.86 (s, 1H), 7.74 (s, 1H), 7.25 (d, J=7.6 Hz, 1H), 3.65 (s, 2H), 3.03 (s, 3H), 2.83 (s, 3H), 2.78-2.70 (m, 4H), 2.57-2.51 (m, 2H), 2.31 (s, 3H), 2.29 (s, 3H), 1.13 (t, J=7.1 Hz, 3H). LCMS $(M+H)^+$=454.6.

Example 128: 4-(2-(2,8-dimethyl-1,2,3,4-tetrahydroisoquinolin-6-yl)-5H-pyrrolo[2,3-b]pyrazin-7-yl)-2-methyl-N,N-bis(methyl-d3)benzamide

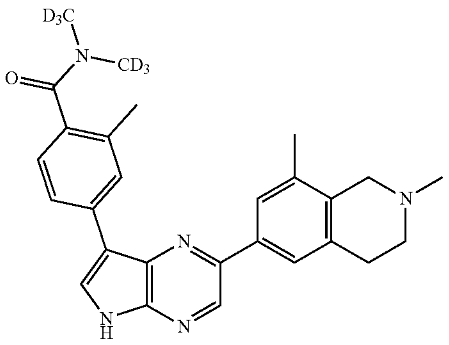 [SMILES: [2H]C([2H])([2H])N(C(=O)c1ccc(-c2c[nH]c3ncc(-c4cc(C)c5c(c4)CCN(C)C5)nc23)cc1C)C([2H])([2H])[2H]]

Step 1: 4-bromo-2-methyl-N,N-bis(methyl-d3)benzamide

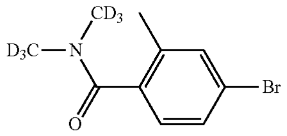 [SMILES: [2H]C([2H])([2H])N(C(=O)c1ccc(Br)cc1C)C([2H])([2H])[2H]]

A mixture of 4-bromo-2-methylbenzoic acid (12.4 g, 57.6 mmol) and $SOCl_2$ (30 mL) was stirred at 60° C. for 3 h under a refluxing condenser. The mixture was cooled to room temperature and concentrated under vacuum. The crude residue was dissolved in anhydrous DCM (50 mL) and the solution was added dropwise into a solution of bis(methyl-d3)amine HCl salt (5.0 g, 57 mmol) and $Et_3N$ (20 g, 200 mmol) in anhydrous DCM (200 mL) at 0° C. The mixture was warmed to room temperature, stirred for 2 h then diluted with water (200 mL). The organic layer was separated, dried over $Na_2SO_4$ then concentrated under reduced pressure to give the title compound (12.7 g, 88%). LC-MS $(M+H)^+$= 248.1.

Step 2: 2-methyl-N,N-bis(methyl-d3)-4-(4,4,5,5-tetramethyl-1,3,2-dioxaborolan-2-yl)benzamide

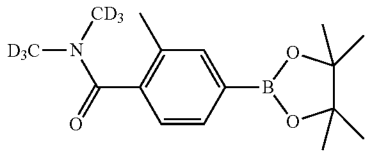 [SMILES: [2H]C([2H])([2H])N(C(=O)c1ccc(B2OC(C)(C)C(C)(C)O2)cc1C)C([2H])([2H])[2H]]

The title compound (7.4 g, 62%) was prepared in a manner similar to that in Example 2 step 2 from 4-bromo-2-methyl-N,N-bis(methyl-d3)benzamide and BPD. $^1H$ NMR (400 MHz, $CDCl_3$) δ 7.68-7.62 (m, 2H), 7.17 (d, J=6.9 Hz, 1H), 2.29 (s, 3H), 1.35 (s, 12H). LC-MS $(M+H)^+$=296.2.

Step 3: (2,8-dimethyl-1,2,3,4-tetrahydroisoquinolin-6-yl)boronic acid

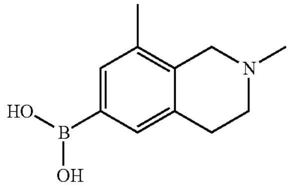

To a solution of 6-bromo-2,8-dimethyl-1,2,3,4-tetrahydroisoquinoline (46 g, 191 mmol) in THF (500 mL) was added n-BuLi (2.4 M, 95 mL, 228 mmol) dropwise at −78° C. and the mixture was stirred at −78° C. for 30 min. To the mixture was added triisopropyl borate (54 g, 287 mmol) dropwise and the mixture was stirred at −78° C. for 2 h. The mixture was quenched with water (500 mL), and most of THF was evaporated under reduced pressure. The mixture was washed with EtOAc (100 mL×2) and the aqueous layer was neutralized with HCl (2 M) until its pH reached 9. The precipitate was collected by filtration and dried under vacuum to give the title compound (28 g, 71%). LC-MS $(M+H)^+$=206.1.

Step 4: 2,8-dimethyl-6-(5H-pyrrolo[2,3-b]pyrazin-2-yl)-1,2,3,4-tetrahydroisoquinoline

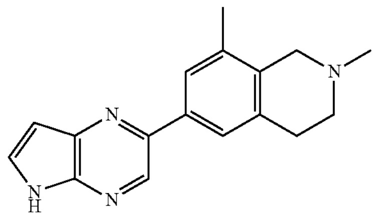 [SMILES: Cc1cc(-c2cnc3[nH]ccc3n2)cc2c1CN(C)CC2]

To a solution of 2-bromo-5H-pyrrolo[2,3-b]pyrazine (16.0 g, 81.3 mmol) and (2,8-dimethyl-1,2,3,4-tetrahydroisoquinolin-6-yl)boronic acid (20.0 g, 97.6 mmol) in dioxane (300 mL) and water (75 mL) was added $K_2CO_3$ (22.5 g, 163 mmol) and Pd(dppf)$Cl_2$ (1.78 g, 2.44 mmol) under nitrogen atmosphere. After being stirred for 15 h at 90° C., the reaction mixture was cooled to room temperature and extracted with EtOAc (100 mL×2). The combined organic layer was concentrated under reduced pressure. The residue was partitioned in between aq. HCl (200 mL, 1 N) and DCM (100 mL), then stirred at 20 minutes. The organic layer was discarded and the pH of aqueous layer was adjusted to 8-9 with aq. NaOH (6 M). The mixture was extracted DCM (200 mL×3). The combined organic layer was washed with brine (100 mL), dried over anhydrous $Na_2SO_4$ and concentrated under reduced pressure. The crude was triturated with TBME (100 mL) for 30 minutes, and the solid was collected by filtration to give the title compound (16.4 g, 60%). $^1H$ NMR (400 MHz, DMSO-d6) δ 12.07 (s, 1H), 8.79 (s, 1H), 7.87 (app s, 1H), 7.75 (s, 1H), 7.72 (s, 1H), 6.65 (app s, 1H), 3.45 (s, 2H), 2.96-2.87 (m, 2H), 2.64-2.57 (m, 2H), 2.41 (s, 3H), 2.25 (s, 3H). LCMS $(M+H)^+$=279.0.

Step 5: 6-(7-iodo-5H-pyrrolo[2,3-b]pyrazin-2-yl)-2,8-dimethyl-1,2,3,4-tetrahydroisoquinoline

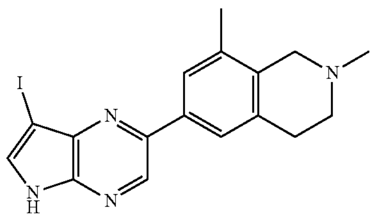 [SMILES: Cc1cc(-c2cnc3[nH]cc(I)c3n2)cc2c1CN(C)CC2]

To a solution of 2,8-dimethyl-6-(5H-pyrrolo[2,3-b]pyrazin-2-yl)-1,2,3,4-tetrahydroisoquinoline (16.4 g, 59 mmol) in DMF (200 mL) was added NIS (13.3 g, 59 mmol) in portions at 0° C. After being stirred for 30 minutes, water (600 mL) and saturated $Na_2S_2O_3$ (50 mL) was added with vigorous stirring. After 10 minutes, lots of solid appeared and the precipitate was collected by filtration to give the title compound (21.0 g, 88%). LCMS $(M+H)^+$=405.0.

Step 6: (2,6-dichlorophenyl)(2-(2,8-dimethyl-1,2,3,4-tetrahydroisoquinolin-6-yl)-7-iodo-5H-pyrrolo[2,3-b]pyrazin-5-yl)methanone

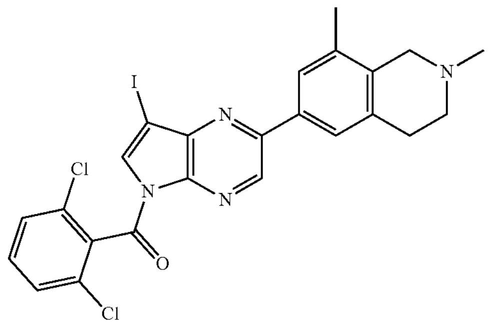 [SMILES: Cc1cc(-c2cnc3c(n2)c(I)cn3C(=O)c2c(Cl)cccc2Cl)cc2c1CN(C)CC2]

To a solution of 6-(7-iodo-5H-pyrrolo[2,3-b]pyrazin-2-yl)-2,8-dimethyl-1,2,3,4-tetrahydroisoquinoline (21.0 g, 51.85 mmol) in 2-methyl-THF (400 mL) was added triethylamine (11.2 mL, 77.8 mmol) and DMAP (634 mg, 5.2 mmol) at 0° C., followed by dropwise addition of a solution of 2,6-dichlorobenzoyl chloride (13.0 g, 62.2 mmol) in 2-methyl-THF (50 mL). The mixture was warmed to room temperature and stirred for 2 h, then quenched with water (200 mL). The organic layer was separated, and the aqueous layer was extracted with EtOAc (200 mL). The combined organic layer was washed with brine (100 mL), dried over anhydrous $Na_2SO_4$ and concentrated under reduced pressure. The residue was triturated with MTBE (200 mL) for 30 minutes, and the precipitate was collected by filtration to give the title compound (24.0 g, 80%). LCMS $(M+H)^+$=577.0.

Step 7: 4-(5-(2,6-dichlorobenzoyl)-2-(2,8-dimethyl-1,2,3,4-tetrahydroisoquinolin-6-yl)-5H-pyrrolo[2,3-b]pyrazin-7-yl)-2-methyl-N,N-bis(methyl-d3)benzamide

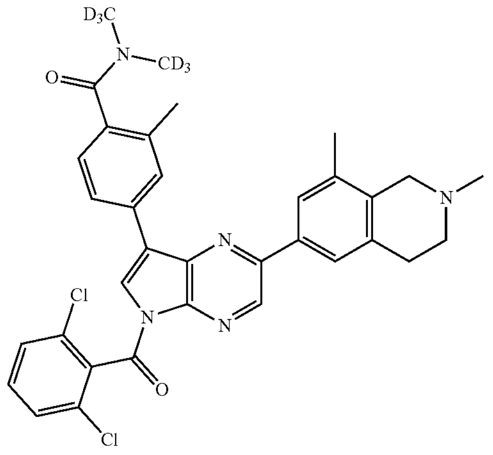 [SMILES: [2H]C([2H])([2H])N(C(=O)c1ccc(-c2cn(C(=O)c3c(Cl)cccc3Cl)c3ncc(-c4cc(C)c5c(c4)CCN(C)C5)nc23)cc1C)C([2H])([2H])[2H]]

To a mixture of (2,6-dichlorophenyl)(2-(2,8-dimethyl-1,2,3,4-tetrahydroisoquinolin-6-yl)-7-iodo-5H-pyrrolo[2,3-b]pyrazin-5-yl)methanone (7.3 g, 12.7 mmol) and 2-methyl-N,N-bis(methyl-d3)-4-(4,4,5,5-tetramethyl-1,3,2-dioxaborolan-2-yl)benzamide (4.1 g, 13.9 mmol) in 1,4-dioxane (100 mL) and water (50 mL) was added $K_2CO_3$ (4.4 g, 31.8 mmol) and $Pd(dppf)Cl_2$ (470 mg, 0.60 mmol). The mixture was stirred at 100° C. for 3 h under $N_2$, then cooled to room temperature. The mixture was successively extracted with EtOAc (100 mL×3). The combined organic layer was washed with brine (100 mL), dried over $Na_2SO_4$, filtered and concentrated. The residue was purified by silica gel column chromatography, eluting with MeOH/DCM (1:20) to give the title compound (6.7 g, 86%). LC-MS $(M+H)^+$=618.2.

Step 8: 4-(2-(2,8-dimethyl-1,2,3,4-tetrahydroisoquinolin-6-yl)-5H-pyrrolo[2,3-b]pyrazin-7-yl)-2-methyl-N,N-bis(methyl-d3)benzamide To a suspension of 4-(5-(2,6-dichlorobenzoyl)-2-(2,8-dimethyl-1,2,3,4-tetrahydroisoquinolin-6-yl)-5H-pyrrolo[2,3-b]pyrazin-7-yl)-2-methyl-N,N-bis(methyl-d3)benzamide (6.7 g, 10.9 mmol) in dioxane (100 mL) was added a solution of NaOH (2.0 g, 50 mmol) in water (50 mL). The mixture was stirred at 100° C. for 3 h. The mixture was cooled to room temperature then extracted with EtOAc (100 mL×3). The combined organic phase was washed with brine (100 mL), dried over $Na_2SO_4$, filtered and concentrated. The residue was purified by crystallization in EtOH to give Example 128 (3.5 g, 72%). $^1H$ NMR (400 MHz, DMSO) δ 12.34 (s, 1H), 8.88 (s, 1H), 8.46 (s, 1H), 8.26 (s, 1H), 8.19 (d, J=6.6 Hz, 1H), 7.84 (s, 1H), 7.80 (s, 1H), 7.24 (d, J=7.3 Hz, 1H), 3.46 (brs, 2H), 2.95 (brs, 2H), 2.62 (brs, 2H), 2.41 (s, 3H), 2.29 (brs, 6H). LC-MS $(M+H)^+$=446.5.

Biological Activity

HPK1 Kinase Activity Assay at 1 mM ATP

Compounds disclosed herein were tested for inhibition of HPK1 kinase (aa1-346, Life Technologies) activity in assays based on the time-resolved fluorescence-resonance energy transfer (TR-FRET) methodology. The assays were carried out in 384-well low volume black plates in a reaction mixture containing HPK1 kinase (40 nM), 1 mM ATP, 0.5 μM STK1 substrate and 0-10 μM compound in buffer containing 50 mM HEPES, 0.01% BSA, 0.1 mM Orthovanadate, 10 mM $MgCl_2$, 1 mM DTT, pH=7.0, 0.005% Tween-20. The kinase was incubated with the compounds disclosed herein or DMSO for 60 minutes at room temperature and the reaction was initiated by the addition of ATP and STK1 substrate. After reaction at room temperature for 120 minutes, an equal volume of stop/detection solution was added according to the manufacturer's instruction (CisBio). The stop/detection solution contained STK Antibody-Cryptate and XL665-conjugated streptavidin in Detection Buffer. The TR-FRET signals (ratio of fluorescence emission at 665 nm over emission at 620 nm with excitation at 337 nm wavelength) were recorded on a PHERAstar FS plate reader (BMG Labtech). Phosphorylation of STK1 substrate led to the binding of STK Antibody-Cryptate to the biotinylated STK1 substrate, which places fluorescent donor ($Eu^{3+}$ cryptate) in close proximity to the accepter (Streptavidin-XL665), thus resulting in a high degree of fluorescence resonance energy transfer. The inhibition of HPK1 in presence of increasing concentrations of compounds was calculated based on the ratio of fluorescence at 665 nm to that at 620 nm. The $IC_{50}$ for each compound was derived from fitting the data to the four-parameter logistic equation by Graphpad Prism software. The compounds disclosed herein showed the enzymatic activity values as in Table 1.

TABLE 1

Enzymatic activity $IC_{50}$ (nM) for the compounds disclosed herein

| Comp No. | Enzymatic activity $IC_{50}$ (nM) | Comp No. | Enzymatic activity $IC_{50}$ (nM) |
|---|---|---|---|
| 1 | 24 | 2 | 26 |
| 3 | 12 | 4 | 92 |
| 5 | 21 | 6 | 32 |
| 7A | 34 | 7B | 31 |
| 8 | 36 | 9 | 62 |
| 10 | 11 | 11 | 74 |
| 12 | 52 | 13 | 45 |
| 14 | 12 | 15 | 17 |
| 16 | 88 | 17 | 24 |
| 18 | 7 | 19 | 13 |
| 20 | 65 | 21 | 75 |
| 22 | 11 | 23 | 122 |
| 24 | 75 | 25 | 49 |
| 26 | 63 | 27 | 26 |
| 28 | 67 | 29 | 46 |
| 30 | 63 | 31 | 53 |
| 32 | 71 | 33 | 49 |
| 34 | 42 | 35 | 19 |
| 36 | 39 | 37 | 35 |
| 38 | 65 | 39 | 186 |
| 40 | 17 | 41 | 54 |
| 42 | 85 | 43 | 37 |
| 44 | 82 | 45 | 52 |
| 46 | 65 | 47 | 22 |
| 48 | 65 | 49 | 67 |
| 50 | 137 | 51 | 36 |
| 52 | 74 | 53 | 78 |
| 54 | 68 | 55 | 89 |
| 56 | 93 | 57 | 14 |
| 58 | 21 | 59 | 16 |
| 95 | 71 | 126 | 43 |
| 127 | 86 | 128 | 21 |

Cytotoxicity on HEK293 Cells Proliferation (HEK293 Cell Viability Assay)

Methods

HEK293 cell line were used in this study. Cell lines were maintained in DMEM (Dulbecco's Modified Eagle Medium) supplemented with 10% fetal bovine serum (Thermo Fisher), 50 units/mL penicillin and streptomycin (Thermo Fisher) and kept at 37° C. in a humidified atmosphere containing 5% $CO_2$ in air. Cell lines were reinstated from frozen stocks that were laid down within 50 passages from the original cells purchased. The growth-inhibitory activity of compounds in HEK293 cells was determined using CellTiter-Glo luminescent cell viability assay (Promega). 3000 cells per well were seeded into a 96-well plate to ensure logarithmic growth for 3 days treatment period. Cells were treated with a 10-point dilution series. The final compound concentration was from 0 to 10 μM. Following a 3-day exposure to the test compounds, 30 μL of CellTiter-Glo reagent was added into 100 μL cell culture medium per well. Mixture was mixed on an orbital shaker for 2 minutes to allow cell lysis, followed by 10 minutes of incubation at room temperature to allow development and stabilization of luminescent signal, which corresponded to the quantity of ATP and thus the quantity of metabolically active cells. Luminescent signal was measured using PHERAstar FS reader (BMG Labtech). $IC_{50}$ values for cell viability were determined with Dotmatics.

| Comp No. | HEK293 cell viability $IC_{50}$ (nM) | Comp No. | HEK293 cell viability $IC_{50}$ (nM) |
|---|---|---|---|
| 1 | 3646 | 2 | 3338 |
| 3 | 1272 | 6 | 5559 |
| 10 | 1417 | 15 | 1037 |
| 16 | >10000 | 20 | 3872 |
| 38 | 2187 | 95 | 5181 |
| 126 | >10000 | 127 | 3128 |

It is to be understood that, if any prior art publication is referred to herein; such reference does not constitute an admission that the publication forms a part of the common general knowledge in the art in any country.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A compound of formula (I):

(I)

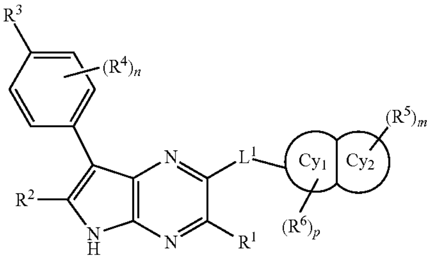

or a pharmaceutically acceptable salt thereof, or a stereoisomer thereof, wherein:

$R^1$ and $R^2$ are each hydrogen;

n is 0, 1, 2, 3 or 4;

$R^3$ and $R^4$, at each of its occurrence, are independently F, Cl, —$C_{1-8}$alkyl, cycloalkyl, heterocyclyl, —$C_{1-8}$alkyl-heterocyclyl, —$C_{1-8}$alkyl-cycloalkyl, aryl, heteroaryl, oxo, —CN, —$NO_2$, —$OR^{3a}$, —$SO_2R^{3a}$, —$SO_2NR^{3a}R^{3b}$, —$COR^{3a}$, —$CO^2R^{3a}$, —$CONR^{3a}R^{3b}$, —C(=$NR^{3a}$) $NR^{3b}R^{3c}$, —$NR^{3a}R^{3b}$, —$NR^{3a}$ $COR^{3b}$, —$NR^{3a}$ $CONR_3R^{3c}$, —$NR^{3a}$ $CO_2R^{3b}$, —$NR^{3a}$ $SONR^{3b}R^{3c}$, —$NR^{3a}$ $SO_2NR^{3b}R^{3c}$, or —$NR^{3a}$ $SO_2R^{3b}$, each of said —$C_{1-8}$alkyl, cycloalkyl, heterocyclyl, or —$C_{1-8}$alkyl-heterocyclyl, aryl, or heteroaryl is optionally substituted with at least one substituents $R^{3d}$; or $R^3$ and $R^4$, when on adjacent carbon atoms of the phenyl ring, together with the two intervening carbon atoms to which they are attached, form a 5- to 8-membered ring comprising 0, 1 or 2 heteroatoms independently selected from nitrogen, oxygen or optionally oxidized sulfur as ring member(s), said ring is optionally substituted with at least one substituents $R^{3e}$;

or two $R^4$, when on adjacent carbon atoms of the phenyl ring, together with the two intervening carbon atoms to which they are attached, form a 5- to 8-membered ring comprising 0, 1 or 2 heteroatoms independently selected from nitrogen, oxygen or optionally oxidized sulfur as ring member(s);

$R^{3a}$, $R^{3b}$, and $R^{3c}$ are each independently hydrogen, —$C_{1-8}$alkyl, cycloalkyl, or heterocyclyl, each of said-$C_{1-8}$alkyl, cycloalkyl, or heterocyclyl is optionally substituted with at least one substituents $R^{3e}$; or ($R^{3a}$ and $R^{3b}$), ($R^{3b}$ and $R^{3c}$), or ($R^{3c}$ and $R^{3a}$), together with the atom(s) to which they are attached, form a 3- to 12-membered ring, said ring comprising 0, 1 or 2 additional heteroatoms independently selected from nitrogen, oxygen or optionally oxidized sulfur as ring member(s), said ring is optionally substituted with at least one substituents $R^{3e}$, $R^{3d}$ and $R^{3e}$ are each independently F, Cl, —$C_{1-8}$alkyl, cycloalkyl, heterocyclyl, aryl, heteroaryl, oxo, —CN, —$NO_2$, —$OR^{3f}$, —$SO_2R^{3f}$, —$SO_2NR^3R^{3g}$, —$COR^{3f}$, —$CO_2R^{3f}$, —$CONR^{3d}R^{3e}$, —C(=$NR^{3f}$) $NR^{3g}R^{3h}$, —$NR^3R^{3g}$, —$NR^{3f}COR^{3g}$, —$NR^3CONR^{3g}R^{3h}$, —$NR^3CO_2R^{3f}$, —$NR^{3f}SONR^3R^{3g}$, —$NR^{3f}SO_2NR^{3g}R^{3h}$, or —$NR^3SO_2R^{38}$, each of said —$C_{1-8}$alkyl, —$C_{2-8}$alkenyl, —$C_{2-8}$alkynyl, cycloalkyl, heterocyclyl, aryl, or heteroaryl is optionally substituted with at least one substituents selected from F, Cl, —$C_{1-8}$alkyl, —$OR^{3i}$, —$NR^{3i}R^{3j}$, cycloalkyl, heterocyclyl, aryl, or heteroaryl;

$R^{3f}$, $R^{3g}$, $R^{3h}$, $R^{3i}$, and $R^{3j}$ are each independently hydrogen, —$C_{1-8}$ alkyl, $C_{1-8}$alkoxy-$C_{1-8}$alkyl-cycloalkyl, heterocyclyl, aryl, or heteroaryl;

$L^1$ is a single bond;

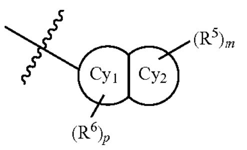 is

-continued

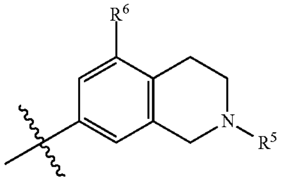 or

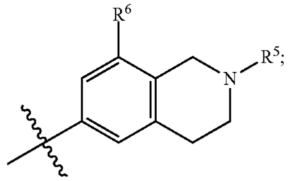;

$R^5$ at each of its occurrence, is each independently —$C_{1-8}$ alkyl, cycloalkyl, —$C_{1-8}$alkyl-cycloalkyl, heterocyclyl, —$COR^{5a}$, $CO_2R^{5a}$, —$CONR^{5a}R^{5b}$, $CH_2CONR^{5a}R^{5b}$, —$CH_2CH_2CONR^{5a}R^{5b}$, —$CH_2CH_2CH_2CONR^{5a}R^{5b}$ $CH_2CH_2NR^{5a}R^{5b}$, or —$CH_2CH_2CH_2NR^{5a}R^{5b}$, each of said —$C_{1-8}$alkyl, cycloalkyl, —$C_{1-8}$alkyl-cycloalkyl, or heterocyclyl, is optionally substituted with at least one substituents $R^{5d}$;

$R^{5a}$ and $R^{5b}$ are each independently hydrogen, —$C_{1-8}$alkyl, —$C_{1-8}$alkyl-$C_{1-8}$alkoxy, cycloalkyl, —$C_{1-8}$alkyl-heterocyclyl, —$C_{1-8}$alkyl-aryl, heterocyclyl, aryl, or heteroaryl, each of said —$C_{1-8}$alkyl, $C_{1-8}$alkyl-$C_{1-8}$ alkoxy, cycloalkyl, —$C_{1-8}$alkyl-heterocyclyl, —$C_{1-8}$ alkyl-aryl, heterocyclyl, aryl, or heteroaryl is optionally substituted with at least one substituents $R^{5e}$; or $R^{5a}$ and $R^{5b}$, together with the atom(s) to which they are attached, form a 3- to 12-membered ring, said ring comprising 0, 1 or 2 additional heteroatoms independently selected from nitrogen, oxygen or optionally oxidized sulfur as ring member(s), said ring is optionally substituted with at least one substituents $R^{5e}$;

$R^{5d}$ and $R^{5e}$ are each independently hydrogen, F, Cl, —$C_{1-8}$alkyl, cycloalkyl, heterocyclyl, aryl, heteroaryl, oxo, —CN, —$NO_2$—, —$CF_3$, —$OR^{5f}$, —$SO_2R^{5f}$, —$SO_2NR^{5f}R^{5g}$, —$POR^{5f}R^{5g}$, —$COR^{5f}$, —$CO_2R^{5f}$, —$CONR^{5f}R^{5g}$, —C(=$NR^{5h}$) $NRSR^{5g}$, —$NRSR^{5g}$, —$NR^{5f}COR^{5g}$, —$NR^{5h}CONR^{5f}R^{5g}$, —$NR^{5g}CO_2R^{5h}$, —$NR^{5h}SONR^{5f}R^{5g}$, —$NR^{5h}SO_2NR^{5f}R^{5g}$, or —$NR^{5f}SO_2R^{5g}$, each of said —$C_{1-8}$alkyl, cycloalkyl, heterocyclyl, aryl, or heteroaryl is optionally substituted with at least one substituents selected from halogen, —$C_{1-8}$alkyl, —$OR^{5i}$, —$NR^{5i}R^{5j}$, cycloalkyl, heterocyclyl, aryl, or heteroaryl;

$R^{5f}$, $R^{5g}$, $R^{5h}$, $R^{5i}$, and $R^{5j}$ are each independently hydrogen, —$C_{1-8}$alkyl, —$C_{1-8}$alkoxy, hydroxy, $C_{1-8}$alkoxy-$C_{1-8}$alkyl-, —$C_{2-8}$alkenyl, —$C_{2-8}$alkynyl, cycloalkyl, heterocyclyl, aryl, or heteroaryl;

$R^6$ is hydrogen, —$C_{1-8}$alkyl, —$OR^{6a}$, or —$NR^{6a}R^{6b}$, said —$C_{1-8}$alkyl is optionally substituted with at least one substituents $R^{6d}$;

$R^{6a}$ and $R^{6b}$ are each independently hydrogen or —$C_{1-8}$alkyl;

each Rod is independently F, Cl, or —$OR^{6f}$; and $R^{6f}$ is hydrogen or $C_{1-8}$alkyl.

2. The compound of claim 1, wherein:

a) $R^3$ is —$C_{1-8}$alkyl, —$C_{1-8}$alkyl-heterocyclyl or —$C_{1-8}$ alkyl-cycloalkyl, wherein said —$C_{1-8}$alkyl, —$C_{1-8}$alkyl-heterocyclyl or —$C_{1-8}$alkyl-cycloalkyl is optionally substituted with at least one substituent $R^{3d}$; $R^{3d}$ is independently selected from —$C_{1-8}$alkyl or —$OR^{3f}$; $R^{3f}$ is each independently hydrogen, —$C_{1-8}$alkyl; or b) $R^3$ is —$CONR^{3a}R^{3b}$, $R^{3a}$ and $R^{3b}$ are each independently hydrogen or —$C_{1-8}$alkyl, each of said —$C_{1-8}$ alkyl is substituted with at least one substituent selected from hydrogen, —$OR^{3f}$, CN, or 4-to-7 membered heterocyclyl comprising 1 or 2 heteroatoms selected from nitrogen or oxygen; and $R^{3f}$ is hydrogen or —$C_{1-8}$alkyl; or c) $R^3$ is —$CONR^{3a}R^{3b}$ or —$NR^{3a}R^{3b}$; $R^{3a}$ and $R^{3b}$ together with the nitrogen atom to which they are attached forms a 4- to 12-membered ring comprising 1 or 2 additional nitrogen or oxygen heteroatoms as ring members, said ring is optionally substituted with at least one substituent $R^{3e}$; $R^{3e}$ each is selected from oxo, —$C_{1-8}$alkyl, —$OR_{3f}$, or —$NR^{3f}R^{3g}$, said —$C_{1-8}$alkyl is optionally substituted with at least one halogen; and wherein $R^{3f}$ and $R^{3g}$ are each independently hydrogen, or —$C_{1-8}$alkyl; or d) $R^3$ is selected from

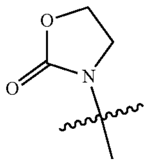 or 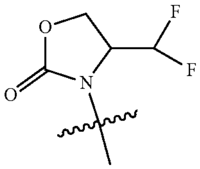.

3. The compound of claim 2, wherein $R^3$ is selected from

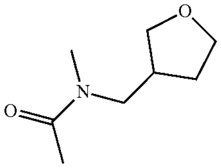, 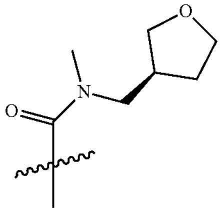,

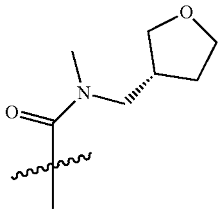, 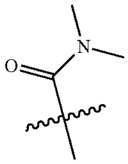,

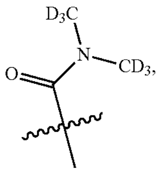 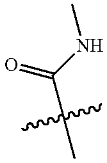 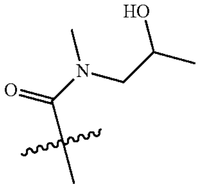,

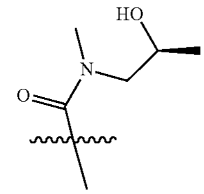, 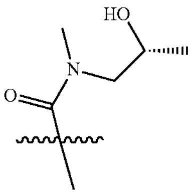,

-continued

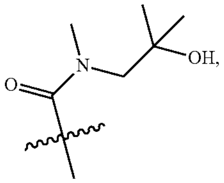 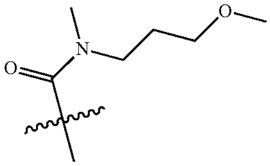,

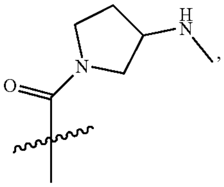

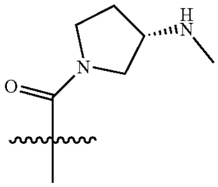, 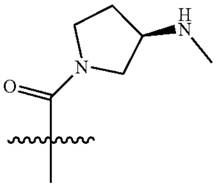,

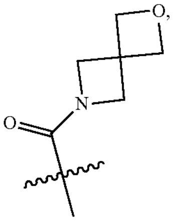 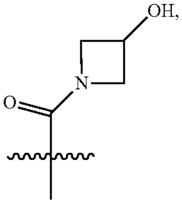

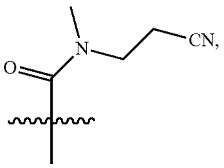 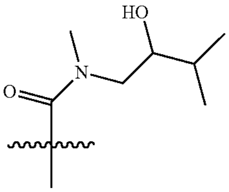,

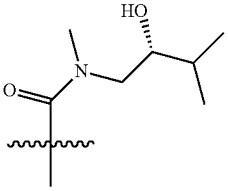, 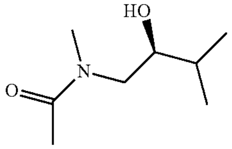,

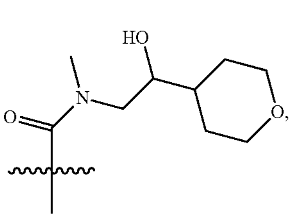

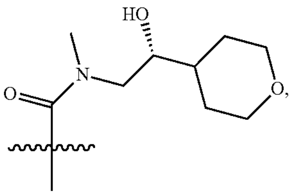

-continued

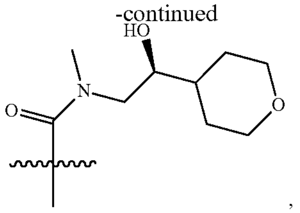

, or

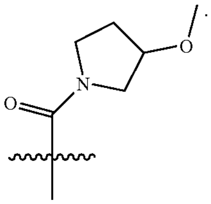

4. The compound of claim 1, wherein n is 0, 1 or 2; $R^4$ is selected from F halogen, —$C_{1-8}$alkyl, CN, —$OR^{3a}$ or —$NR^{3a}$ $CONR^{3b}R^{3c}$, said-$C_{1-8}$alkyl is optionally substituted with at least one substituent $R^{3d}$, $R^{3a}$, $R^{3b}$ and $R^{3c}$ are each independently hydrogen or —$C_{1-8}$alkyl; and $R^{3d}$ is each independently F, Cl, or —$C_{1-8}$alkyl.

5. The compound of claim 4, wherein:

a) n is 1; $R^4$ is selected from —$C_{1-8}$alkyl, F, CN, $OR^{3a}$ or —$NR^{3a}CONR^{3b}R^{3c}$, said —$C_{1-8}$alkyl is optionally substituted with at least one substituent $R^{3d}$, $R^{3a}$, $R^{3b}$ and $R^{3c}$ are each independently hydrogen or —$C_{1-8}$ alkyl; and $R^{3d}$ is each independently F, Cl, or —$C_{1-8}$ alkyl; or b) n is 2; and $R^4$ is F; or c) n is 1 or 2; and $R^4$ is selected from methyl, F, OH, CN, or —$CHF_2$; or d) n is 0; and $R^3$ is selected from

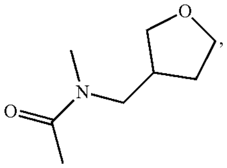

,

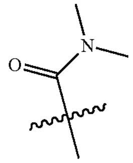

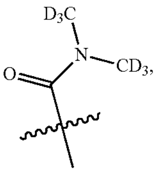

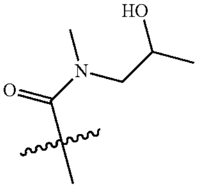

,

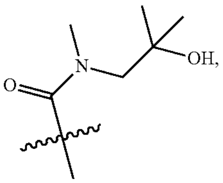

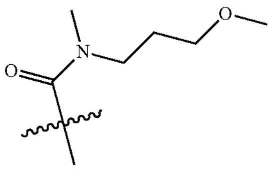

,

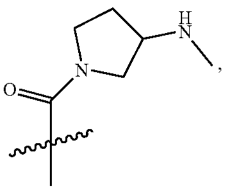

,

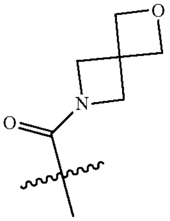

,

-continued

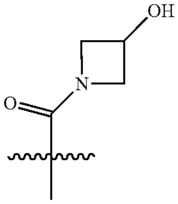

or

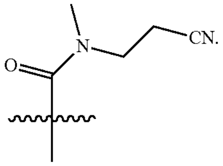

6. The compound of claim 5, wherein:

a) n is 1; $R^3$ is selected from

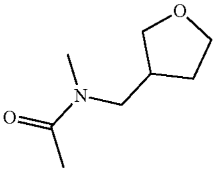

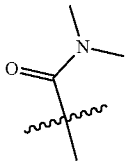

,

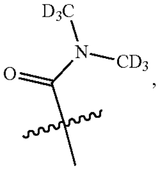

,

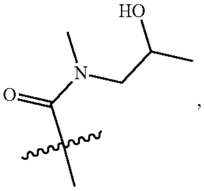

,

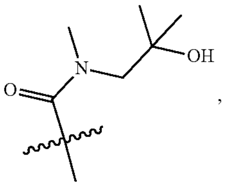

,

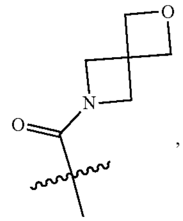

,

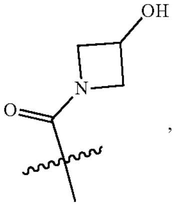

, or

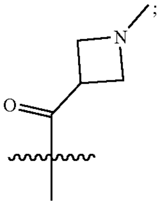

and $R^4$ is methyl, F, OH, CN, or —$CHF_2$; or b) n is 2; $R^3$ is

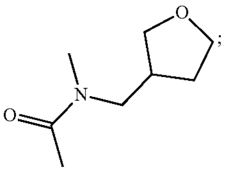

and $R^4$ is F.

7. The compound of claim 1, wherein $R^3$ and $R^4$, when on adjacent carbon atoms of the phenyl ring, together with the two intervening carbon atoms to which they are attached, form a 5- to 8-membered ring comprising 0, 1 or 2 heteroatoms independently selected from nitrogen, oxygen or optionally oxidized sulfur as ring member(s), said ring is optionally substituted with at least one substituents $R^{3e}$, and each $R^{3e}$ is independently selected from —$C_{1-8}$alkyl or oxo.

8. The compound of claim 7, wherein:

a)

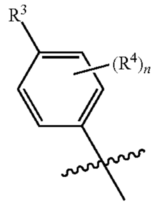 is 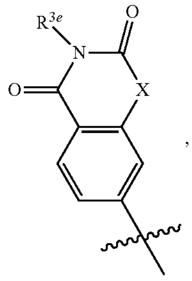,

X═NH or O, and $R^{3e}$ is —$C_{1-8}$alkyl; or b)

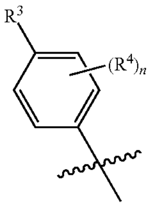 is 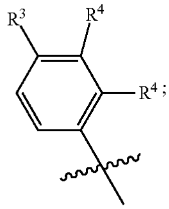;

n=2; two $R^4$ together with the two intervening carbon atoms to which they are attached, form a 5-membered ring comprising 2 heteroatoms independently selected from nitrogen, oxygen or optionally oxidized sulfur as ring member(s); or c)

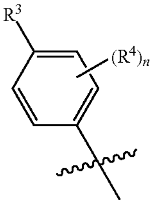 is 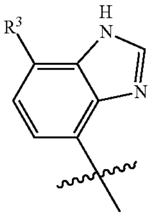 or 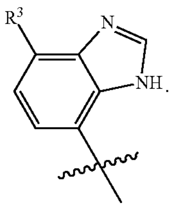.

9. The compound of claim 1, wherein:

$R^5$ is selected from —$C_{1-8}$alkyl, —$C_{1-8}$alkyl-cycloalkyl, heterocyclyl, heteroaryl, —$CONR_{5a}R^{5b}$, $CH_2CONR_{5a}R^{5b}$, —$CH_2CH_2CONR^{5a}R^{5b}$, —$NR^{5a}R^{5b}$, —$CH_2NR^{5a}R^{5b}$, or —$CH_2CH_2NR^{5a}R^{5b}$, said —$C_{1-8}$alkyl, —$C_{1-8}$alkyl-cycloalkyl or heterocyclyl or heteroaryl is optionally substituted with at least one $R^{5d}$, $R^6$ is selected from —$C_{1-8}$alkyl, —$OR^{6a}$ or —$NR^{6a}R^{6b}$, said —$C_{1-8}$alkyl is optionally substituted with at least one substituents Rod, $R^{6a}$ and $R^{6b}$ are each independently hydrogen or —$C_{1-8}$ alkyl; and $R^{6d}$ is each independently hydrogen or E halogen.

10. The compound of claim 1, wherein:

a) $R^5$ is selected from methyl, ethyl, 1-propyl, 2-propyl, 1-butyl, 2-methyl-1-propyl, 1-methylpropyl, t-butyl, —$C_{1-8}$alkyl-cycloalkyl, or heterocyclyl, said methyl, ethyl, 1-propyl, 2-propyl, 1-butyl, 2-methyl-1-propyl, 1-methylpropyl, t-butyl, —$C_{1-8}$alkyl-cycloalkyl, or heterocyclyl is optionally substituted with at least one substituents $R^{5d}$; $R^d$ is selected from —$C_{1-8}$alkyl, —$OR^{5f}$, —$NR^{5f}R^{5g}$, —$CO_2R^f$, heteroaryl, heterocyclyl, —$SO_2R^{5f}$, —$POR^{5f}R^{5g}$, —$CONR^{5f}R^{5g}$, oxo or —$CF_3$; and $R^{5f}$ and $R^{5g}$ are each independently hydrogen, —$C_{1-8}$alkyl, —$C_{1-8}$alkoxy or hydroxy; or b) $R^5$ is —$NR^{5a}R^{5b}$, —$CH_2NR^{5a}R^{5b}$, or —$CH_2CH_2NR^{5a}R^{5b}$; $R^{5a}$ and $R^{5b}$ together with the nitrogen atom to which they are attached form a 4- to 7-membered ring, said ring comprising 0, 1 or 2 additional heteroatoms independently selected from nitrogen or oxygen, said ring is optionally substituted with at least one substituents $R^{5e}$; $R^{5e}$ is each independently selected from $C_{1-8}$alkyl or $OR^{5f}$; and $R^{5f}$ is each independently selected from hydrogen or —$C_{1-8}$alkyl; or c) $R^5$ is selected from —$CONR_{5a}R^{5b}$, —$CH_2CONR_{5a}R^{5b}$, or —$CH_2CH_2CONR^{5a}R^{5b}$, $R^{5a}$ is hydrogen, methyl, or ethyl; $R^{5b}$ is selected from —$C_{1-8}$ alkyl, cycloalkyl, —$C_{1-8}$alkyl-heterocyclyl, —$C_{1-8}$alkyl-aryl, heterocyclyl, or aryl, said —$C_{1-8}$alkyl, cycloalkyl, —$C_{1-8}$alkyl-heterocyclyl, —$C_{1-8}$alkyl-aryl, heterocyclyl, or aryl is optionally substituted with at least one substituents $R^{5e}$, $R^{5e}$ is selected from halogen, —$CH_2OH$ or $OR^{5f}$; and $R^{5f}$ is selected from hydrogen, cycloalkyl or —$C_{1-8}$alkyl.

11. The compound of claim 10, wherein, $R^5$ is methyl, ethyl, propyl, butyl, pentyl or hexyl, —$CH_2OH$, —$C_2H_4OH$, $C_2H_4NHCH_3$, —$C_2H_4OCH_3$,

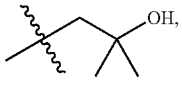 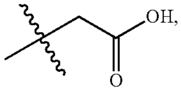

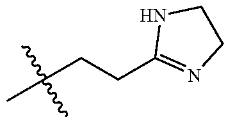, 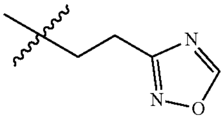,

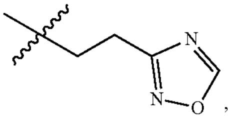,

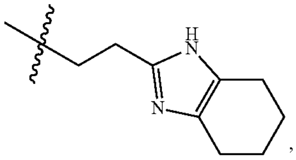,

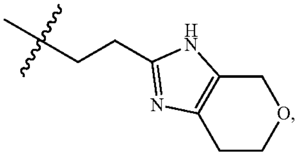

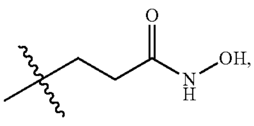 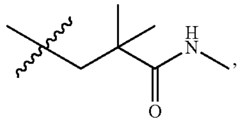,

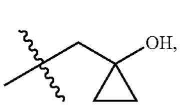 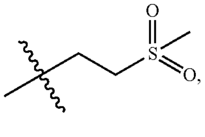

-continued
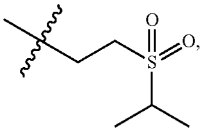
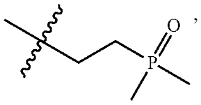 ,
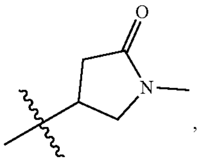 ,
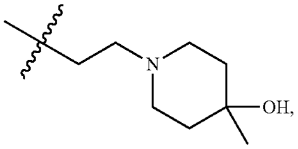
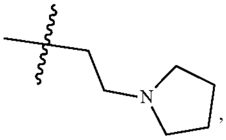 ,
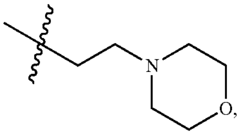
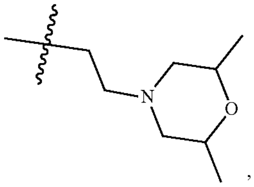 ,
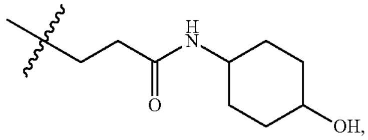
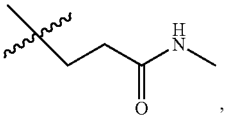 ,
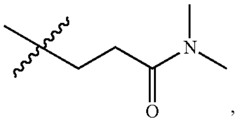 ,
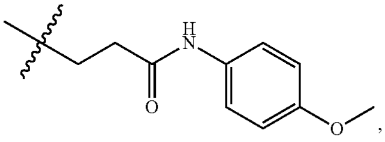 ,
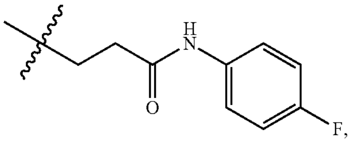
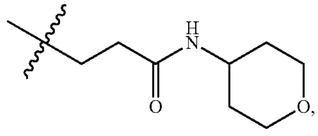
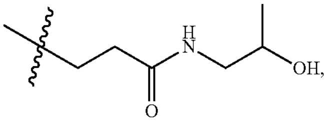
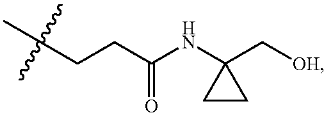
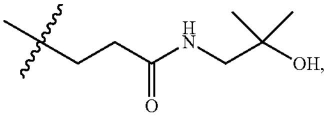
-continued
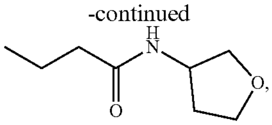
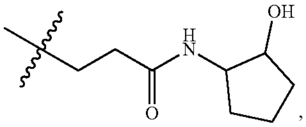 ,
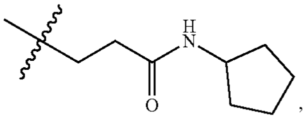 ,
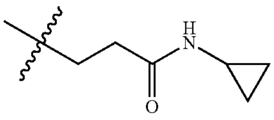 ,
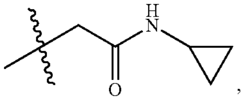 ,
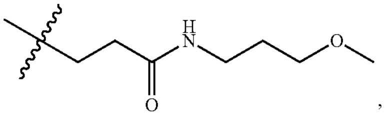 ,
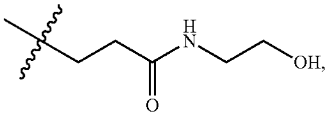
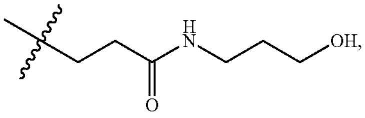
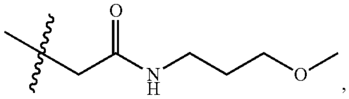 ,
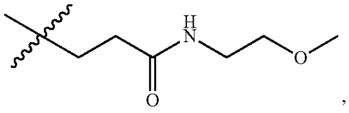 ,
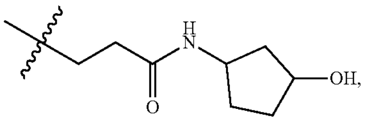
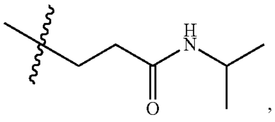 ,
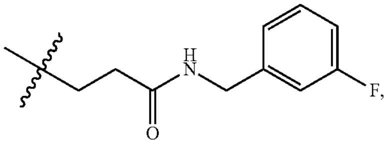
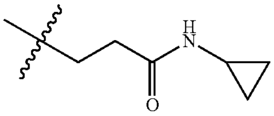 ,
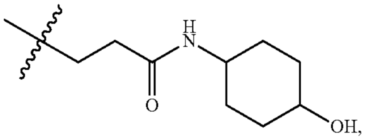

-continued

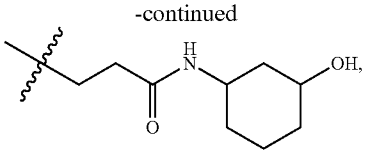

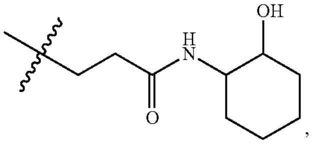
,

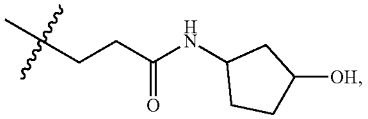

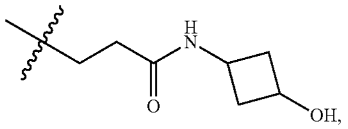

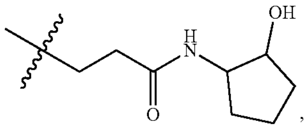
,

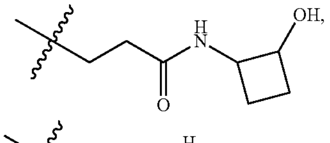

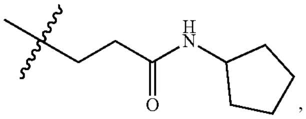
, or

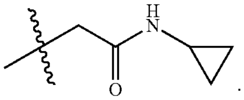
.

12. The compound of claim 10, wherein $R^5$ is $—CONR^{5a}R^{5b}$ $CH_2CONR^{5a}R^{5b}$ or $—CH_2CH_2CONR^{5a}R^{5b}$; $R^{5a}$ is hydrogen or methyl; and $R^{5b}$ is selected from cyclopropyl, cyclobutyl, cyclopentyl, cyclohexenyl, cyclohexadienyl, cycloheptyl, cyclooctyl, cyclononyl, cyclodecyl, cycloundecyl, or cyclododecyl.

13. The compound of claim 1, wherein:

a) $R^5$ is $—CONR_{5a}R^{5b}$, $CH_2CONR_{5a}R^{5b}$ or $—CH_2CH_2CONR_{5a}R^{5b}$; $R^{5a}$ is hydrogen or methyl; $R^{5b}$ is heterocyclyl selected from

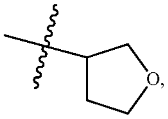
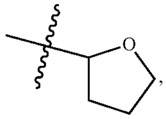
,
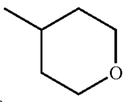
,
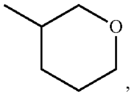
, or
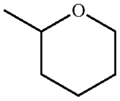
, or phenyl, said heterocyclyl or phenyl is optionally substituted with at least one substituents $R^{5e}$ selected from F, Cl, $—C_{1-8}$alkyl or $—OR^{5f}$; and $R^{5f}$ is each independently hydrogen or $—C_{1-8}$alkyl; or b) $R^5$ is selected from $—CONR^{5a}R^{5b}$, $CH_2CONR^{5a}R^{5b}$, or $—CH_2CH_2CONR^{5a}R^{5b}$; $R^{5a}$ and $R^{5b}$ together with the nitrogen atom to which they are attached, form a 4- to 7-membered ring, said ring comprising 0, 1 or 2 additional heteroatoms independently selected from nitrogen, oxygen or optionally oxidized sulfur as ring member(s), said ring is optionally substituted with at least one substituents $R^{5e}$; $R^{5e}$ is each independently F, Cl, $—C_{1-8}$alkyl, or $—OR^{5f}$, and $R^{5f}$ is each independently hydrogen or $—C_{1-8}$alkyl.

14. The compound of claim 1, wherein $R^5$ is selected from methyl, ethyl, propyl, butyl, pentyl, hexyl, $—CH_2OH$, $—C_2H_4OH$, $C_2H_4NHCH_3$, $—C_2H_4OCH_3$,

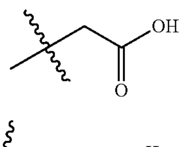
,
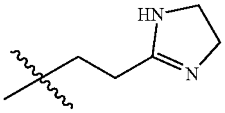
,
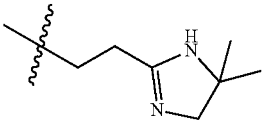
,
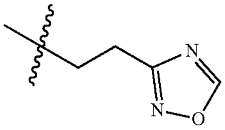
,
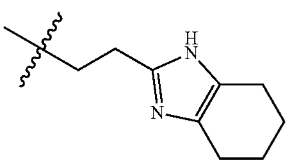
,
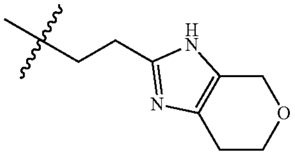
,
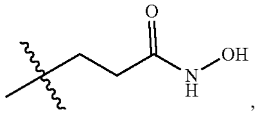
,
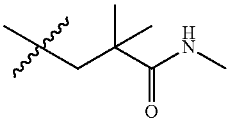
,
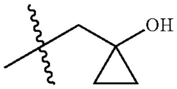
,
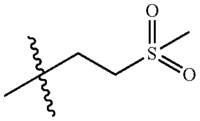
,
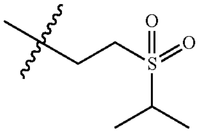
,
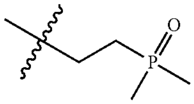
,
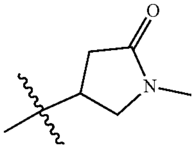
,
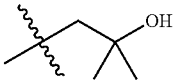
,
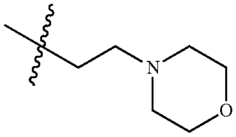
,
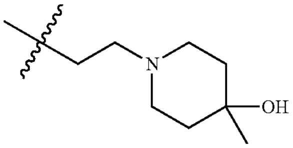
,
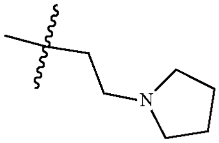
, -continued
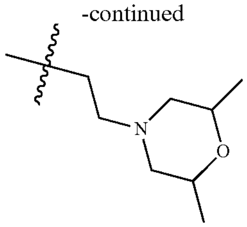
,
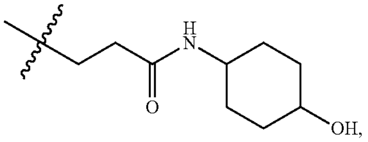
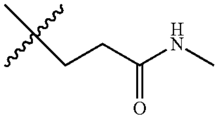
,
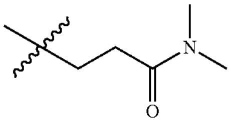
,
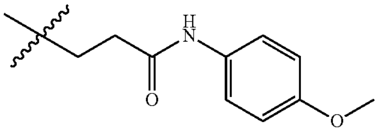
,
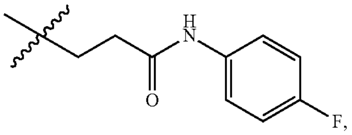
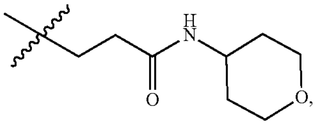
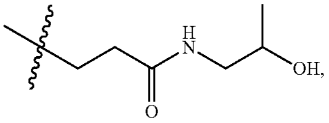
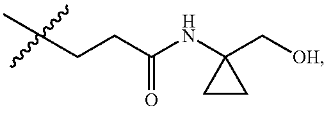
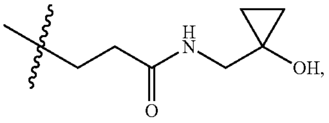
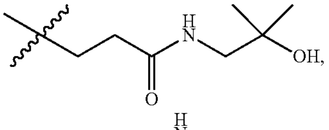
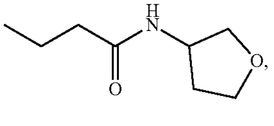
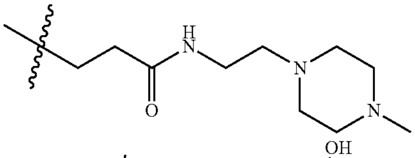
,
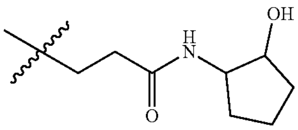
,
-continued
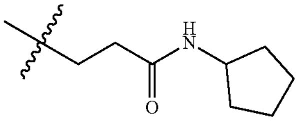
,
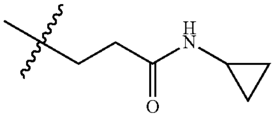
,
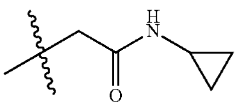
,
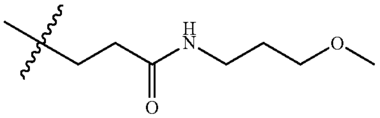
,
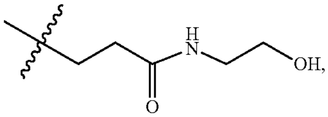
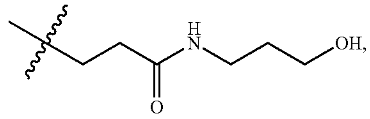
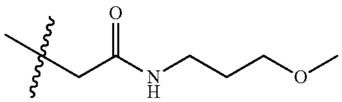
,
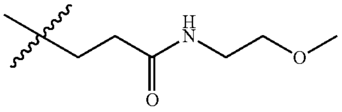
,
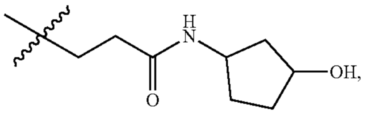
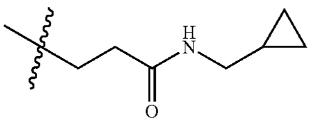
,
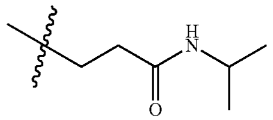
, or
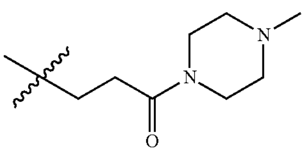
.
15. The compound of claim 1, wherein $R^5$ is —$C_{1-8}$alkyl or —$CONR^{5a}R^{5b}$; $R^{5a}$ and $R^{5b}$ are hydrogen or —$C_{1-8}$alkyl; $R^6$ is selected from —$C_{1-8}$alkyl, —$OR_{6a}$ or —$NR^{6a}R^{6b}$, said —$C_{1-8}$alkyl is optionally substituted with at least one substituents $R^{6d}$, $R^{6a}$ and $R^{6b}$ are each hydrogen or —$C_{1-8}$alkyl; and $R^{6d}$ is each independently F or Cl.

16. A compound, wherein the compound is selected from:
1
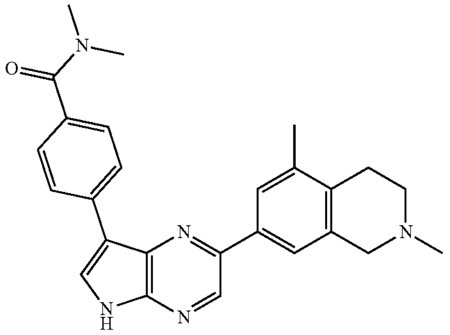
2
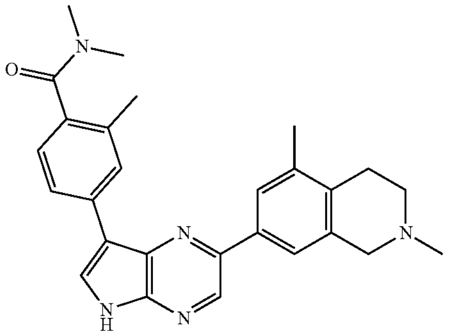
3
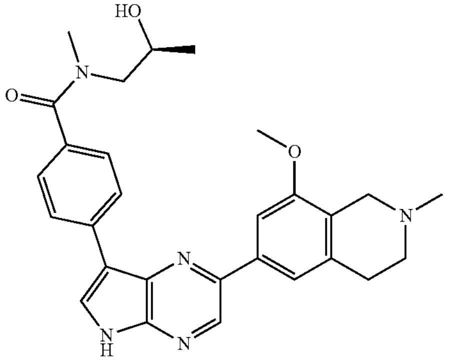
4
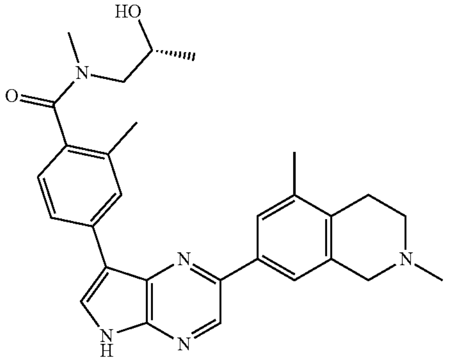
-continued
5
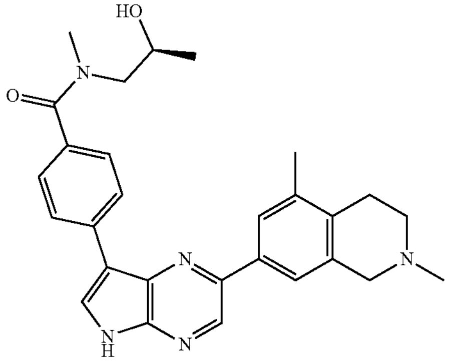
6
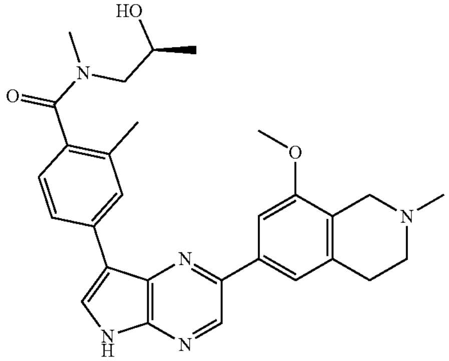
7A
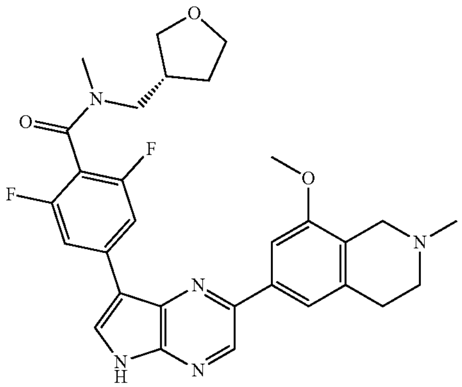
7B
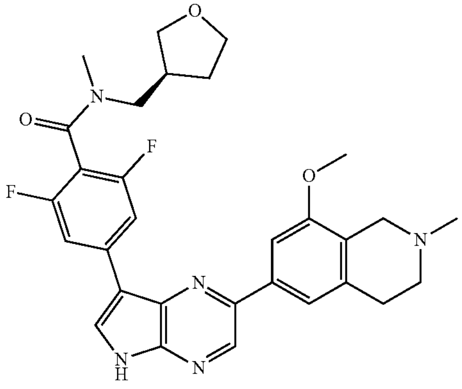

-continued
8
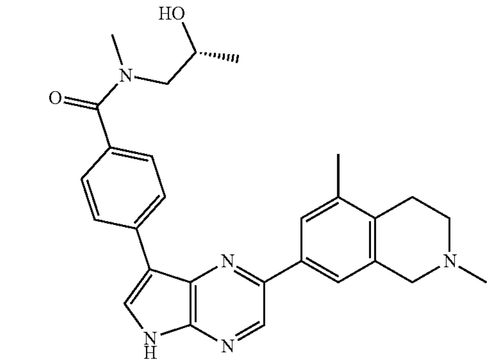
9
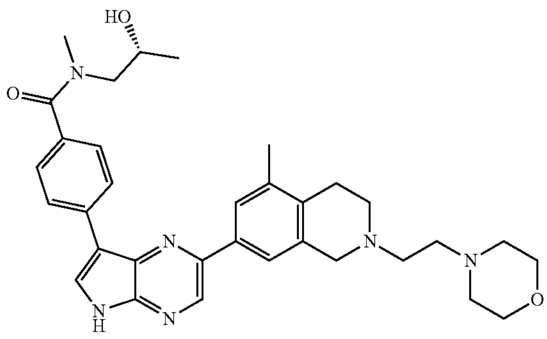
10
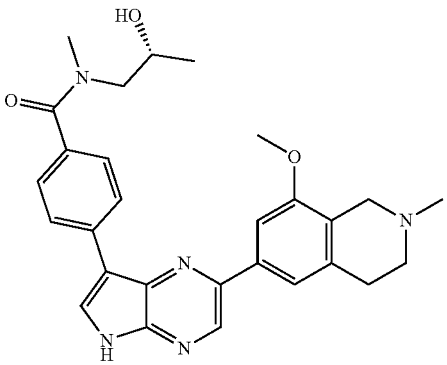
11
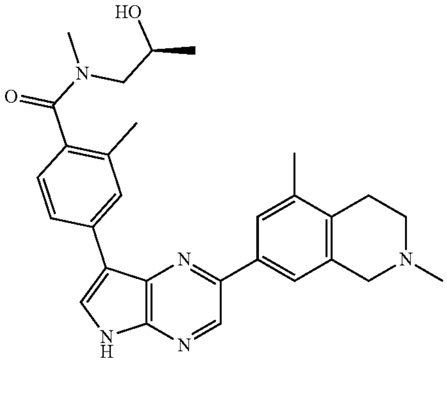
-continued
12
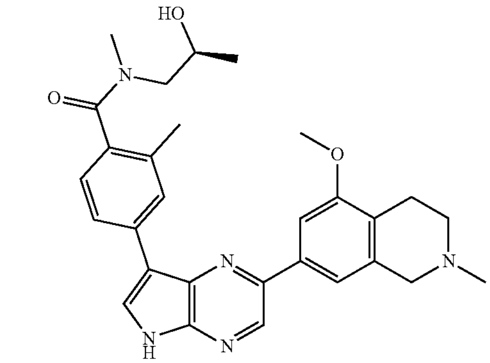
13
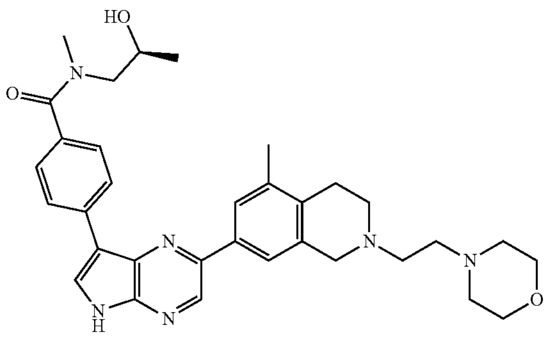
14
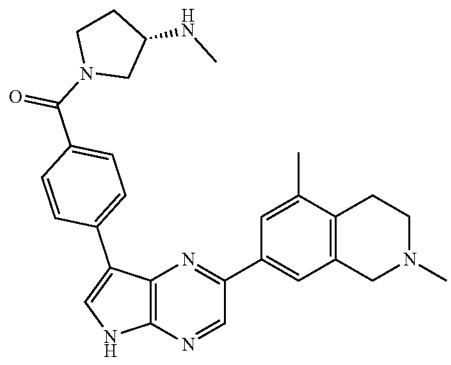
15
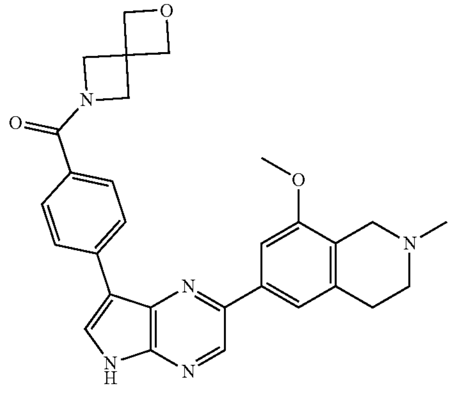

-continued
16
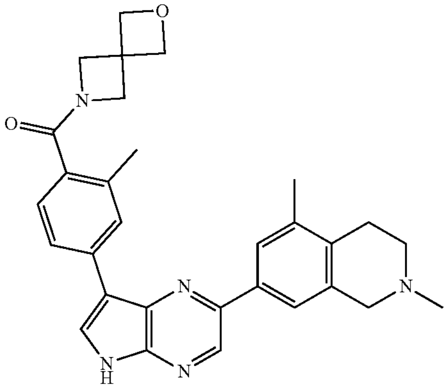
17
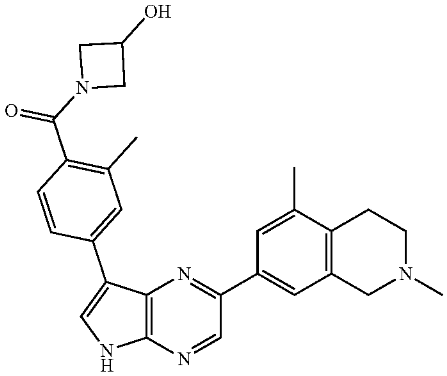
18
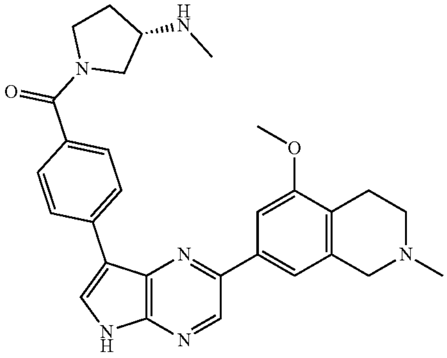
19
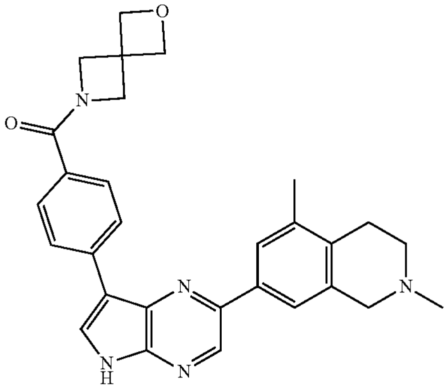
-continued
20
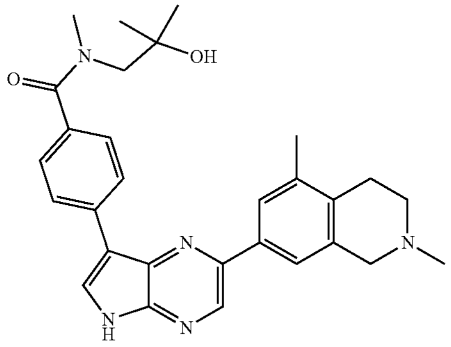
21
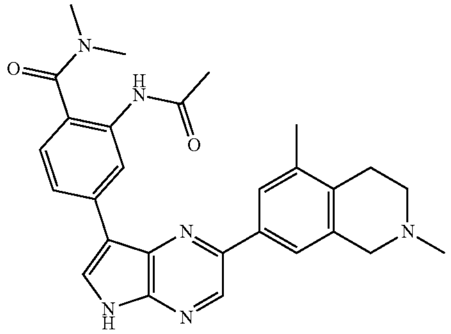
22
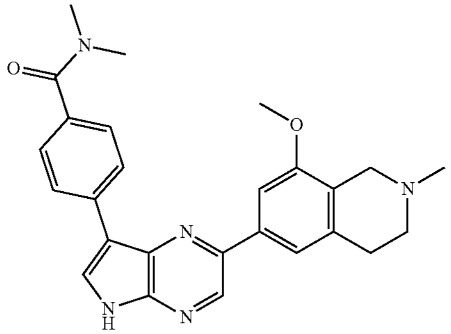
23
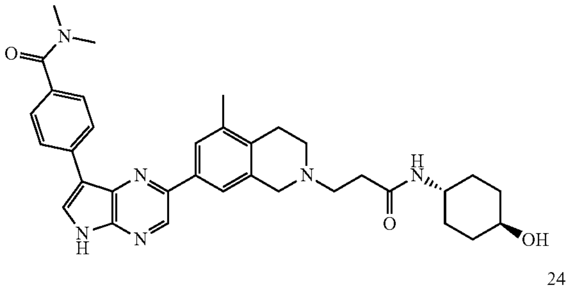
24
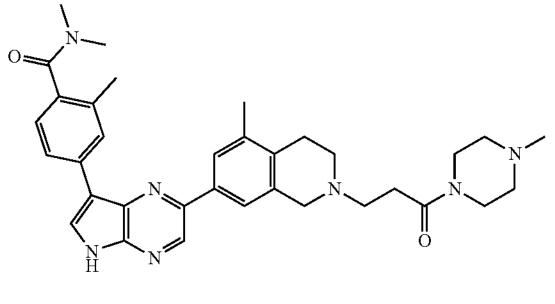

-continued
25
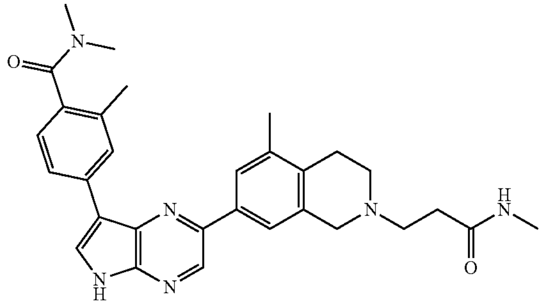
26
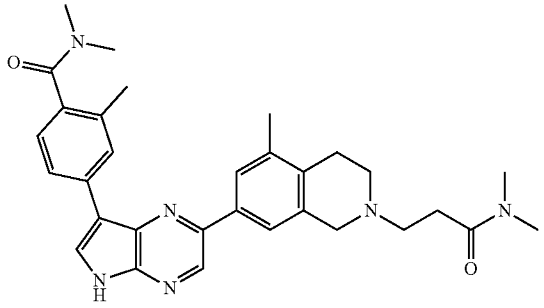
27
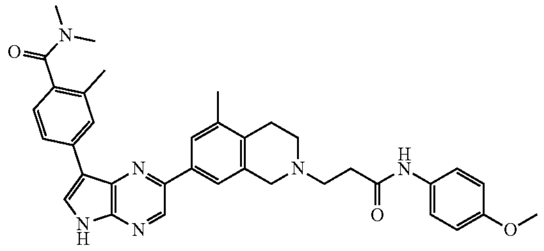
28
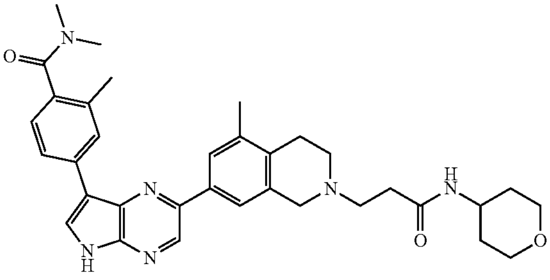
29
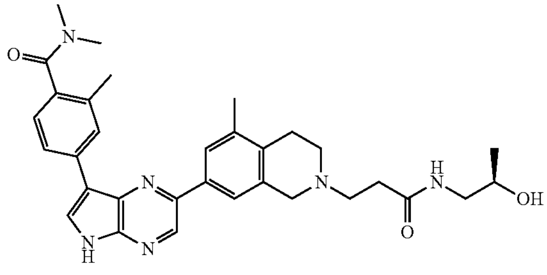
-continued
30
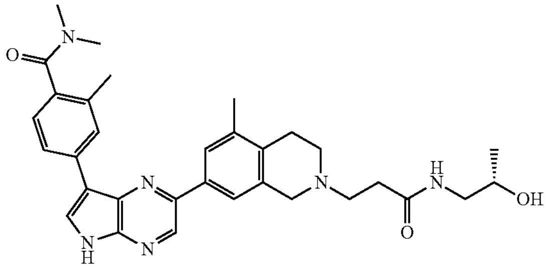
31
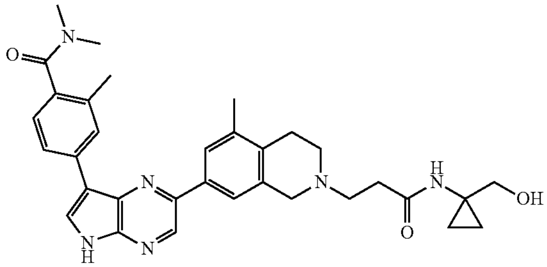
32
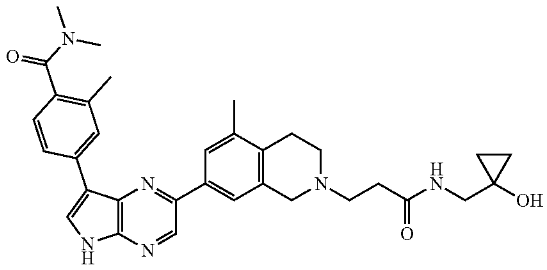
33
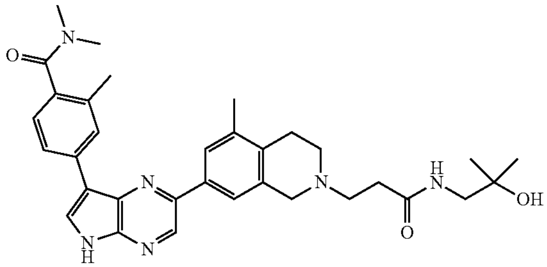
34
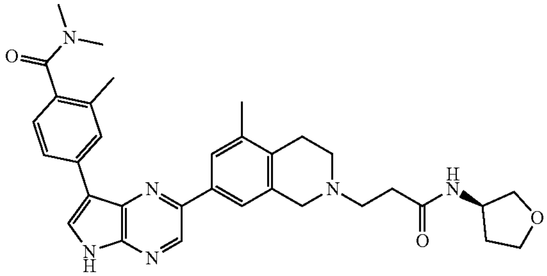

-continued
35
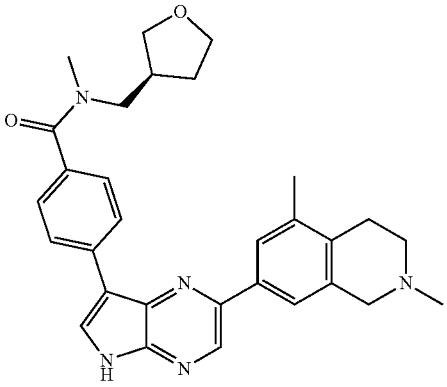
36
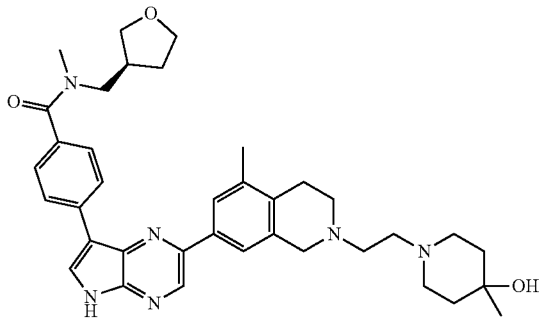
37
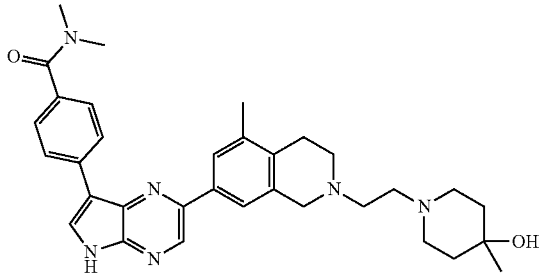
38
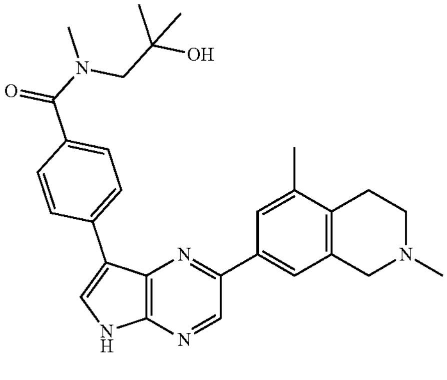
-continued
39
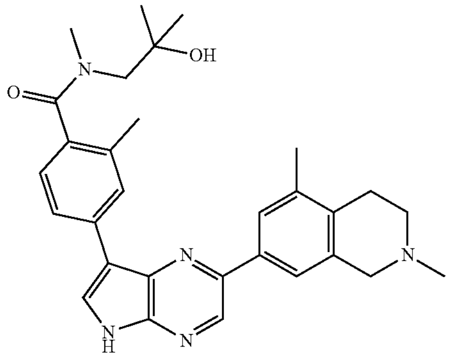
40
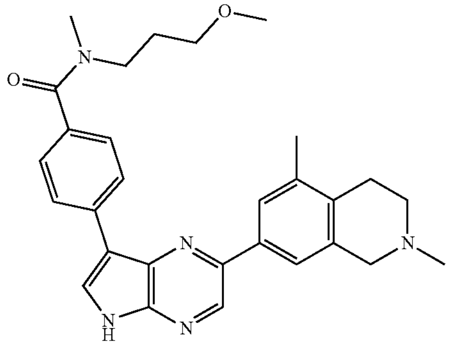
41
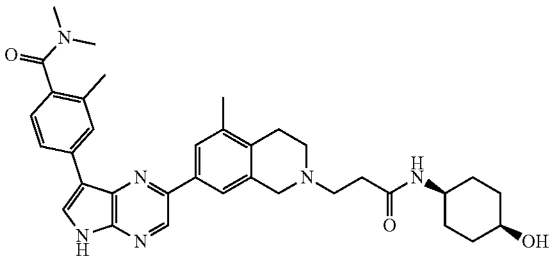
42
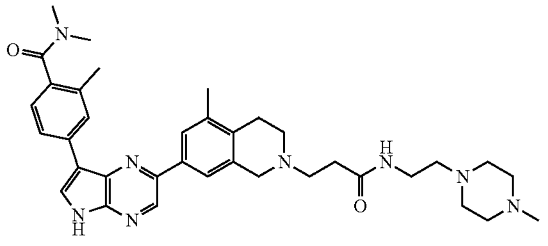
43
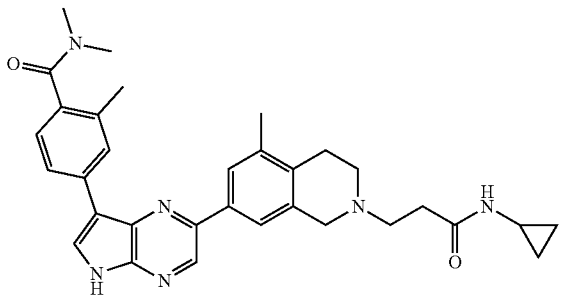

-continued
44
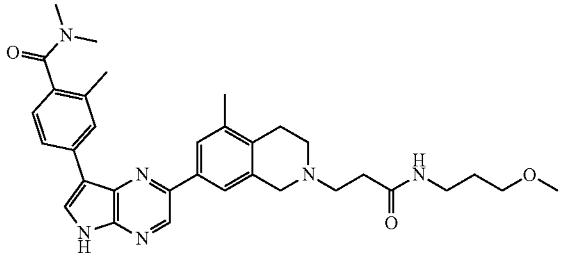
45
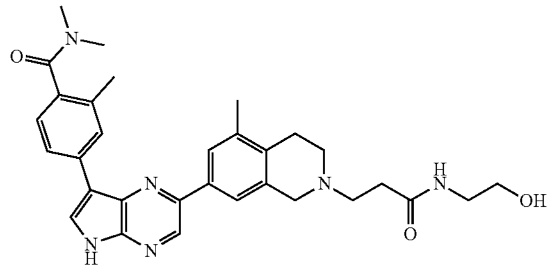
46
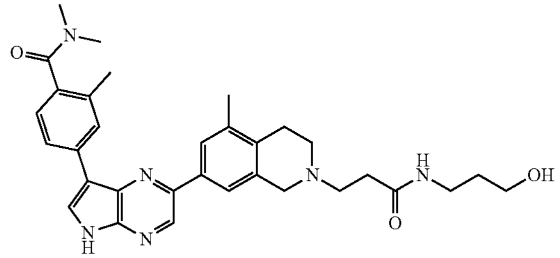
47
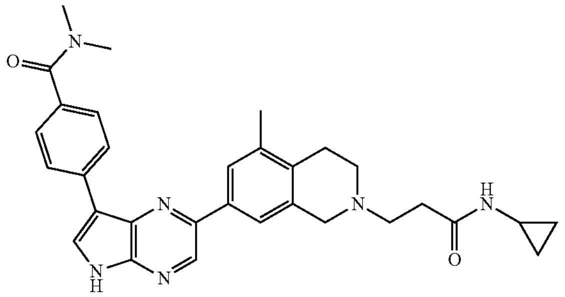
48
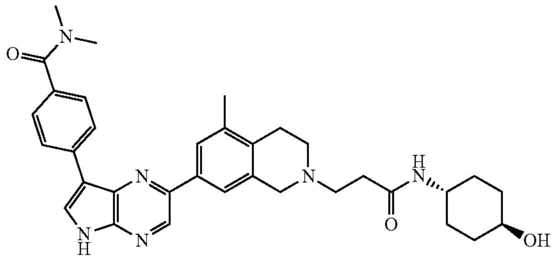
-continued
49
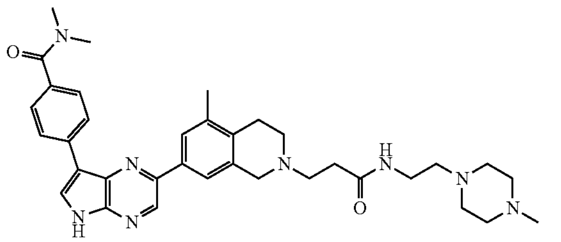
50
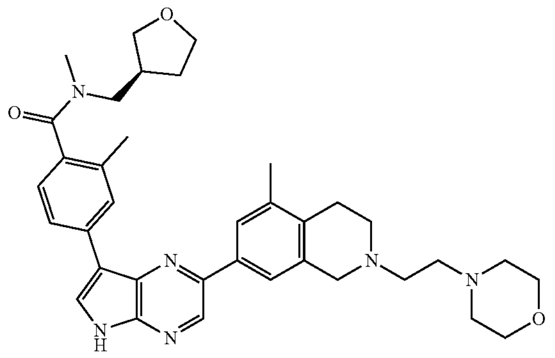
51
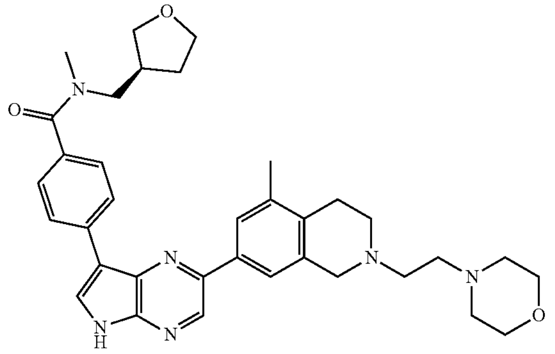
52
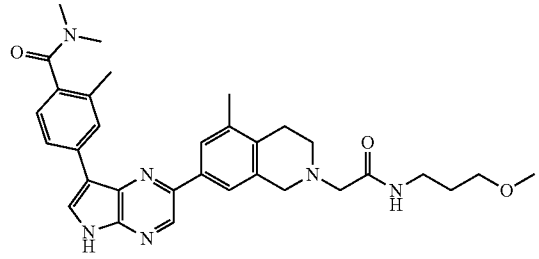
53
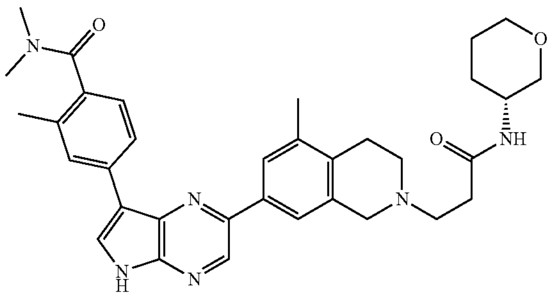

-continued
54
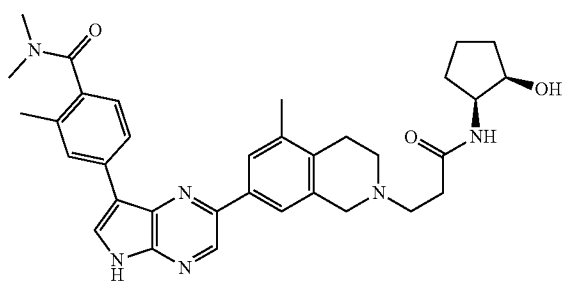
55
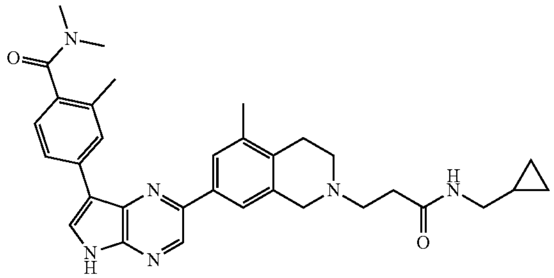
56
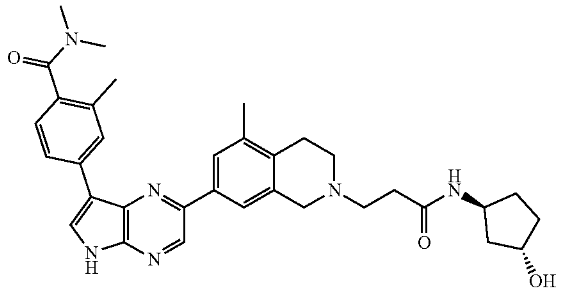
57
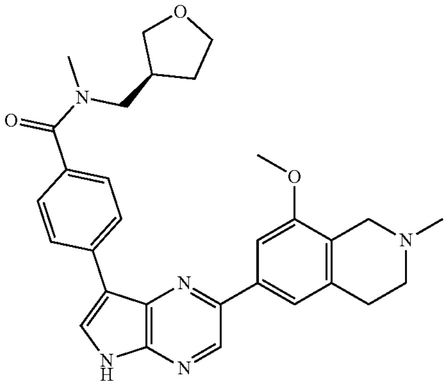
-continued
58
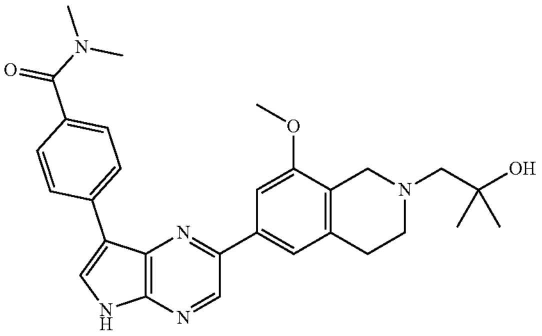
59
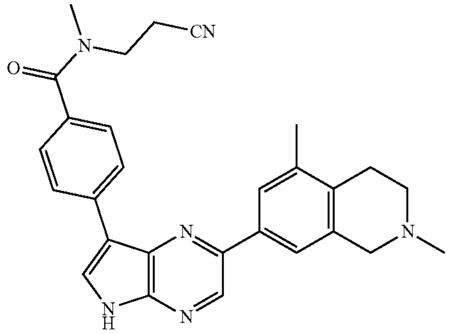
60
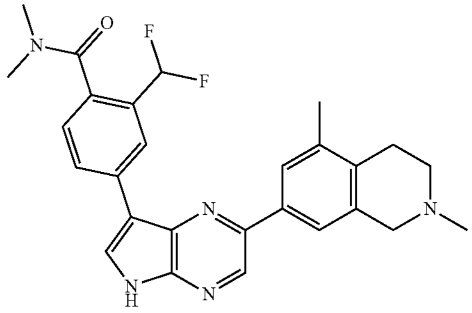
61
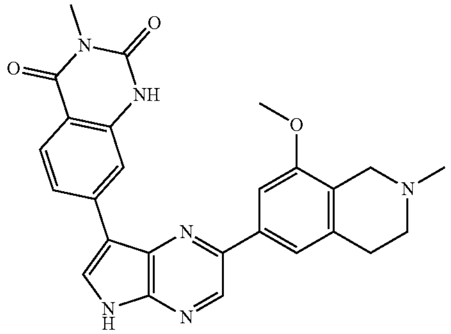

-continued
62
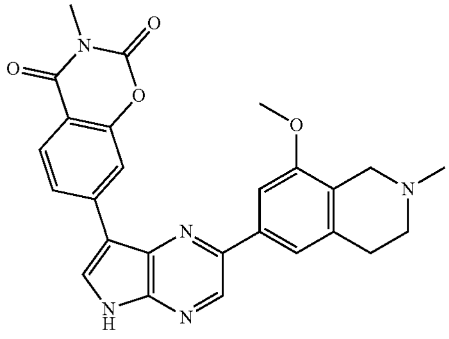
63
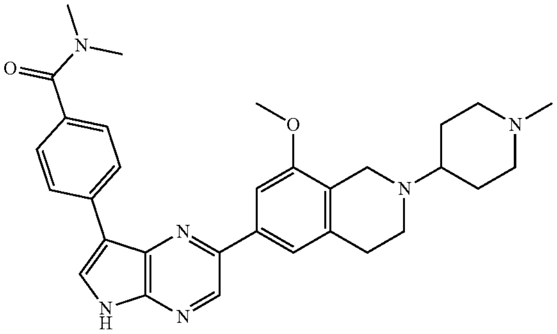
64
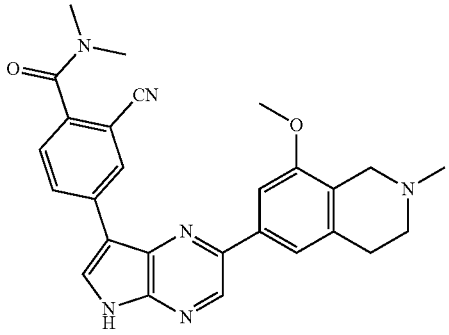
65
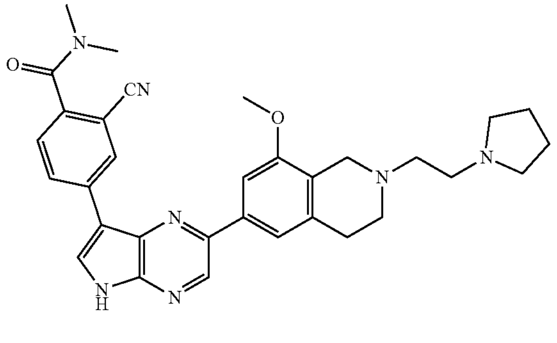
-continued
66
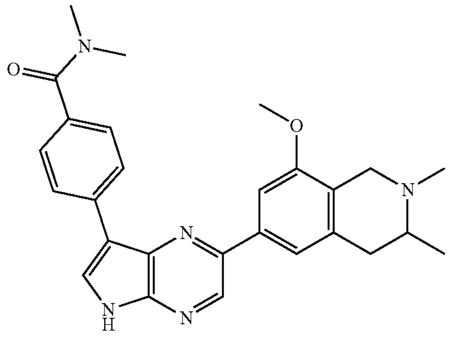
67
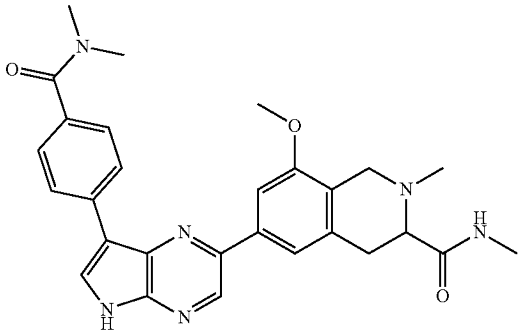
68
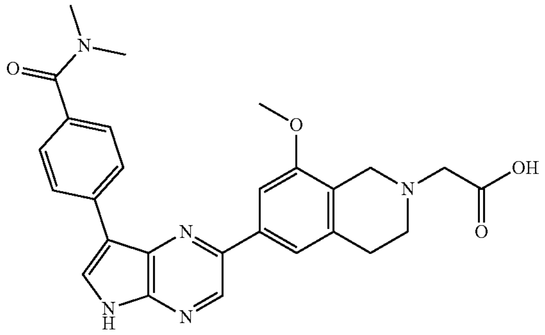
69
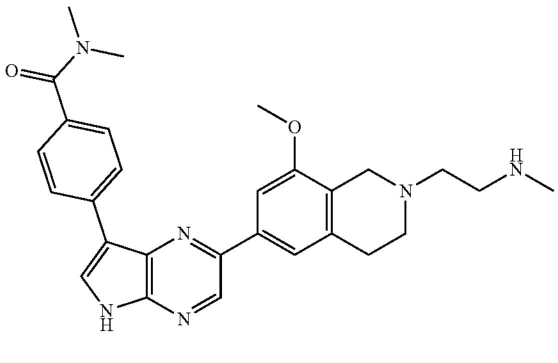

-continued
70
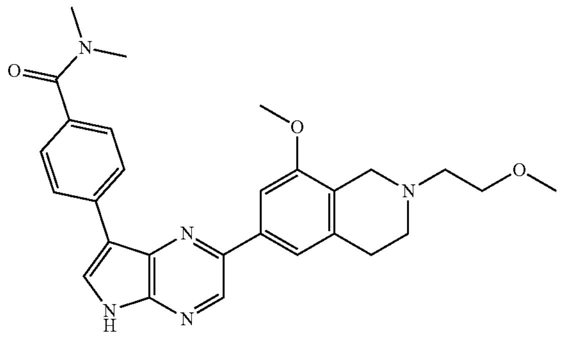
71
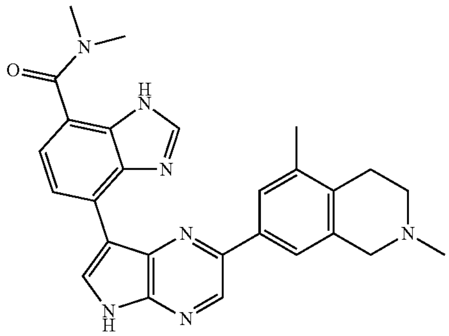
72
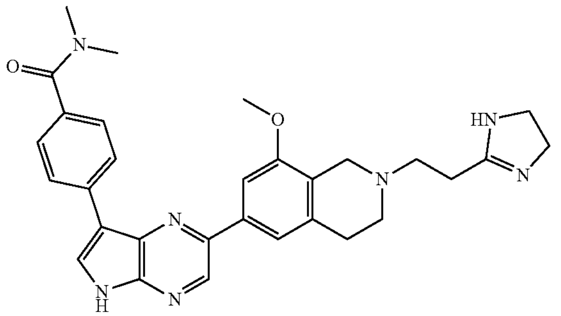
73
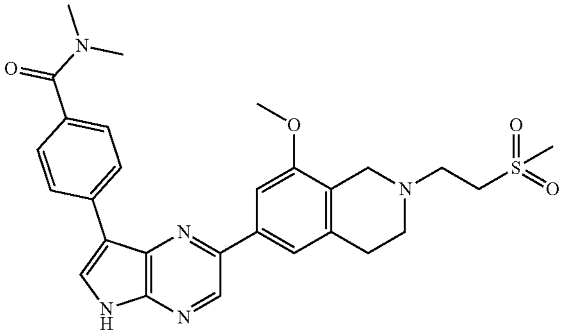
-continued
74
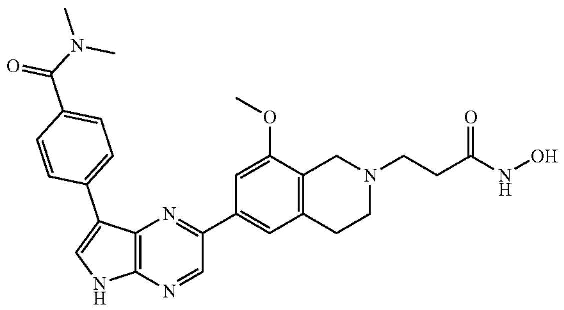
75
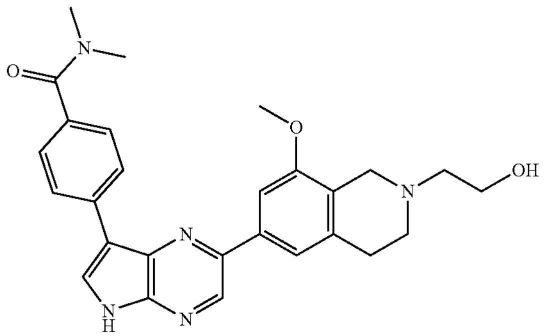
76
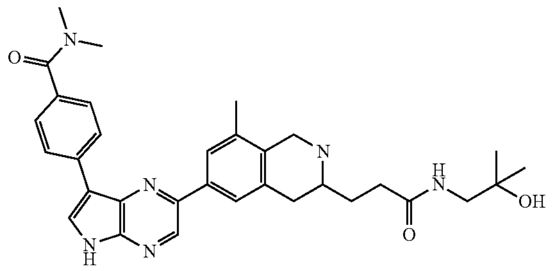
77
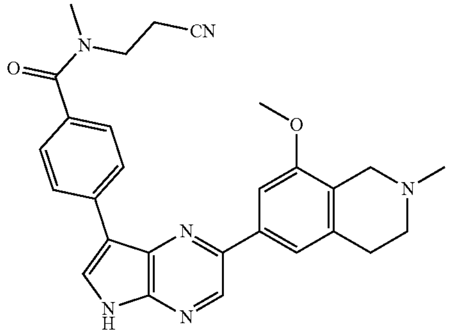

-continued
78
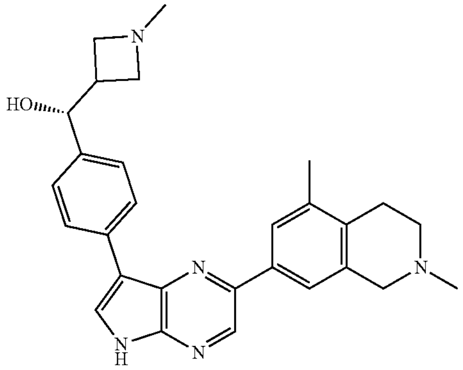
79
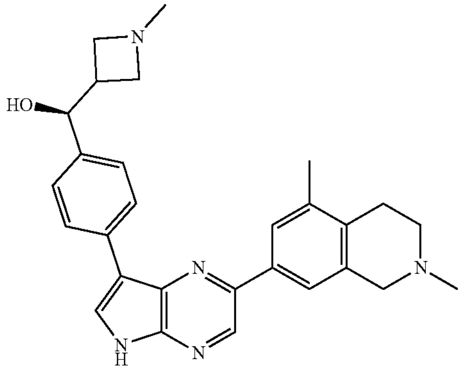
80
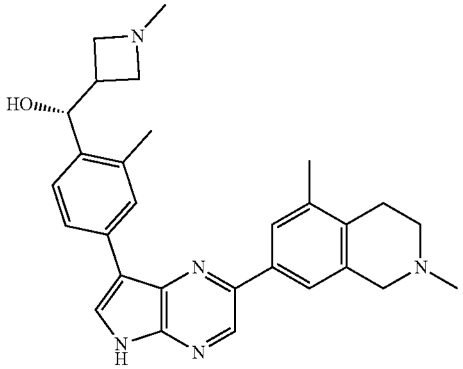
81
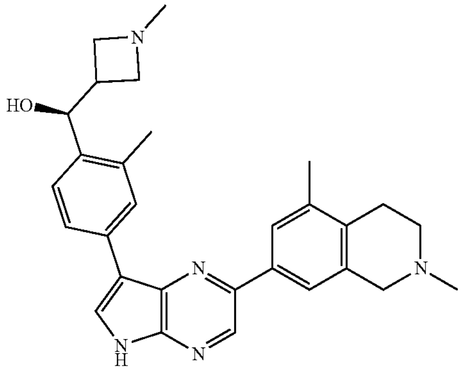
-continued
82
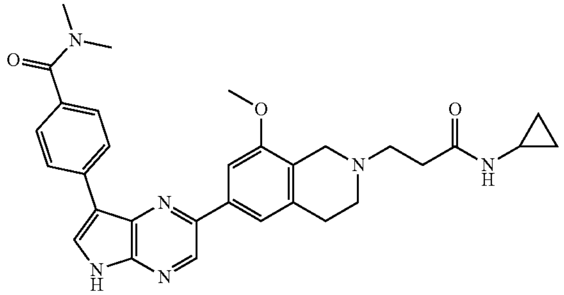
83
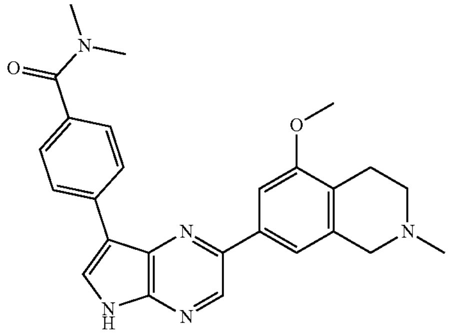
84
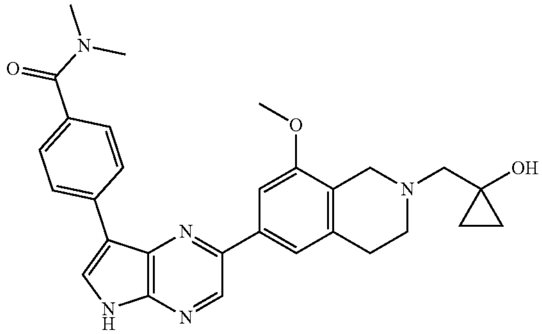
85
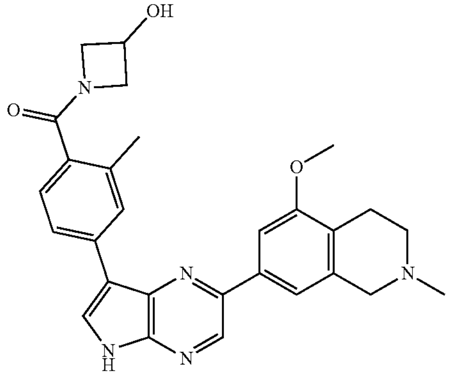

-continued
86
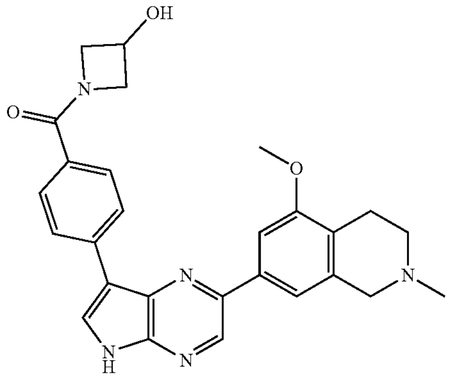
87
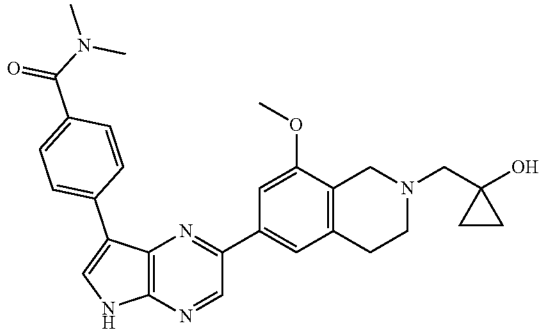
88
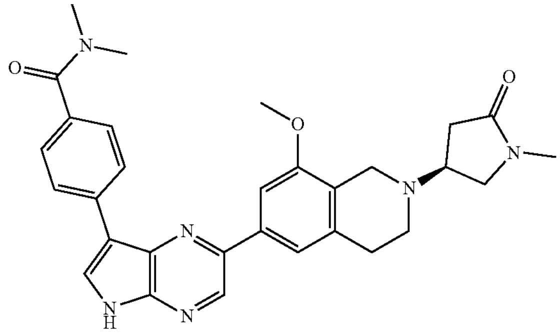
89
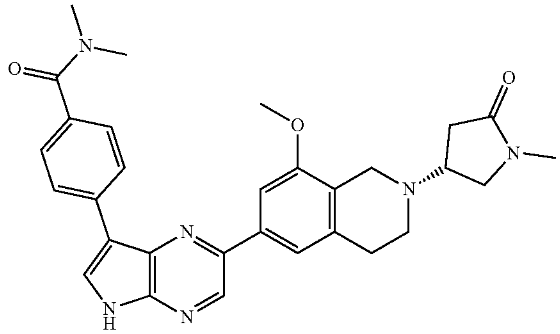
-continued
90
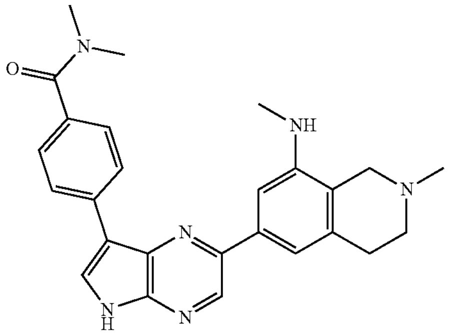
91
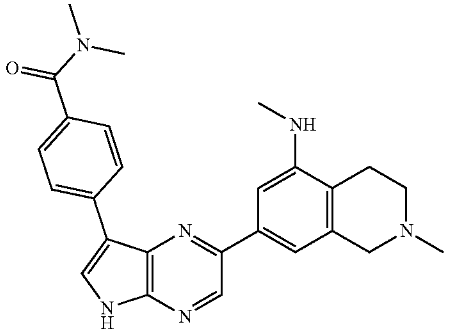
92
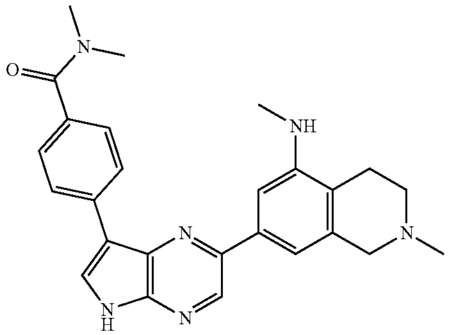
93
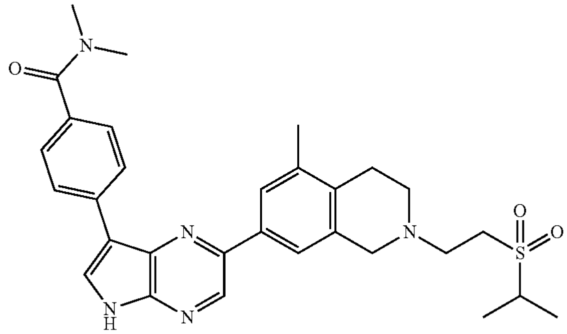

-continued
94
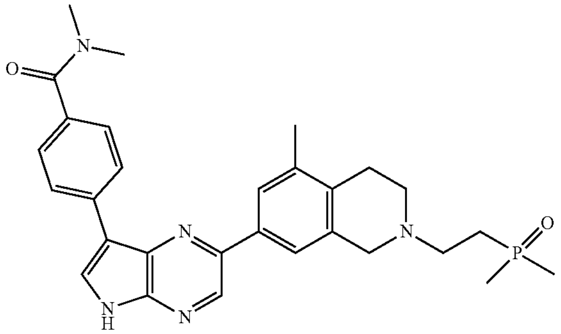
95
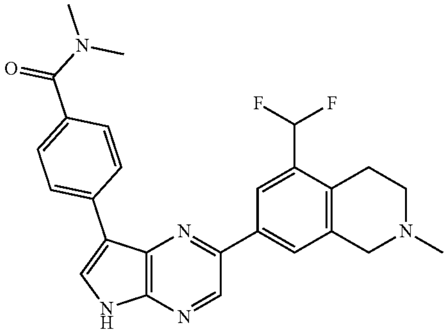
96
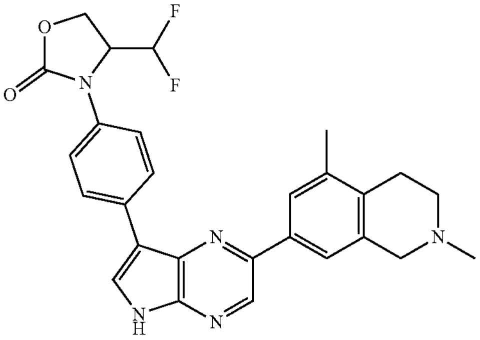
97
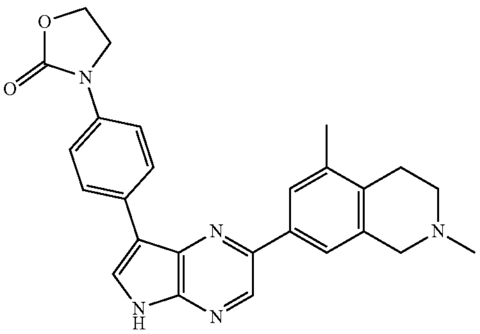
-continued
98
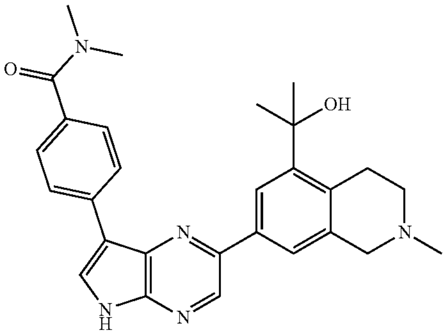
99
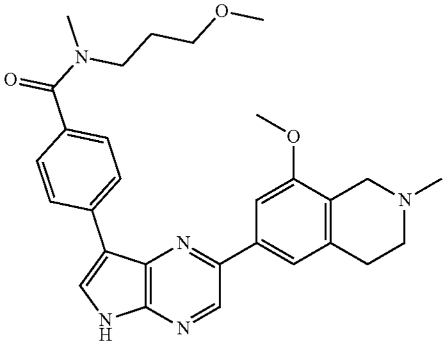
100
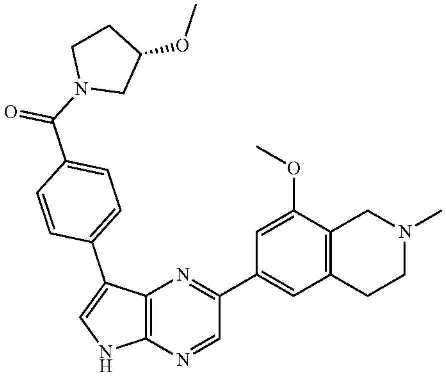
101
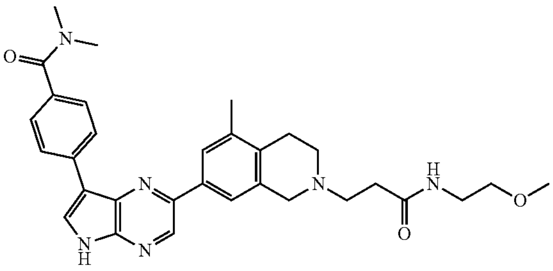

-continued
102
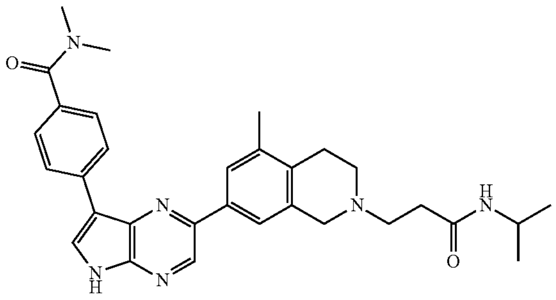
103
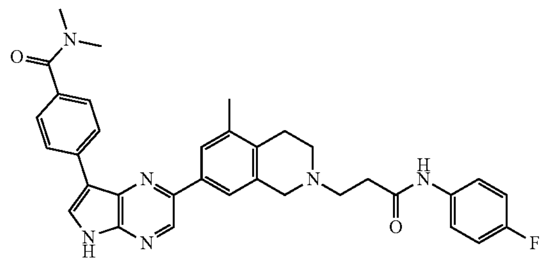
104
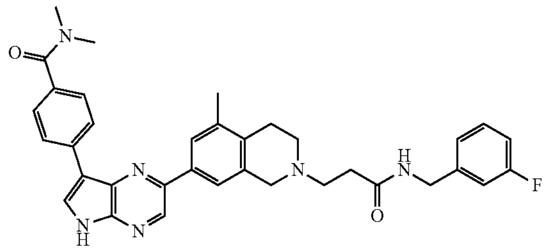
105
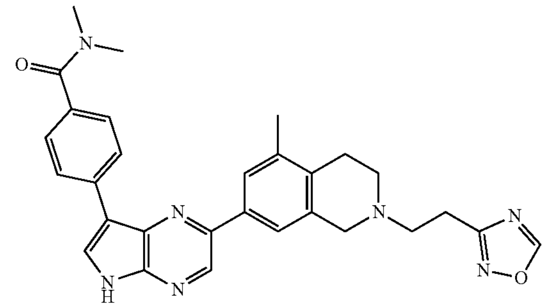
106
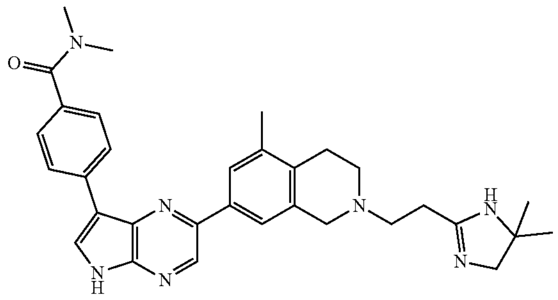
-continued
107
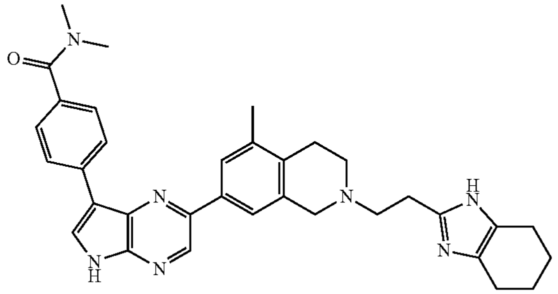
108
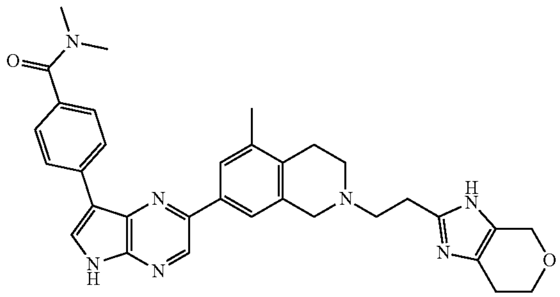
109
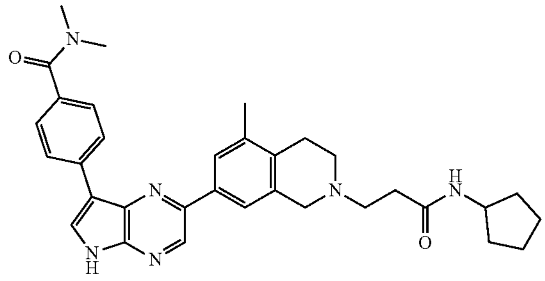
110
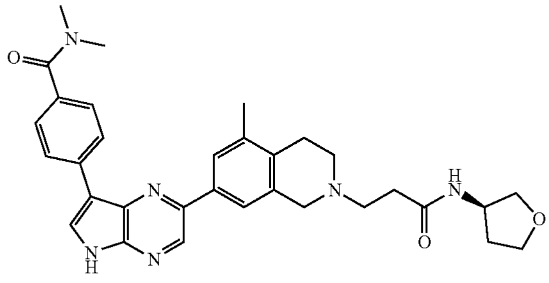
111
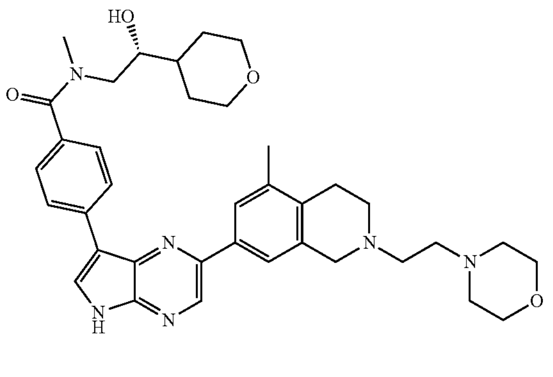

-continued
112
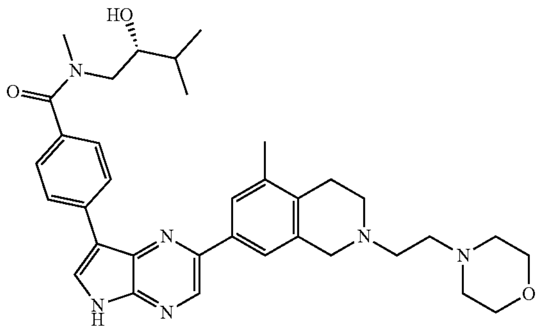
113
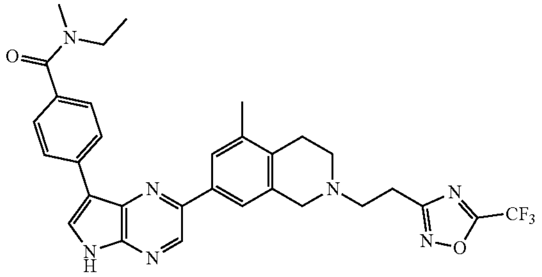
114
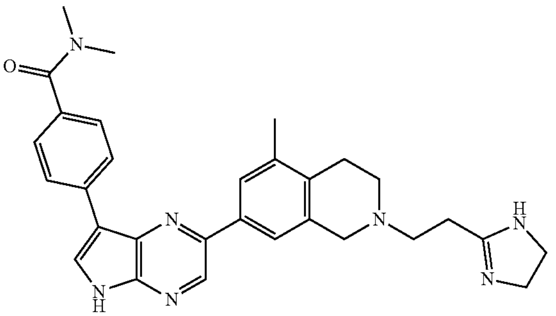
115
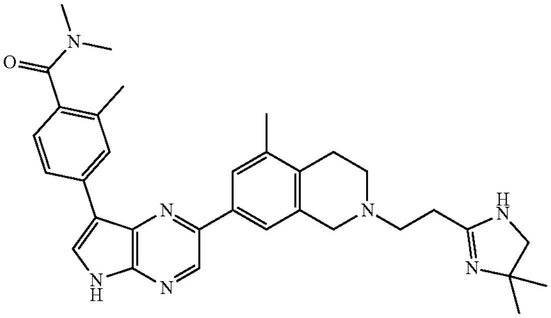
-continued
116
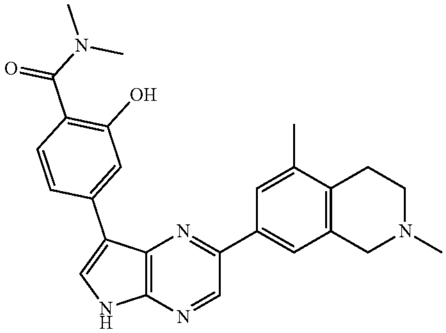
117
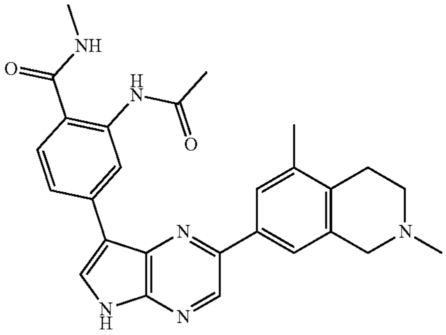
118
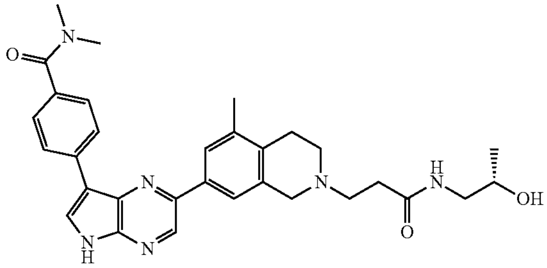
119
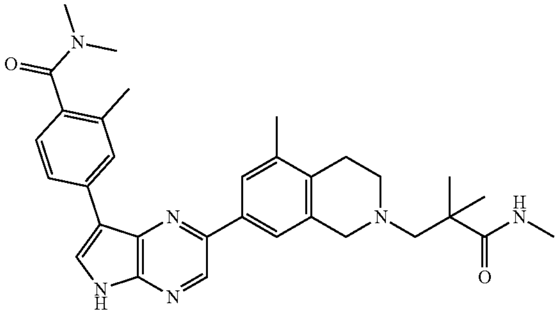
120
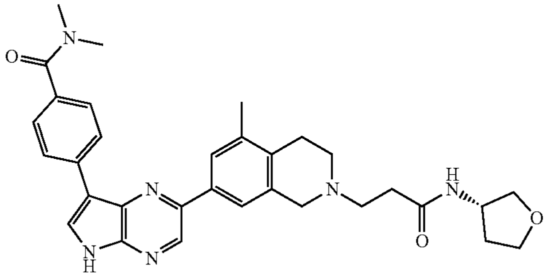

-continued

121

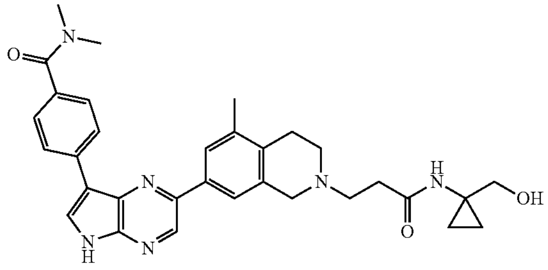

122

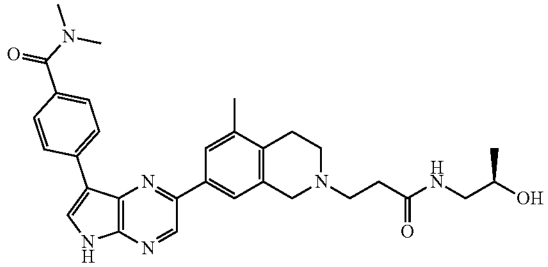

123

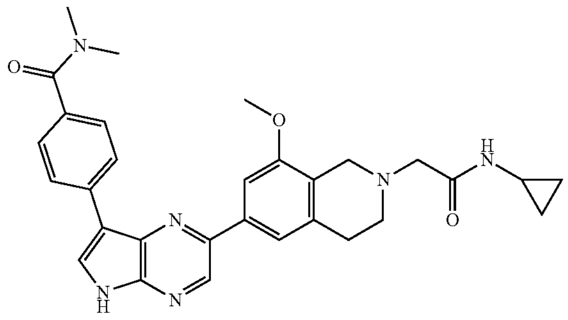

124

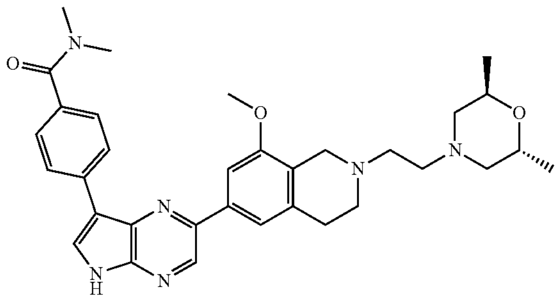

125

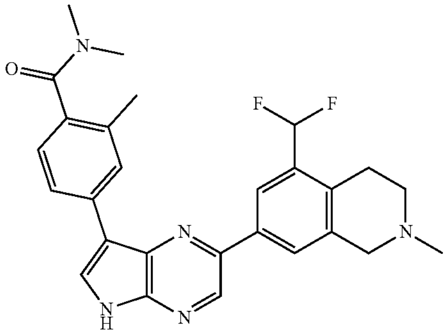

-continued

126

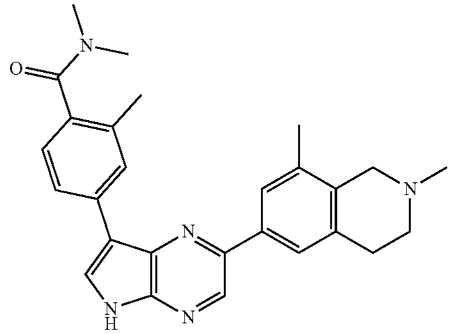

127

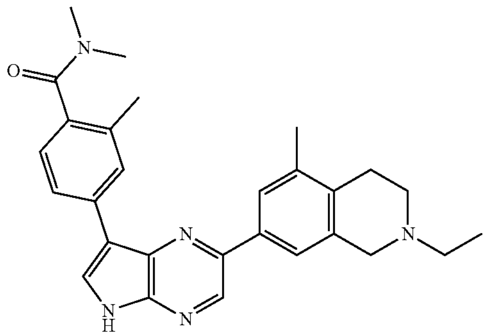

128

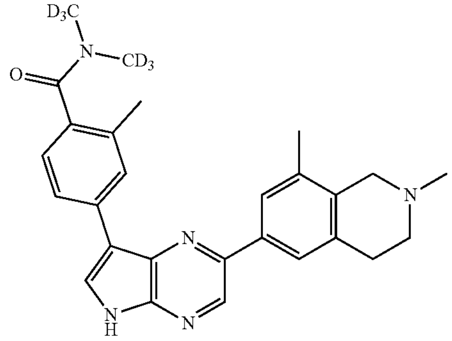

.

or a pharmaceutically acceptable salt thereof.

17. A pharmaceutical composition comprising the compound of claim 1 or a stereoisomer thereof, or a pharmaceutically acceptable salt thereof and a pharmaceutically acceptable excipient.

18. A method of inhibiting HPK1 activity, comprising administering a subject in need thereof the compound of claim 1 or a stereoisomer thereof, or a pharmaceutically acceptable salt thereof.

19. The compound of claim 1, wherein:

$R^5$ is methyl, ethyl, 1-propyl, 2-propyl, 1-butyl, 2-methyl-1-propyl, 1-methylpropyl or t-butyl; and $R^6$ is $-CH_3$, $-OCH_3$, $-NHCH_3$, $-CHF_2$, or $-C(CH_3)_2$ OH.

20. The compound of claim 16, wherein the compound is

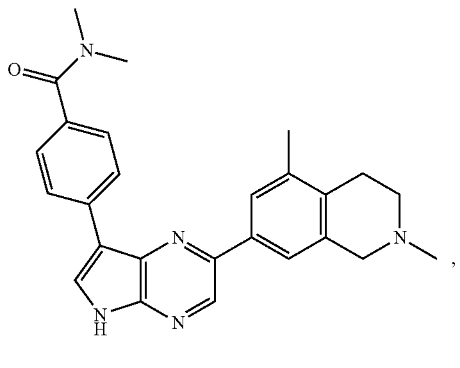 [SMILES: Cc1cc(-c2cnc3[nH]cc(-c4ccc(C(=O)N(C)C)cc4)c3n2)cc2c1CCN(C)C2]

or a pharmaceutically acceptable salt thereof.

21. The compound of claim 16, wherein the compound is

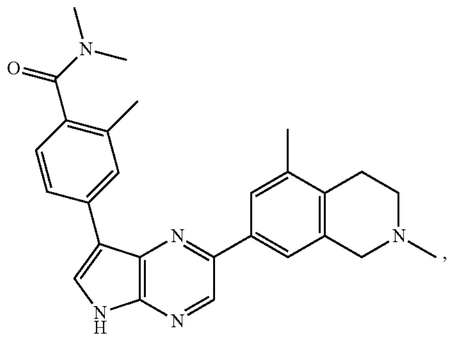 [SMILES: Cc1cc(-c2c[nH]c3ncc(-c4cc(C)c5c(c4)CN(C)CC5)nc23)ccc1C(=O)N(C)C]

or a pharmaceutically acceptable salt thereof.

22. The compound of claim 16, wherein the compound is

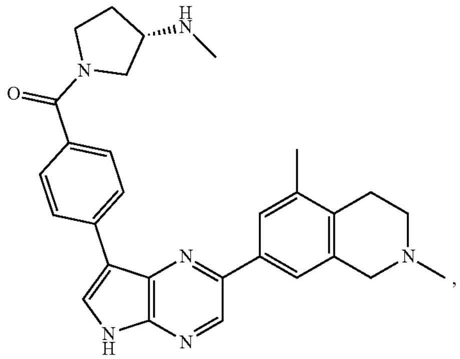 [SMILES: CN[C@H]1CCN(C(=O)c2ccc(-c3c[nH]c4ncc(-c5cc(C)c6c(c5)CN(C)CC6)nc34)cc2)C1]

or a stereoisomer thereof, or a pharmaceutically acceptable salt thereof.

23. The compound of claim 13, wherein the compound is

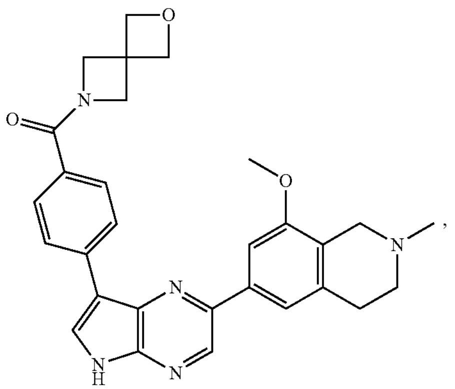 [SMILES: COc1cc(-c2cnc3[nH]cc(-c4ccc(C(=O)N5CC6(COC6)C5)cc4)c3n2)cc2c1CN(C)CC2]

or a pharmaceutically acceptable salt thereof.

24. The compound of claim 16, wherein the compound is

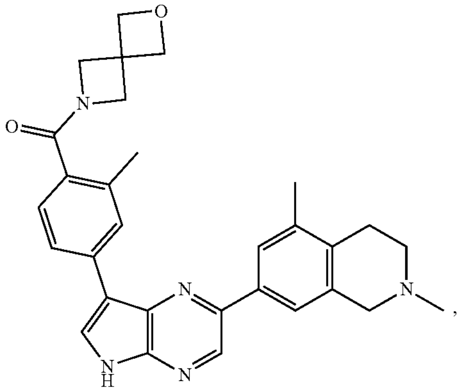 [SMILES: Cc1cc(-c2c[nH]c3ncc(-c4cc(C)c5c(c4)CN(C)CC5)nc23)ccc1C(=O)N1CC2(COC2)C1]

or a pharmaceutically acceptable salt thereof.

25. The compound of claim 16, wherein the compound is

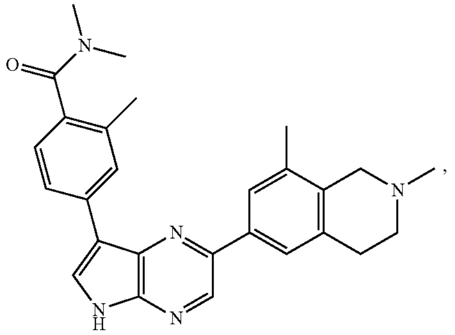 [SMILES: Cc1cc(-c2c[nH]c3ncc(-c4cc(C)c5c(c4)CCN(C)C5)nc23)ccc1C(=O)N(C)C]

or a pharmaceutically acceptable salt thereof.

* * * * *